United States Patent
Liu et al.

(10) Patent No.: US 10,550,143 B2
(45) Date of Patent: Feb. 4, 2020

(54) C,O-SPIRO ARYL GLYCOSIDE COMPOUNDS, PREPARATION THEREFOR AND USE THEREOF

(71) Applicant: SHANGHAI INSTITUTE OF MATERIA MEDICA, CHINESE ACADEMY OF SCIENCES, Pudong, Shanghai (CN)

(72) Inventors: Hong Liu, Shanghai (CN); Jia Li, Shanghai (CN); Jiang Wang, Shanghai (CN); Jingya Li, Shanghai (CN); Hui Chen, Shanghai (CN); Dan Li, Shanghai (CN); Jian Li, Shanghai (CN); Yibing Wang, Shanghai (CN); Hualiang Jiang, Shanghai (CN); Kaixian Chen, Shanghai (CN)

(73) Assignee: Shanghai Institute of Materia Medica, Chinese Academy of Sciences, Shanghai (CN)

( * ) Notice: Subject to any disclaimer, the term of this patent is extended or adjusted under 35 U.S.C. 154(b) by 94 days.

(21) Appl. No.: 15/738,675

(22) PCT Filed: Jun. 23, 2016

(86) PCT No.: PCT/CN2016/086892
§ 371 (c)(1),
(2) Date: Mar. 15, 2018

(87) PCT Pub. No.: WO2016/206604
PCT Pub. Date: Dec. 29, 2016

(65) Prior Publication Data
US 2018/0305390 A1 Oct. 25, 2018

(30) Foreign Application Priority Data

Jun. 23, 2015 (CN) .......................... 2015 1 0353843

(51) Int. Cl.
*C07H 19/01* (2006.01)
*A61P 3/08* (2006.01)

(52) U.S. Cl.
CPC ................ *C07H 19/01* (2013.01); *A61P 3/08* (2018.01)

(58) Field of Classification Search
None
See application file for complete search history.

(56) References Cited

FOREIGN PATENT DOCUMENTS

| CN | 101111508 A | 1/2008 |
|---|---|---|
| CN | 101495495 A | 7/2009 |
| WO | 2007140191 A2 | 12/2007 |

OTHER PUBLICATIONS

Adachi et al., Metabolism, vol. 49, No. 8, 2000, 990-995.*
Lv et al., Bioorganic and Medicinal Chemistry Letters, 19, 2009, 6877-6881.*
Patani et al., Chem. Rev., 1996, 96, 3147-3176.*
Lv et al., "Exploration of O-spiroketal C-arylglucosides as Novel and Selective Renal Sodium-dependent Glucose Co-transporter 2 (SGLT2) Inhibitors." Bioorganic & Medicinal Chemistry Letters, vol. 19, pp. 6877-6881 (2009).
Tang et al, "A Specific Pharmacophore Model of Sodium-dependent Glucose Co-Transporter 2 (SGLT2) Inhibitors," J. Mol. Model, vol. 18, pp. 2795-2804 (2012).

* cited by examiner

*Primary Examiner* — Traviss C McIntosh, III
(74) *Attorney, Agent, or Firm* — Panitch Schwarze Belisario & Nadel LLP

(57) ABSTRACT

C, O-spiro aryl glycoside compounds are provided. Specifically provided are C, O-spiro aryl glycoside compounds represented by the formula (I), wherein the definitions of each variable group are described in the specification. Also provided are methods of preparing and using the C, O-spiro aryl glycoside compounds. The C, O-spiro aryl glycoside compounds can be used as SGLT2 inhibitors and for treating diseases, such as diabetes, atherosclerosis, and adiposity.

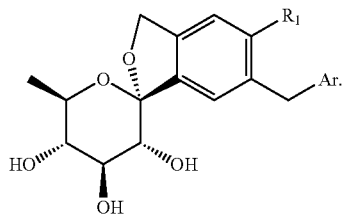

Formula I

20 Claims, 2 Drawing Sheets

C,O-SPIRO ARYL GLYCOSIDE COMPOUNDS, PREPARATION THEREFOR AND USE THEREOF

CROSS-REFERENCE TO RELATED APPLICATION

This application is a Section 371 of International Application No. PCT/CN2016/086892, filed Jun. 23, 2016, which was published in the Chinese language on Dec. 29, 2016, under International Publication No. WO 2016/206604 A1, which claims priority under 35 U.S.C. § 119(b) to Chinese Application No. 201510353843.4, filed Jun. 23, 2015, the disclosures of which are incorporated herein by reference in their entirety.

FIELD OF THE INVENTION

The present invention relates to the field of pharmaceutical chemistry and pharmacotherapy, in particular to a class of C. O-spiro aryl glycoside compounds, the preparation thereof, pharmaceutical compositions comprising such compounds and their use as sodium-glucose cotransporter 2 inhibitors, in particular, for the preparation of medicaments for the treatment of metabolic diseases such as diabetes, atherosclerosis and obesity.

BACKGROUND OF THE INVENTION

Diabetes Mellitus (DM) is a chronic, systemic and metabolic disease caused by long-term interaction between genetic and environmental factors and characterized by increased plasma glucose levels, and is a disease that affect the normal physiological activity mainly due to sugar, fat, protein metabolism disorders caused by insufficient insulin secretion or dysfunction in the body (insulin resistance). Diabetic complications can be divided into acute and chronic complications, in which the acute complications comprises diabetic ketoacidosis, hyperosmolar diabetic coma, various acute infections and lactic acidosis, In addition, hypoglycemia which occurs during the course of diabetes treatment is also one of the most common acute complications; chronic complications include diabetic eye disease, diabetic nephropathy, diabetic neuropathy, diabetic cardiovascular and cerebrovascular diseases, diabetic foot and skin lesions, etc. The main clinical manifestations of diabetes are polydipsia, polyuria, polyphagia and weight loss.

Diabetes is divided into insulin-dependent diabetes mellitus (IDDM, i.e., type I diabetes) and noninsulin-dependent diabetes mellitus (NIDDM, i.e., type II diabetes), of which type II diabetes is most common, accounting for more than 90% of diabetic patients. The exact etiopathogenesis and pathogenesis of type I diabetes is not fully understood. Its etiology is involved by both genetic and environmental factors. It is mainly due to the in vivo β-cell injury that leads to the inability to produce insulin in the body. Patients need daily injections of insulin to control their blood insulin levels. Type II diabetes is a group of metabolic syndromes that fail to control blood glucose levels in the body and are characterized primarily by hyperglycemia, insulin resistance, and lack of insulin secretion. The cause of type II diabetes is mainly due to insulin resistance which makes the body unable to effectively use insulin, or the reduced insulin secretion can not meet the needs of the body, etc. Since those diabetes patients can secrete insulin, generally, insulin treatment is not necessary and blood sugar can be controlled by diet adjustment or oral hypoglycemic agents.

According to figures released by the International Diabetes Federation (IDF), the number of diabetic patients in the world reached 387 million in 2014 and is expected to reach 592 million by 2035, wherein 77% of them are in low and middle income countries. According to the survey, 4.9 million people died of diabetes in 2014, which means that there is one person dies of diabetes almost every 7 seconds, and up to 61.2 billion U.S. dollars are spent for the treatment of diabetes. In addition, about a half of patients do not know they already have diabetes, which presents great difficulties and inconveniences to diabetes prevention and treatment worldwide.

At present, the drugs suitable for the treatment of type II diabetes mainly include insulin and its analogues, sulfonylureas, biguanides, α-glucosidase inhibitors, thiazole diketones, Glucagon-like peptide-1 (GLP-1) analogs, Dipeptidyl peptidase IV (DPP IV) inhibitors, etc. Although existing drugs can control blood sugar levels and reduce the incidence of complications, most of them have serious side effects such as gastrointestinal toxicity, weight gain, edema and hypoglycemia, etc. Therefore, the treatment of type II diabetes remains a difficult problem. It is a hot issue to find and develop therapeutic drugs with new action mechanism and little toxic side effects that both academia and industry have paid close attention to.

Sodium-glucose cotransporter 2 (SGLT2) was first proposed in the 1990s and its importance was confirmed by familial renal glycation. Mutations in SGLT2 cause only familial renal diabetes. Long-term observation of these populations has no other abnormalities and blood glucose levels is in the normal range except for increased glucose excretion in the urine, with good health and normal life expectancy. In addition, animal experiments also showed that in addition to showing obvious urinary sugars, SGLT2 knockout mice has no significant health changes, and after oral glucose test, its glucose tolerance has been found to be enhanced. In contrast, SGLT1 gene defects can cause glucose-galactose malabsorption syndrome, causing severe diarrhea and even life-threatening. Therefore, inhibition of SGLT2 activity can block renal reabsorption of glucose, the excess glucose is excreted in the form of urinary sugars to lower blood sugar without the risk of weight gain and hypoglycemia, and selective inhibition of SGLT2 activity does not interfere with the physiological effects of SGLT1 in the gastrointestinal tract, and does not lead to glucose-galactose malabsorption and other adverse reactions. Therefore, the selective SGLT2 inhibitors become a hot research topic.

Compared with other antidiabetic drugs, SGLT2 inhibitors mainly have the following advantages: (1) reduce the energy retention of sodium and water, and reduce the risk of causing cardiovascular diseases; (2) not easy to cause hypoglycemia, and can improve β cell function as well as insulin resistance; (3) a wider use range, especially for the improvement of blood glucose in patients with renal diabetes; (4) reduce the body weight of diabetic patients by excreting glucose from urine to provide negative energy balance; (5) SGLT2 mainly distributed in the kidney, the selective SGLT2 inhibitors may not affect other body tissues and organs, with fewer adverse reactions.

SGLT2 inhibitors have made major breakthroughs in research, there are already six compounds marketed for the treatment of type II diabetes, many compounds are in clinical research stage, but the development of novel SGLT2 inhibitors to increase their selectivity is still an urgent problem to be solved. Therefore, the research on SGLT2 inhibitors remains a big challenge.

In summary, there is a lack of novel SGLT2 inhibitors with better selectivity in this field.

SUMMARY OF THE INVENTION

An object of the present invention is to provide a C, O-spiro aryl glycoside compound of formula I, pharmaceutically acceptable salts, racemates, R-isomers and S-isomers thereof, or mixtures thereof.

Another object of the present invention is to provide a method for preparing the C. O-spiro aryl glycoside compound represented by the above formula I.

Still another object of the present invention is to provide a pharmaceutical composition comprising a therapeutically effective amount of a C, O-spiro aryl glycoside selected from the group consisting of formula I, pharmaceutically acceptable salts, racemates, R-isomer, S-isomer thereof, or mixtures thereof.

Still another object of the present invention is to provide an SGLT2 inhibitor comprising one or more selected from the group consisting of C, O-spiro aryl glycoside compounds of formula I, pharmaceutically acceptable salts, racemates, R-isomers, S-isomers thereof or mixtures thereof.

Still another object of the present invention is to provide C, O-spiro aryl glycoside compounds of formula I, pharmaceutically acceptable salts, racemates, R-isomers and S-isomers thereof, or mixtures thereof for the preparation of a medicine for use in the treatment of metabolic diseases associated with the glucagon receptor such as diabetes, atherosclerosis, obesity and the like.

Still another object of the present invention is to provide a method for treating metabolic diseases associated with SGLT2, such as diabetes, atherosclerosis and obesity, which comprises administering to a patient in need one or more selected from the group consisting of a C, O-spiro aryl glycoside compound of formula I, pharmaceutically acceptable salts, racemates, R-isomers, S-isomers thereof, or mixtures thereof.

In the first aspect of the present invention, a compound of formula (I) or (II) is provided:

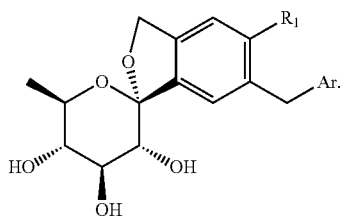

Formula I wherein:

$R_1$ is a hydrogen, halogen, or a substituted or unsubstituted group selected from the group consisting of $C_1$-$C_6$ alkyl, $C_2$-$C_6$ alkenyl, $C_1$-$C_6$ alkoxy, $C_2$-$C_6$ alkynyl, $C_3$-$C_{10}$ cycloalkyl, $C_3$-$C_{10}$ cycloalkenyl, ($C_{2-10}$) alkoxycarbonyl, ($C_{3-10}$) cycloalkyl, hetero ($C_{3-12}$) cycloalkyl, aryl ($C_{1-10}$) alkyl, ($C_{9-12}$) bicycloaryl, hetero ($C_{4-12}$) bicycloaryl, carbonyl ($C_{1-3}$) alkyl, thiocarbonyl ($C_{1-3}$) alkyl, sulfonyl ($C_{1-3}$) alkyl, sulfinyl ($C_{1-3}$) alkyl, imino ($C_{1-3}$) alkyl, amino, cyano, $C_6$-$C_{12}$ aryl, 3-12 membered heteroaryl, hydroxy, hydrocarbyloxy, $C_6$-$C_{12}$ aryloxy, 3-12 membered heteroaryloxy, sulfonyl, and sulfinyl;

Ar is a group selected from the group consisting of substituted or unsubstituted $C_6$-$C_{12}$ aryl, and substituted or unsubstituted 3-12 membered heterocyclic group;

wherein said substitution means that one or more hydrogen atoms on the group are replaced by a substituent selected from the group consisting of cyano, $C_1$-$C_6$ alkyl, $C_1$-$C_6$ alkoxy, halogen, $C_1$-$C_6$ haloalkyl, carbonyl ($C_{2-10}$) alkoxy, carbonyl ($C_{7-10}$) aryloxy, acylamino ($C_{2-10}$) alkyl, $C_6$-$C_{12}$ aryl or 3-12 membered heterocyclic group unsubstituted or substituted by 1 to 3 substituents selected from the group consisting of: halogen, unsubstituted or halogenated $C_1$-$C_6$ alkyl, $C_2$-$C_6$ alkoxy:

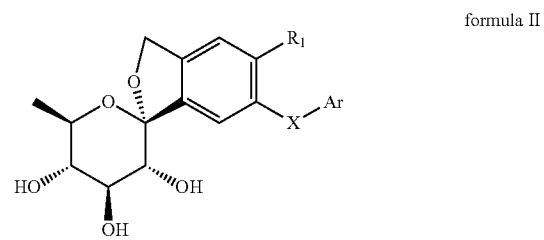

formula II wherein:

$R_1$ is a hydrogen, halogen, or a substituted or unsubstituted group selected from the group consisting of $C_1$-$C_6$ alkyl, $C_2$-$C_6$ alkenyl, $C_1$-$C_6$ alkoxy, $C_2$-$C_6$ alkynyl, $C_3$-$C_{10}$ cycloalkyl, $C_3$-$C_{10}$ cycloalkenyl, ($C_{2-10}$) alkoxycarbonyl, ($C_{3-12}$) cycloalkyl, hetero ($C_{3-12}$) cycloalkyl, aryl ($C_{1-10}$) alkyl, ($C_{9-12}$) bicycloaryl, hetero ($C_{4-12}$) bicycloaryl, carbonyl ($C_{1-3}$) alkyl, thiocarbonyl ($C_{1-3}$) alkyl, sulfonyl ($C_{1-3}$) alkyl, sulfinyl ($C_{1-3}$) alkyl, imino ($C_{1-3}$) alkyl, amino, cyano, $C_6$-$C_{12}$ aryl, 3-12 membered heteroaryl, hydroxy, hydrocarbyloxy, $C_6$-$C_{12}$ aryloxy, 3-12 membered heteroaryloxy, sulfonyl, or sulfinyl;

X is selected from the group consisting of —$CH_2$—, —C(=O)—, —CH(—OH)—;

Ar is a group selected from the group consisting of substituted or unsubstituted $C_6$-$C_{12}$ aryl, and substituted or unsubstituted 3-12 membered heterocyclic group;

wherein the substitution means that one or more hydrogen atoms on the group are substituted with a substituent selected from the group consisting of cyano, $C_1$-$C_6$ alkyl, $C_1$-$C_6$ alkoxy, $C_2$-$C_{10}$ ether group, $C_2$-$C_{10}$ ester group, $C_1$-$C_{10}$ hydroxy alkyl, $C_1$-$C_{10}$ carboxyalkyl, $C_2$-$C_6$ acyl, $C_3$-$C_{10}$ ester-alkyl, $C_1$-$C_4$ alkyl-3 to 12 membered heterocyclic group, halogen, $C_1$-$C_6$ haloalkyl, carbonyl ($C_{2-10}$) alkoxy, carbonyl ($C_{7-10}$) aryloxy, carbonyl ($C_{7-10}$) heterocyclic group, amido ($C_{2-10}$) alkyl, acyl ($C_{2-10}$) 3-12 membered heterocyclic group, $C_3$-$C_6$ cycloalkyl, $C_6$-$C_{12}$ aryl, or 3-12 membered heterocyclic group; wherein said $C_3$-$C_6$ cycloalkyl, $C_6$-$C_{12}$ aryl or 3-12 membered heterocyclic group are unsubstituted or substituted with 1 to 3 substituents selected from the group consisting of halogen, cyano, unsubstituted or halogenated $C_1$-$C_6$ alkyl, $C_1$-$C_6$ haloalkyl, and $C_1$-$C_6$ alkoxy.

In another preferred embodiment, Ar is a substituted or unsubstituted group selected from the group consisting of phenyl, furanyl, thiophenyl, pyrrolyl, pyrazolyl, triazolyl, isoxazolyl, oxazolyl, thiazolyl, isothiazolyl, oxadiazolyl, pyridinyl, pyridazinyl, pyrimidinyl, pyrazinyl, triazinyl, benzofuranyl, isobenzofuranyl, benzothiophenyl, isobenzothiophenyl, imidazolyl, benzoimidazolyl, indolyl, isoindolyl, quinolinyl, isoquinolinyl, cinnolinyl, quinazolinyl, naphthyridinyl, pyridopyridinyl, quinoxalinyl, phthalazinyl, and benzothiazolyl.

In another preferred embodiment, $R_1$ is a hydrogen, halogen, or substituted or unsubstituted group selected from the group consisting of $C_1$-$C_6$ alkyl, $C_2$-$C_6$ alkenyl, $C_1$-$C_6$ alkoxy, $C_2$-$C_6$ alkynyl, $C_3$-$C_{10}$ cycloalkyl, $C_3$-$C_{10}$ cycloalkenyl, $(C_{2-10})$ alkoxycarbonyl, $(C_{3-12})$ cycloalkyl, hetero $(C_{3-12})$ cycloalkyl, carbonyl $(C_{1-3})$ alkyl, thiocarbonyl $(C_{1-3})$ alkyl, sulfonyl $(C_{1-3})$ alkyl, sulfinyl $(C_{1-3})$ alkyl, cyano, $C_6$-$C_{12}$ aryl, 3-12 membered heteroaryl, hydroxy, hydrocarbyloxy, $C_6$-$C_{12}$ aryloxy, 3-12 membered heteroaryloxy, imino, sulfonyl, or sulfinyl; and/or said Ar is a substituted or unsubstituted group selected from the group consisting of phenyl, furanyl, thiophenyl, pyrrolyl, pyrazolyl, triazolyl, isoxazolyl, oxazolyl, thiazolyl, isothiazolyl, oxadiazolyl, pyridinyl, pyridazinyl, pyrimidinyl, benzofuranyl, isobenzofuranyl, benzothiophenyl, isobenzothiophenyl, imidazolyl, benzoimidazolyl, indolyl, isoindolyl, quinolinyl, isoquinolinyl, naphthyridinyl, pyridopyridinyl, or benzothiazolyl.

In another preferred embodiment, $R_1$ is a hydrogen, halogen, or a substituted or unsubstituted group selected from the group consisting of methyl, methoxy, ethyl, ethylenyl, amino, hydroxy, cyano, nitro, ester group, amide, acetyl, carboxamido, carbamoyl, formyloxy, methoxycarbonyl, trifluoromethyl and trifluoromethoxy; and/or said Ar is a substituted or unsubstituted group selected from the group consisting of phenyl, furanyl, thiophenyl, pyrrolyl, thiazolyl, isothiazolyl, pyridinyl, pyridazinyl, pyrimidinyl, benzofuranyl, isobenzofuranyl, benzothiophenyl, isobenzothiophenyl, imidazolyl, benzoimidazolyl, indolyl, isoindolyl, quinolinyl, isoquinolinyl, naphthyridinyl, pyridopyridinyl, or benzothiazolyl.

In another preferred embodiment, $R_1$ is a hydrogen, halogen, or a substituted or unsubstituted group selected from the group consisting of methyl, methoxy, ethyl, ethylenyl, amino, hydroxy, cyano, nitro, ester, amide, acetyl, carboxamido, trifluoromethyl and trifluoromethoxy; and/or said Ar is a substituted or unsubstituted group selected from the group consisting of phenyl, furanyl, thiophenyl, pyrrolyl, thiazolyl, isothiazolyl, benzofuranyl, or benzothiophenyl.

In another preferred embodiment, the $R_1$ is selected from the group consisting of hydrogen, halogen, methyl, ethyl; and/or said Ar is a substituted or unsubstituted group selected from the group consisting of phenyl, thiophenyl, benzofuranyl, and benzothiophenyl; wherein the substitution means that one or more hydrogen atoms on the group are replaced by a group selected from the group consisting of halogen, and $C_1$-$C_4$ alkyl, phenyl unsubstituted or substituted by 1-3 halogen atoms.

In another preferred embodiment, in the compound, any of $R_1$ and Ar is the corresponding group in the specific compound described in Table 1 respectively.

In another preferred embodiment, the compound of formula (I) is the specific compound described in Table 1.

In the second aspect of the present invention, a preparation method of compound of formula (I) of the first aspect of the present invention is provided, which comprises the following steps:

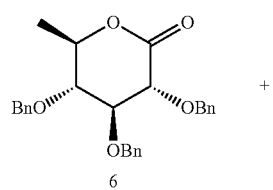

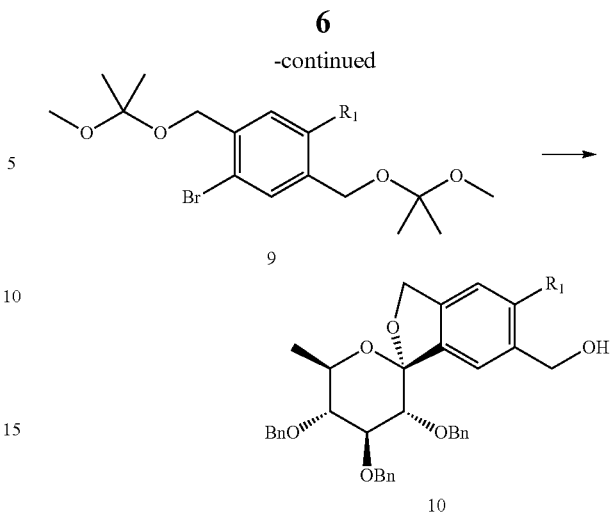

(a) in an inert solvent, reacting compound of formula 6 with compound of formula 9, thus obtaining compound of formula 10; and preparing compound of formula (I) using compound of formula 10.

In another preferred embodiment, the step (a) comprises the steps:

(a1) in an inert solvent, in the presence of alkyllithium reagent (preferably n-butyllithium), reacting the compound of formula 6 with compound of formula 9 to give a reaction mixture:

(a2) in a mixed solvent, in the presence of p-toluenesulfonic acid, further reacting the above reaction mixture to provide the compound of formula 10.

In another preferred embodiment, in the step (a1), the inert solvent is tetrahydrofuran.

In another preferred embodiment, in the step (a2), the mixed solvent is tetrahydrofuran-methanol.

In another preferred embodiment, in the step (a1), the reaction temperature is −100 to −50° C.

In another preferred embodiment, in the step (a2), the reaction temperature is 10 to 40° C.

In another preferred embodiment, the compound of formula 6 is prepared by the following method:

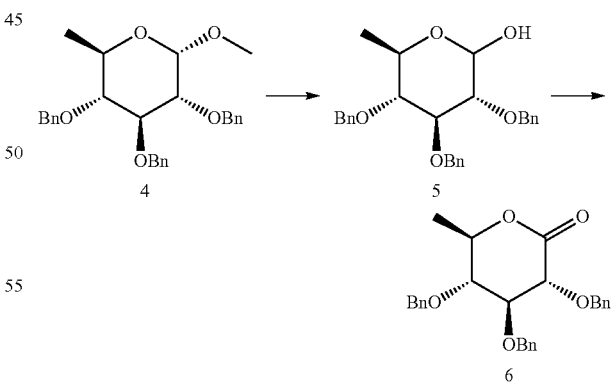

(b1) in an inert solvent, in the presence of acid, reacting compound of formula 4 to give compound of formula 5;

(b2) in an inert solvent, in the presence of acetic anhydride, reacting compound of formula 5 to give compound of formula 6.

In another preferred embodiment, in the step (b1), the acid is sulfuric acid.

In another preferred embodiment, in the step (b1), the reaction temperature is 60-95° C.

In another preferred embodiment, in the step (b2), the reaction temperature is 10 to 40° C.

In the third aspect of the present invention, a pharmaceutical composition comprising a therapeutically effective amount of compound of formula (I) according to the first aspect of the present invention, or a pharmaceutically acceptable salt, racemates, R-isomer, S-isomer thereof, or a mixture thereof, and optionally a pharmaceutically acceptable carrier, vehicle, adjuvant, excipient and/or diluent is provided.

In the fourth aspect of the present invention, a sodium-glucose cotransporter 2 inhibitor is provided, which comprising: an effective inhibitory amount of compound of formula (I) according to the first aspect of the present invention, or a pharmaceutically acceptable salt, racemates, R-isomer, S-isomer thereof, or a mixture thereof, and optionally a pharmaceutically acceptable carrier, vehicle, adjuvant, excipient and/or diluent.

In another preferred embodiment, the inhibition is selective inhibition.

In another preferred embodiment, the selective inhibition is selective inhibition of SGLT2 but not inhibition of SGLT1.

In the fifth aspect of the invention, uses of a compound of formula (I) according to the first aspect of the present invention are provided, wherein the uses comprise one or more uses selected from the group consisting of (i) treating or preventing metabolic disorders associated with sodium-glucose cotransporter 2; (ii) inhibiting the activity of sodium-glucose cotransporter 2, or decreasing the expression quantity of sodium-glucose cotransporter 2; (iii) preparing a pharmaceutical composition for the treatment or prevention of metabolic system diseases associated with sodium-glucose cotransporter 2; (iv) preparing a sodium-glucose cotransporter 2 inhibitor.

In another preferred embodiment, the disease is selected from the group consisting of diabetes, atherosclerosis, and obesity.

In the sixth aspect of the present invention, a method for treating or preventing a metabolic system disorder associated with sodium-glucose cotransporter 2 is provided, which comprising: administering to a subject a compound of formula (I), or the pharmaceutically acceptable salt, racemate, R-isomer, S-isomer thereof, or a mixture thereof.

It should be understood that, in the present invention, each of the technical features specifically described above and below (such as those in the Examples) can be combined with each other, thereby constituting new or preferred technical solutions which need not be specified again herein.

EMBODIMENTS FOR CARRYING OUT THE INVENTION

Figure 1:
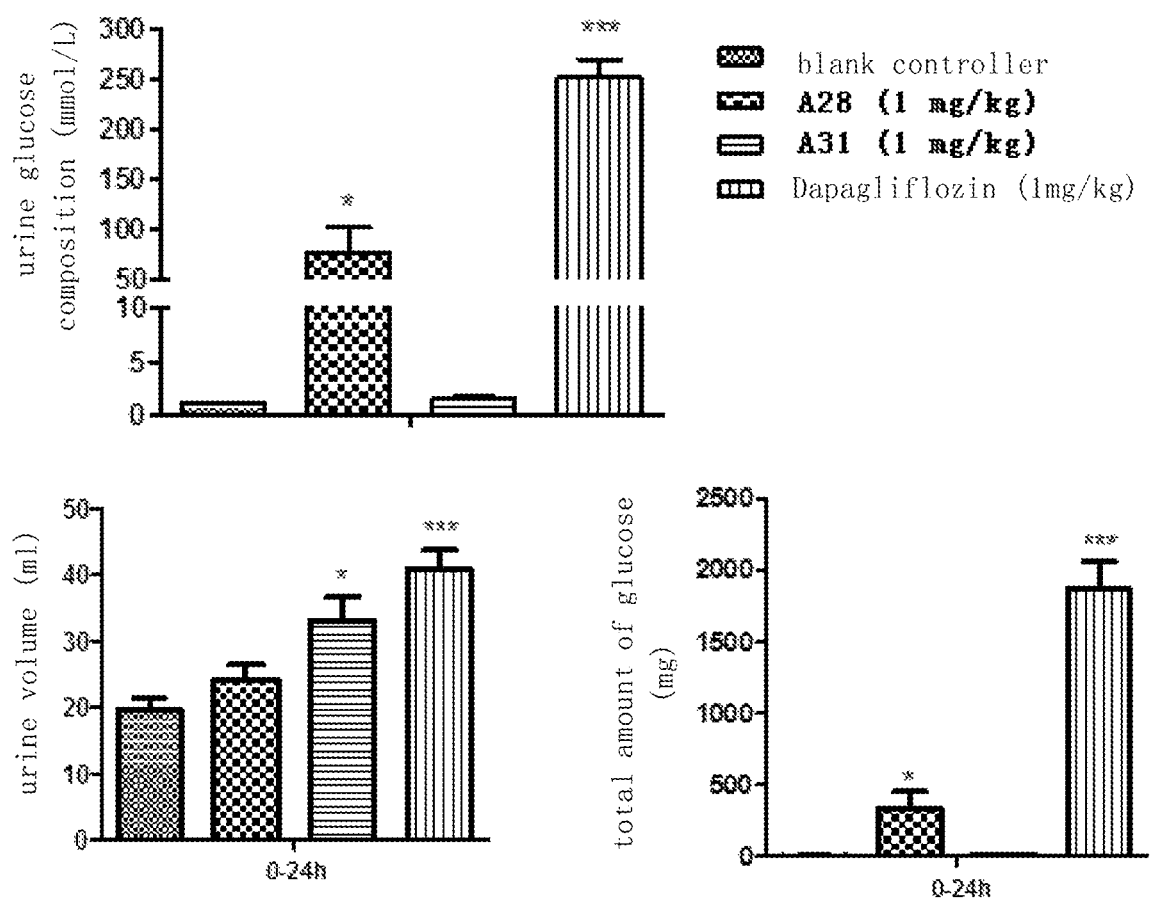
FIG. 1. Effect of single administration of test substance on each index in urine of SD rats; note: *: $p<0.05$; , $p<0.01$; *, $p<0.001$, compared with the blank control.

After a long and deep research, the inventors designed and prepared a series of novel C, O-spiro aryl glycoside compounds. The compounds can selectively inhibit SGLT2 and show superior properties over the existing compounds in the art in in-vivo experiments and pharmacokinetic experiments. The present invention is completed on this basis.

Terms

As used herein, the term "$C_1$-$C_6$ alkyl" refers to a linear or branched alkyl having 1 to 6 carbon atoms, including, but not limited to methyl, ethyl, propyl, isopropyl, butyl, isobutyl, sec-butyl, tert-butyl, pentyl and hexyl, and the like; preferably ethyl, propyl, isopropyl, butyl, isobutyl, sec-butyl and tert-butyl.

The term "$C_1$-$C_6$ alkoxy" refers to a liner or branched alkoxy group having 1 to 6 carbon atoms, including, but not limited to methoxy, ethoxy, propoxy, isopropoxy and butoxy, iso-butoxy, and the like.

The term "$C_2$-$C_6$ alkenyl" refers to a liner or branched alkenyl having one double bond and having 2 to 6 carbon atoms, including, but not limited to ethenyl, propenyl, butenyl, isobutenyl, pentenyl, hexenyl and the like.

The term "$C_2$-$C_6$ alkynyl" refers to a linear or branched alkynyl having one triple bond and having 2 to 6 carbon atoms, including but not limited to ethynyl, propynyl, butynyl, isobutynyl, pentynyl and hexynyl and the like.

The term "$C_3$-$C_{10}$ cycloalkyl" refers to a cyclic alkyl group having 3 to 10 carbon atoms on the ring, including, but not limited to cyclopropyl, cyclobutyl, cyclopentyl, cyclohexyl, cycloheptyl, cyclooctyl and cyclodecyl and the like. The terms "$C_3$-$C_8$ cycloalkyl", "$C_3$-$C_7$ cycloalkyl", and "$C_3$-$C_6$ cycloalkyl" have similar meanings.

The term "$C_3$-$C_{10}$ cycloalkenyl" refers to a cyclic alkenyl group having from 3 to 10 carbon atoms on the ring including, but not limited to, cyclopropenyl, cyclobutenyl, cyclopentenyl, cyclohexenyl, cycloheptenyl, cyclooctenyl, cyclodecanylene and the like. The term "$C_3$-$C_7$ cycloalkenyl" has a similar meaning.

The term "$C_6$-$C_2$ aryl" refers to aryl groups having 6 to 12 carbon atoms which do not comprise heteroatoms on the ring, such as phenyl, naphthyl and the like. The term "$C_6$-$C_{10}$ aryl" has a similar meaning.

The term "3-12 membered heterocyclyl" refers to a saturated or unsaturated 3-12 membered ring group having 1 to 3 heteroatoms selected from oxygen, sulfur and nitrogen on the ring, such as oxepanyl and the like. The term "3-7 membered heterocyclyl" has a similar meaning.

C, O-Spiro Aryl Glycoside Compounds

Based on the above object, the present invention provides a C, O-spiro aryl glycoside compound having the structure of the following formula I or II, and racemates, R-isomers, S-isomers, pharmaceutically acceptable salts thereof, or mixtures thereof:

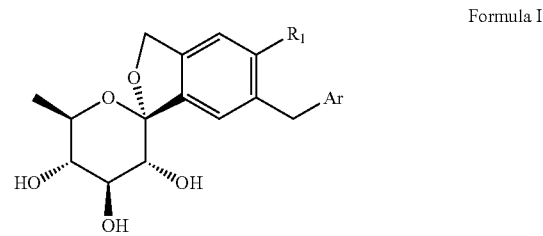

Formula I

-continued

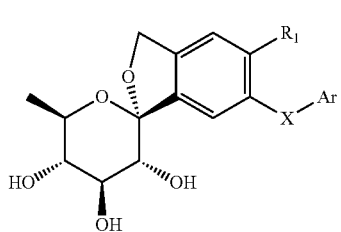

formula II

In another preferred embodiment, in the compound, any of $R_1$ and Ar is the corresponding group in the specific compound described in table 1 respectively.

In another preferred embodiment, the compound of formula I is a compound selected from the table 1.

In the present invention, the halogen is F, Cl, Br or I.

In the present invention, unless otherwise specified, the terms used have the general meaning known by those skilled in the art.

In a more preferred embodiment of the present invention, the compounds of general formula I of the present invention are preferably specific compounds as follows:

TABLE 1

Specific compounds

| No. | Name | Structure |
|---|---|---|
| A1 | (1S,3'R,4'S,5'S,6'R)-6'-methyl-6-(4-methylbenzyl)-3',4',5',6'-tetrahydro-3H-spiro[isobenzofuran-1,2'-pyran]-3',4',5'-triol | A1 |
| A2 | (1S,3'R,4'S,5'S,6'R)-6'-methyl-6-(4-ethylbenzyl)-3',4',5',6'-tetrahydro-3H-spiro[isobenzofuran-1,2'-pyran]-3',4',5'-triol | A2 |
| A3 | (1S,3'R,4'S,5'S,6'R)-6'-methyl-6-(4-propylbenzyl)-3',4',5',6'-tetrahydro-3H-spiro[isobenzofuran-1,2'-pyran]-3',4',5'-triol | A3 |
| A4 | (1S,3'R,4'S,5'S,6'R)-6'-methyl-6-(4-isopropylbenzyl)-3',4',5',6'-tetrahydro-3H-spiro[isobenzofuran-1,2'-pyran]-3',4',5'-triol | A4 |

TABLE 1-continued

Specific compounds

| No. | Name | Structure |
|---|---|---|
| A5 | (1S,3'R,4'S,5'S,6'R)-6'-methyl-6-(4-methoxybenzyl)-3',4',5',6'-tetrahydro-3H-spiro[isobenzofuran-1,2'-pyran]-3',4',5'-triol | 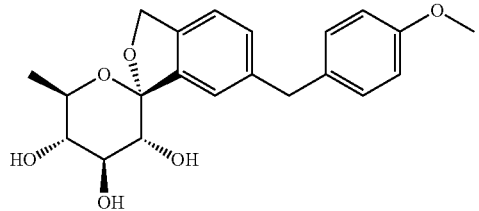<br>A5 |
| A6 | (1S,3'R,4'S,5'S,6'R)-6'-methyl-6-(4-ethyoxylbenzyl)-3',4',5',6'-tetrahydro-3H-spiro[isobenzofuran-1,2'-pyran]-3',4',5'-triol | 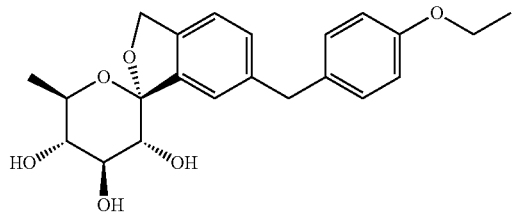<br>A6 |
| A7 | (1S,3'R,4'S,5'S,6'R)-6'-methyl-6-((5-methylthienyl)-2-methyl)-3',4',5',6'-tetrahydro-3H-spiro[isobenzofuran-1,2'-pyran]-3',4',5'-triol | 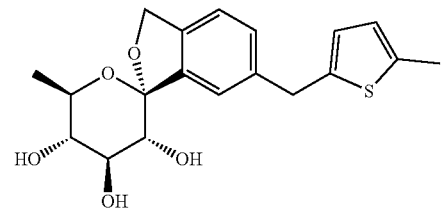<br>A7 |
| A8 | (1S,3'R,4'S,5'S,6'R)-6'-methyl-6-((5-ethylthienyl)-2-methyl)-3',4',5',6'-tetrahydro-3H-spiro[isobenzofuran-1,2'-pyran]-3',4',5'-triol | 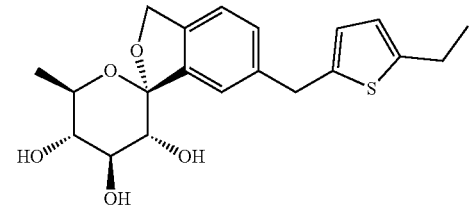 [SMILES: CCc1ccc(Cc2ccc3c(c2)[C@]2(OC3)O[C@H](C)[C@@H](O)[C@H](O)[C@H]2O)s1]<br>A8 |
| A9 | (1S,3'R,4'S,5'S,6'R)-6'-methyl-6-((5-propylthienyl)-2-methyl)-3',4',5',6'-tetrahydro-3H-spiro[isobenzofuran-1,2'-pyran]-3',4',5'-triol | 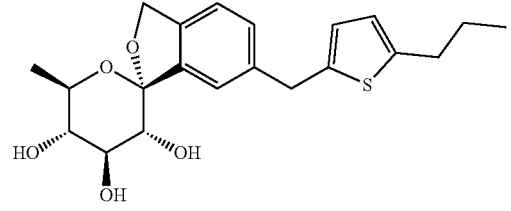 [SMILES: CCCc1ccc(Cc2ccc3c(c2)[C@]2(OC3)O[C@H](C)[C@@H](O)[C@H](O)[C@H]2O)s1]<br>A9 |
| A10 | (1S,3'R,4'S,5'S,6'R)-6'-methyl-6-((5-chlorothienyl)-2-methyl)-3',4',5',6'-tetrahydro-3H-spiro[isobenzofuran-1,2'-pyran]-3',4',5'-triol | 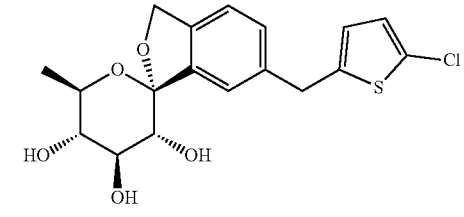 [SMILES: C[C@H]1O[C@]2(OCc3ccc(Cc4ccc(Cl)s4)cc32)[C@H](O)[C@@H](O)[C@@H]1O]<br>A10 |

TABLE 1-continued

Specific compounds

| No. | Name | Structure |
|---|---|---|
| A11 | (1S,3'R,4'S,5'S,6'R)-6'-methyl-6-((5-(4-fluorophenyl)thienyl)-2-methyl)-3',4',5',6'-tetrahydro-3H-spiro[isobenzofuran-1,2'-pyran]-3',4',5'-triol | 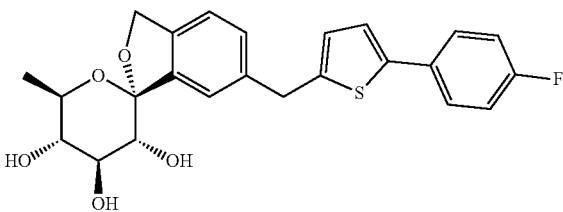 [SMILES: C[C@H]1O[C@]2(OCc3ccc(Cc4ccc(-c5ccc(F)cc5)s4)cc32)[C@H](O)[C@@H](O)[C@@H]1O]<br>A11 |
| A12 | (1S,3'R,4'S,5'S,6'R)-6'-methyl-6-((5-phenylthienyl)-2-methyl)-3',4',5',6'-tetrahydro-3H-spiro[isobenzofuran-1,2'-pyran]-3',4',5'-triol | 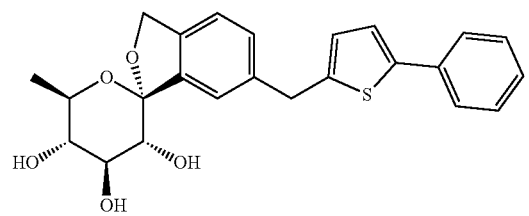 [SMILES: C[C@H]1O[C@]2(OCc3ccc(Cc4ccc(-c5ccccc5)s4)cc32)[C@H](O)[C@@H](O)[C@@H]1O]<br>A12 |
| A13 | (1S,3'R,4'S,5'S,6'R)-6'-methyl-6-((5-(2-pyridyl)thienyl)-2-methyl)-3',4',5',6'-tetrahydro-3H-spiro[isobenzofuran-1,2'-pyran]-3',4',5'-triol | 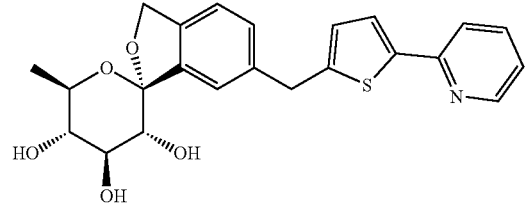 [SMILES: C[C@H]1O[C@]2(OCc3ccc(Cc4ccc(-c5ccccn5)s4)cc32)[C@H](O)[C@@H](O)[C@@H]1O]<br>A13 |
| A14 | (1S,3'R,4'S,5'S,6'R)-6'-methyl-6-(naphthyl-2-methyl)-3',4',5',6'-tetrahydro-3H-spiro[isobenzofuran-1,2'-pyran]-3',4',5'-triol | 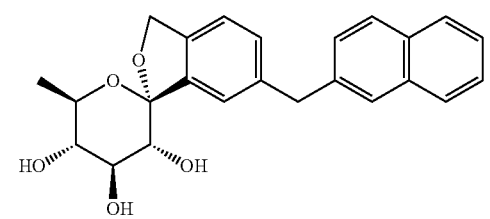 [SMILES: C[C@H]1O[C@]2(OCc3ccc(Cc4ccc5ccccc5c4)cc32)[C@H](O)[C@@H](O)[C@@H]1O]<br>A14 |
| A15 | (1S,3'R,4'S,5'S,6'R)-6'-methyl-6-(benzo[b]thiophene-2-methyl)-3',4',5',6'-tetrahydro-3H-spiro[isobenzofuran-1,2'-pyran]-3',4',5'-triol | 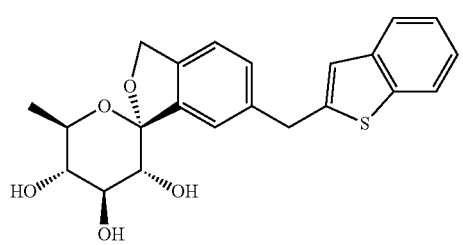<br>A15 |

TABLE 1-continued

Specific compounds

| No. | Name | Structure |
|---|---|---|
| A16 | (1S,3'R,4'S,5'S,6'R)-6'-methyl-6-(benzo[b]furan-2-methyl)-3',4',5',6'-tetrahydro-3H-spiro[isobenzofuran-1,2'-pyran]-3',4',5'-triol | 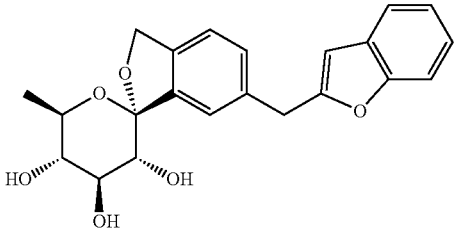<br>A16 |
| A17 | (1S,3'R,4'S,5'S,6'R)-6'-methyl-6-((5-(2-furyl)thiazolyl)-2-methyl)-3',4',5',6'-tetrahydro-3H-spiro[isobenzofuran-1,2'-pyran]-3',4',5'-triol | 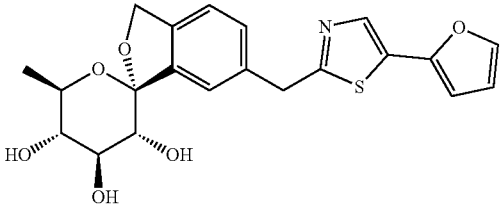 [SMILES: C[C@H]1O[C@]2(OCc3ccc(Cc4ncc(-c5ccco5)s4)cc32)[C@H](O)[C@@H](O)[C@@H]1O]<br>A17 |
| A18 | (1S,3'R,4'S,5'S,6'R)-6'-methyl-6-((5-(2-thienyl)thiazolyl)-2-methyl)-3',4',5',6'-tetrahydro-3H-spiro[isobenzofuran-1,2'-pyran]-3',4',5'-triol | 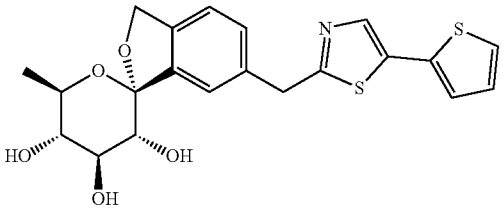 [SMILES: C[C@H]1O[C@]2(OCc3ccc(Cc4ncc(-c5cccs5)s4)cc32)[C@H](O)[C@@H](O)[C@@H]1O]<br>A18 |
| A19 | (1S,3'R,4'S,5'S,6'R)-6'-methyl-6-((5-(4-fluorophenyl)thiazolyl)-2-methyl)-3',4',5',6'-tetrahydro-3H-spiro[isobenzofuran-1,2'-pyran]-3',4',5'-triol | 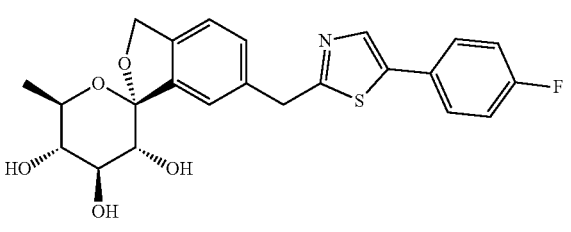<br>A19 |
| A20 | (1S,3'R,4'S,5'S,6'R)-6'-methyl-6-((5-phenylthiazolyl)-2-methyl)-3',4',5',6'-tetrahydro-3H-spiro[isobenzofuran-1,2'-pyran]-3',4',5'-triol | 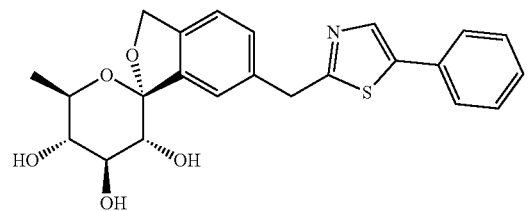 [SMILES: C[C@H]1O[C@]2(OCc3ccc(Cc4ncc(-c5ccccc5)s4)cc32)[C@H](O)[C@@H](O)[C@@H]1O]<br>A20 |

TABLE 1-continued

| No. | Name | Structure |
|---|---|---|
| A21 | (1S,3'R,4'S,5'S,6'R)-6'-methyl-6-(4-methylbenzyl)-5-chloro-3',4',5',6'-tetrahydro-3H-spiro[isobenzofuran-1,2'-pyran]-3',4',5'-triol | A21 |
| A22 | (1S,3'R,4'S,5'S,6'R)-6'-methyl-6-(4-ethylbenzyl)-5-chloro-3',4',5',6'-tetrahydro-3H-spiro[isobenzofuran-1,2'-pyran]-3',4',5'-triol | A22 |
| A23 | (1S,3'R,4'S,5'S,6'R)-6'-methyl-6-(4-propylbenzyl)-5-chloro-3',4',5',6'-tetrahydro-3H-spiro[isobenzofuran-1,2'-pyran]-3',4',5'-triol | A23 |
| A24 | (1S,3'R,4'S,5'S,6'R)-6'-methyl-6-(4-isopropylbenzyl)-5-chloro-3',4',5',6'-tetrahydro-3H-spiro[isobenzofuran-1,2'-pyran]-3',4',5'-triol | A24 |
| A25 | (1S,3'R,4'S,5'S,6'R)-6'-methyl-6-(4-methoxybenzyl)-5-chloro-3',4',5',6'-tetrahydro-3H-spiro[isobenzofuran-1,2'-pyran]-3',4',5'-triol | A25 |

TABLE 1-continued

Specific compounds

| No. | Name | Structure |
|---|---|---|
| A26 | (1S,3'R,4'S,5'S,6'R)-6'-methyl-6-(4-ethyoxylbenzyl)-5-chloro-3',4',5',6'-tetrahydro-3H-spiro[isobenzofuran-1,2'-pyran]-3',4',5'-triol | A26 |
| A27 | (1S,3'R,4'S,5'S,6'R)-6'-methyl-6-((5-methylthienyl)-2-methyl)-5-chloro-3',4',5',6'-tetrahydro-3H-spiro[isobenzofuran-1,2'-pyran]-3',4',5'-triol | A27 |
| A28 | (1S,3'R,4'S,5'S,6'R)-6'-methyl-6-((5-ethylthienyl)-2-methyl)-5-chloro-3',4',5',6'-tetrahydro-3H-spiro[isobenzofuran-1,2'-pyran]-3',4',5'-triol | A28 |
| A29 | (1S,3'R,4'S,5'S,6'R)-6'-methyl-6-((5-propylthienyl)-2-methyl)-5-chloro-3',4',5',6'-tetrahydro-3H-spiro[isobenzofuran-1,2'-pyran]-3',4',5'-triol | A29 |
| A30 | (1S,3'R,4'S,5'S,6'R)-6'-methyl-6-((5-chlorothienyl)-2-methyl)-5-chloro-3',4',5',6'-tetrahydro-3H-spiro[isobenzofuran-1,2'-pyran]-3',4',5'-triol | A30 |

TABLE 1-continued

Specific compounds

| No. | Name |
|---|---|
| A31 | (1S,3'R,4'S,5'S,6'R)-6'-methyl-6-((5-(4-fluorophenyl)-thienyl)-2-methyl)-5-chloro-3',4',5',6'-tetrahydro-3H-spiro[isobenzofuran-1,2'-pyran]-3',4',5'-triol |
| A32 | (1S,3'R,4'S,5'S,6'R)-6'-methyl-6-((5-phenylthienyl)-2-methyl)-5-chloro-3',4',5',6'-tetrahydro-3H-spiro[isobenzofuran-1,2'-pyran]-3',4',5'-triol |
| A33 | (1S,3'R,4'S,5'S,6'R)-6'-methyl-6-((5-(2-pyridyl)-thienyl)-2-methyl)-5-chloro-3',4',5',6'-tetrahydro-3H-spiro[isobenzofuran-1,2'-pyran]-3',4',5'-triol |
| A34 | (1S,3'R,4'S,5'S,6'R)-6'-methyl-6-(naphthyl-2-methyl)-5-chloro-3',4',5',6'-tetrahydro-3H-spiro[isobenzofuran-1,2'-pyran]-3',4',5'-triol |
| A35 | (1S,3'R,4'S,5'S,6'R)-6'-methyl-6-(benzo[b]thiophene-2-methyl)-5-chloro-3',4',5',6'-tetrahydro-3H-spiro[isobenzofuran-1,2'-pyran]-3',4',5'-triol |

TABLE 1-continued

Specific compounds

| No. | Name |
|---|---|
| A36 | (1S,3'R,4'S,5'S,6'R)-6'-methyl-6-(benzo[b]furan-2-methyl)-5-chloro-3',4',5',6'-tetrahydro-3H-spiro[isobenzofuran-1,2'-pyran]-3',4',5'-triol |
| A37 | (1S,3'R,4'S,5'S,6'R)-6'-methyl-6-((5-(2-furyl)thiazolyl)-2-methyl)-5-chloro-3',4',5',6'-tetrahydro-3H-spiro[isobenzofuran-1,2'-pyran]-3',4',5'-triol |
| A38 | (1S,3'R,4'S,5'S,6'R)-6'-methyl-6-(4-methylbenzyl)-5-fluoro-3',4',5',6'-tetrahydro-3H-spiro[isobenzofuran-1,2'-pyran]-3',4',5'-triol |
| A39 | (1S,3'R,4'S,5'S,6'R)-6'-methyl-6-(4-methoxybenzyl)-5-fluoro-3',4',5',6'-tetrahydro-3H-spiro[isobenzofuran-1,2'-pyran]-3',4',5'-triol |
| A40 | (1S,3'R,4'S,5'S,6'R)-6'-methyl-6-(4-ethyoxylbenzyl)-5-fluoro-3',4',5',6'-tetrahydro-3H-spiro[isobenzofuran-1,2'-pyran]-3',4',5'-triol |

TABLE 1-continued

Specific compounds

| No. | Name | Structure |
|---|---|---|
| A41 | (1S,3'R,4'S,5'S,6'R)-6'-methyl-6-((5-methylthienyl)-2-methyl)-5-fluoro-3',4',5',6'-tetrahydro-3H-spiro[isobenzofuran-1,2'-pyran]-3',4',5'-triol | 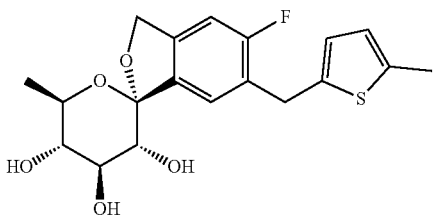<br>A41 |
| A42 | (1S,3'R,4'S,5'S,6'R)-6'-methyl-6-((5-ethylthienyl)-2-methyl)-5-fluoro-3',4',5',6'-tetrahydro-3H-spiro[isobenzofuran-1,2'-pyran]-3',4',5'-triol | 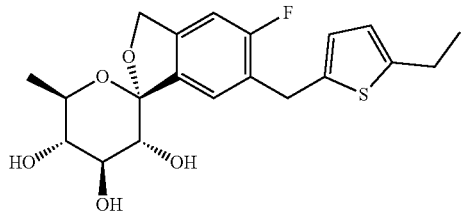<br>A42 |
| A43 | (1S,3'R,4'S,5'S,6'R)-6'-methyl-6-((5-chlorothienyl)-2-methyl)-5-fluoro-3',4',5',6'-tetrahydro-3H-spiro[isobenzofuran-1,2'-pyran]-3',4',5'-triol | 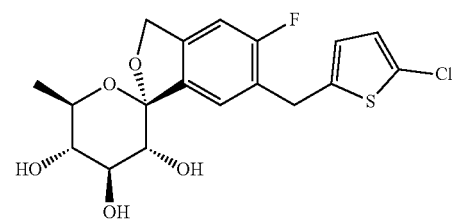<br>A43 |
| A44 | (1S,3'R,4'S,5'S,6'R)-6'-methyl-6-((5-(4-fluorophenyl)-thienyl)-2-methyl)-5-fluoro-3',4',5',6'-tetrahydro-3H-spiro[isobenzofuran-1,2'-pyran]-3',4',5'-triol | 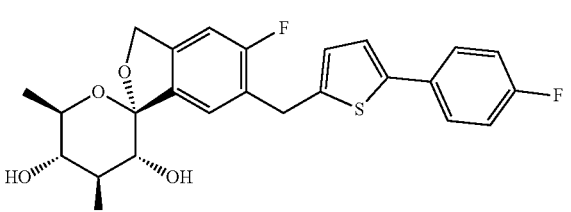<br>A44 |
| A45 | (1S,3'R,4'S,5'S,6'R)-6'-methyl-6-((5-phenylthienyl)-2-methyl)-5-fluoro-3',4',5',6'-tetrahydro-3H-spiro[isobenzofuran-1,2'-pyran]-3',4',5'-triol | 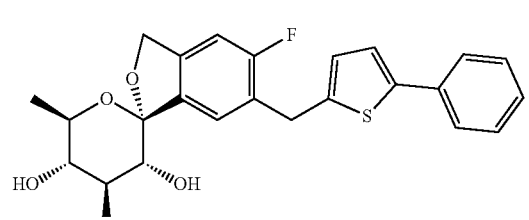<br>A45 |

TABLE 1-continued

Specific compounds

| No. | Name | Structure |
|---|---|---|
| A46 | (1S,3'R,4'S,5'S,6'R)-6'-methyl-6-((5-(2-pyridyl)-thienyl)-2-methyl)-5-fluoro-3',4',5',6'-tetrahydro-3H-spiro[isobenzofuran-1,2'-pyran]-3',4',5'-triol | 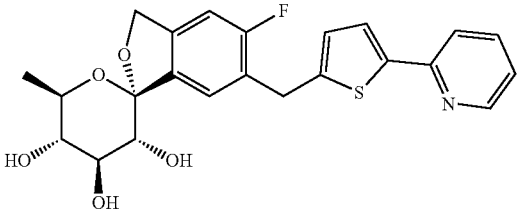 [SMILES: C[C@H]1O[C@]2(OCc3cc(Cl)c(Cc4ccc(-c5ccccn5)s4)cc32)[C@H](O)[C@@H](O)[C@@H]1O]<br>A46 |
| A47 | (1S,3'R,4'S,5'S,6'R)-6'-methyl-6-(benzo[b]thiophene-2-methyl)-5-fluoro-3',4',5',6'-tetrahydro-3H-spiro[isobenzofuran-1,2'-pyran]-3',4',5'-triol | 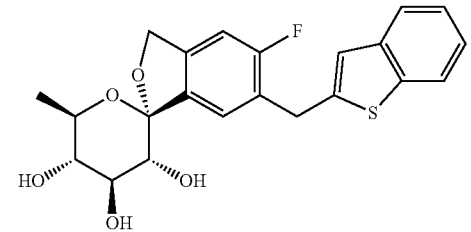<br>A47 |
| A48 | (1S,3'R,4'S,5'S,6'R)-6'-methyl-6-(benzo[b]furan-2-methyl)-5-fluoro-3',4',5',6'-tetrahydro-3H-spiro[isobenzofuran-1,2'-pyran]-3',4',5'-triol | 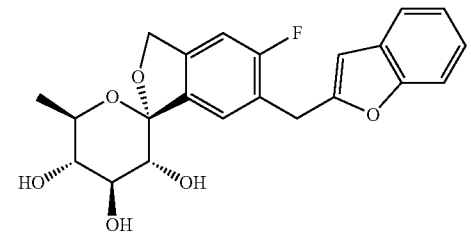<br>A48 |
| A49 | (1S,3'R,4'S,5'S,6'R)-6'-methyl-6-((5-(2-furyl)thiazolyl)-2-methyl)-5-fluoro-3',4',5',6'-tetrahydro-3H-spiro[isobenzofuran-1,2'-pyran]-3',4',5'-triol | 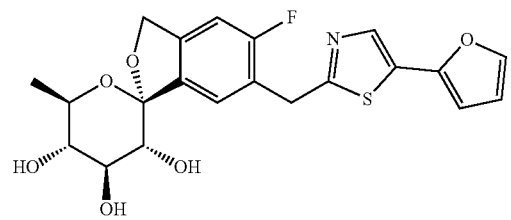<br>A49 |
| A50 | (1S,3'R,4'S,5'S,6'R)-5,6'-dimethyl-6-(4-methylbenzyl)-3',4',5',6'-tetrahydro-3H-spiro[isobenzofuran-1,2'-pyran]-3',4',5'-triol | 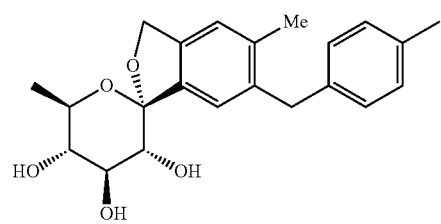<br>A50 |

TABLE 1-continued

Specific compounds

| No. | Name |
|-----|------|
| A51 | (1S,3'R,4'S,5'S,6'R)-5,6'-dimethyl-6-(4-ethylbenzyl)-3',4',5',6'-tetrahydro-3H-spiro[isobenzofuran-1,2'-pyran]-3',4',5'-triol |
| A52 | (1S,3'R,4'S,5'S,6'R)-5,6'-dimethyl-6-(4-propylbenzyl)-3',4',5',6'-tetrahydro-3H-spiro[isobenzofuran-1,2'-pyran]-3',4',5'-triol |
| A53 | (1S,3'R,4'S,5'S,6'R)-5,6'-dimethyl-6-(4-isopropylbenzyl)-3',4',5',6'-tetrahydro-3H-spiro[isobenzofuran-1,2'-pyran]-3',4',5'-triol |
| A54 | (1S,3'R,4'S,5'S,6'R)-5,6'-dimethyl-6-(4-methoxybenzyl)-3',4',5',6'-tetrahydro-3H-spiro[isobenzofuran-1,2'-pyran]-3',4',5'-triol |
| A55 | (1S,3'R,4'S,5'S,6'R)-5,6'-dimethyl-6-(4-ethyoxylbenzyl)-3',4',5',6'-tetrahydro-3H-spiro[isobenzofuran-1,2'-pyran]-3',4',5'-triol |

TABLE 1-continued

Specific compounds

| No. | Name | Structure |
|---|---|---|
| A56 | (1S,3'R,4'S,5'S,6'R)-5,6'-dimethyl-6-((5-methylthienyl)-2-methyl)-3',4',5',6'-tetrahydro-3H-spiro[isobenzofuran-1,2'-pyran]-3',4',5'-triol | 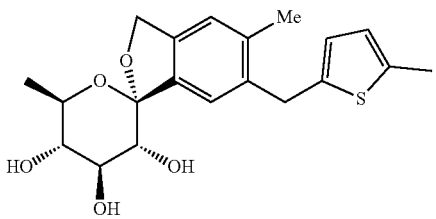<br>A56 |
| A57 | (1S,3'R,4'S,5'S,6'R)-5,6'-dimethyl-6-((5-ethylthienyl)-2-methyl)-3',4',5',6'-tetrahydro-3H-spiro[isobenzofuran-1,2'-pyran]-3',4',5'-triol | 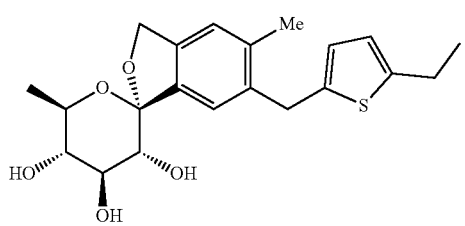<br>A57 |
| A58 | (1S,3'R,4'S,5'S,6'R)-5,6'-dimethyl-6-((5-propylthienyl)-2-methyl)-3',4',5',6'-tetrahydro-3H-spiro[isobenzofuran-1,2'-pyran]-3',4',5'-triol | 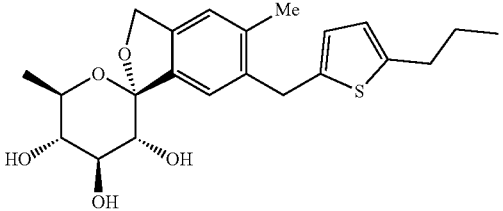<br>A58 |
| A59 | (1S,3'R,4'S,5'S,6'R)-5,6'-dimethyl-6-((5-chlorothienyl)-2-methyl)-3',4',5',6'-tetrahydro-3H-spiro[isobenzofuran-1,2'-pyran]-3',4',5'-triol | 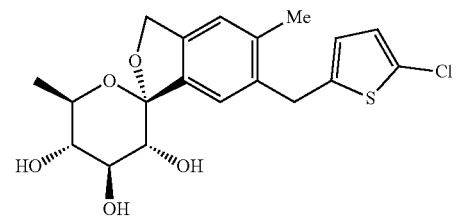<br>A59 |
| A60 | (1S,3'R,4'S,5'S,6'R)-5,6'-dimethyl-6-((5-(4-fluorophenyl)thienyl)-2-methyl)-5-chloro-3',4',5',6'-tetrahydro-3H-spiro[isobenzofuran-1,2'-pyran]-3',4',5'-triol | 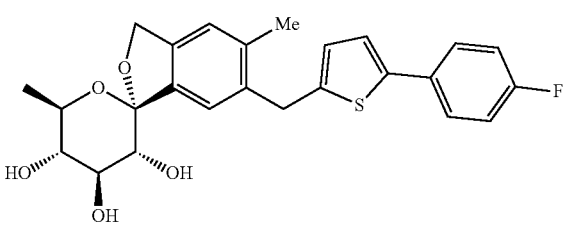<br>A60 |

TABLE 1-continued

Specific compounds

| No. | Name | Structure |
|---|---|---|
| A61 | (1S,3'R,4'S,5'S,6'R)-5,6'-dimethyl-6-((5-phenylthienyl)-2-methyl)-3',4',5',6'-tetrahydro-3H-spiro[isobenzofuran-1,2'-pyran]-3',4',5'-triol | <br>A61 |
| A62 | (1S,3'R,4'S,5'S,6'R)-5,6'-dimethyl-6-((5-(2-pyridyl)thienyl)-2-methyl)-3',4',5',6'-tetrahydro-3H-spiro[isobenzofuran-1,2'-pyran]-3',4',5'-triol | 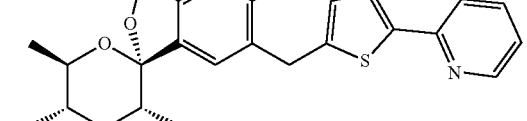<br>A62 |
| A63 | (1S,3'R,4'S,5'S,6'R)-5,6'-dimethyl-6-(naphthyl-2-methyl)-3',4',5',6'-tetrahydro-3H-spiro[isobenzofuran-1,2'-pyran]-3',4',5'-triol | 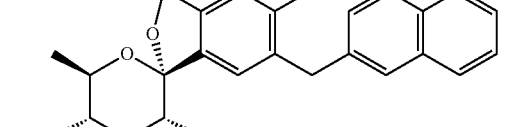<br>A63 |
| A64 | (1S,3'R,4'S,5'S,6'R)-5,6'-dimethyl-6-(benzo[b]thiophene-2-methyl)-3',4',5',6'-tetrahydro-3H-spiro[isobenzofuran-1,2'-pyran]-3',4',5'-triol | 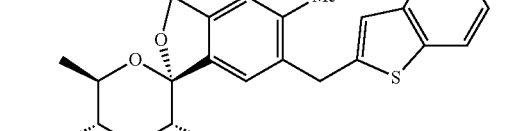<br>A64 |
| A65 | (1S,3'R,4'S,5'S,6'R)-5,6'-dimethyl-6-(benzo[b]furan-2-methyl)-3',4',5',6'-tetrahydro-3H-spiro[isobenzofuran-1,2'-pyran]-3',4',5'-triol | 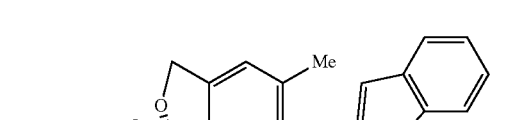<br>A65 |

TABLE 1-continued

Specific compounds

| No. | Name | Structure |
|---|---|---|
| A66 | (1S,3'R,4'S,5'S,6'R)-5,6'-dimethyl-6-((5-(2-furyl)thiazolyl)-2-methyl)-3',4',5',6'-tetrahydro-3H-spiro[isobenzofuran-1,2'-pyran]-3',4',5'-triol | 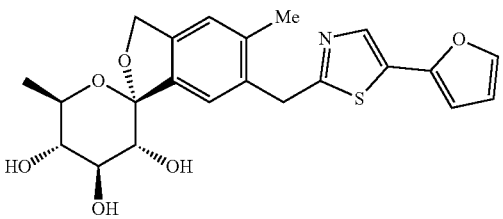 A66 |
| A67 | (1S,3'R,4'S,5'S,6'R)-5,6'-dimethyl-6-((5-(2-thienyl)thiazolyl)-2-methyl)-3',4',5',6'-tetrahydro-3H-spiro[isobenzofuran-1,2'-pyran]-3',4',5'-triol | 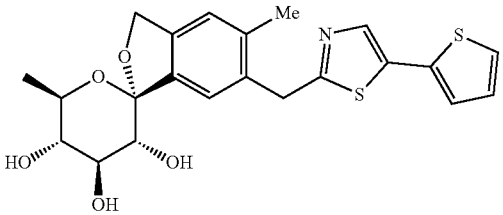 A67 |
| A68 | (1S,3'R,4'S,5'S,6'R)-5,6'-dimethyl-6-((5-(4-fluorophenyl)thiazolyl)-2-methyl)-3',4',5',6'-tetrahydro-3H-spiro[isobenzofuran-1,2'-pyran]-3',4',5'-triol | 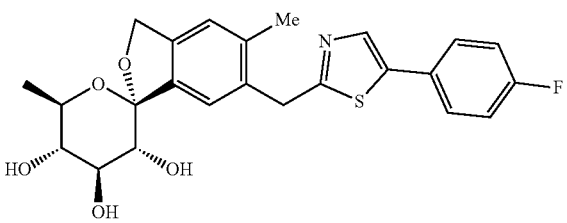 A68 |
| A69 | (1S,3'R,4'S,5'S,6'R)-5,6'-dimethyl-6-((5-phenylthiazolyl)-2-methyl)-3',4',5',6'-tetrahydro-3H-spiro[isobenzofuran-1,2'-pyran]-3',4',5'-triol | 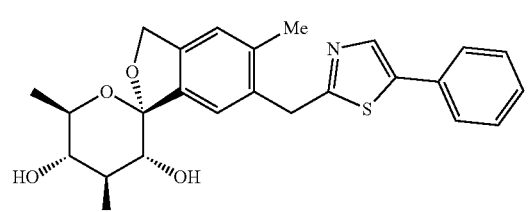 A69 |
| A70 | (1S,3'R,4'S,5'S,6'R)-5,6'-dimethyl-6-((5-(4-trifluoromethyl)phenyl)thienyl)-2-methyl)-5-chloro-3',4',5',6'-tetrahydro-3H-spiro[isobenzofuran-1,2'-pyran]-3',4',5'-triol | 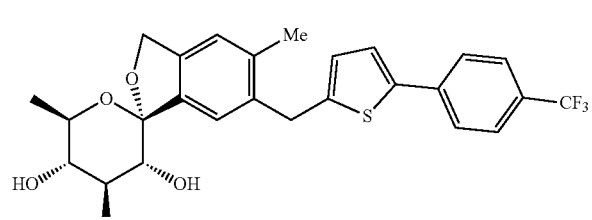 A70 |

TABLE 1-continued

| No. | Name | Structure |
|-----|------|-----------|
| A71 | (1S,3'R,4'S,5'S,6'R)-5,6'-dimethyl-6-((5-(4-methyl)phenyl)thienyl)-2-methyl)-5-chloro-3',4',5',6'-tetrahydro-3H-spiro[isobenzofuran-1,2'-pyran]-3',4',5'-triol | A71 |
| A72 | (1S,3'R,4'S,5'S,6'R)-5,6'-dimethyl-6-((5-(3-fluorophenyl)thienyl)-2-methyl)-5-chloro-3',4',5',6'-tetrahydro-3H-spiro[isobenzofuran-1,2'-pyran]-3',4',5'-triol | A72 |
| A73 | (1S,3'R,4'S,5'S,6'R)-5,6'-dimethyl-6-((5-(2,4-difluorophenyl)thienyl)-2-methyl)-5-chloro-3',4',5',6'-tetrahydro-3H-spiro[isobenzofuran-1,2'-pyran]-3',4',5'-triol | A73 |
| A74 | (1S,3'R,4'S,5'S,6'R)-5,6'-dimethyl-6-((5-(2-fluorophenyl)thienyl)-2-methyl)-5-chloro-3',4',5',6'-tetrahydro-3H-spiro[isobenzofuran-1,2'-pyran]-3',4',5'-triol | A74 |
| A75 | (1S,3'R,4'S,5'S,6'R)-5,6'-dimethyl-6-((5-(4-methoxyphenyl)thienyl)-2-methyl)-5-chloro-3',4',5',6'-tetrahydro-3H-spiro[isobenzofuran-1,2'-pyran]-3',4',5'-triol | A75 |

TABLE 1-continued

Specific compounds

| No. | Name |
|---|---|
| A76 | (1S,3'R,4'S,5'S,6'R)-5,6'-dimethyl-6-((5-methoxythienyl)-2-methyl)-3',4',5',6'-tetrahydro-3H-spiro[isobenzofuran-1,2'-pyran]-3',4',5'-triol |
| A77 | (1S,3'R,4'S,5'S,6'R)-5,6'-dimethyl-6-((5-trifluoromethylthienyl)-2-methyl)-3',4',5',6'-tetrahydro-3H-spiro[isobenzofuran-1,2'-pyran]-3',4',5'-triol |
| A78 | 5-(((1S,3'R,4'S,5'S,6'R)-3',4',5'-trihydroxy-5,6'-dimethyl-3',4',5',6'-tetrahydro-3H-spiro[isobenzofuran-1,2'-pyran]yl)-6-methyl)thiophene-2-nitrile |
| A79 | 5-(((1S,3'R,4'S,5'S,6'R)-3',4',5'-trihydroxy-5,6'-dimethyl--3',4',5',6'-tetrahydro-3H-spiro[isobenzofuran-1,2'-pyran]yl)-6-methyl)thiophene-2-methyl formate |
| A80 | 5-(((1S,3'R,4'S,5'S,6'R)-3',4',5'-trihydroxy-5,6'-dimethyl-3',4',5',6'-tetrahydro-3H-spiro[isobenzofuran-1,2'-pyran]yl)-6-methyl)thiophene-2-phenyl formate |

TABLE 1-continued

Specific compounds

| No. | Name |
|---|---|
| A81 | N-methyl-5-(((1S,3'R,4'S,5'S,6'R)-3',4',5'-trihydroxy-5,6'-dimethyl--3',4',5',6'-tetrahydro-3H-spiro[isobenzofuran-1,2'-pyran]yl)-6-methyl)thiophene-2-formamide |
| A82 | (1S,3'R,4'S,5'S,6'R)-5-ethynyl-6'-methyl-6-(4-methylbenzyl)-3',4',5',6'-tetrahydro-3H-spiro[isobenzofuran-1,2'-pyran]-3',4',5'-triol |
| A83 | (1S,3'R,4'S,5'S,6'R)-5-ethynyl-6'-methyl-6-(5-(4-fluorophenyl)thienyl)-2-methyl)-3',4',5',6'-tetrahydro-3H-spiro[isobenzofuran-1,2'-pyran]-3',4',5'-triol |
| A84 | (1S,3'R,4'S,5'S,6'R)-5-ethynyl-6'-methyl-6-(5-(2-furyl)thiazolyl)-2-methyl)-3',4',5',6'-tetrahydro-3H-spiro[isobenzofuran-1,2'-pyran]-3',4',5'-triol |
| A85 | (1S,3'R,4'S,5'S,6'R)-5-ethynyl-6'-methyl-6-(5-ethylthienyl)-2-methyl)-3',4',5',6'-tetrahydro-3H-spiro[isobenzofuran-1,2'-pyran]-3',4',5'-triol |

TABLE 1-continued

Specific compounds

| No. | Name | Structure |
|---|---|---|
| A86 | (1S,3'R,4'S,5'S,6'R)-5-ethynyl-6'-methyl-6-(4-methoxybenzyl)-3',4',5',6'-tetrahydro-3H-spiro[isobenzofuran-1,2'-pyran]-3',4',5'-triol | 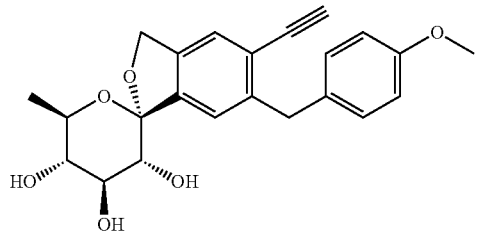<br>A86 |
| A87 | (1S,3'R,4'S,5'S,6'R)-5-ethynyl-6'-methyl-6-(4-ethoxylbenzyl)-3',4',5',6'-tetrahydro-3H-spiro[isobenzofuran-1,2'-pyran]-3',4',5'-triol | 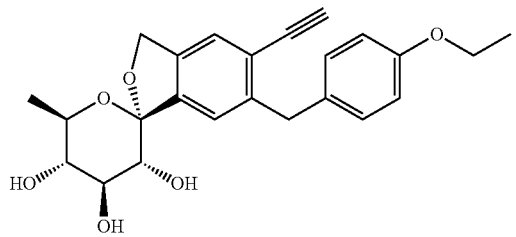 [SMILES: C#Cc1cc2c(cc1Cc1ccc(OCC)cc1)[C@]1(OC2)O[C@H](C)[C@@H](O)[C@H](O)[C@H]1O]<br>A87 |
| A88 | (1S,3'R,4'S,5'S,6'R)-3',4',5'-trihydroxy-6'-methyl-6-(4-methylphenyl)-3',4',5',6'-tetrahydro-3H-spiro[isobenzofuran-1,2'-pyran]-5-nitrile | 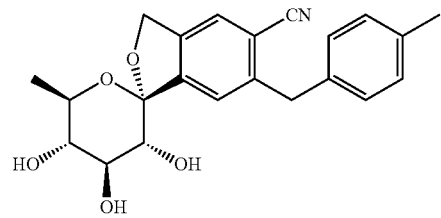<br>A88 |
| A89 | (1S,3'R,4'S,5'S,6'R)-6-((5-(4-fluorophenyl)thienyl)-2-methyl)-3',4',5'-trihydroxy-6'-methyl-3',4',5',6'-tetrahydro-3H-spiro[isobenzofuran-1,2'-pyran]-5-nitrile | 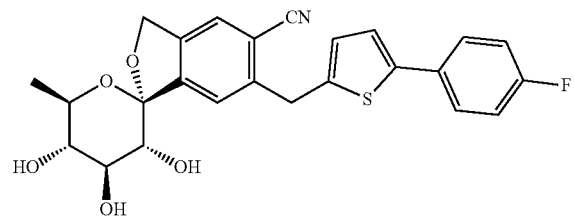<br>A89 |
| A90 | (1S,3'R,4'S,5'S,6'R)-6-((5-(2-furyl)thiazolyl)-2-methyl)-3',4',5'-trihydroxy-6'-methyl-3',4',5',6'-tetrahydro-3H-spiro[isobenzofuran-1,2'-pyran]-5-nitrile | 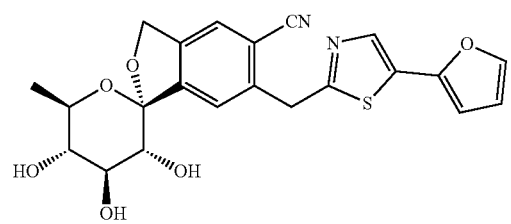<br>A90 |

TABLE 1-continued

Specific compounds

| No. | Name |
|---|---|
| A91 | (1S,3'R,4'S,5'S,6'R)-6-((5-ethylthienyl)-2-methyl)-3',4',5'-trihydroxy-6'-methyl-3',4',5',6'-tetrahydro-3H-spiro[isobenzofuran-1,2'-pyran]-5-nitrile |
| A92 | (1S,3'R,4'S,5'S,6'R)-3',4',5'-trihydroxy-6-(4-methoxyphenyl)-6'-methyl-3',4',5'-trihydroxy-6'-methyl-3',4',5',6'-tetrahydro-3H-spiro[isobenzofuran-1,2'-pyran]-5-nitrile |
| A93 | (1S,3'R,4'S,5'S,6'R)-3',4',5'-trihydroxy-6-(4-ethyoxylphenyl)-6'-methyl-3',4',5'-trihydroxy-6'-methyl-3',4',5',6'-tetrahydro-3H-spiro[isobenzofuran-1,2'-pyran]-5-nitrile |
| A94 | (1S,3'R,4'S,5'S,6'R)-6'-methyl-6-(4-methylbenzyl)-5-bromo-3',4',5',6'-tetrahydro-3H-spiro[isobenzofuran-1,2'-pyran]-3',4',5'-triol |
| A95 | (1S,3'R,4'S,5'S,6'R)-6'-methyl-6-((5-(4-fluorophenyl)thienyl)-2-methyl)-5-bromo-3',4',5',6'-tetrahydro-3H-spiro[isobenzofuran-1,2'-pyran]-3',4',5'-triol |

TABLE 1-continued

Specific compounds

| No. | Name |
|---|---|
| A96 | (1S,3'R,4'S,5'S,6'R)-6'-methyl-6-((5-(2-furyl)thiazolyl)-2-methyl)-5-bromo-3',4',5',6'-tetrahydro-3H-spiro[isobenzofuran-1,2'-pyran]-3',4',5'-triol |
| A97 | (1S,3'R,4'S,5'S,6'R)-6'-methyl-6-((5-ethylthienyl)-2-methyl)-5-fluoro-3',4',5',6'-tetrahydro-3H-spiro[isobenzofuran-1,2'-pyran]-3',4',5'-triol |
| A98 | (1S,3'R,4'S,5'S,6'R)-6'-methyl-6-(4-methoxybenzyl)-5-bromo-3',4',5',6'-tetrahydro-3H-spiro[isobenzofuran-1,2'-pyran]-3',4',5'-triol |
| A99 | (1S,3'R,4'S,5'S,6'R)-6'-methyl-6-(4-ethyoxylbenzyl)-5-bromo-3',4',5',6'-tetrahydro-3H-spiro[isobenzofuran-1,2'-pyran]-3',4',5'-triol |
| A100 | (1S,3'R,4'S,5'S,6'R)-5-methoxy-6'-methyl-6-(4-methylbenzyl)-3',4',5',6'-tetrahydro-3H-spiro[isobenzofuran-1,2'-pyran]-3',4',5'-triol |

TABLE 1-continued

Specific compounds

| No. | Name |
|---|---|
| A101 | (1S,3'R,4'S,5'S,6'R)-6-((5-(4-fluorophenyl)thienyl)-2-methyl-5-methoxy-6'-methyl-3',4',5',6'-tetrahydro-3H-spiro[isobenzofuran-1,2'-pyran]-3',4',5'-triol |
| A102 | (1S,3'R,4'S,5'S,6'R)-6-((5-(2-furyl)thiazolyl)-2-methyl-5-methoxy-6'-methyl-3',4',5',6'-tetrahydro-3H-spiro[isobenzofuran-1,2'-pyran]-3',4',5'-triol |
| A103 | (1S,3'R,4'S,5'S,6'R)-6-((5-ethylthienyl)-2-methyl-5-methoxy-6'-methyl-3',4',5',6'-tetrahydro-3H-spiro[isobenzofuran-1,2'-pyran]-3',4',5'-triol |
| A104 | (1S,3'R,4'S,5'S,6'R)-5-methoxy-6-(4-methoxyphenyl)-6'-methyl-3',4',5',6'-tetrahydro-3H-spiro[isobenzofuran-1,2'-pyran]-3',4',5'-triol |
| A105 | (1S,3'R,4'S,5'S,6'R)-5-methoxy-6-(4-ethyoxylphenyl)-6'-methyl-3',4',5',6'-tetrahydro-3H-spiro[isobenzofuran-1,2'-pyran]-3',4',5'-triol |

TABLE 1-continued

Specific compounds

| No. | Name |
|---|---|
| A106 | (1S,3'R,4'S,5'S,6'R)-6-(benzofuran-5-ylmethyl)-5-chloro-6'-methyl-3',4',5',6'-tetrahydro-3H-spiro[isobenzofuran-1,2'-pyran]-3',4',5'-triol |
| A107 | (1S,3'R,4'S,5'S,6'R)-5-chloro-6-(4-ethyoxyl-3-fluorophenyl)-6'-methyl-3',4',5',6'-tetrahydro-3H-spiro[isobenzofuran-1,2'-pyran]-3',4',5'-triol |
| A108 | 1-(4-(((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)methyl)phenyl)cyclopropane-1-formonitrile |
| A109 | 1-(5-(((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)methyl)thiophene-2-yl)cyclopropane-1-formonitrile |
| A110 | (1S,3'R,4'S,5'S,6'R)-5-chloro-6'-methyl-6-(4-trifluoromethylphenyl)-3',4',5',6'-tetrahydro-3H-spiro[isobenzofuran-1,2'-pyran]-3',4',5'-triol |
| A111 | ((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)(4-(trifluoromethyl)phenyl)ketone |

TABLE 1-continued

Specific compounds

| No. | Name | Structure |
| --- | --- | --- |
| A112 | ((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl) (3-fluoro-4-(trifluoromethyl)phenyl)ketone | A112 |
| A113 | ((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl) (5-ethylthiophene-2-yl)ketone | A113 |
| A114 | (1S,3'R,4'S,5'S,6'R)-5-chloro-6-((5-(2-methoxyethyl)thiophene-2-yl)methyl)-6'-methyl-3',4',5',6'-tetrahydro-3H-spiro[isobenzofuran-1,2'-pyran]-3',4',5'-triol | A114 |
| A115 | (1S,3'R,4'S,5'S,6'R)-5-chloro-6-((5-(2-ethyoxylethyl)thiophene-2-yl)methyl)-6'-methyl-3',4',5',6'-tetrahydro-3H-spiro[isobenzofuran-1,2'-pyran]-3',4',5'-triol | A115 |
| A116 | (1S,3'R,4'S,5'S,6'R)-5-chloro-6-((5-(2-propoxyethyl)thiophene-2-yl)methyl)-6'-methyl-3',4',5',6'-tetrahydro-3H-spiro[isobenzofuran-1,2'-pyran]-3',4',5'-triol | A116 |

TABLE 1-continued

Specific compounds

| No. | Name | Structure |
|-----|------|-----------|
| A117 | 1-(5-((((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)methyl)thiophene-2-yl)ethanone | 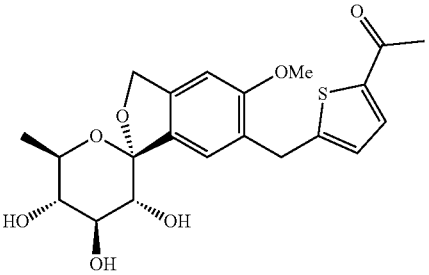 [SMILES: COc1cc2c(cc1Cc1ccc(C(C)=O)s1)[C@]1(OC2)O[C@H](C)[C@@H](O)[C@H](O)[C@H]1O]<br>A117 |
| A118 | (1S,3'R,4'S,5'S,6'R)-5-chloro-6-((5-(1-hydroxyethyl)thiophene-2-yl)methyl)-6'-methyl-3',4',5',6'-tetrahydro-3H-spiro[isobenzofuran-1,2'-pyran]-3',4',5'-triol | 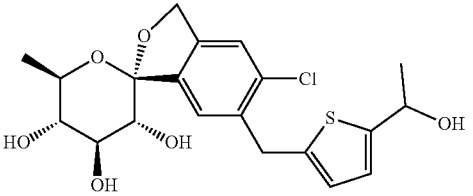<br>A118 |
| A119 | (1S,3'R,4'S,5'S,6'R)-5-chloro-6-((5-(2-hydroxyethyl)thiophene-2-yl)methyl)-6'-methyl-3',4',5',6'-tetrahydro-3H-spiro[isobenzofuran-1,2'-pyran]-3',4',5'-triol | 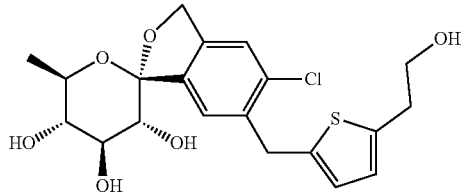 [SMILES: C[C@H]1O[C@]2(OCc3cc(Cl)c(Cc4ccc(CCO)s4)cc32)[C@H](O)[C@@H](O)[C@@H]1O]<br>A119 |
| A120 | (1S,3'R,4'S,5'S,6'R)-5-chloro-6-((5-ethylthiophene-2-yl)(hydroxymethyl)-6'-methyl-3',4',5',6'-tetrahydro-3H-spiro[isobenzofuran-1,2'-pyran]-3',4',5'-triol | 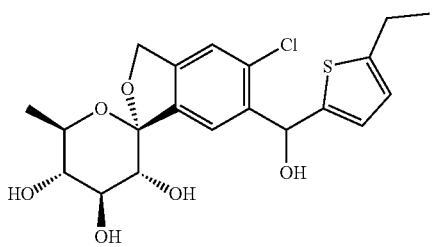 [SMILES: CCc1ccc(C(O)c2cc3c(cc2Cl)CO[C@]32O[C@H](C)[C@@H](O)[C@H](O)[C@H]2O)s1]<br>A120 |
| A121 | 2-(5-((((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)methyl)thiophene-2-yl) acetic acid | 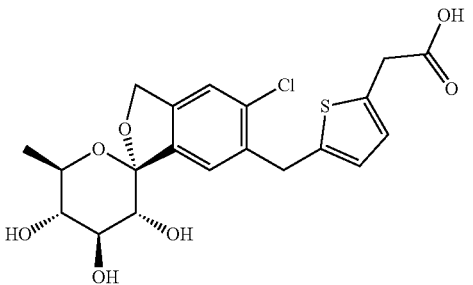 [SMILES: C[C@H]1O[C@]2(OCc3cc(Cl)c(Cc4ccc(CC(=O)O)s4)cc32)[C@H](O)[C@@H](O)[C@@H]1O]<br>A121 |

TABLE 1-continued

Specific compounds

| No. | Name | Structure |
|-----|------|-----------|
| A122 | 2-(5-((((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)methyl)thiophene-2-yl) methyl acetate | A122 |
| A123 | 2-(5-((((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)methyl)thiophene-2-yl) ethyl acetate | A123 |
| A124 | 2-(5-((((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)methyl)thiophene-2-yl)-N-methylacetamide | A124 |
| A125 | 2-(5-((((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)methyl)thiophene-2-yl)-N-ethylacetamide | A125 |

TABLE 1-continued

Specific compounds

| No. | Name | Structure |
| --- | --- | --- |
| A126 | 2-(5-(((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)methyl)thiophene-2-yl)-N,N-dimethylacetamide | 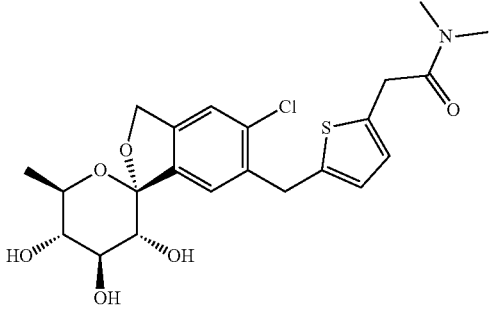<br>A126 |
| A127 | 2-(5-(((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)methyl)thiophene-2-yl)-1-(pyrrolidine-1-yl)ethyl-1-one | 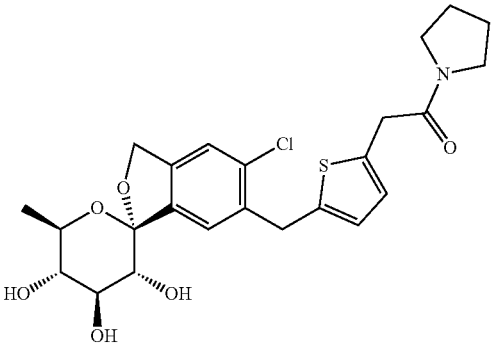 [SMILES: C[C@H]1O[C@]2(OCc3cc(Cl)c(Cc4ccc(CC(=O)N5CCCC5)s4)cc32)[C@H](O)[C@@H](O)[C@@H]1O]<br>A127 |
| A128 | 2-(5-(((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)methyl)thiophene-2-yl)-1-morpholineethyl-1-one | 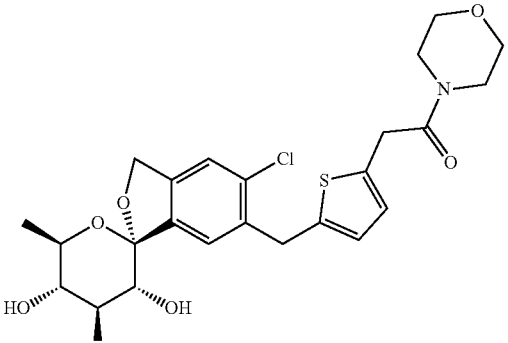<br>A128 |
| A129 | 5-(((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)methyl)thiophene-2-formaldehyde | 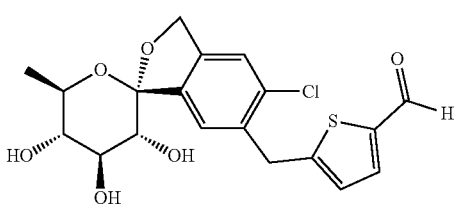 [SMILES: C[C@H]1O[C@]2(OCc3cc(Cl)c(Cc4ccc(C=O)s4)cc32)[C@H](O)[C@@H](O)[C@@H]1O]<br>A129 |

TABLE 1-continued

Specific compounds

| No. | Name |
|---|---|
| A130 | (1S,3'R,4'S,5'S,6'R)-5-chloro-6-((5-(hydroxymethyl)thiophene-2-yl)methyl)-6'-methyl-3',4',5',6'-tetrahydro-3H-spiro[isobenzofuran-1,2'-pyran]-3',4',5'-triol |
| A131 | (1S,3'R,4'S,5'S,6'R)-5-chloro-6-((5-(difluoromethyl)thiophene-2-yl)methyl)-6'-methyl-3',4',5',6'-tetrahydro-3H-spiro[isobenzofuran-1,2'-pyran]-3',4',5'-triol |
| A132 | (1S,3'R,4'S,5'S,6'R)-5-chloro-6'-methyl-6-((5-(pyrrolidine-1-ylmethyl)thiophene-2-yl)methyl)-3',4',5',6'-tetrahydro-3H-spiro[isobenzofuran-1,2'-pyran]-3',4',5'-triol |
| A133 | (1S,3'R,4'S,5'S,6'R)-5-chloro-6'-methyl-6-((5-morpholinemethyl)thiophene-2-yl)methyl)-3',4',5',6'-tetrahydro-3H-spiro[isobenzofuran-1,2'-pyran]-3',4',5'-triol |
| A134 | 2-(5-(((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)methyl)thiophene-2-methyl formate |
| A135 | 2-(5-(((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)methyl)thiophene-2-ethyl formate |

TABLE 1-continued

Specific compounds

| No. | Name | Structure |
|---|---|---|
| A136 | (5-(((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)methyl)thiophene-2-yl)(pyrrolidine-1-yl)ketone | 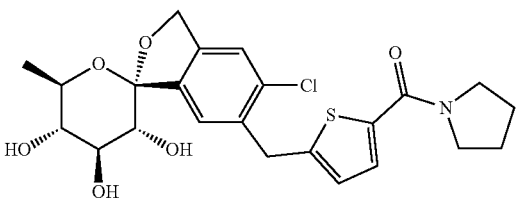 [SMILES: C[C@H]1O[C@]2(OCc3cc(Cl)c(Cc4ccc(C(=O)N5CCCC5)s4)cc32)[C@H](O)[C@@H](O)[C@@H]1O]<br>A136 |
| A137 | (5-(((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)methyl)thiophene-2-yl) (morpholineyl)ketone | 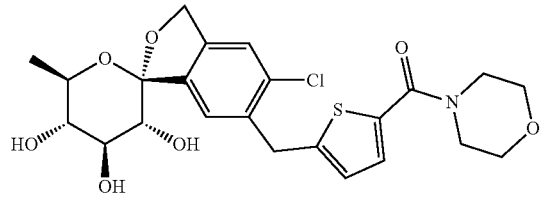 [SMILES: C[C@H]1O[C@]2(OCc3cc(Cl)c(Cc4ccc(C(=O)N5CCOCC5)s4)cc32)[C@H](O)[C@@H](O)[C@@H]1O]<br>A137 |
| A138 | (5-(((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)methyl)-N-methylthiophene-2-formamide | 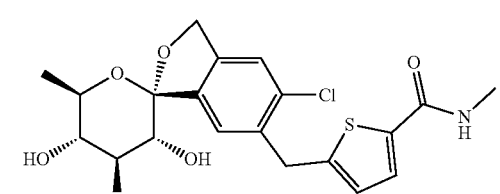<br>A138 |
| A139 | (5-(((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)methyl)-N-ethylthiophene-2-formamide | 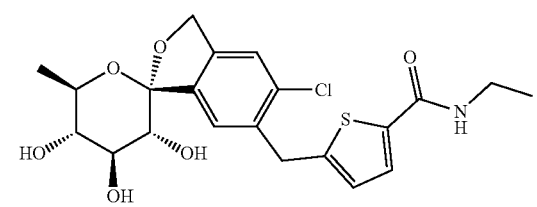 [SMILES: CCNC(=O)c1ccc(Cc2cc3c(cc2Cl)CO[C@]32O[C@H](C)[C@@H](O)[C@H](O)[C@H]2O)s1]<br>A139 |
| A140 | (5-(((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)methyl)-N,N-dimethylthiophene-2-formamide | 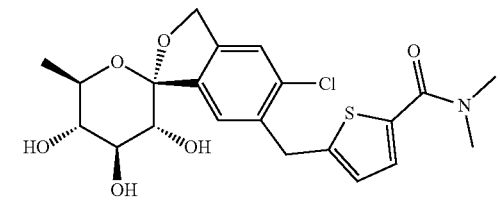<br>A140 |
| A141 | (1S,3'R,4'S,5'S,6'R)-5-chloro-6-((5-ethyl-4-methylthiophene-2-yl)methyl)-6'-methyl-3',4',5',6'-tetrahydro-3H-spiro[isobenzofuran-1,2'-pyran]-3',4',5'-triol | 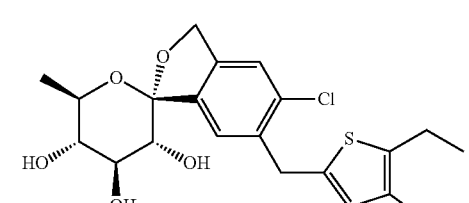<br>A141 |

TABLE 1-continued

Specific compounds

| No. | Name |
|---|---|
| A142 | (1S,3'R,4'S,5'S,6'R)-5-chloro-6-((5-(2-hydroxyethyl)-4-methylthiophene-2-yl)methyl)-6'-methyl-3',4',5',6'-tetrahydro-3H-spiro[isobenzofuran-1,2'-pyran]-3',4',5'-triol |
| A143 | (1S,3'R,4'S,5'S,6'R)-5-chloro-6-((5-ethyl-4-fluorothiophene-2-yl)methyl)-6'-methyl-3',4',5',6'-tetrahydro-3H-spiro[isobenzofuran-1,2'-pyran]-3',4',5'-triol |
| A144 | (1S,3'R,4'S,5'S,6'R)-5-chloro-6-((4-fluoro-5-(2-hydroxyethyl)thiophene-2-yl)methyl)-6'-methyl-3',4',5',6'-tetrahydro-3H-spiro[isobenzofuran-1,2'-pyran]-3',4',5'-triol |
| A145 | (1S,3'R,4'S,5'S,6'R)-5-chloro-6-((4,5-dimethylthiophene-2-yl)methyl)-6'-methyl-3',4',5',6'-tetrahydro-3H-spiro[isobenzofuran-1,2'-pyran]-3',4',5'-triol |
| A146 | (1S,3'R,4'S,5'S,6'R)-5-chloro-6-((5-chloro-4-methylthiophene-2-yl)methyl)-6'-methyl-3',4',5',6'-tetrahydro-3H-spiro[isobenzofuran-1,2'-pyran]-3',4',5'-triol |
| A147 | (1S,3'R,4'S,5'S,6'R)-5-chloro-6-((5-fluoro-4-methylthiophene-2-yl)methyl)-6'-methyl-3',4',5',6'-tetrahydro-3H-spiro[isobenzofuran-1,2'-pyran]-3',4',5'-triol |

TABLE 1-continued

Specific compounds

| No. | Name | Structure |
|---|---|---|
| A148 | (1S,3'R,4'S,5'S,6'R)-5-chloro-6-((5-((R)-1-hydroxyethyl)thiophene-2-yl)methyl-6'-methyl-3',4',5',6'-tetrahydro-3H-spiro[isobenzofuran-1,2'-pyran]-3',4',5'-triol | A148 |
| A149 | (1S,3'R,4'S,5'S,6'R)-5-chloro-6-((5-((S)-1-hydroxyethyl)thiophene-2-yl)methyl-6'-methyl-3',4',5',6'-tetrahydro-3H-spiro[isobenzofuran-1,2'-pyran]-3',4',5'-triol | A149 |
| A150 | (1S,3'R,4'S,5'S,6'R)-5-chloro-6-((S)-(5-ethylthiophene-2-yl)(hydroxyl)methyl)-6'-methyl-3',4',5',6'-tetrahydro-3H-spiro[isobenzofuran-1,2'-pyran]-3',4',5'-triol | A150 |
| A151 | (1S,3'R,4'S,5'S,6'R)-5-chloro-6-((R)-(5-ethylthiophene-2-yl)(hydroxyl)methyl)-6'-methyl-3',4',5',6'-tetrahydro-3H-spiro[isobenzofuran-1,2'-pyran]-3',4',5'-triol | A151 |

The compounds of the present invention have asymmetric centers, chiral axises, and chiral planes, and may exist as racemates, R-isomers, or S-isomers. One skilled in the art can obtain R-isomers and/or S-isomers from racemates using conventional techniques.

The present invention provides a pharmaceutically acceptable salt of a compound of formula I, in particular a conventional pharmaceutically acceptable salt formed by the reaction of a compound of formula I with an inorganic or organic acid. For example, conventional pharmaceutically acceptable salts may be prepared by reacting a compound of formula I with an inorganic acid, such as hydrochloric acid, hydrobromic acid, sulfuric acid, nitric acid, aminosulfonic acid and phosphoric acid, and the like, and organic acids include citric acid, tartaric acid, lactic acid, pyruvic acid, acetic acid, benzenesulfonic acid, p-toluenesulfonic acid, methanesulfonic acid, naphthalenesulfonic acid, ethanesulfonic acid, naphthalene disulfonic acid, maleic acid, malic acid, malonic acid, fumaric acid, succinic acid, propionic acid, oxalic acid, trifluoroacetic acid, stearic acid, pamoic acid, hydroxymaleic acid, phenylacetic acid, benzoic acid, salicylic acid, glutamic acid, ascorbic acid, p-anilinesulfonic acid, 2-acetoxybenzoic acid and isethionic acid and the like; or sodium, potassium, calcium, aluminum or ammonium salts of the compound of formula I with an inorganic base; or a salt formed by compound of formula I with an organic base, such as methanamine salt, ethylamine salt or ethanolamine salt.

The Preparation of C, O-Spirocyclic Aryl Glycoside Compound

The invention also provides a method for preparing the compound represented by the general formula I, and the preparation method is as the scheme 1.

Scheme 1:

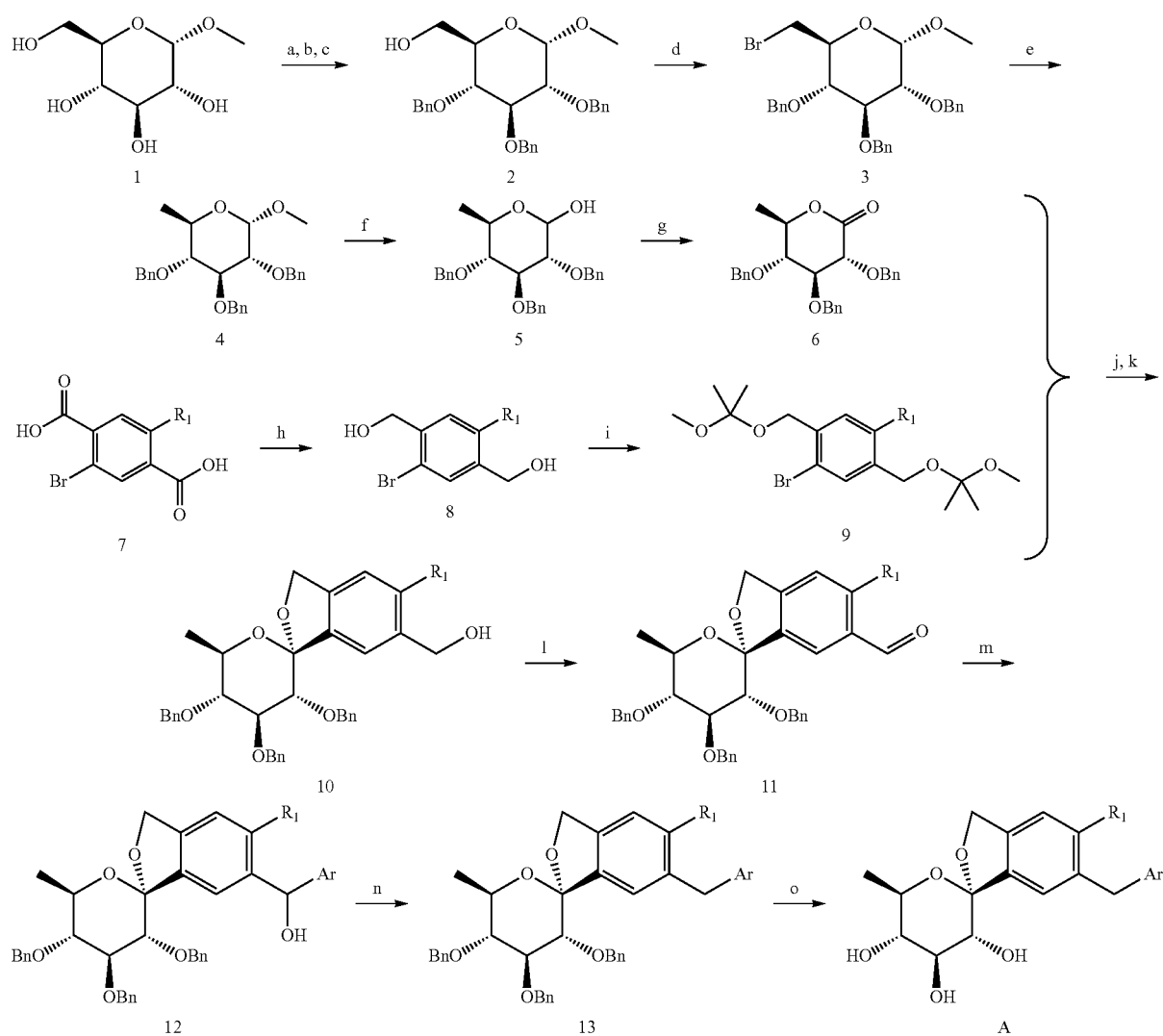

wherein the definition of $R_1$ and Ar have the same definitions as in formula I above.

Steps a, b and c:

Methyl α-D-pyran glucosidase 1 and imidazole are dissolved in DMF, and TIPSCl is slowly added dropwise under an ice bath. After the addition is completed, the mixture is stirred at room temperature for 1 to 2 days. TLC monitors (alkaline potassium permanganate color) that the reaction is completed, then the reaction solution is added an appropriate amount of water, extracted with dichloromethane, the organic layer is combined, washed with saturated sodium chloride solution twice, dried over anhydrous sodium sulfate, concentrated, and the crude product is directly used in the next reaction.

The crude product of the previous step and benzyl bromide are dissolved in DMF. After sodium hydride is added in portions under ice-cooling, the mixture is slowly warmed to room temperature and stirred at room temperature for 6-18 hours. TLC monitors (alkaline potassium permanganate color) that the reaction is completed, then the reaction solution is slowly added an appropriate amount of water to quench, extracted with ethylacetate, the organic layer is combined, washed with saturated sodium chloride solution for twice, dried over anhydrous sodium sulfate, concentrated, and the crude product is directly used in the next reaction.

The crude product of the previous step and TBAF are dissolved in tetrahydrofuran and stirred for 6-18 hours at room temperature. TLC monitors (UV color) that the reaction is completed, then the reaction solution is slowly added an appropriate amount of water to quench, extracted with ethylacetate, the organic layer is combined, washed with saturated sodium chloride solution twice, dried over anhydrous sodium sulfate, concentrated, and the crude product is isolated and purified by silica gel column to provide colorless syrup 2, yield 70-90% (three consecutive steps).

Step d:

Compound 2 is dissolved in tetrahydrofuran, $Ph_3P$ and $CBr_4$ were added at 0-20° C., and the mixture was stirred in an ice bath for 1-5 hours after the addition was completed. TLC monitored (UV color) that the reaction was completed, then the filtrate was suction filtered and the filtrate was concentrated. The crude product was isolated and purified by silica gel column chromatography (petroleum ether/ethylacetate) to give colorless syrup 3 in 98%-100% yield.

Step e:

Compound 3 was dissolved in anhydrous toluene and Bu$_3$SnH and AIBN were added at room temperature. After the addition was completed, the temperature was raised to 40-120° C. and stirred for 2-8 hours. TLC monitored (UV color) that the reaction was completed, then the reaction was cooled to room temperature and concentrated. The crude product was isolated and purified by silica gel column chromatography (petroleum ether/ethylacetate) to give colorless syrup 4 in 80-95% yield.

Step f:

Compound 4 was dissolved in glacial acetic acid and 3 M of sulfuric acid solution was added at room temperature. After the addition was completed, the mixture was stirred at 60-95° C. for 1-5 hours. TLC monitored (UV color) that the reaction was completed, then the reaction was cooled to room temperature and saturated sodium bicarbonate solution was slowly added until no bubbles formed. The mixture was extracted with methylene chloride. The combined organic layers were washed twice with saturated sodium chloride solution and dried over anhydrous sodium sulfate and concentrated. The crude product was isolated and purified by silica gel column chromatography (petroleum ether/ethylacetate) to give white solid 5 in 85-95% yield.

Step g:

Compound 5 was dissolved in DMSO and acetic anhydride was added at room temperature. After the addition was complete, it was stirred at room temperature overnight. TLC monitored (UV color) that the reaction was completed, then saturated sodium bicarbonate solution was slowly added until no bubbles were formed. The mixture was extracted with ethylacetate. The combined organic layers were washed twice with saturated sodium chloride solution, dried over anhydrous sodium sulfate and concentrated. The crude product was purified by silica gel column chromatography (petroleum ether/ethylacetate) to provide white solid 6 in 85-100% yield.

Step h:

Compound 7 was dissolved in anhydrous tetrahydrofuran and borane dimethylsulfide complex was added under ice-cooling. After addition was completed, the mixture was stirred at 40-100° C. for 2-8 hours. TLC monitored (UV color) that the reaction was completed, then the reaction was cooled to room temperature, slowly poured into ice-water, extracted with ethylacetate and the combined organic layers were washed twice with saturated sodium chloride solution, dried over anhydrous sodium sulfate and concentrated to give an off-white solid 8, yield 85-95%.

Step i:

Compound 8 was dissolved in anhydrous tetrahydrofuran and 4-methylbenzenesulfonate pyridine and 2-methoxypropylene were added under ice-cooling. After the addition was completed, the mixture was stirred in an ice bath for 1 to 5 hours. TLC monitored (UV color) that the reaction was completed, then saturated sodium bicarbonate solution was added and extracted with ethylacetate-triethylamine. The combined organic layers were washed twice with saturated sodium chloride solution, dried over anhydrous sodium sulfate and concentrated. The crude product was isolated and purified by silica gel column chromatography (petroleum ether/ethylacetate) to give colorless oily liquid 9, yield 65-85%.

Step j, k:

Compound 9 was dissolved in anhydrous tetrahydrofuran and n-butyllithium was added dropwise at −78° C. under nitrogen. After the addition was completed and the mixture was stirred at −78° C. for 0.5-4 hours, a solution of compound 6 in anhydrous tetrahydrofuran was added and the mixture was stirred for 1 to 5 hours at −78° C. TLC monitored (UV color) that the reaction was completed, then the reaction was transferred to room temperature and an appropriate amount of water was added. After the reaction was warmed to room temperature, the mixture was extracted with ethylacetate, washed twice with saturated sodium chloride solution, dried over anhydrous sodium sulfate and concentrated. The crude product was directly used in the next reaction.

The crude product of the previous step was dissolved in tetrahydrofuran-methanol and p-toluenesulfonic acid was added at room temperature. After the addition was completed, the mixture was stirred at room temperature for 10 to 24 hours. TLC monitored (UV color) that the reaction was completed, then the reaction solution was concentrated to remove most of the methanol and extracted with ethylacetate. The combined organic layer was washed twice with saturated sodium bicarbonate solution, washed twice with saturated sodium chloride solution, dried over anhydrous sodium sulfate. After concentration, the crude product was isolated and purified by silica gel column chromatography (petroleum ether/ethylacetate) to give 10 as a colorless oil in 50-60% yield (two consecutive steps).

Step l:

Compound 10 was dissolved in methylene chloride and PCC and silica gel were added at room temperature. After the addition was completed, the mixture was stirred at room temperature for 2-7 hours. TLC monitored (UV color) that the reaction was completed, then the reaction mixture was concentrated and the crude product was isolated and purified by silica gel column chromatography (petroleum ether/ethylacetate) to give white solid 11 in 80-90% yield.

Step m:

Bromobenzotoluene was dissolved in anhydrous tetrahydrofuran and n-butyllithium was added dropwise at −78° C. under nitrogen. After the addition was completed and the mixture was stirred at −78° C. for 0.5-4 hours, a solution of compound 11 in anhydrous tetrahydrofuran was added and the mixture was stirred for 2 hours at −78° C. TLC monitored (UV color) that the reaction was completed, then the reaction was transferred to room temperature, and an appropriate amount of water was added. Extracted with ethylacetate after the reaction was warmed to room temperature, and the combined organic layers were washed twice with saturated sodium chloride solution and dried over anhydrous sodium sulfate. After concentration, the crude product was isolated and purified by silica gel column chromatography (petroleum ether/ethylacetate) to give colorless oil 12, yield 90-95%.

Step n:

Compound 12 was dissolved in dichloromethane, Et$_3$SiH and BF$_3$.OEt2 were added at −20 to −40° C. under nitrogen atmosphere. After addition, the mixture was stirred at −20 to −40° C. for 0.5 to 4 hours. TLC monitored (UV color) that the reaction was completed, then the reaction was transferred to room temperature, and an appropriate amount of water was added. Extracted with dichloromethane after the reaction was warmed to room temperature, and the combined organic layers were washed twice with saturated sodium chloride solution and dried over anhydrous sodium sulfate. After concentration, the crude product was isolated and purified by silica gel column chromatography (petroleum ether/ethylacetate) to give colorless oil 13, yield 90-95%.

Step o:

Compound 13 and pentamethylbenzene were dissolved in methylene chloride and boron trichloride was added at −78° C. under nitrogen. After the addition was complete, the mixture was stirred overnight at −78° C. TLC monitored (UV color) that the reaction was completed, then methanol was added and the reaction was transferred to room temperature. After that, the residue was concentrated and the crude product was isolated and purified by silica gel column chromatography (methylene chloride/methanol) to obtain white solid A in 50-85% yield.

Pharmaceutical Composition and Use Thereof

In another aspect of the present invention, a pharmaceutical composition is provided, which comprises one or more in a therapeutically effective amount selected from the group consisting of the compounds of formula (I), their pharmaceutically acceptable salts, enantiomers, diastereomers or racemates, and optionally one or more pharmaceutically acceptable carriers, excipients, adjuvants, ingredients and/or diluents. The ingredients comprises, for example, odorants, fragrances, sweeteners, etc.

The pharmaceutical composition provided by the present invention preferably comprises 1-99% of the active ingredient by weight, the preferred ratio is that the compound of formula I as the active ingredient in a total amount of 65%-99% by weight, and the rest is pharmaceutically acceptable carriers, diluents, solutions or salt solutions.

The compounds and pharmaceutical compositions provided herein can be in a variety of forms such as tablets, capsules, powders, syrups, solutions, suspensions, aerosols and the like, and can be presented in suitable solid or liquid carriers or diluents, and in suitable disinfecting equipment for injection or infusion.

Various dosage forms of the pharmaceutical composition of the present invention can be prepared by conventional preparation methods in pharmacy field. The unit dose of the formulation contains from 0.05 to 200 mg of a compound of formula I, preferably from 0.1 mg to 100 mg of a compound of formula I in unit dose of the formulation.

The compounds and pharmaceutical compositions of this invention may be used clinically in mammals, including humans and animals, via routes of administration such as mouth, nose, skin, lungs or gastrointestinal tract. Most preferably oral. The most preferred daily dose is 0.01-200 mg/kg body weight, taken once, or 0.01-100 mg/kg body weight, used in multiple times. Regardless of the method of administration, the optimal dose for the individual should depend on the particular treatment. Usually, it starts with a small dose and gradually increases the dose until the most suitable dose is found.

In a further aspect of the present invention, a sodium-glucose cotransporter 2 inhibitor is provided, which comprises one or more compounds selected from the group consisting of the compound of formula I, pharmaceutically acceptable salts, racemates, R-isomers, S-isomers thereof or mixtures thereof, and optionally one or more pharmaceutically acceptable carriers, excipients, adjuvants, ingredients and/or diluents.

The compounds and compositions of the present invention are useful for the treatment and prevention of metabolic system disorders associated with sodium-glucose cotransporter 2 including, but not limited to, diseases such as diabetes, atherosclerosis, obesity, etc.

Therefore, according to a further aspect of the present invention, the use of a compound of formula I, a pharmaceutically acceptable salt, racemate, R-isomer, S-isomer thereof or a mixture thereof in the preparation of medicine for the treatment of metabolic system diseases associated with sodium-glucose cotransporter 2 (such as diabetes, atherosclerosis, and obesity) is provided.

Still in another aspect of the present invention, a method for treating metabolic diseases associated with sodium-glucose cotransporter 2, such as diabetes, atherosclerosis and obesity and the like is to provided, which comprises administering to a patient in need one or more compounds selected from the group consisting of compound of formula I, pharmaceutically acceptable salts, racemates, R-isomers, S-isomers thereof, or mixtures thereof.

In a preferred embodiment of the invention, the compound of formula I is used for lowering the blood glucose level of a subject.

In a preferred embodiment of the invention, the compound of formula I is used to increase the glucose tolerance of a patient suffering from diabetes or to improve their glucose-stimulated insulin release.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacturer's instructions. Unless indicated otherwise, parts and percentage are calculated by weight.

Example 1 Preparation of (1S,3'R,4'S,5'S,6'R)-6'-methyl-6-(4-methylbenzyl)-3',4',5',6'-tetrahydro-3H-spiro[isobenzofuran-1,2'-pyran]-3',4',5'-triol (A1)

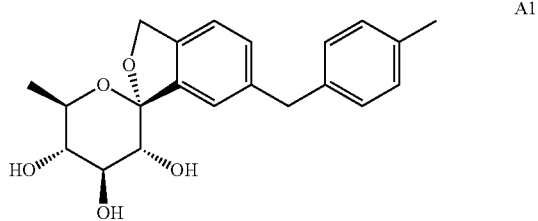 [SMILES: Cc1ccc(Cc2ccc3c(c2)[C@]2(OC3)O[C@H](C)[C@@H](O)[C@H](O)[C@H]2O)cc1]

Synthetic Route

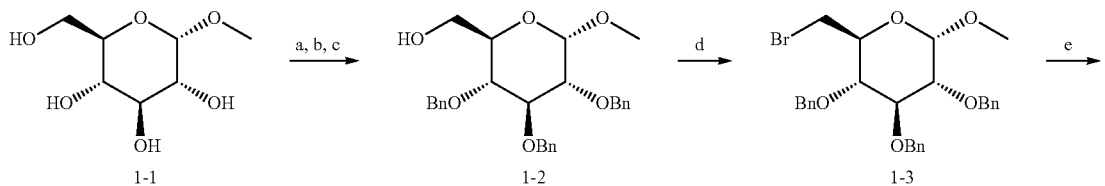

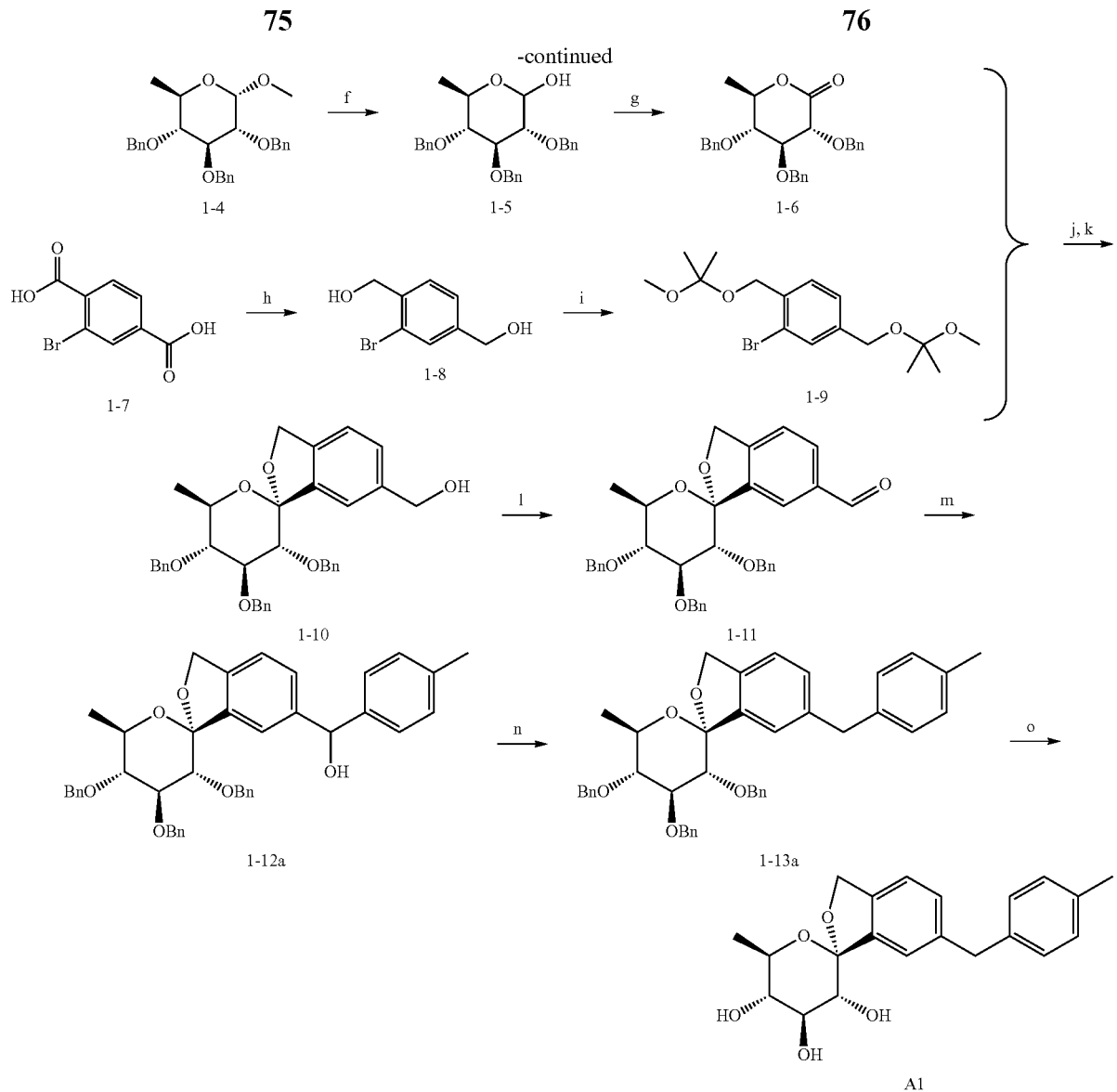

((2R,3R,4S,5R,6S)-3,4,5-tri(benzyloxy)-6-methoxytetrahydro-2H-pyran-2-yl)methanol (1-2)

Methyl α-D-pyran glucoside 1-1 (20.00 g, 103.00 mmol) and imidazole (21.04 g, 308.99 mmol) were dissolved in 180 mL of DMF and TIPSCl (24.27 mL, 113.30 mmol) was slowly added dropwise under ice-cooling for about 1 hour. After the addition was completed, the mixture was stirred at room temperature for 24 hours. TLC monitored (alkaline potassium permanganate color) that the reaction was completed, then the reaction solution was added an appropriate amount of water, extracted with dichloromethane, the organic layer was combined, washed with saturated sodium chloride solution twice, dried over anhydrous sodium sulfate, concentrated, and the crude product was directly used in the next reaction.

The crude product of the previous step and benzyl bromide (61.17 mL, 514.98 mmol) were dissolved in 350 mL of DMF and sodium hydride (60% dispersion in mineral oil) (20.60 g, 514.98 mmol) was added in portions under ice-cooling. After that, the mixture was slowly warmed to room temperature and stirred at room temperature for 12 hours. TLC monitored (alkaline potassium permanganate color) that the reaction was completed, then the reaction solution was slowly added an appropriate amount of water to quench, extracted with ethylacetate, the organic layer was combined, washed with saturated sodium chloride solution twice, dried over anhydrous sodium sulfate, concentrated, and the crude product was directly used in the next reaction.

The crude product of the previous step and TBAF (53.86 g, 205.99 mmol) were dissolved in 350 mL of tetrahydrofuran and stirred for 12 hours at room temperature. TLC monitored (UV color) that the reaction was completed, then the reaction solution was slowly added an appropriate amount of water to quench, extracted with ethylacetate, the organic layer was combined, washed with saturated sodium chloride solution twice, dried over anhydrous sodium sulfate, concentrated, and the crude product was isolated and purified by silica gel column (petroleum ether/ethylacetate 2/1, v/v) to provide 37.50 g colorless syrup 1-2, yield 78% (three consecutive steps).

$^1$H NMR (400 MHz, Chloroform-d) δ 7.40-7.27 (m, 15H), 4.99 (d, J=10.9 Hz, 1H), 4.92-4.77 (m, 3H), 4.70-4.61 (m, 2H), 4.56 (d, J=3.6 Hz, 1H), 4.01 (t, J=9.3 Hz, 1H), 3.81-3.61 (m, 3H), 3.58-3.45 (m, 2H), 3.37 (s, 3H).
LRMS (ESI, m/z): 487 [M+Na]$^+$.

(2S,3S,4S,5R,6S)-3,4,5-tri(benzyloxy)-2-(bromomethyl)-6-methoxytetrahydro-2H-pyran (1-3)

Compound 1-2 (30.00 g, 64.58 mmol) was dissolved in 300 mL of tetrahydrofuran, Ph$_3$P (25.41 g, 96.87 mmol) and CBr$_4$ (32.12 g, 96.87 mmol) were added under ice-cooling. After that, the mixture was stirred in ice bath for 1 hour. TLC monitored (UV color) that the reaction was completed, then the filtrate was suction filtered and the filtrate was concentrated.
The crude product was isolated and purified by silica gel column chromatography (petroleum ether/ethylacetate 10/1, v/v) to give 33.70 g colorless syrup 1-3 in 99% yield.
LRMS (ESI, m/z): 549 [M+Na]$^+$.

(2S,3R,4S,5R,6R)-3,4,5-tri(benzyloxy)-2-methoxy-6-methyltetrahydro-2H-pyran (1-4)

Compound 1-3 (31.89 g, 60.46 mmol) was dissolved in 250 mL of anhydrous toluene, Bu$_3$SnH (19.45 mL, 72.55 mmol) and AIBN (992.82 mg, 6.05 mmol) were added at room temperature, and then stirred under 80° C. for 4 hours. TLC monitored (UV color) that the reaction was completed, then the reaction was cooled to room temperature and concentrated. The crude product was isolated and purified by silica gel column chromatography (petroleum ether/ethylacetate 10/1, v/v) to give 23.59 g colorless syrup 1-4 in 87% yield.
$^1$H NMR (400 MHz, Chloroform-d) δ 7.42-7.22 (m, 15H), 4.98 (d, J=10.9 Hz, 1H), 4.90 (d, J=10.9 Hz, 1H), 4.86-4.76 (m, 2H), 4.72-4.60 (m, 2H), 4.53 (d, J=3.6 Hz, 1H), 3.95 (t, J=9.3 Hz, 1H), 3.79-3.66 (m, 1H), 3.52 (dd, J=9.7, 3.6 Hz, 1H), 3.37 (s, 3H), 3.13 (t, J=9.3 Hz, 1H), 1.24 (d, J=6.3 Hz, 3H).
LRMS (ESI, nm/z): 471 [M+Na]$^+$.

(3R,4S,5R,6R)-3,4,5-tri(benzyloxy)-6-methyltetrahydro-2H-pyran-2-nol (1-5)

Compound 1-4 (15.10 g, 33.66 mmol) was dissolved in 300 mL of glacial acetic acid and 3 M sulfuric acid solution (33.66 mL, 100.99 mmol) was added at room temperature. After the addition was completed, the mixture was stirred at 85° C. for 2.5 hours. TLC monitored (UV color) that the reaction was completed, then the reaction was cooled to room temperature and saturated sodium bicarbonate solution was slowly added until no bubbles formed. The mixture was extracted with methylene chloride. The combined organic layers were washed twice with saturated sodium chloride solution and dried over anhydrous sodium sulfate and concentrated. The crude product was isolated and purified by silica gel column chromatography (petroleum ether/ethylacetate 2/1, v/v) to give 13.01 g white solid 1-5 in 89% yield.
LRMS (ESI, m/z): 457 [M+Na]$^+$.

(3R,4S,5R,6R)-3,4,5-tri(benzyloxy)-6-methyltetrahydro-2H-pyran-2-one (1-6)

Compound 1-5 (25.20 g, 57.99 mmol) was dissolved in 200 mL of DMSO, 50 mL of acetic anhydride was added at room temperature. After the addition was completed, stirred at room temperature overnight. TLC monitored (UV color) that the reaction was completed, then saturated sodium bicarbonate solution was slowly added until no bubbles were formed. The mixture was extracted with ethylacetate. The combined organic layers were washed twice with saturated sodium chloride solution, dried over anhydrous sodium sulfate and concentrated. The crude product was purified by silica gel column chromatography (petroleum ether/ethylacetate 10/1, v/v) to provide 24.70 g white solid 1-6 in 98% yield.
$^1$H NMR (400 MHz, Chloroform-d) δ 7.48-7.19 (m, 15H), 4.95 (d, J=11.5 Hz, 1H), 4.74-4.61 (m, 3H), 4.61-4.48 (m, 3H), 4.12 (d, J=5.0 Hz, 1H), 3.97-3.87 (m, 1H), 3.46 (dd, J=8.8, 5.7 Hz, 1H), 1.41 (d, J=6.4 Hz, 3H).
LRMS (ESI, m/z): 433 [M+H]$^+$.

(2-bromo-1,4-phenylene) dimethyl carbinol (1-8)

2-bromoterephthalic acid 1-7 (15.00 g, 61.22 mmol) was dissolved in 200 mL of anhydrous tetrahydrofuran, and borane dimethylsulfide complex (2.0 M tetrahydrofuran solution) (91.83 mL, 183.65 mmol) was added in ice-bath. Stirred at 70° C. for 4 hours after the addition was completed. TLC monitored (UV color) that the reaction was completed, then the reaction was cooled to room temperature, slowly poured into ice-water, extracted with ethylacetate and the combined organic layers were washed twice with saturated sodium chloride solution, dried over anhydrous sodium sulfate and concentrated to give 11.90 g off-white solid 1-8, yield 89%.

2-bromo-1,4-di(((2-methoxypropan-2-yl)oxy)methyl)benzene (1-9)

Compound 1-8 (11.90 g, 54.82 mmol) was dissolved in 200 mL of anhydrous tetrahydrofuran and 4-methylbenzenesulfonate pyridine (275.55 mg, 1.10 mmol) and 2-methoxypropylene (51.61 mL, 548.24 mmol) were added under ice-cooling. After the addition was completed, the mixture was stirred in an ice bath for 2 hours. TLC monitored (UV color) that the reaction was completed, then saturated sodium bicarbonate solution was added and extracted with ethylacetate-triethylamine (ethylacetate/triethylamine 320/1, v/v). The combined organic layers were washed twice with saturated sodium chloride solution, dried over anhydrous sodium sulfate and concentrated. The crude product was isolated and purified by silica gel column chromatography (petroleum ether/ethylacetate 20/1, v/v) to give 13.62 g colorless oily liquid 1-9, yield 69%.
$^1$H NMR (400 MHz, Chloroform-d) δ 7.54 (d, J=1.3 Hz, 1H), 7.50 (d, J=7.9 Hz, 1H), 7.28 (dd, J=7.9, 1.6 Hz, 1H), 4.53 (s, 2H), 4.44 (s, 2H), 3.24 (s, 3H), 3.23 (s, 3H), 1.45 (s, 6H), 1.42 (s, 6H).

((1S,3'R,4'S,5'R,6'R)-3',4',5'-tri(benzyloxy)-6'-methyl-3',4',5',6'-tetrahydro-3H-spiro [isobenzofuran-1,2'-pyran]-6-yl) methanol (1-10)

Compound 1-9 (10.00 g, 27.68 mmol) was dissolved in anhydrous tetrahydrofuran and n-butyllithium (2.4 M in hexane) (12.69 mL, 30.45 mmol) was added dropwise at −78° C. under nitrogen. After the addition was completed and the mixture was stirred at −78° C. for 1 hours, a solution of compound 1-6 (10.54 g, 24.36 mmol) in anhydrous tetrahydrofuran was added and the mixture was stirred for 2 hours at −78° C. TLC monitored (UV color) that the reaction was completed, then the reaction was transferred to room temperature and an appropriate amount of water was added. After the reaction was warmed to room temperature, the mixture was extracted with ethylacetate, washed twice with saturated sodium chloride solution, dried over anhydrous sodium sulfate and concentrated. The crude product was directly used in the next reaction.

The crude product of the previous step was dissolved in 150 mL of tetrahydrofuran-methanol (tetrahydrofuran/methanol 2/1, v/v) and p-toluenesulfonic acid (5.24 g, 30.45 mmol) was added at room temperature. After the addition was completed, the mixture was stirred at room temperature for 15 hours. TLC monitored (UV color) that the reaction was completed, then the reaction solution was concentrated to remove most of the methanol and extracted with ethylacetate. The combined organic layer was washed twice with saturated sodium bicarbonate solution, twice with saturated sodium chloride solution, dried over anhydrous sodium sulfate. After concentration, the crude product was isolated and purified by silica gel column chromatography (petroleum ether/ethylacetate 4/1, v/v) to give 7.67 g 1-10 as a colorless oil in 57% yield (two consecutive steps).

LRMS (ESI, m/z): 553 [M+H]$^+$.

(1S,3'R,4'S,5'R,6'R)-3',4',5'-tri(benzyloxy)-6'-methyl-3',4',5',6'-tetrahydro-3H-spiro [isobenzofuran-1,2'-pyran]-6-formaldehyde (1-11)

Compound 1-10 (11.20 g, 20.27 mmol) was dissolved in 120 mL of methylene chloride, PCC (6.55 g, 30.40 mmol) and 200-300 mesh silica gel (15.00 g) were added at room temperature. After the addition was completed, the mixture was stirred at room temperature for 4 hours. TLC monitored (UV color) that the reaction was completed, then the reaction mixture was concentrated and the crude product was isolated and purified by silica gel column chromatography (petroleum ether/ethylacetate 10/1, v/v) to give 9.00 g white solid 1-11 in 81% yield.

$^1$H NMR (400 MHz, Chloroform-d) δ 9.86 (s, 1H), 7.88 (d, J=7.7 Hz, 1H), 7.50 (s, 1H), 7.41 (d, J=7.8 Hz, 1H), 7.38-7.27 (m, 10H), 7.13 (t, J=7.2 Hz, 1H), 7.07 (t, J=7.3 Hz, 2H), 6.77 (d, J=7.3 Hz, 2H), 5.24 (s, 2H), 4.97 (d, J=11.1 Hz, 3H), 4.73 (d, J=10.9 Hz, 1H), 4.65 (d, J=11.4 Hz, 1H), 4.25 (d, J=11.2 Hz, 1H), 4.15 (t, J=9.3 Hz, 1H), 4.11-4.01 (m, 1H), 3.92 (d, J=9.5 Hz, 1H), 3.36 (t, J=9.3 Hz, 1H), 1.26 (d, J=6.2 Hz, 3H).

LRMS (ESI, m/z): 573 [M+Na]$^+$.

(1S,3'R,4'S,5'S,6'R)-6'-methyl-6-(4-methylbenzyl)-3',4',5',6'-tetrahydro-3H-spiro[isobenzofuran-1,2'-pyran]-3',4',5'-triol (A1)

Parabromotoluene (1.00 g, 5.85 mmol) was dissolved in 30 mL anhydrous tetrahydrofuran and n-butyllithium (2.4 M in hexane) (2.44 mL, 5.85 mmol) was added dropwise at −78° C. under nitrogen. After the addition was completed and the mixture was stirred at −78° C. for 1 hours, a solution of compound 1-11 (321.95 mg, 0.58 mmol) in anhydrous tetrahydrofuran was added and the mixture was stirred for 2 hours at −78° C. TLC monitored (UV color) that the reaction was completed, then the reaction was transferred to room temperature, and an appropriate amount of water was added. Extracted with ethylacetate after the reaction was warmed to room temperature, and the combined organic layers were washed twice with saturated sodium chloride solution and dried over anhydrous sodium sulfate. After concentration, the crude product was isolated and purified by silica gel column chromatography (petroleum ether/ethylacetate 4/1, v/v) to give 338.45 mg colorless oil 1-12a, yield 90%.

Compound 1-12a (338.00 mg, 0.53 mmol) was dissolved in 30 mL of dichloromethane, Et$_3$SiH (0.42 mL, 2.63 mmol) and BF$_3$.OEt$_2$ (0.071 mL, 0.58 mmol) were added at −40° C. under nitrogen atmosphere. After addition, the mixture was stirred at −40° C. for 1 hour. TLC monitored (UV color) that the reaction was completed, then the reaction was transferred to room temperature, and an appropriate amount of water was added. Extracted with dichloromethane after the reaction was warmed to room temperature, and the combined organic layers were washed twice with saturated sodium chloride solution and dried over anhydrous sodium sulfate. After concentration, the crude product was isolated and purified by silica gel column chromatography (petroleum ether/ethylacetate 10/1, v/v) to give 310.00 mg colorless oil 1-13a, yield 94%.

$^1$H NMR (400 MHz, Chloroform-d) δ 7.36-7.27 (m, 10H), 7.25-7.09 (m, 6H), 6.99 (s, 4H), 6.76-6.70 (m, 2H), 5.18 (q, J=12.5 Hz, 2H), 4.99-4.83 (m, 3H), 4.72 (d, J=11.0 Hz, 1H), 4.46 (d, J=10.7 Hz, 1H), 4.14-4.03 (m, 2H), 3.98 (d, J=12.8 Hz, 3H), 3.83 (d, J=9.6 Hz, 1H), 3.32 (t, J=9.4 Hz, 1H), 2.27 (s, 3H), 1.28 (d, J=6.3 Hz, 3H).

Compound 1-13a (310.00 g, 0.49 mmol) and pentamethylbenzene (733.21 mg, 4.95 mmol) were dissolved in 30 mL of dichloromethane and boron trichloride (1.0 M toluene solution) (4.95 mL, 4.95 mmol) was added at −78° C. under nitrogen. Stirred at −78° C. overnight after the addition was completed. TLC monitored (UV color) that the reaction was completed, then 15 mL of methanol was added and the reaction was transferred to room temperature. After that, the residue was concentrated and the crude product was isolated and purified by silica gel column chromatography (methylene chloride/methanol 20/1, v/v) to obtain 100.00 mg white solid A1 in 57% yield.

$^1$H NMR (400 MHz, Methanol-d$_4$) δ 7.24-7.18 (m, 2H), 7.16-7.12 (m, 1H), 7.12-7.05 (m, 4H), 5.15-5.04 (m, 2H), 3.96 (s, 2H), 3.91-3.81 (m, 1H), 3.77-3.66 (m, 2H), 3.18-3.10 (m, 1H), 2.29 (s, 3H), 1.20 (d, J=6.3 Hz, 3H).

LRMS (ESI, nm/z): 357 [M+H]$^+$.

Example 2 (1S,3'R,4'S,5'S,6'R)-6-(4-ethylbenzyl)-6'-methyl-3',4',5',6'-tetrahydro-3H-spiro[isobenzofuran-1,2'-pyran]-3',4',5'-triol (A2)

The target compound A2 was synthesized according to the synthetic method of A1, wherein p-bromomethylbenzene was replaced by p-bromoethylbenzene.

$^1$H NMR (400 MHz, Methanol-d$_4$) δ 7.24-7.17 (m, 2H), 7.16 (s, 1H), 7.11 (d, J=1.8 Hz, 4H), 5.16-5.03 (m, 2H), 3.97 (s, 2H), 3.91-3.81 (m, 1H), 3.77-3.66 (m, 2H), 3.18-3.10 (m, 1H), 2.59 (q, J=7.6 Hz, 2H), 1.24-1.16 (m, 6H).

LRMS (ESI, m/z): 371 [M+H]$^+$.

Example 3 (1S,3'R,4'S,5'S,6'R)-6'-methyl-6-(4-n-propylbenzyl)-3',4',5',6'-tetrahydro-3H-spiro[isobenzofuran-1,2'-pyran]-3',4',5'-triol (A3)

The target compound A3 was synthesized according to the synthetic method of A1, wherein p-bromomethylbenzene was replaced by 1-bromo-4-propylbenzene.

$^1$H NMR (400 MHz, Methanol-d$_4$) δ 7.25-7.18 (m, 2H), 7.17 (s, 1H), 7.10 (q, J=8.2 Hz, 4H), 5.14-5.05 (m, 2H), 3.97 (s, 2H), 3.92-3.80 (m, 1H), 3.77-3.67 (m, 2H), 3.19-3.10 (m, 1H), 2.60-2.48 (m, 2H), 1.69-1.54 (m, 2H), 1.20 (d, J=6.3 Hz, 3H), 0.92 (t, J=7.4 Hz, 3H).

LRMS (ESI, m/z): 385 [M+H]$^+$.

Example 4 (1S,3'R,4'S,5'S,6'R)-6-(4-isopropylbenzyl)-6'-methyl-3',4',5',6'-tetrahydro-3H-spiro[isobenzofuran-1,2'-pyran]-3',4',5'-triol (A4)

The target compound A4 was synthesized according to the synthetic method of A1, wherein p-bromomethylbenzene was replaced by 1-bromo-4-isopropylbenzene.

$^1$H NMR (400 MHz, Methanol-$d_4$) δ 7.25-7.18 (m, 2H), 7.17 (s, 1H), 7.13 (s, 4H), 5.14-5.05 (m, 2H), 3.97 (s, 2H), 3.91-3.82 (m, 1H), 3.78-3.67 (m, 2H), 3.18-3.10 (m, 1H), 2.91-2.80 (m, 1H), 1.24-1.18 (m, 9H).

LRMS (ESI, m/z): 385 [M+H]$^+$.

Example 5 (1S,3'R,4'S,5'S,6'R)-6-(4-methoxybenzyl)-6'-methyl-3',4',5',6'-tetrahydro-3H-spiro[isobenzofuran-1,2'-pyran]-3',4',5'-triol (A5)

The target compound A5 was synthesized according to the synthetic method of A1, wherein p-bromomethylbenzene was replaced by 1-bromo-4-methoxybenzene.

$^1$H NMR (400 MHz, Methanol-$d_4$) δ 7.24-7.18 (m, 2H), 7.16-7.09 (m, 3H), 6.86-6.79 (m, 2H), 5.14-5.05 (m, 2H), 3.95 (s, 2H), 3.91-3.82 (m, 1H), 3.75 (s, 3H), 3.74-3.68 (m, 2H), 3.18-3.10 (m, 1H), 1.20 (d, J=6.3 Hz, 3H).

LRMS (ESI, nm/z): 373 [M+H]$^+$.

Example 6 (1S,3'R,4'S,5'S,6'R)-6-(4-ethoxybenzyl)-6'-methyl-3',4',5',6'-tetrahydro-3H-spiro[isobenzofuran-1,2'-pyran]-3',4',5'-triol (A6)

The target compound A6 was synthesized according to the synthetic method of A1, wherein p-bromomethylbenzene was replaced by 1-bromo-4-ethoxybenzene.

$^1$H NMR (400 MHz, Methanol-$d_4$) δ 7.25-7.17 (m, 2H), 7.17-7.07 (m, 3H), 6.85-6.78 (m, 2H), 5.16-5.04 (m, 2H), 3.99 (q, J=7.0 Hz, 2H), 3.94 (s, 2H), 3.91-3.81 (m, 1H), 3.77-3.66 (m, 2H), 3.14 (t, J=8.9 Hz, 1H), 1.36 (t, J=7.0 Hz, 3H), 1.20 (d, J=6.3 Hz, 3H).

LRMS (ESI, nm/z): 387 [M+H]$^+$.

Example 7 (1S,3'R,4'S,5'S,6'R)-6'-methyl-6-((5-meththiophene-2-yl)methyl)-3',4',5',6'-tetrahydro-3H-spiro[isobenzofuran-1,2'-pyran]-3',4',5'-triol (A7)

The target compound A7 was synthesized according to the synthetic method of A1, wherein p-bromomethylbenzene was replaced by 2-methylthiophene.

$^1$H NMR (400 MHz, Methanol-$d_4$) δ 7.27 (dd, J=7.8, 1.3 Hz, 1H), 7.24-7.18 (m, 2H), 6.60 (d, J=3.3 Hz, 1H), 6.57-6.54 (m, 1H), 5.16-5.05 (m, 2H), 4.10 (s, 2H), 3.92-3.82 (m, 1H), 3.78-3.67 (m, 2H), 3.19-3.11 (m, 1H), 2.43-2.35 (m, 3H), 1.21 (d, J=6.3 Hz, 3H).

LRMS (ESI, nm/z): 363 [M+H]$^+$.

Example 8 (1S,3'R,4'S,5'S,6'R)-6-((5-ethylthiophene-2-yl)methyl)-6'-methyl-3',4',5',6'-tetrahydro-3H-spiro[isobenzofuran-1,2'-pyran]-3',4',5'-triol (A8)

The target compound A8 was synthesized according to the synthetic method of A1, wherein p-bromomethylbenzene was replaced by 2-ethylthiophene.

$^1$H NMR (500 MHz, Methanol-$d_4$) δ 7.29-7.25 (m, 1H), 7.22 (d, J=8.5 Hz, 2H), 6.62 (d, J=3.3 Hz, 1H), 6.58 (d, J=3.4 Hz, 1H), 5.17-5.04 (m, 2H), 4.11 (s, 2H), 3.95-3.82 (m, 1H), 3.81-3.63 (m, 2H), 3.26-3.08 (m, 1H), 2.75 (q, J=7.5 Hz, 2H), 1.32-1.15 (m, 6H).

LRMS (ESI, m/z): 377 [M+H]$^+$.

Example 9 (1S,3'R,4'S,5'S,6'R)-6'-methyl-6-((5-(n-propyl)thiophene-2-yl)methyl)-3',4',5',6'-tetrahydro-3H-spiro[isobenzofuran-1,2'-pyran]-3',4',5'-triol (A9)

The target compound A9 was synthesized according to the synthetic method of A1, wherein p-bromomethylbenzene was replaced by 2-(n-propyl)thiophene.

$^1$H NMR (400 MHz, Methanol-$d_4$) δ 7.25 (dd, J=20.4, 9.3 Hz, 3H), 6.62 (d, J=3.2 Hz, 1H), 6.58 (d, J=3.1 Hz, 1H), 5.21-5.03 (m, 2H), 4.12 (s, 2H), 3.96-3.82 (m, 1H), 3.81-3.65 (m, 2H), 3.15 (t, J=9.0 Hz, 1H), 2.70 (t, J=7.4 Hz, 2H), 1.70-1.56 (m, 2H), 1.21 (d, J=6.3 Hz, 3H), 0.94 (t, J=7.3 Hz, 3H).

LRMS (ESI, m/z): 391 [M+H]$^+$.

Example 10 (1S,3'R,4'S,5'S,6'R)-6-((5-chlorothiophene-2-yl)methyl)-6'-methyl-3',4',5',6'-tetrahydro-3H-spiro[isobenzofuran-1,2'-pyran]-3',4',5'-triol (A10)

The target compound A10 was synthesized according to the synthetic method of A1, wherein p-bromomethylbenzene was replaced by 2-chlorothiophene.

$^1$H NMR (400 MHz, Methanol-$d_4$) δ 7.33-7.18 (m, 3H), 6.77 (d, J=3.7 Hz, 1H), 6.68 (d, J=3.7 Hz, 1H), 5.18-5.05 (m, 2H), 4.13 (s, 2H), 3.93-3.82 (m, 1H), 3.80-3.66 (m, 2H), 3.21-3.10 (m, 1H), 1.21 (d, J=6.3 Hz, 3H).

LRMS (ESI, m/z): 383 [M+H]$^+$.

Example 11 (1S,3'R,4'S,5'S,6'R)-6-((5-(4-fluorophenyl) thiophene-2-yl) methyl)-6'-methyl-3',4',5',6'-tetrahydro-3H-spiro[isobenzofuran-1,2'-pyran]-3',4',5'-triol (A11)

The target compound A11 was synthesized according to the synthetic method of A1, wherein p-bromomethylbenzene was replaced by 2-(4-fluorophenyl)thiophene.

$^1$H NMR (400 MHz, Methanol-$d_4$) δ 7.54 (dd, J=8.7, 5.3 Hz, 2H), 7.32 (d, J=8.1 Hz, 1H), 7.25 (d, J=7.8 Hz, 2H), 7.13 (d, J=3.5 Hz, 1H), 7.07 (t, J=8.7 Hz, 2H), 6.82 (d, J=3.5 Hz, 1H), 5.17-5.06 (m, 2H), 4.19 (s, 2H), 3.96-3.83 (m, 1H), 3.82-3.65 (m, 2H), 3.16 (t, J=9.1 Hz, 1H), 1.21 (d, J=6.2 Hz, 3H).

$^{13}$C NMR (125 MHz, Methanol-$d_4$) δ 163.48 (d, J=243.6 Hz), 145.03, 142.95, 141.45, 140.50, 140.34, 132.43, 132.40, 130.88, 128.18 (d, J=8.0 Hz), 127.59, 124.03, 123.26, 122.06, 116.63 (d, J=21.9 Hz), 111.53, 77.38, 76.11, 75.26, 73.47, 71.48, 36.81, 18.20.

LRMS (ESI, m/z): 443 [M+H]$^+$.

Example 12 (1S,3'R,4'S,5'S,6'R)-6'-methyl-6-((5-phenylthiophene-2-yl)methyl)-3',4',5',6'-tetrahydro-3H-spiro[isobenzofuran-1,2'-pyran]-3',4',5'-triol (A12)

The target compound A12 was synthesized according to the synthetic method of A1, wherein p-bromomethylbenzene was replaced by 2-phenylthiophene.

$^1$H NMR (500 MHz, Methanol-$d_4$) δ 7.53 (d, J=7.5 Hz, 2H), 7.36-7.28 (m, 3H), 7.28-7.19 (m, 3H), 7.18 (d, J=3.6 Hz, 1H), 6.82 (d, J=3.5 Hz, 1H), 5.16-5.07 (m, 2H), 4.19 (s, 2H), 3.95-3.84 (m, 1H), 3.78 (d, J=9.6 Hz, 1H), 3.72 (t, J=9.2 Hz, 1H), 3.17 (t, J=9.2 Hz, 1H), 1.22 (d, J=6.2 Hz, 3H).
LRMS (ESI, m/z): 425 [M+H]$^+$.

Example 13 (1S,3'R,4'S,5'S,6'R)-6'-methyl-6-((5-(pyridin-2-yl) thiophene-2-yl) methyl)-3',4',5',6'-tetrahydro-3H-spiro [isobenzofuran-1,2'-pyran]-3',4',5'-triol (A13)

The target compound A13 was synthesized according to the synthetic method of A1, wherein p-bromomethylbenzene was replaced by 2-(2-thiophene)pyridine.
$^1$H NMR (400 MHz, Methanol-d$_4$) δ 8.65-8.58 (m, 1H), 8.45 (td, J=8.3, 1.5 Hz, 1H), 8.19 (d, J=8.3 Hz, 1H), 7.89 (d, J=3.9 Hz, 1H), 7.82-7.74 (m, 1H), 7.41-7.34 (m, 1H), 7.30 (d, J=7.5 Hz, 2H), 7.16 (d, J=3.9 Hz, 1H), 5.13 (d, J=2.7 Hz, 2H), 4.35 (s, 2H), 3.93-3.83 (m, 1H), 3.79-3.68 (m, 2H), 3.19-3.11 (m, 1H), 1.21 (d, J=6.3 Hz, 3H).
LRMS (ESI, m/z): 426 [M+H]$^+$.

Example 14 (1S,3'R,4'S,5'S,6'R)-6'-methyl-6-(naphthalene-2-ylmethyl)-3',4',5',6'-tetrahydro-3H-spiro [isobenzofuran-1,2'-pyran]-3',4',5'-triol (A14)

The target compound A14 was synthesized according to the synthetic method of A1, wherein p-bromomethylbenzene was replaced by 2-bromonaphthalene.
$^1$H NMR (500 MHz, Methanol-d$_4$) δ 7.82-7.72 (m, 3H), 7.67 (s, 1H), 7.46-7.37 (m, 2H), 7.34 (dd, J=8.4, 1.6 Hz, 1H), 7.31-7.26 (m, 1H), 7.22 (d, J=8.6 Hz, 2H), 5.20-5.02 (m, 2H), 4.17 (s, 2H), 3.94-3.82 (m, 1H), 3.79-3.64 (m, 2H), 3.20-3.07 (m, 1H), 1.20 (d, J=6.2 Hz, 3H).
LRMS (ESI, m/z): 393 [M+H]$^+$.

Example 15 (1S,3'R,4'S,5'S,6'R)-6-(benzo [b] thiophene-2-ylmethyl) 6'-methyl-3',4',5',6'-tetrahydro-3H-spiro [isobenzofuran-1,2'-pyran]-3',4',5'-triol (A15)

The target compound A15 was synthesized according to the synthetic method of A1, wherein p-bromomethylbenzene was replaced by benzothiophene.
$^1$H NMR (400 MHz, Methanol-d$_4$) δ 7.73 (d, J=7.8 Hz, 1H), 7.67 (d, J=7.5 Hz, 1H), 7.36 (dd, J=7.7, 1.5 Hz, 1H), 7.32-7.19 (m, 4H), 7.09 (s, 1H), 5.19-5.06 (m, 2H), 4.29 (s, 2H), 3.87 (dd, J=9.6, 6.3 Hz, 1H), 3.80-3.64 (m, 2H), 3.20-3.09 (m, 1H), 1.21 (d, J=6.3 Hz, 3H).
LRMS (ESI, nm/z): 399 [M+H]$^+$.

Example 16 (1S,3'R,4'S,5'S,6'R)-6-(benzofuran-2-ylmethyl)-6'-methyl-3',4',5',6'-tetrahydro-3H-spiro [isobenzofuran-1,2'-pyran]-3',4',5'-triol (A16)

The target compound A16 was synthesized according to the synthetic method of A1, wherein p-bromomethylbenzene was replaced by 2,3-benzofuran.
$^1$H NMR (400 MHz, Methanol-d$_4$) δ 7.51-7.44 (m, 1H), 7.36 (d, J=7.4 Hz, 2H), 7.33-7.24 (m, 2H), 7.23-7.11 (m, 2H), 6.54-6.44 (m, 1H), 5.18-5.07 (m, 2H), 4.17 (s, 2H), 3.93-3.82 (m, 1H), 3.80-3.67 (m, 2H), 3.20-3.10 (m, 1H), 1.21 (d, J=6.3 Hz, 3H).
LRMS (ESI, m/z): 383 [M+H]$^+$.

Example 17 (1S,3'R,4'S,5'S,6'R)-6'-methyl-6-((5-(2-furyl)thiazolyl)-2-methyl)-3',4',5',6'-tetrahydro-3H-spiro[isobenzofuran-1,2'-pyran]-3',4',5'-triol (A17)

The target compound A17 was synthesized according to the synthetic method of A1, wherein p-bromomethylbenzene was replaced by 5-(furan-2-yl)thiazole.
$^1$H NMR (400 MHz, DMSO-d$_6$) δ 7.66 (dd, J=7.5, 1.4 Hz, 1H), 7.60 (s, 2H), 7.53 (s, 1H), 7.44-7.37 (m, 1H), 6.87 (dd, J=7.5, 1.5 Hz, 1H), 6.63 (t, J=7.5 Hz, 1H), 4.98 (d, J=5.0 Hz, 1H), 4.80 (d, J=5.0 Hz, 1H), 4.73-4.64 (m, 2H), 4.58 (dd, J=8.1, 1.0 Hz, 1H), 4.50 (d, J=5.0 Hz, 1H), 4.23 (dd, J=6.9, 5.0 Hz, 1H), 4.10 (dt, J=12.4, 1.2 Hz, 1H), 3.70 (p, J=6.9 Hz, 1H), 3.55 (td, J=7.0, 5.0 Hz, 1H), 3.31 (td, J=7.0, 5.0 Hz, 1H), 1.11 (d, J=6.8 Hz, 3H).
LRMS (ESI, m/z): 416 [M+H]$^+$.

Example 18 (1S,3'R,4'S,5'S,6'R)-6'-methyl-6-((5-(2-thienyl)thiazolyl)-2-methyl)-3',4',5',6'-tetrahydro-3H-spiro[isobenzofuran-1,2'-pyran]-3',4',5'-triol (A18)

The target compound A18 was synthesized according to the synthetic method of A1, wherein p-bromomethylbenzene was replaced by 5-(thiophene-2-yl)thiazole.
$^1$H NMR (400 MHz, DMSO-d$_6$) δ 7.72 (s, 1H), 7.64-7.55 (m, 2H), 7.51-7.37 (m, 3H), 7.03 (t, J=7.5 Hz, 1H), 4.98 (d, J=5.0 Hz, 1H), 4.80 (d, J=5.0 Hz, 1H), 4.73-4.65 (m, 2H), 4.58 (dd, J=8.1, 1.0 Hz, 1H), 4.50 (d, J=5.0 Hz, 1H), 4.23 (dd, J=7.0, 5.0 Hz, 1H), 4.12 (dt, J=12.4, 1.2 Hz, 1H), 3.70 (p, J=6.9 Hz, 1H), 3.55 (td, J=7.0, 5.0 Hz, 1H), 3.32 (td, J=7.0, 5.0 Hz, 1H), 1.11 (d, J=6.8 Hz, 3H).
LRMS (ESI, nm/z): 432 [M+H]$^+$.

Example 19 (1S,3'R,4'S,5'S,6'R)-6'-methyl-6-((5-(4-fluorophenyl)thiazolyl)-2-methyl)-3',4',5',6'-tetrahydro-3H-spiro[isobenzofuran-1,2'-pyran]-3',4',5'-triol (A19)

The target compound A19 was synthesized according to the synthetic method of A1, wherein p-bromomethylbenzene was replaced by 5-(4-fluorophenyl)thiazole.
$^1$H NMR (400 MHz, DMSO-d$_6$) δ 7.74-7.63 (m, 6H), 7.51 (dt, J=2.0, 1.1 Hz, 1H), 7.51-7.46 (m, 3H), 7.41 (dt, J=7.6, 1.0 Hz, 2H), 7.32-7.21 (m, 4H), 4.93 (d, J=5.0 Hz, 2H), 4.74 (dt, J=12.5, 1.2 Hz, 2H), 4.68 (dd, J=7.9, 1.0 Hz, 2H), 4.58 (dd, J=8.1, 1.0 Hz, 2H), 4.51 (dd, J=7.5, 5.0 Hz, 4H), 4.26 (dd, J=7.0, 5.0 Hz, 2H), 4.09 (dt, J=12.5, 1.2 Hz, 2H), 3.70 (p, J=6.9 Hz, 2H), 3.55 (td, J=7.0, 5.0 Hz, 2H), 3.31 (td, J=7.0, 5.0 Hz, 2H), 1.11 (d, J=6.7 Hz, 6H).
LRMS (ESI, m/z): 444 [M+H]$^+$.

Example 20

(1S,3'R,4'S,5'S,6'R)-6'-methyl-6-((5-phenylthiazolyl)-2-methyl)-3',4',5',6'-tetrahydro-3H-spiro [isobenzofuran-1,2'-pyran]-3',4',5'-triol (A20)

The target compound A20 was synthesized according to the synthetic method of A1, wherein p-bromomethylbenzene was replaced by 5-phenylthiazole.
$^1$H NMR (400 MHz, DMSO-d$_6$) δ 7.93-7.84 (m, 2H), 7.67 (p, J=0.9 Hz, 1H), 7.58-7.53 (m, 1H), 7.53-7.36 (m, 5H), 4.98 (d, J=5.0 Hz, 1H), 4.79 (d, J=5.0 Hz, 1H), 4.76-4.64 (m, 2H), 4.58 (dd, J=8.1, 1.0 Hz, 1H), 4.50 (d, J=5.0 Hz, 1H), 4.24 (dd, J=7.0, 5.0 Hz, 1H), 4.09 (dt, J=12.5, 1.0 Hz, 1H), 3.70 (p, J=6.9 Hz, 1H), 3.55 (td. J=7.0, 5.0 Hz, 1H), 3.32 (td, J=7.0, 5.0 Hz, 1H), 1.11 (d, J=6.8 Hz, 3H).
LRMS (ESI, m/z): 426 [M+H]$^+$.

Example 21 (1S,3'R,4'S,5'S,6'R)-6'-methyl-6-(4-methylbenzyl)-5-chloro-3',4',5',6'-tetrahydro-3H-spiro[isobenzofuran-1,2'-pyran]-3',4',5'-triol (A21)

The target compound A21 was synthesized according to the synthetic method of A1, wherein 2-bromo-1,4-bis(((2- methoxy-propan-2-yl)oxy)methyl)benzene (1-9) was replaced by 1-bromo-4-chloro-2,5-bis(((2-methoxypropane-2-yl)oxy)methyl)benzene.

$^1$H NMR (400 MHz, DMSO-d$_6$) δ 7.67 (d, J=1.2 Hz, 1H), 7.47 (d, J=1.2 Hz, 1H), 7.37-7.28 (m, 2H), 7.13 (dq, J=7.4, 1.2 Hz, 2H), 4.96 (d, J=5.0 Hz, 1H), 4.78-4.64 (m, 2H), 4.58 (dd, J=8.1, 1.0 Hz, 1H), 4.50 (d, J=5.0 Hz, 1H), 4.32-4.23 (m, 1H), 4.12 (dd, J=6.9, 5.0 Hz, 1H), 3.76-3.64 (m, 2H), 3.51 (td, J=7.0, 5.0 Hz, 1H), 3.28 (td, J=7.0, 5.0 Hz, 1H), 2.21 (d, J=1.2 Hz, 3H), 1.09 (d, J=6.7 Hz, 3H).

LRMS (ESI, m/z): 391 [M+H]$^+$.

Example 22 (1S,3'R,4'S,5'S,6'R)-6'-methyl-6-(4-ethylbenzyl)-5-chloro-3',4',5',6'-tetrahydro-3H-spiro[isobenzofuran-1,2'-pyran]-3',4',5'-triol (A22)

The target compound A22 was synthesized according to the synthetic method of A1, wherein 2-bromo-1,4-bis(((2-methoxy-propan-2-yl)oxy)methyl)benzene (1-9) and p-bromomethylbenzene were replaced by 1-bromo-4-chloro-2,5-bis (((2-methoxypropane-2-yl)oxy)methyl)benzene and p-bromoethylbenzene.

$^1$H NMR (400 MHz, DMSO-d$_6$) δ 7.67 (s, 1H), 7.47 (d, J=1.3 Hz, 1H), 7.40-7.31 (m, 2H), 7.15 (dt, J=7.4, 1.1 Hz, 2H), 4.96 (d, J=5.0 Hz, 1H), 4.78-4.64 (m, 2H), 4.58 (dd, J=8.1, 1.0 Hz, 1H), 4.50 (d, J=5.0 Hz, 1H), 4.28 (dq, J=12.5, 1.1 Hz, 1H), 4.12 (dd, J=7.0, 5.0 Hz, 1H), 3.76-3.64 (m, 2H), 3.51 (td, J=7.0, 5.0 Hz, 1H), 3.28 (td, J=7.0, 5.0 Hz, 1H), 2.69-2.56 (m, 2H), 1.19 (t, J=8.0 Hz, 3H), 1.09 (d, J=6.7 Hz, 3H).

LRMS (ESI, m/z): 405 [M+H]$^+$.

Example 23 (1S,3'R,4'S,5'S,6'R)-6'-methyl-6-(4-propylbenzyl)-5-chloro-3',4',5',6'-tetrahydro-3H-spiro[isobenzofuran-1,2'-pyran]-3',4',5'-triol (A23)

The target compound A23 was synthesized according to the synthetic method of A1, wherein 2-bromo-1,4-bis(((2-methoxy-propan-2-yl)oxy)methyl)benzene (1-9) and p-bromomethylbenzene were replaced by 1-bromo-4-chloro-2,5-bis (((2-methoxypropane-2-yl)oxy)methyl)benzene and 1-bromo-4-propylbenzene.

$^1$H NMR (400 MHz, DMSO-d$_6$) δ 7.68 (s, 1H), 7.39-7.31 (m, 2H), 7.17-7.10 (m, 2H), 4.91 (d, J=5.0 Hz, 1H), 4.68 (dd, J=7.9, 1.0 Hz, 1H), 4.58 (dd, J=8.1, 1.0 Hz, 1H), 4.53-4.34 (m, 3H), 4.11 (dd, J=7.0, 5.0 Hz, 1H), 3.70 (p, J=6.9 Hz, 1H), 3.61-3.47 (m, 2H), 3.27 (td, J=7.0, 5.0 Hz, 1H), 2.67-2.52 (m, 2H), 1.61-1.44 (m, 2H), 1.11 (d, J=6.8 Hz, 3H), 0.94 (t, J=8.0 Hz, 3H).

LRMS (ESI, m/z): 419 [M+H]$^+$.

Example 24 (1S,3'R,4'S,5'S,6'R)-6'-methyl-6-(4-isopropylbenzyl)-5-chloro-3-3',4',5',6'-tetrahydro-3H-spiro[isobenzofuran-1,2'-pyran]-3',4',5'-triol (A24)

The target compound A24 was synthesized according to the synthetic method of A1, wherein 2-bromo-1,4-bis(((2-methoxy-propan-2-yl)oxy)methyl)benzene (1-9) and p-bromomethylbenzene were replaced by 1-bromo-4-chloro-2,5-bis (((2-methoxypropane-2-yl)oxy)methyl)benzene and 1-bromo-4-isopropylbenzene.

$^1$H NMR (400 MHz, DMSO-d$_6$) δ 7.68 (d, J=1.1 Hz, 1H), 7.55 (d, J=1.1 Hz, 1H), 7.42-7.34 (m, 2H), 7.24-7.16 (m, 2H), 4.96 (d, J=5.0 Hz, 1H), 4.75 (d, J=5.0 Hz, 1H), 4.68 (dd, J=7.9, 1.0 Hz, 1H), 4.58 (dd, J=8.1, 1.0 Hz, 1H), 4.50 (d, J=5.0 Hz, 1H), 4.39-4.31 (m, 1H), 4.15 (dd, J=6.9, 5.0 Hz, 1H), 3.70 (p, J=6.9 Hz, 1H), 3.60-3.47 (m, 2H), 3.30 (td, J=7.0, 5.0 Hz, 1H), 2.94-2.78 (m, 1H), 1.20 (dd, J=19.9, 6.8 Hz, 6H), 1.10 (d, J=6.9 Hz, 3H).

LRMS (ESI, m/z): 419 [M+H]$^+$.

Example 25 (1S,3'R,4'S,5'S,6'R)-6'-methyl-6-(4-methoxybenzyl)-5-chloro-3',4',5',6'-tetrahydro-3H-spiro[isobenzofuran-1,2'-pyran]-3',4',5'-triol (A25)

The target compound A25 was synthesized according to the synthetic method of A1, wherein 2-bromo-1,4-bis(((2-methoxy-propan-2-yl)oxy)methyl)benzene (1-9) and p-bromomethylbenzene were replaced by 1-bromo-4-chloro-2,5-bis (((2-methoxypropane-2-yl)oxy)methyl)benzene and 1-bromo-4-methoxybenzene.

$^1$H NMR (400 MHz, DMSO-d$_6$) δ 7.67 (s, 1H), 7.59 (t, J=1.1 Hz, 1H), 7.09 (dt, J=7.5, 1.1 Hz, 2H), 6.90-6.82 (m, 2H), 4.91 (d, J=5.0 Hz, 1H), 4.68 (dd, J=7.9, 1.0 Hz, 1H), 4.58 (dd, J=8.1, 1.0 Hz, 1H), 4.49 (dd, J=10.3, 5.0 Hz, 2H), 4.32-4.23 (m, 1H), 4.15 (dd, J=6.9, 5.0 Hz, 1H), 3.79 (s, 3H), 3.70 (p, J=6.9 Hz, 1H), 3.64-3.57 (m, 1H), 3.54 (td, J=7.0, 5.0 Hz, 1H), 3.29 (td, J=7.0, 5.0 Hz, 1H), 1.12 (d, J=6.7 Hz, 3H).

LRMS (ESI, nm/z): 407 [M+H]$^+$.

Example 26 (1S,3'R,4'S,5'S,6'R)-6'-methyl-6-(4-ethoxybenzyl)-5-chloro-3',4',5',6'-tetrahydro-3H-spiro[isobenzofuran-1,2'-pyran]-3',4',5'-triol (A26)

The target compound A26 was synthesized according to the synthetic method of A1, wherein 2-bromo-1,4-bis(((2-methoxy-propan-2-yl)oxy)methyl)benzene (1-9) and p-bromomethylbenzene were replaced by 1-bromo-4-chloro-2,5-bis (((2-methoxypropane-2-yl)oxy)methyl)benzene and 1-bromo-4-ethoxybenzene.

$^1$H NMR (400 MHz, DMSO-d$_6$) δ 7.66 (s, 1H), 7.59 (d, J=1.0 Hz, 1H), 7.13-7.05 (m, 2H), 6.89-6.81 (m, 2H), 4.97 (d, J=5.0 Hz, 1H), 4.78 (d, J=5.0 Hz, 1H), 4.68 (dd, J=7.9, 1.0 Hz, 1H), 4.58 (dd, J=8.1, 1.0 Hz, 1H), 4.50 (d, J=5.0 Hz, 1H), 4.25-4.08 (m, 4H), 3.76-3.58 (m, 2H), 3.54 (td, J=7.0, 5.0 Hz, 1H), 3.31 (td, J=7.0, 5.0 Hz, 1H), 1.34 (t, J=8.0 Hz, 3H), 1.11 (d, J=6.7 Hz, 3H).

LRMS (ESI, m/z): 421 [M+H]$^+$.

Example 27 (1S,3'R,4'S,5'S,6'R)-6'-methyl-6-((5-methylthienyl)-2-methyl)-5-chloro-3',4',5',6'-tetrahydro-3H-spiro[isobenzofuran-1,2'-pyran]-3',4',5'-triol (A27)

The target compound A27 was synthesized according to the synthetic method of A1, wherein 2-bromo-1,4-bis(((2-methoxy-propan-2-yl)oxy)methyl)benzene (1-9) and p-bromomethylbenzene were replaced by 1-bromo-4-chloro-2,5-bis (((2-methoxypropane-2-yl)oxy)methyl)benzene and 2-methylthiophene.

$^1$H NMR (400 MHz, DMSO-d$_6$) δ 7.60 (s, 1H), 7.55 (d, J=1.1 Hz, 1H), 6.52 (s, 2H), 4.98 (d, J=5.0 Hz, 1H), 4.79 (d, J=5.0 Hz, 1H), 4.68 (dd, J=7.9, 1.0 Hz, 1H), 4.65-4.54 (m, 2H), 4.50 (d, J=5.0 Hz, 1H), 4.22 (dd, J=6.9, 5.0 Hz, 1H), 3.82 (dd, J=12.5, 1.0 Hz, 1H), 3.70 (p. J=6.9 Hz, 1H), 3.54 (td, J=6.9, 5.0 Hz, 1H), 3.31 (td, J=7.0, 5.0 Hz, 1H), 2.37 (s, 3H), 1.11 (d, J=6.9 Hz, 3H).

LRMS (ESI, m/z): 397 [M+H]$^+$.

Example 28 (1S,3'R,4'S,5'S,6'R)-6'-methyl-6-((5-ethylthienyl)-2-methyl)-5-chloro-3',4',5',6'-tetrahydro-3H-spiro[isobenzofuran-1,2'-pyran]-3',4',5'-triol (A28)

The target compound A28 was synthesized according to the synthetic method of A1, wherein 2-bromo-1,4-bis(((2-methoxy-propan-2-yl)oxy)methyl)benzene (1-9) and p-bromomethylbenzene were replaced by 1-bromo-4-chloro-2,5-bis (((2-methoxypropane-2-yl)oxy)methyl)benzene and 2-ethylthiophene.

$^1$H NMR (400 MHz, DMSO-$d_6$) δ 7.61 (d, J=1.1 Hz, 1H), 6.80 (dd, J=7.5, 0.9 Hz, 1H), 6.73 (d, J=7.5 Hz, 1H), 4.98 (d, J=5.0 Hz, 1H), 4.79 (d, J=5.0 Hz, 1H), 4.68 (dd, J=7.9, 1.0 Hz, 1H), 4.62-4.52 (m, 2H), 4.50 (d, J=5.0 Hz, 1H), 4.21 (dd, J=7.0, 5.1 Hz, 1H), 3.84 (dd, J=12.5, 1.0 Hz, 1H), 3.70 (p, J=6.9 Hz, 1H), 3.54 (td, J=7.0, 5.0 Hz, 1H), 3.31 (td, J=7.0, 5.0 Hz, 1H), 2.96 (dq, J=12.3, 8.0 Hz, 1H), 2.82 (dq, J=12.3, 8.0 Hz, 1H), 1.30 (t, J=8.0 Hz, 3H), 1.11 (d, J=6.9 Hz, 3H).

LRMS (ESI, m/z): 411 [M+H]$^+$.

Example 29 (1S,3'R,4'S,5'S,6'R)-6'-methyl-6-((5-propylthienyl)-2-methyl)-5-chloro-3',4',5',6'-tetrahydro-3H-spiro[isobenzofuran-1,2'-pyran]-3',4',5'-triol (A29)

The target compound A29 was synthesized according to the synthetic method of A1, wherein 2-bromo-1,4-bis(((2-methoxy-propan-2-yl)oxy)methyl)benzene (1-9) and p-bromomethylbenzene were replaced by 1-bromo-4-chloro-2,5-bis (((2-methoxypropane-2-yl)oxy)methyl)benzene and 2-propylthiophene.

$^1$H NMR (400 MHz, DMSO-$d_6$) δ 7.58 (dt, J=21.1, 1.0 Hz, 2H), 6.86 (d, J=7.5 Hz, 1H), 6.73 (d, J=7.5 Hz, 1H), 4.85 (d, J=5.0 Hz, 1H), 4.72-4.54 (m, 4H), 4.50 (d, J=5.0 Hz, 1H), 4.22 (dd, J=6.9, 5.0 Hz, 1H), 3.87-3.79 (m, 1H), 3.70 (p, J=6.9 Hz, 1H), 3.54 (td, J=6.9, 5.0 Hz, 1H), 3.31 (td, J=7.0, 5.0 Hz, 1H), 2.93 (td, J=12.7, 3.0 Hz, 1H), 2.81 (td, J=12.5, 2.8 Hz, 1H), 1.90 (ddtd, J=20.6, 12.6, 8.0, 2.9 Hz, 1H), 1.81-1.63 (m, 1H), 1.11 (d, J=6.8 Hz, 3H), 0.96 (t, J=8.0 Hz, 3H).

LRMS (ESI, nm/z): 424 [M+H]$^+$.

Example 30 (1S,3'R,4'S,5'S,6'R)-6'-methyl-6-((5-chlorothienyl)-2-methyl)-5-chloro-3',4':5',6'-tetrahydro-3H-spiro[isobenzofuran-1,2'-pyran]-3',4',5'-triol (A30)

The target compound A30 was synthesized according to the synthetic method of A1, wherein 2-bromo-1,4-bis(((2-methoxy-propan-2-yl)oxy)methyl)benzene (1-9) and p-bromomethylbenzene were replaced by 1-bromo-4-chloro-2,5-bis (((2-methoxypropane-2-yl)oxy)methyl)benzene and 2-chlorothiophene.

$^1$H NMR (400 MHz, DMSO-$d_6$) δ 7.64-7.55 (m, 2H), 6.99-6.92 (m, 1H), 6.75 (d, J=7.5 Hz, 1H), 4.93 (d, J=5.0 Hz, 1H), 4.72-4.54 (m, 3H), 4.50 (dd, J=5.0, 3.5 Hz, 2H), 4.22 (dd, J=7.0, 5.0 Hz, 1H), 3.86 (dd, J=12.5, 1.0 Hz, 1H), 3.70 (p, J=6.9 Hz, 1H), 3.55 (td. J=6.9, 5.0 Hz, 1H), 3.30 (td, J=7.0, 5.0 Hz, 1H), 1.11 (d, J=6.7 Hz, 3H).

LRMS (ESI, m/z): 417 [M+H]$^+$.

Example 31 (1S,3'R,4'S,5'S,6'R)-6'-methyl-6-((5-(4-fluorophenyl)thienyl-2-methyl)-5-chloro-3',4',5',6'-tetrahydro-3H-spiro[isobenzofuran-1,2'-pyran]-3',4',5'-triol (A31)

The target compound A31 was synthesized according to the synthetic method of A1, wherein 2-bromo-1,4-bis(((2-methoxy-propan-2-yl)oxy)methyl)benzene (1-9) and p-bromomethylbenzene were replaced by 1-bromo-4-chloro-2,5-bis (((2-methoxypropane-2-yl)oxy)methyl)benzene and 2-(4-fluorophenyl)thiophene.

$^1$H NMR (400 MHz, DMSO-$d_6$) δ 7.73-7.62 (m, 4H), 7.34-7.21 (m, 3H), 7.12 (dd, J=7.5, 1.2 Hz, 1H), 4.93 (d, J=5.0 Hz, 1H), 4.76-4.64 (m, 2H), 4.58 (dd, J=8.1, 1.0 Hz, 1H), 4.51 (dd, J=8.9, 5.0 Hz, 2H), 4.25 (dd, J=6.9, 5.0 Hz, 1H), 3.99 (dd, J=12.3, 1.0 Hz, 1H), 3.70 (p, J=6.9 Hz, 1H), 3.57 (td, J=7.0, 5.0 Hz, 1H), 3.32 (td, J=7.0, 5.0 Hz, 1H), 1.12 (d, J=6.7 Hz, 3H).

LRMS (ESI, m/z): 477 [M+H]$^+$.

Example 32 (1S,3'R,4'S,5'S,6'R)-6'-methyl-6-((5-phenylthienyl)-2-methyl)-5-chloro-3',4',5',6'-tetrahydro-3H-spiro[isobenzofuran-1,2'-pyran]-3',4',5'-triol (A32)

The target compound A32 was synthesized according to the synthetic method of A1, wherein 2-bromo-1,4-bis(((2-methoxy-propan-2-yl)oxy)methyl)benzene (1-9) and p-bromomethylbenzene were replaced by 1-bromo-4-chloro-2,5-bis (((2-methoxypropane-2-yl)oxy)methyl)benzene and 2-phenylthiophene.

$^1$H NMR (400 MHz, DMSO-$d_6$) δ 7.87-7.77 (m, 2H), 7.67 (dt, J=18.1, 1.0 Hz, 2H), 7.48 (pd, J=3.9, 2.0 Hz, 3H), 7.35 (d, J=7.4 Hz, 1H), 7.15 (dd, J=7.5, 1.0 Hz, 1H), 4.98 (d, J=5.0 Hz, 1H), 4.80 (d, J=5.0 Hz, 1H), 4.77-4.64 (m, 2H), 4.58 (dd, J=8.1, 1.0 Hz, 1H), 4.50 (d, J=5.0 Hz, 1H), 4.24 (dd, J=7.0, 5.0 Hz, 1H), 3.95 (dd, J=12.3, 1.0 Hz, 1H), 3.70 (p, J=6.9 Hz, 1H), 3.55 (td, J=7.0, 5.0 Hz, 1H), 3.32 (td, J=7.0, 5.0 Hz, 1H), 1.11 (d, J=6.7 Hz, 3H).

LRMS (ESI, m/z): 459 [M+H]$^+$.

Example 33 (1S,3'R,4'S,5'S,6'R)-6'-methyl-6-((5-(2-pyridyl)thienyl-2-methyl)-5-chloro-3',4',5',6'-tetrahydro-3H-spiro[isobenzofuran-1,2'-pyran]-3',4',5'-triol (A33)

The target compound A33 was synthesized according to the synthetic method of A1, wherein 2-bromo-1,4-bis(((2-methoxy-propan-2-yl)oxy)methyl)benzene (1-9) and p-bromomethylbenzene were replaced by 1-bromo-4-chloro-2,5-bis (((2-methoxypropane-2-yl)oxy)methyl)benzene and 2-(thiophene-2-yl)pyridine.

$^1$H NMR (400 MHz, DMSO-$d_6$) δ 8.47 (d, J=5.0 Hz, 1H), 7.86-7.76 (m, 2H), 7.74-7.61 (m, 3H), 7.39-7.32 (m, 1H), 7.17 (h, J=4.4 Hz, 1H), 4.93 (d, J=5.1 Hz, 1H), 4.76-4.64 (m, 2H), 4.58 (dd, J=8.1, 1.0 Hz, 1H), 4.51 (dd, J=7.6, 5.0 Hz, 2H), 4.26 (dd, J=7.0, 5.1 Hz, 1H), 3.98 (dt, J=12.2, 0.9 Hz, 1H), 3.70 (p, J=6.9 Hz, 1H), 3.55 (td, J=7.0, 5.0 Hz, 1H), 3.33 (td, J=7.0, 5.0 Hz, 1H), 1.13 (d, J=6.8 Hz, 3H).

LRMS (ESI, m/z): 460 [M+H]$^+$.

Example 34 (1S,3'R,4'S,5'S,6'R)-6'-methyl-6-(naphthyl-2-methyl)-5-chloro-3',4',5',6'-tetrahydro-3H-spiro[isobenzofuran-1,2'-pyran]-3',4',5'-triol (A34)

The target compound A34 was synthesized according to the synthetic method of A1, wherein 2-bromo-1,4-bis(((2-methoxy-propan-2-yl)oxy)methyl)benzene (1-9) and p-bromomethylbenzene were replaced by 1-bromo-4-chloro-2,5-bis (((2-methoxypropane-2-yl)oxy)methyl)benzene and 2-bromonaphthalene.

$^1$H NMR (400 MHz, DMSO-$d_6$) δ 7.99-7.87 (m, 2H), 7.87-7.79 (m, 2H), 7.76-7.66 (m, 2H), 7.63-7.47 (m, 3H), 4.96 (d, J=5.0 Hz, 1H), 4.76-4.64 (m, 2H), 4.58 (dd, J=8.1, 1.0 Hz, 1H), 4.53-4.45 (m, 2H), 4.15 (dd, J=7.0, 5.0 Hz, 1H), 3.76-3.64 (m, 2H), 3.51 (td, J=7.0, 5.0 Hz, 1H), 3.30 (td, J=7.0, 5.0 Hz, 1H), 1.11 (d, J=6.7 Hz, 3H).
LRMS (ESI, m/z): 427 [M+H]$^+$.

Example 35 (1S,3'R,4'S,5'S,6'R)-6'-methyl-6-(benzo[b]thiophene-2-methyl)-5-chloro-3',4',5',6'-tetrahydro-3H-spiro[isobenzofuran-1,2'-pyran]-3',4',5'-triol (A35)

The target compound A35 was synthesized according to the synthetic method of A1, wherein 2-bromo-1,4-bis(((2-methoxypropan-2-yl)oxy)methyl)benzene (1-9) and p-bromomethylbenzene were replaced by 1-bromo-4-chloro-2,5-bis (((2-methoxypropane-2-yl)oxy)methyl)benzene and benzothiophene.
$^1$H NMR (400 MHz, DMSO-d$_6$) δ 7.78 (dd, J=7.6, 1.5 Hz, 1H), 7.67 (dt, J=7.5, 1.6 Hz, 1H), 7.57-7.43 (m, 3H), 7.32 (td, J=7.5, 1.5 Hz, 1H), 7.22 (t, J=1.2 Hz, 1H), 4.97 (d, J=5.0 Hz, 1H), 4.78 (d, J=5.0 Hz, 1H), 4.68 (dd, J=7.9, 1.0 Hz, 1H), 4.62-4.47 (m, 3H), 4.20 (dd, J=7.0, 5.1 Hz, 1H), 4.02 (dd, J=12.4, 1.0 Hz, 1H), 3.70 (p, J=6.9 Hz, 1H), 3.53 (td, J=7.0, 5.0 Hz, 1H), 3.30 (td, J=7.0, 5.0 Hz, 1H), 1.10 (d, J=6.8 Hz, 3H).
LRMS (ESI, m/z): 433 [M+H]$^+$.

Example 36 (1S,3'R,4'S,5'S,6'R)-6'-methyl-6-(benzo[b]furan-2-methyl)-5-chloro-3',4',5',6'-tetrahydro-3H-spiro[iso benzofuran-1,2'-pyran]-3',4',5'-triol (A36)

The target compound A36 was synthesized according to the synthetic method of A1, wherein 2-bromo-1,4-bis(((2-methoxypropan-2-yl)oxy)methyl)benzene (1-9) and p-bromomethylbenzene were replaced by 1-bromo-4-chloro-2,5-bis (((2-methoxypropane-2-yl)oxy)methyl)benzene and 2,3-benzofuran.
$^1$H NMR (400 MHz, DMSO-d$_6$) δ 7.57-7.43 (m, 4H), 7.40 (td, J=7.5, 1.5 Hz, 1H), 7.19 (td, J=7.4, 1.6 Hz, 1H), 6.81-6.75 (m, 1H), 4.96 (d, J=5.0 Hz, 1H), 4.77 (d, J=5.0 Hz, 1H), 4.68 (dd, J=7.9, 1.0 Hz, 1H), 4.58 (dd, J=8.1, 1.0 Hz, 1H), 4.53-4.45 (m, 2H), 4.18 (dd, J=6.9, 5.0 Hz, 1H), 3.95-3.87 (m, 1H), 3.70 (p, J=6.9 Hz, 1H), 3.52 (td, J=7.0, 5.0 Hz, 1H), 3.29 (td, J=7.0, 5.0 Hz, 1H), 1.10 (d, J=6.7 Hz, 3H).
LRMS (ESI, m/z): 417 [M+H]$^+$.

Example 37 (1S,3'R,4'S,5'S,6'R)-6'-methyl-6-((5-(2-furyl)thiazolyl)-2-methyl)-5-chloro-3',4',5',6'-tetrahydro-3H-spiro[isobenzofuran-1,2'-pyran]-3',4',5'-triol (A37)

The target compound A37 was synthesized according to the synthetic method of A1, wherein 2-bromo-1,4-bis(((2-methoxypropan-2-yl)oxy)methyl)benzene (1-9) and p-bromomethylbenzene were replaced by 1-bromo-4-chloro-2,5-bis (((2-methoxypropane-2-yl)oxy)methyl)benzene and 5-(furan-2-yl)thiazole.
$^1$H NMR (400 MHz, DMSO-d$_6$) δ 7.73-7.63 (m, 2H), 7.61 (d, J=1.3 Hz, 1H), 7.53 (s, 1H), 6.85 (dd, J=7.6, 1.6 Hz, 1H), 6.62 (t, J=7.5 Hz, 1H), 5.04 (dd, J=12.4, 1.0 Hz, 1H), 4.92 (d, J=5.0 Hz, 1H), 4.68 (dd, J=7.9, 1.0 Hz, 1H), 4.58 (dd, J=8.1, 1.0 Hz, 1H), 4.51 (t, J=5.3 Hz, 2H), 4.27-4.13 (m, 2H), 3.70 (p, J=6.9 Hz, 1H), 3.56 (td, J=7.0, 5.0 Hz, 1H), 3.31 (td, J=7.0, 5.0 Hz, 1H), 1.12 (d, J=6.7 Hz, 3H).
LRMS (ESI, m/z): 450 [M+H]$^+$.

Example 38 (1S,3'R,4'S,5'S,6'R)-6'-methyl-6-(4-methylbenzyl)-5-fluoro-3',4',5',6'-tetrahydro-3H-spiro[isobenzofuran-1,2'-pyran]-3',4',5'-triol (A38)

The target compound A38 was synthesized according to the synthetic method of A1, wherein 2-bromo-1,4-bis(((2-methoxypropan-2-yl)oxy)methyl)benzene (1-9) was replaced by 1-bromo-4-fluoro-2,5-bis(((2-methoxypropane-2-yl)oxy)methyl)benzene.
$^1$H NMR (400 MHz, DMSO-d$_6$) δ 7.59-7.52 (m, 1H), 7.37-7.29 (m, 2H), 7.21 (dt, J=8.7, 1.1 Hz, 1H), 7.11 (dq, J=7.5, 1.2 Hz, 2H), 4.97 (d, J=5.0 Hz, 1H), 4.76 (d, J=5.0 Hz, 1H), 4.68 (dd, J=7.9, 1.0 Hz, 1H), 4.58 (dd, J=8.1, 1.0 Hz, 1H), 4.50 (d, J=5.0 Hz, 1H), 4.17 (dd, J=7.0, 5.0 Hz, 1H), 4.01-3.92 (m, 1H), 3.76-3.61 (m, 2H), 3.53 (td, J=7.0, 5.0 Hz, 1H), 3.30 (td, J=7.0, 5.0 Hz, 1H), 2.21 (d, J=1.2 Hz, 3H), 1.10 (d, J=6.7 Hz, 3H).
LRMS (ESI, m/z): 375 [M+H]$^+$.

Example 39 (1S,3'R,4'S,5'S,6'R)-6'-methyl-6-(4-methoxybenzyl)-5-fluoro-3',4',5',6'-tetrahydro-3H-spiro[isobenzofuran-1,2'-pyran]-3',4',5'-triol (A39)

The target compound A39 was synthesized according to the synthetic method of A1, wherein 2-bromo-1,4-bis(((2-methoxypropan-2-yl)oxy)methyl)benzene (1-9) and p-bromomethylbenzene were replaced by 1-bromo-4-fluoro-2,5-bis (((2-methoxypropane-2-yl)oxy)methyl)benzene and 1-bromo-4-methoxybenzene.
$^1$H NMR (400 MHz, DMSO-d$_6$) δ 7.46 (d, J=5.7 Hz, 1H), 7.23 (d, J=8.9 Hz, 1H), 7.13-7.05 (m, 2H), 6.92-6.84 (m, 2H), 4.90 (d, J=5.0 Hz, 1H), 4.68 (d, J=8.1 Hz, 1H), 4.58 (d, J=7.9 Hz, 1H), 4.47 (dd, J=22.1, 5.0 Hz, 2H), 4.14-4.02 (m, 2H), 3.78 (d, J=10.3 Hz, 4H), 3.71 (dd, J=13.4, 6.7 Hz, 2H), 3.52 (td, J=7.0, 5.0 Hz, 1H), 3.25 (td, J=7.0, 5.0 Hz, 1H), 1.09 (d, J=6.7 Hz, 3H).
LRMS (ESI, m/z): 391 [M+H]$^+$.

Example 40 (1S,3'R,4'S,5'S,6'R)-6'-methyl-6-(4-ethoxybenzyl)-5-fluoro-3',4',5',6'-tetrahydro-3H-spiro[isobenzofuran-1,2'-pyran]-3',4',5'-triol (A40)

The target compound A40 was synthesized according to the synthetic method of A1, wherein 2-bromo-1,4-bis(((2-methoxypropan-2-yl)oxy)methyl)benzene (1-9) and p-bromomethylbenzene were replaced by 1-bromo-4-fluoro-2,5-bis (((2-methoxypropane-2-yl)oxy)methyl)benzene and 1-bromo-4-ethoxybenzene.
$^1$H NMR (400 MHz, DMSO-d$_6$) δ 7.56 (d, J=5.7 Hz, 1H), 7.21 (d, J=8.9 Hz, 1H), 7.13-7.05 (m, 2H), 6.89-6.81 (m, 2H), 4.97 (d, J=5.0 Hz, 1H), 4.76 (d, J=5.0 Hz, 1H), 4.68 (d, J=8.1 Hz, 1H), 4.58 (d, J=7.9 Hz, 1H), 4.50 (d, J=5.0 Hz, 1H), 4.23-4.04 (m, 3H), 3.96 (d, J=12.5 Hz, 1H), 3.76-3.62 (m, 2H), 3.53 (td, J=6.9, 5.0 Hz, 1H), 3.30 (td, J=7.0, 5.0 Hz, 1H), 1.34 (t, J=8.0 Hz, 3H), 1.10 (d, J=6.9 Hz, 3H).
LRMS (ESI, m/z): 405 [M+H]$^+$.

Example 41 (1S,3'R,4'S,5'S,6'R)-6'-methyl-6-((5-methylthienyl)-2-methyl)-5-fluoro-3',4',5',6'-tetrahydro-3H-spiro[isobenzofuran-1,2'-pyran]-3',4',5'-triol (A41)

The target compound A41 was synthesized according to the synthetic method of A1, wherein 2-bromo-1,4-bis(((2-methoxypropan-2-yl)oxy)methyl)benzene (1-9) and p-bromomethylbenzene were replaced by 1-bromo-4-fluoro-2,5-bis (((2-methoxypropane-2-yl)oxy)methyl)benzene and 2-methylthiophene.
$^1$H NMR (400 MHz, DMSO-d$_6$) δ 7.55 (dt, J=5.7, 1.1 Hz, 1H), 7.15 (dt, J=8.9, 1.2 Hz, 1H), 6.52 (s, 2H), 4.98 (d, J=5.0 Hz, 1H), 4.79 (d, J=5.0 Hz, 1H), 4.68 (dd, J=7.9, 1.0 Hz, 1H), 4.58 (dd, J=8.1, 1.0 Hz, 1H), 4.50 (d, J=5.0 Hz, 1H), 4.29 (dd, J=12.3, 1.0 Hz, 1H), 4.21 (dd, J=7.0, 5.0 Hz, 1H), 3.96-3.88 (m, 1H), 3.70 (p, J=6.9 Hz, 1H), 3.54 (td, J=7.0, 5.0 Hz, 1H), 3.31 (td, J=7.0, 5.0 Hz, 1H), 2.37 (s, 3H), 1.11 (d, J=6.9 Hz, 3H).
LRMS (ESI, m/z): 381 [M+H]$^+$.

Example 42 (1S,3'R,4'S,5'S,6'R)-6'-methyl-6-((5-ethylthienyl)-2-methyl)-5-fluoro-3',4',5',6'-tetrahydro-3H-spiro[iso benzofuran-1,2'-pyran]-3',4',5'-triol (A42)

The target compound A42 was synthesized according to the synthetic method of A1, wherein 2-bromo-1,4-bis(((2-methoxypropan-2-yl)oxy)methyl)benzene (1-9) and p-bromomethylbenzene were replaced by 1-bromo-4-fluoro-2,5-bis (((2-methoxypropane-2-yl)oxy)methyl)benzene and 2-ethylthiophene.

$^1$H NMR (400 MHz, DMSO-$d_6$) δ 7.60 (dt, J=5.7, 1.1 Hz, 1H), 7.15 (dt, J=8.9, 1.1 Hz, 1H), 6.83-6.70 (m, 2H), 4.98 (d, J=5.0 Hz, 1H), 4.79 (d, J=5.0 Hz, 1H), 4.68 (dd, J=7.9, 1.0 Hz, 1H), 4.58 (dd, J=8.1, 1.0 Hz, 1H), 4.50 (d, J=5.0 Hz, 1H), 4.31 (dd. J=12.5, 1.0 Hz, 1H), 4.22 (dd, J=7.0, 5.0 Hz, 1H), 4.06-3.98 (min, 1H), 3.70 (p, J=6.9 Hz, 1H), 3.54 (td, J=7.0, 5.0 Hz, 1H), 3.31 (td, J=7.0, 5.0 Hz, 1H), 2.97 (dq, J=12.4, 8.0 Hz, 1H), 2.83 (dq, J=12.5, 8.0 Hz, 1H), 1.30 (t, J=8.0 Hz, 3H), 1.11 (d, J=6.7 Hz, 3H).

LRMS (ESI, m/z): 395 [M+H]$^+$.

Example 43 (1S,3'R,4'S,5'S,6'R)-6'-methyl-6-((5-chlorothienyl)-2-methyl)-5-fluoro-3',4',5',6'-tetrahydro-3H-spiro[isobenzofuran-1,2'-pyran]-3',4',5'-triol (A43)

The target compound A43 was synthesized according to the synthetic method of A1, wherein 2-bromo-1,4-bis(((2-methoxypropan-2-yl)oxy)methyl)benzene (1-9) and p-bromomethylbenzene were replaced by 1-bromo-4-fluoro-2,5-bis (((2-methoxypropane-2-yl)oxy)methyl)benzene and 2-chlorothiophene.

$^1$H NMR (400 MHz, DMSO-$d_6$) δ 7.57 (dt, J=5.8, 1.1 Hz, 1H), 7.16 (dt, J=9.0, 1.1 Hz, 1H), 6.94-6.87 (m, 1H), 6.74 (d, J=7.5 Hz, 1H), 4.93 (d, J=5.0 Hz, 1H), 4.68 (dd, J=7.9, 1.0 Hz, 1H), 4.58 (dd, J=8.1, 1.0 Hz, 1H), 4.50 (dd, J=5.0, 2.5 Hz, 2H), 4.31 (dd, J=12.5, 1.0 Hz, 1H), 4.22 (dd, J=7.0, 5.0 Hz, 1H), 4.00-3.91 (m, 1H), 3.70 (p, J=6.9 Hz, 1H), 3.55 (td, J=7.0, 5.0 Hz, 1H), 3.30 (td, J=6.9, 5.0 Hz, 1H), 1.11 (d, J=6.8 Hz, 3H).

LRMS (ESI, m/z): 401 [M+H]$^+$.

Example 44 (1S,3'R,4'S,5'S,6'R)-6'-methyl-6-((5-(4-fluorophenyl)thienyl)-2-methyl)-5-fluoro-3',4',5',6'-tetrahydro-3H-spiro[isobenzofuran-1,2'-pyran]-3',4',5'-triol (A44)

The target compound A44 was synthesized according to the synthetic method of A1, wherein 2-bromo-1,4-bis(((2-methoxy-propan-2-yl)oxy)methyl)benzene (1-9) and p-bromomethylbenzene were replaced by 1-bromo-4-fluoro-2,5-bis (((2-methoxypropane-2-yl)oxy)methyl)benzene and 2-(4-fluorophenyl)thiophene.

$^1$H NMR (400 MHz, DMSO-$d_6$) δ 7.76-7.64 (m, 3H), 7.35-7.20 (m, 4H), 7.08 (dd, J=7.6, 1.0 Hz, 1H), 4.92 (d, J=5.0 Hz, 1H), 4.68 (dd, J=7.9, 1.0 Hz, 1H), 4.58 (dd, J=8.1, 1.0 Hz, 1H), 4.50 (d, J=5.0 Hz, 2H), 4.42 (dd, J=12.5, 1.0 Hz, 1H), 4.23 (dd, J=7.0, 5.0 Hz, 1H), 4.16 (dt, J=12.5, 1.1 Hz, 1H), 3.70 (p, J=6.9 Hz, 1H), 3.56 (td, J=7.0, 5.0 Hz, 1H), 3.31 (td, J=7.0, 5.0 Hz, 1H), 1.12 (d, J=6.7 Hz, 3H).

LRMS (ESI, m/z): 461 [M+H]$^+$.

Example 45 (1S,3'R,4'S,5'S,6'R)-6'-methyl-6-((5-phenylthienyl)-2-methyl)-5-fluoro-3',4',5',6'-tetrahydro-3H-spiro[isobenzofuran-1,2'-pyran]-3',4',5'-triol (A45)

The target compound A45 was synthesized according to the synthetic method of A1, wherein 2-bromo-1,4-bis(((2-methoxypropan-2-yl)oxy)methyl)benzene (1-9) and p-bromomethylbenzene were replaced by 1-bromo-4-fluoro-2,5-bis (((2-methoxypropane-2-yl)oxy)methyl)benzene and 2-phenylthiophene.

$^1$H NMR (400 MHz, DMSO-$d_6$) δ 7.87-7.77 (m, 2H), 7.65 (dd, J=5.7, 1.1 Hz, 1H), 7.48 (pd, J=3.9, 2.0 Hz, 3H), 7.33 (d, J=7.5 Hz, 1H), 7.24 (dt, J=8.9, 1.1 Hz, 1H), 7.10 (d, J=7.7 Hz, 1H), 4.98 (d, J=5.0 Hz, 1H), 4.79 (d, J=5.0 Hz, 1H), 4.68 (dd, J=7.9, 1.0 Hz, 1H), 4.58 (dd, J=8.1, 1.0 Hz, 1H), 4.50 (d, J=5.0 Hz, 1H), 4.41 (dd, J=12.5, 1.0 Hz, 1H), 4.24 (dd, J=7.0, 5.0 Hz, 1H), 4.08-4.00 (m, 1H), 3.70 (p, J=6.9 Hz, 1H), 3.55 (td, J=7.0, 5.0 Hz, 1H), 3.32 (td, J=7.0, 5.0 Hz, 1H), 1.11 (d, J=6.8 Hz, 3H).

LRMS (ESI, m/z): 443 [M+H]$^+$.

Example 46 (1S,3'R,4'S,5'S,6'R)-6'-methyl-6-((5-(2-pyridyl)thienyl)-2-methyl)-5-fluoro-3',4',5',6'-tetrahydro-3H-spiro[isobenzofuran-1,2'-pyran]-3',4',5'-triol (A46)

The target compound A46 was synthesized according to the synthetic method of A1, wherein 2-bromo-1,4-bis(((2-methoxy-propan-2-yl)oxy)methyl)benzene (1-9) and p-bromomethylbenzene were replaced by 1-bromo-4-fluoro-2,5-bis (((2-methoxypropane-2-yl)oxy)methyl)benzene and 2-(thiophene-2-yl)pyridine.

$^1$H NMR (400 MHz, DMSO-$d_6$) δ 8.47 (d, J=5.0 Hz, 1H), 7.86-7.76 (m, 2H), 7.71 (dt, J=5.8, 1.1 Hz, 1H), 7.64 (d, J=7.4 Hz, 1H), 7.33-7.22 (m, 2H), 7.22-7.12 (m, 1H), 4.93 (d, J=5.0 Hz, 1H), 4.68 (dd, J=7.9, 1.0 Hz, 1H), 4.58 (dd, J=8.1, 1.0 Hz, 1H), 4.51 (t, J=4.7 Hz, 2H), 4.39 (dd, J=12.5, 1.0 Hz, 1H), 4.25 (dd, J=7.0, 5.0 Hz, 1H), 4.08 (dt, J=12.6, 1.2 Hz, 1H), 3.70 (p, J=6.9 Hz, 1H), 3.55 (td, J=7.0, 5.0 Hz, 1H), 3.32 (td, J=7.0, 5.0 Hz, 1H), 1.12 (d, J=6.7 Hz, 3H).

LRMS (ESI, m/z): 444 [M+H]$^+$.

Example 47 (1S,3'R,4'S,5'S,6'R)-6'-methyl-6-(benzo[b]thiophene-2-methyl)-5-fluoro-3,4',5',6'-tetrahydro-3H-spiro [isobenzofuran-1,2'-pyran]-3',4',5'-triol (A47)

The target compound A47 was synthesized according to the synthetic method of A1, wherein 2-bromo-1,4-bis(((2-methoxypropan-2-yl)oxy)methyl)benzene (1-9) and p-bromomethylbenzene were replaced by 1-bromo-4-fluoro-2,5-bis (((2-methoxypropane-2-yl)oxy)methyl)benzene and benzothiophene.

$^1$H NMR (400 MHz, DMSO-$d_6$) δ 7.78 (dd, J=7.5, 1.7 Hz, 1H), 7.66 (dt, J=7.6, 1.6 Hz, 1H), 7.56-7.43 (m, 2H), 7.32 (td, J=7.5, 1.5 Hz, 1H), 7.19 (d, J=1.3 Hz, 1H), 7.09 (dt, J=8.9, 1.0 Hz, 1H), 4.97 (d, J=5.0 Hz, 1H), 4.77 (d, J=5.0 Hz, 1H), 4.68 (dd, J=7.9, 1.0 Hz, 1H), 4.58 (dd, J=8.1, 1.0 Hz, 1H), 4.50 (d, J=5.0 Hz, 1H), 4.29 (dd, J=12.5, 1.0 Hz, 1H), 4.19 (dd, J=7.0, 5.0 Hz, 1H), 3.99 (dt, J=12.2, 0.9 Hz, 1H), 3.70 (p, J=6.9 Hz, 1H), 3.53 (td, J=7.0, 5.0 Hz, 1H), 3.30 (td, J=7.0, 5.0 Hz, 1H), 1.10 (d, J=6.8 Hz, 3H).

LRMS (ESI, m/z): 417 [M+H]$^+$.

Example 48 (1S,3'R,4'S,5'S,6'R)-6'-methyl-6-(benzo[b]furan-2-methyl)-5-fluoro-3',4',5',6'-tetrahydro-3H-spiro[isobenzofuran-1,2'-pyran]-3',4',5'-triol (A48)

The target compound A48 was synthesized according to the synthetic method of A1, wherein 2-bromo-1,4-bis(((2-methoxypropan-2-yl)oxy)methyl)benzene (1-9) and p-bromomethylbenzene were replaced by 1-bromo-4-fluoro-2,5-bis (((2-methoxypropane-2-yl)oxy)methyl)benzene and 2,3-benzofuran.

$^1$H NMR (400 MHz, DMSO-d$_6$) δ 7.53-7.43 (m, 3H), 7.40 (td, J=7.5, 1.5 Hz, 1H), 7.19 (td, J=7.4, 1.7 Hz, 1H), 7.09 (dd, J=9.0, 1.2 Hz, 1H), 6.74 (t, J=1.2 Hz, 1H), 4.97 (d, J=5.0 Hz, 1H), 4.76 (d, J=5.0 Hz, 1H), 4.68 (dd, J=7.9, 1.0 Hz, 1H), 4.58 (dd, J=8.1, 1.0 Hz, 1H), 4.50 (d, J=5.0 Hz, 1H), 4.22-4.14 (m, 2H), 3.88 (dd, J=12.4, 1.0 Hz, 1H), 3.70 (p, J=6.9 Hz, 1H), 3.52 (td, J=7.0, 5.0 Hz, 1H), 3.31 (td, J=7.0, 5.0 Hz, 1H), 1.11 (d, J=6.9 Hz, 3H).

LRMS (ESI, m/z): 401 [M+H]$^+$.

Example 49 (1S,3'R,4'S,5'S,6'R)-6'-methyl-6-((5-(2-furyl)thiazolyl)-2-methyl)-5-fluoro-3',4',5',6'-tetrahydro-3H-spiro[isobenzofuran-1,2'-pyran]-3',4',5'-triol (A49)

The target compound A49 was synthesized according to the synthetic method of A1, wherein 2-bromo-1,4-bis(((2-methoxypropan-2-yl)oxy)methyl)benzene (1-9) and p-bromomethylbenzene were replaced by 1-bromo-4-fluoro-2,5-bis (((2-methoxypropane-2-yl)oxy)methyl)benzene and 5-(furan-2-yl)thiazole.

$^1$H NMR (400 MHz, DMSO-d$_6$) δ 7.75-7.62 (m, 2H), 7.53 (s, 1H), 7.24 (dt, J=9.0, 1.1 Hz, 1H), 6.88 (dd, J=7.6, 1.6 Hz, 1H), 6.63 (t, J=7.5 Hz, 1H), 4.93 (d, J=5.0 Hz, 1H), 4.68 (dd, J=7.9, 1.0 Hz, 1H), 4.62-4.54 (m, 2H), 4.51 (dd, J=7.8, 5.0 Hz, 2H), 4.35-4.21 (m, 2H), 3.70 (p, J=6.9 Hz, 1H), 3.55 (td, J=7.0, 5.0 Hz, 1H), 3.32 (td, J=7.0, 5.0 Hz, 1H), 1.12 (d, J=6.8 Hz, 3H).

LRMS (ESI, m/z): 434 [M+H]$^+$.

Example 50 (1S,3'R,4'S,5'S,6'R)-5,6'-dimethyl-6-(4-methylbenzyl)-3',4',5',6'-tetrahydro-3H-spiro[isobenzofuran-1,2'-pyran]-3',4',5'-triol (A50)

The target compound A50 was synthesized according to the synthetic method of A1, wherein 2-bromo-1,4-bis(((2-methoxypropan-2-yl)oxy)methyl)benzene (1-9) was replaced by 1-bromo-2,5-bis(((2-methoxypropane-2-yl)oxy)methyl)-4-methylbenzene.

$^1$H NMR (400 MHz, DMSO-d$_6$) δ 7.27-7.17 (m, 3H), 7.11 (dd, J=7.5, 1.2 Hz, 2H), 4.91 (d, J=5.0 Hz, 1H), 4.68 (dd, J=7.9, 1.0 Hz, 1H), 4.58 (dd, J=8.1, 1.0 Hz, 1H), 4.49 (dd, J=12.1, 5.0 Hz, 2H), 4.24-4.11 (m, 2H), 3.70 (p, J=6.9 Hz, 1H), 3.59-3.48 (m, 2H), 3.28 (td, J=7.0, 5.0 Hz, 1H), 2.29 (d, J=1.2 Hz, 3H), 2.21 (d, J=1.2 Hz, 3H), 1.11 (d, J=6.9 Hz, 3H).

LRMS (ESI, m/z): 371 [M+H]$^+$.

Example 51 (1S,3'R,4'S,5'S,6'R)-5,6'-dimethyl-6-(4-ethylbenzyl)-3',4',5',6'-tetrahydro-3H-spiro[isobenzofuran-1,2'-pyran]-3',4',5'-triol (A51)

The target compound A51 was synthesized according to the synthetic method of A1, wherein 2-bromo-1,4-bis(((2-methoxypropan-2-yl)oxy)methyl)benzene (1-9) and p-bromomethylbenzene was replaced by 1-bromo-2,5-bis(((2-methoxypropane-2-yl)oxy)methyl)-4-methylbenzene and p-bromoethylbenzene.

$^1$H NMR (400 MHz, DMSO-d$_6$) δ 7.45 (t, J=0.9 Hz, 1H), 7.30-7.17 (m, 3H), 7.16-7.09 (m, 2H), 4.91 (d, J=5.0 Hz, 1H), 4.68 (dd, J=7.9, 1.0 Hz, 1H), 4.58 (dd, J=8.1, 1.0 Hz, 1H), 4.48 (dd, J=14.1, 5.0 Hz, 2H), 4.23 (dp, J=12.2, 1.1 Hz, 1H), 4.14 (dd, J=7.0, 5.0 Hz, 1H), 3.70 (p, J=6.9 Hz, 1H), 3.58-3.48 (m, 2H), 3.27 (td. J=7.0, 5.0 Hz, 1H), 2.67-2.55 (m, 2H), 2.32-2.27 (m, 3H), 1.19 (t, J=8.0 Hz, 3H), 1.10 (d, J=6.8 Hz, 3H).

LRMS (ESI, nm/z): 385 [M+H]$^+$.

Example 52 (1S,3'R,4'S,5'S,6'R)-5,6'-dimethyl-6-(4-propylbenzyl)-3',4',5',6'-tetrahydro-3H-spiro[isobenzofuran-1,2'-pyran]-3',4',5'-triol (A52)

The target compound A52 was synthesized according to the synthetic method of A1, wherein 2-bromo-1,4-bis(((2-methoxypropan-2-yl)oxy)methyl)benzene (1-9) and p-bromomethylbenzene was replaced by 1-bromo-2,5-bis(((2-methoxypropane-2-yl)oxy)methyl)-4-methylbenzene and 1-bromo-4-propylbenzene.

$^1$H NMR (400 MHz, DMSO-d$_6$) δ 7.26 (dt, J=7.4, 1.1 Hz, 2H), 7.22-7.09 (m, 3H), 4.97 (d, J=5.0 Hz, 1H), 4.77 (d, J=5.0 Hz, 1H), 4.68 (dd, J=7.9, 1.0 Hz, 1H), 4.58 (dd, J=8.1, 1.0 Hz, 1H), 4.50 (d, J=5.0 Hz, 1H), 4.22-4.06 (m, 2H), 3.70 (p, J=6.9 Hz, 1H), 3.61-3.49 (m, 2H), 3.30 (td, J=7.0, 5.0 Hz, 1H), 2.64-2.54 (m, 2H), 2.29-2.24 (m, 3H), 1.55 (dddd, J=16.0, 8.0, 4.0, 2.8 Hz, 2H), 1.10 (d, J=6.7 Hz, 3H), 0.94 (t, J=8.0 Hz, 3H).

LRMS (ESI, m/z): 399 [M+H]$^+$.

Example 53 (1S,3'R,4'S,5'S,6'R)-5,6'-dimethyl-6-(4-isopropylbenzyl)-3',4',5',6'-tetrahydro-3H-spiro[isobenzofuran-1,2'-pyran]-3',4',5'-triol (A53)

The target compound A53 was synthesized according to the synthetic method of A1, wherein 2-bromo-1,4-bis(((2-methoxypropan-2-yl)oxy)methyl)benzene (1-9) and p-bromomethylbenzene were replaced by 1-bromo-2,5-bis (((2-methoxypropane-2-yl)oxy)methyl)-4-methylbenzene and 1-bromo-4-isopropylbenzene.

$^1$H NMR (400 MHz, DMSO-d$_6$) δ 7.28-7.15 (m, 5H), 4.79 (dd, J=8.8, 5.0 Hz, 2H), 4.68 (dd, J=7.9, 1.0 Hz, 1H), 4.58 (dd, J=8.1, 1.0 Hz, 1H), 4.50 (d, J=5.0 Hz, 1H), 4.22 (dd, J=7.0, 5.0 Hz, 1H), 3.95 (dt, J=12.4, 1.1 Hz, 1H), 3.76-3.62 (m, 2H), 3.56 (td, J=6.9, 5.0 Hz, 1H), 3.31 (td, J=7.0, 5.0 Hz, 1H), 2.94-2.78 (m, 1H), 2.21 (d, J=1.5 Hz, 3H), 1.26-1.08 (m, 9H).

LRMS (ESI, m/z): 399 [M+H]$^+$.

Example 54 (1S,3'R,4'S,5'S,6'R)-5,6'-dimethyl-6-(4-methoxybenzyl)-3',4',5',6'-tetrahydro-3H-spiro[isobenzofuran-1,2'-pyran]-3',4',5'-triol (A54)

The target compound A54 was synthesized according to the synthetic method of A1, wherein 2-bromo-1,4-bis(((2-methoxypropan-2-yl)oxy)methyl)benzene (1-9) and p-bromomethylbenzene were replaced by 1-bromo-2,5-bis (((2-methoxypropane-2-yl)oxy)methyl)-4-methylbenzene and 1-bromo-4-methoxybenzene.

$^1$H NMR (400 MHz, DMSO-d$_6$) δ 7.19 (q, J=1.1 Hz, 1H), 7.09 (dt, J=7.5, 1.1 Hz, 2H), 6.86 (d, J=7.5 Hz, 2H), 4.97 (d, J=5.0 Hz, 1H), 4.77 (d, J=5.0 Hz, 1H), 4.68 (dd, J=7.9, 1.0 Hz, 1H), 4.58 (dd, J=8.1, 1.0 Hz, 1H), 4.50 (d, J=5.0 Hz, 1H), 4.22-4.06 (m, 2H), 3.79 (s, 3H), 3.70 (p, J=6.9 Hz, 1H), 3.63-3.49 (m, 2H), 3.30 (td, J=7.0, 5.0 Hz, 1H), 2.29-2.23 (m, 3H), 1.10 (d, J=6.7 Hz, 3H).

LRMS (ESI, m/z): 387 [M+H]$^+$.

Example 55 (1S,3'R,4'S,5'S,6'R)-5,6'-dimethyl-6-(4-ethoxybenzyl)-3',4',5',6'-tetrahydro-3H-spiro[isobenzofuran-1,2'-pyran]-3',4',5'-triol (A55)

The target compound A55 was synthesized according to the synthetic method of A1, wherein 2-bromo-1,4-bis(((2- methoxypropan-2-yl)oxy)methyl)benzene (1-9) and p-bromomethylbenzene were replaced by 1-bromo-2,5-bis (((2-methoxypropane-2-yl)oxy)methyl)-4-methylbenzene and 1-bromo-4-ethoxybenzene.

$^1$H NMR (400 MHz, DMSO-d$_6$) δ 7.20 (q, J=1.1 Hz, 1H), 7.09 (dt, J=7.4, 1.1 Hz, 2H), 6.85 (d, J=7.6 Hz, 2H), 4.91 (d, J=5.0 Hz, 1H), 4.68 (dd, J=7.9, 1.0 Hz, 1H), 4.58 (dd, J=8.1, 1.0 Hz, 1H), 4.48 (dd, J=13.0, 5.0 Hz, 2H), 4.27-4.21 (m, 1H), 4.21-4.03 (m, 4H), 3.70 (p, J=6.9 Hz, 1H), 3.59-3.48 (m, 2H), 3.28 (td, J=7.0, 5.0 Hz, 1H), 2.29 (q, J=1.0 Hz, 3H), 1.34 (t, J=8.0 Hz, 3H), 1.11 (d, J=6.7 Hz, 3H).

LRMS (ESI, nm/z): 401 [M+H]$^+$.

Example 56 (1S,3'R,4'S,5'S,6'R)-5,6'-dimethyl-6-((5-methylthienzyl)-2-methyl)-3',4',5',6'-tetrahydro-3H-spiro[isobenzofuran-1,2'-pyran]-3',4',5'-triol (A56)

The target compound A56 was synthesized according to the synthetic method of A1, wherein 2-bromo-1,4-bis(((2-methoxypropan-2-yl)oxy)methyl)benzene (1-9) and p-bromomethylbenzene were replaced by 1-bromo-2,5-bis (((2-methoxypropane-2-yl)oxy)methyl)-4-methylbenzene and 2-methylthiophene.

$^1$H NMR (400 MHz, DMSO-d$_6$) δ 7.14 (q, J=1.1 Hz, 1H), 6.52 (d, J=1.0 Hz, 2H), 4.79 (dd, J=7.0, 5.0 Hz, 2H), 4.68 (dd, J=7.9, 1.0 Hz, 1H), 4.58 (dd, J=8.1, 1.0 Hz, 1H), 4.53-4.39 (m, 2H), 4.20 (dd, J=6.9, 5.0 Hz, 1H), 3.86 (dp, J=12.5, 1.1 Hz, 1H), 3.70 (p, J=6.9 Hz, 1H), 3.55 (td, J=7.0, 5.0 Hz, 1H), 3.30 (td, J=7.0, 5.0 Hz, 1H), 2.40-2.31 (m, 6H), 1.11 (d, J=6.7 Hz, 3H).

LRMS (ESI, m/z): 377 [M+H]$^+$.

Example 57 (1S,3'R,4'S,5'S,6'R)-5,6'-dimethyl-6-((5-ethylthienzyl)-2-methyl)-3',4',5',6'-tetrahydro-3H-spiro[isobenzofuran-1,2'-pyran]-3',4',5'-triol (A57)

The target compound A57 was synthesized according to the synthetic method of A1, wherein 2-bromo-1,4-bis(((2-methoxypropan-2-yl)oxy)methyl)benzene (1-9) and p-bromomethylbenzene were replaced by 1-bromo-2,5-bis (((2-methoxypropane-2-yl)oxy)methyl)-4-methylbenzene and 2-ethylthiophene.

$^1$H NMR (400 MHz, DMSO-d$_6$) δ 7.42 (d, J=1.3 Hz, 1H), 7.13 (q, J=1.2 Hz, 1H), 6.75 (s, 2H), 4.98 (d, J=5.0 Hz, 1H), 4.80 (d, J=5.0 Hz, 1H), 4.68 (dd, J=7.9, 1.0 Hz, 1H), 4.58 (dd, J=8.1, 1.0 Hz, 1H), 4.53-4.41 (m, 2H), 4.21 (dd, J=6.9, 5.0 Hz, 1H), 3.81-3.64 (m, 2H), 3.54 (td, J=7.0, 5.0 Hz, 1H), 3.31 (td, J=7.0, 5.0 Hz, 1H), 2.95 (dq, J=12.4, 8.0 Hz, 1H), 2.80 (dq, J=12.4, 8.0 Hz, 1H), 2.37-2.31 (m, 3H), 1.30 (t, J=8.0 Hz, 3H), 1.10 (d, J=6.8 Hz, 3H).

LRMS (ESI, m/z): 391 [M+H]$^+$.

Example 58 (1S,3'R,4'S,5'S,6'R)-5,6'-dimethyl-6-((5-propylthienzyl)-2-methyl)-3',4',5',6'-tetrahydro-3H-spiro[isobenzofuran-1,2'-pyran]-3',4',5'-triol (A58)

The target compound A58 was synthesized according to the synthetic method of A1, wherein 2-bromo-1,4-bis(((2-methoxypropan-2-yl)oxy)methyl)benzene (1-9) and p-bromomethylbenzene were replaced by 1-bromo-2,5-bis (((2-methoxypropane-2-yl)oxy)methyl)-4-methylbenzene and 2-(n-propyl)thiophene.

$^1$H NMR (400 MHz, DMSO-d$_6$) δ 7.13 (q, J=1.1 Hz, 1H), 6.75-6.61 (m, 2H), 4.97 (d, J=5.0 Hz, 1H), 4.79 (d, J=5.0 Hz, 1H), 4.68 (dd, J=7.9, 1.0 Hz, 1H), 4.58 (dd, J=8.1, 1.0 Hz, 1H), 4.50 (d, J=5.0 Hz, 1H), 4.35 (ddt, J=12.5, 2.5, 1.1 Hz, 1H), 4.20 (dd, J=6.9, 5.0 Hz, 1H), 3.84-3.64 (m, 2H), 3.54 (td, J=7.0, 5.0 Hz, 1H), 3.30 (td, J=7.0, 5.0 Hz, 1H), 3.00 (td, J=12.5, 2.9 Hz, 1H), 2.82 (td, J=12.6, 3.0 Hz, 1H), 2.35 (d, J=1.2 Hz, 3H), 1.88-1.64 (m, 2H), 1.10 (d, J=6.8 Hz, 3H), 0.96 (t, J=8.0 Hz, 3H).

LRMS (ESI, m/z): 405 [M+H]$^+$.

Example 59 (1S,3'R,4'S,5'S,6'R)-5,6'-dimethyl-6-((5-chlorothienzyl)-2-methyl)-3',4',5',6'-tetrahydro-3H-spiro[isobenzofuran-1,2'-pyran]-3',4',5'-triol (A59)

The target compound A59 was synthesized according to the synthetic method of A1, wherein 2-bromo-1,4-bis(((2-methoxypropan-2-yl)oxy)methyl)benzene (1-9) and p-bromomethylbenzene were replaced by 1-bromo-2,5-bis (((2-methoxypropane-2-yl)oxy)methyl)-4-methylbenzene and 2-chlorothiophene.

$^1$H NMR (400 MHz, DMSO-d$_6$) δ 7.42 (s, 1H), 7.14 (q, J=1.2 Hz, 1H), 6.73 (d, J=1.2 Hz, 2H), 4.97 (d, J=5.0 Hz, 1H), 4.79 (d, J=5.0 Hz, 1H), 4.68 (dd, J=7.9, 1.0 Hz, 1H), 4.58 (dd, J=8.1, 1.0 Hz, 1H), 4.50 (d, J=5.0 Hz, 1H), 4.39 (dp, J=12.4, 1.1 Hz, 1H), 4.20 (dd, J=7.0, 5.0 Hz, 1H), 3.81 (dt, J=12.4, 1.0 Hz, 1H), 3.70 (p, J=6.9 Hz, 1H), 3.54 (td, J=7.0, 5.0 Hz, 1H), 3.30 (td, J=7.0, 5.0 Hz, 1H), 2.38-2.32 (m, 3H), 1.10 (d, J=6.8 Hz, 3H). LRMS (ESI, m/z): 397 [M+H]$^+$.

Example 60 (1S,3'R,4'S,5'S,6'R)-5,6'-dimethyl-6-((5-(4-fluorophenyl)thienyl-2-methyl)-5-chloro-3',4',5',6'-tetrahydro-3H-spiro[isobenzofuran-1,2'-pyran]-3',4',5'-triol (A60)

The target compound A60 was synthesized according to the synthetic method of A1, wherein 2-bromo-1,4-bis(((2-methoxy-propan-2-yl)oxy)methyl)benzene (1-9) and p-bromomethylbenzene were replaced by 1-bromo-2,5-bis (((2-methoxypropane-2-yl)oxy)methyl)-4-methylbenzene and 2-(4-fluorophenyl)thiophene.

$^1$H NMR (400 MHz, DMSO-d$_6$) δ 7.74-7.64 (m, 2H), 7.32-7.20 (m, 4H), 6.93 (dd, J=7.5, 2.5 Hz, 1H), 4.98 (d, J=5.0 Hz, 1H), 4.80 (d, J=5.0 Hz, 1H), 4.68 (dd, J=7.9, 1.0 Hz, 1H), 4.62-4.46 (m, 3H), 4.23 (dd, J=6.9, 5.0 Hz, 1H), 3.94 (ddt, J=12.5, 2.5, 1.1 Hz, 1H), 3.70 (p, J=6.9 Hz, 1H), 3.55 (td, J=7.0, 5.0 Hz, 1H), 3.32 (td, J=7.0, 5.0 Hz, 1H), 2.42-2.37 (m, 3H), 1.11 (d, J=6.7 Hz, 3H).

LRMS (ESI, nm/z): 457 [M+H]$^+$.

Example 61 (1S,3'R,4'S,5'S,6'R)-5,6'-dimethyl-6-((5-phenylthienzyl)-2-methyl)-3',4',5',6'-tetrahydro-3H-spiro[isobenzofuran-1,2'-pyran]-3',4',5'-triol (A61)

The target compound A61 was synthesized according to the synthetic method of A1, wherein 2-bromo-1,4-bis(((2-methoxypropan-2-yl)oxy)methyl)benzene (1-9) and p-bromomethylbenzene were replaced by 1-bromo-2,5-bis (((2-methoxypropane-2-yl)oxy)methyl)-4-methylbenzene and 2-phenylthiophene.

$^1$H NMR (400 MHz, DMSO-d$_6$) δ 7.87-7.77 (m, 2H), 7.54-7.44 (m, 4H), 7.32 (d, J=7.5 Hz, 1H), 7.22 (q, J=1.1 Hz, 1H), 6.92 (dd, J=7.5, 2.5 Hz, 1H), 4.98 (d, J=5.0 Hz, 1H), 4.79 (d, J=5.1 Hz, 1H), 4.68 (dd, J=7.9, 1.0 Hz, 1H), 4.58 (dd, J=8.1, 1.0 Hz, 1H), 4.53-4.42 (m, 2H), 4.22 (dd, J=7.0, 5.0 Hz, 1H), 3.92 (dt, J=12.5, 1.1 Hz, 1H), 3.70 (p, J=6.9 Hz,

1H), 3.55 (td, J=6.9, 5.0 Hz, 1H), 3.32 (td, J=7.0, 5.0 Hz, 1H), 2.39 (d, J=1.1 Hz, 3H), 1.12 (d, J=6.9 Hz, 3H).
LRMS (ESI, nm/z): 439 [M+H]+.

Example 62 (1S,3'R,4'S,5'S,6'R)-5,6'-dimethyl-6-((5-(2-pyridyl)thienyl-2-methyl)-3',4',5',6'-tetrahydro-3H-spiro[iso benzofuran-1,2'-pyran]-3',4',5'-triol (A62)

The target compound A62 was synthesized according to the synthetic method of A1, wherein 2-bromo-1,4-bis(((2-methoxy-propan-2-yl)oxy)methyl)benzene (1-9) and p-bromomethylbenzene were replaced by 1-bromo-2,5-bis (((2-methoxypropane-2-yl)oxy)methyl)-4-methylbenzene and 2-(thiophene-2-yl)pyridine.
$^1$H NMR (400 MHz, DMSO-d$_6$) δ 8.47 (d, J=5.0 Hz, 1H), 7.86-7.76 (m, 2H), 7.62 (d, J=7.5 Hz, 1H), 7.51 (s, 1H), 7.25-7.09 (m, 3H), 4.98 (d, J=5.0 Hz, 1H), 4.80 (d, J=5.1 Hz, 1H), 4.68 (dd, J=7.9, 1.0 Hz, 1H), 4.58 (dd, J=8.1, 1.0 Hz, 1H), 4.53-4.44 (m, 2H), 4.22 (dd, J=7.0, 5.0 Hz, 1H), 3.90 (ddt, J=12.4, 2.5, 1.1 Hz, 1H), 3.70 (p, J=6.9 Hz, 1H), 3.55 (td, J=7.0, 5.0 Hz, 1H), 3.32 (td, J=7.0, 5.0 Hz, 1H), 2.40-2.35 (m, 3H), 1.11 (d, J=6.7 Hz, 3H).
LRMS (ESI, m/z): 440 [M+H]+.

Example 63 (1S,3'R,4'S,5'S,6'R)-5,6'-dimethyl-6-(naphthyl-2-methyl)-3',4',5',6'-tetrahydro-3H-spiro[isobenzofuran-1,2'-pyran]-3',4',5'-triol (A63)

The target compound A63 was synthesized according to the synthetic method of A1, wherein 2-bromo-1,4-bis(((2-methoxypropan-2-yl)oxy)methyl)benzene (1-9) and p-bromomethylbenzene was replaced by 1-bromo-2,5-bis(((2-methoxypropane-2-yl)oxy)methyl)-4-methylbenzene and 2-bromonaphthalene.
$^1$H NMR (400 MHz, DMSO-d$_6$) δ 7.94 (ddt, J=21.4, 7.3, 1.7 Hz, 2H), 7.90-7.77 (m, 2H), 7.61-7.49 (m, 3H), 7.23 (q, J=1.1 Hz, 1H), 4.80-4.64 (m, 3H), 4.62-4.46 (m, 3H), 4.08 (dd, J=7.0, 5.1 Hz, 1H), 3.76-3.60 (m, 2H), 3.51 (td, J=7.0, 5.0 Hz, 1H), 3.24 (td, J=7.0, 5.0 Hz, 1H), 2.36 (d, J=1.3 Hz, 3H), 1.10 (d, J=6.7 Hz, 3H).
LRMS (ESI, m/z): 407 [M+H]+.

Example 64 (1S,3'R,4'S,5'S,6'R)-5,6'-dimethyl-6-(benzo[b]thiophene-2-methyl)-3',4',5',6'-tetrahydro-3H-spiro[isobenzofuran-1,2'-pyran]-3',4',5'-triol (A64)

The target compound A64 was synthesized according to the synthetic method of A1, wherein 2-bromo-1,4-bis(((2-methoxypropan-2-yl)oxy)methyl)benzene (1-9) and p-bromomethylbenzene were replaced by 1-bromo-2,5-bis (((2-methoxypropane-2-yl)oxy)methyl)-4-methylbenzene and benzothiophene.
$^1$H NMR (400 MHz, DMSO-d$_6$) δ 7.78 (dd, J=7.5, 1.4 Hz, 1H), 7.63 (dt, J=7.5, 1.6 Hz, 1H), 7.48 (td, J=7.5, 1.5 Hz, 1H), 7.41-7.27 (m, 2H), 7.06 (dq, J=14.8, 1.3 Hz, 2H), 4.93 (d, J=5.0 Hz, 1H), 4.68 (dd, J=7.9, 1.0 Hz, 1H), 4.58 (dd, J=8.1, 1.0 Hz, 1H), 4.50 (dd, J=5.0, 2.5 Hz, 2H), 4.42 (dq, J=12.3, 1.0 Hz, 1H), 4.21 (dd, J=7.0, 5.1 Hz, 1H), 3.79-3.64 (m, 2H), 3.55 (td, J=7.0, 5.0 Hz, 1H), 3.29 (td, J=7.0, 5.0 Hz, 1H), 2.33 (d, J=1.3 Hz, 3H), 1.11 (d, J=6.7 Hz, 3H).
LRMS (ESI, m/z): 413 [M+H]+.

Example 65 (1S,3'R,4'S,5'S,6'R)-5,6'-dimethyl-6-(benzo[b]furan-2-methyl)-3',4',5',6'-tetrahydro-3H-spiro[isobenzofuran-1,2'-pyran]-3',4',5'-triol (A65)

The target compound A65 was synthesized according to the synthetic method of A1, wherein 2-bromo-1,4-bis(((2-methoxypropan-2-yl)oxy)methyl)benzene (1-9) and p-bromomethylbenzene were replaced by 1-bromo-2,5-bis (((2-methoxypropane-2-yl)oxy)methyl)-4-methylbenzene and 2,3-benzofuran.
$^1$H NMR (400 MHz, DMSO-d$_6$) δ 7.52-7.35 (m, 4H), 7.19 (td, J=7.4, 1.6 Hz, 1H), 7.08 (q, J=1.1 Hz, 1H), 6.60 (d, J=1.6 Hz, 1H), 4.92 (d, J=5.0 Hz, 1H), 4.68 (dd, J=7.9, 1.0 Hz, 1H), 4.58 (dd, J=8.1, 1.0 Hz, 1H), 4.50 (dd, J=5.0, 1.0 Hz, 2H), 4.38-4.29 (m, 1H), 4.20 (dd, J=7.0, 5.0 Hz, 1H), 3.76-3.61 (nm, 2H), 3.55 (td, J=6.9, 5.0 Hz, 1H), 3.29 (td, J=7.0, 5.0 Hz, 1H), 2.30 (d, J=1.3 Hz, 3H), 1.11 (d, J=6.9 Hz, 3H).
LRMS (ESI, m/z): 397 [M+H]+.

Example 66 (1S,3'R,4'S,5'S,6'R)-5,6'-dimethyl-6-((5-(2-furyl)thiazolyl-2-methyl)-3',4',5',6'-tetrahydro-3H-spiro[iso benzofuran-1,2'-pyran]-3',4',5'-triol (A66)

The target compound A66 was synthesized according to the synthetic method of A1, wherein 2-bromo-1,4-bis(((2-methoxypropan-2-yl)oxy)methyl)benzene (1-9) and p-bromomethylbenzene were replaced by 1-bromo-2,5-bis (((2-methoxypropane-2-yl)oxy)methyl)-4-methylbenzene and 5-(furan-2-yl)thiazole.
$^1$H NMR (400 MHz, DMSO-d$_6$) δ 7.66 (dd, J=7.5, 1.5 Hz, 1H), 7.55-7.47 (m, 2H), 7.22 (q, J=1.1 Hz, 1H), 6.87 (dd, J=7.4, 1.6 Hz, 1H), 6.63 (t, J=7.5 Hz, 1H), 5.01-4.89 (m, 2H), 4.80 (d, J=5.0 Hz, 1H), 4.68 (dd, J=7.9, 1.0 Hz, 1H), 4.58 (dd, J=8.1, 1.0 Hz, 1H), 4.50 (d, J=5.0 Hz, 1H), 4.23 (dd, J=7.0, 5.0 Hz, 1H), 3.94 (dt, J=12.4, 1.1 Hz, 1H), 3.70 (p, J=6.9 Hz, 1H), 3.55 (td, J=7.0, 5.0 Hz, 1H), 3.32 (td, J=7.0, 5.0 Hz, 1H), 2.43-2.38 (m, 3H), 1.11 (d, J=6.7 Hz, 3H).
LRMS (ESI, m/z): 430 [M+H]+.

Example 67 (1S,3'R,4'S,5'S,6'R)-5,6'-dimethyl-6-((5-(2-thienyl)thiazolyl-2-methyl)-3',4',5',6'-tetrahydro-3H-spiro[isobenzofuran-1,2'-pyran]-3',4',5'-triol (A67)

The target compound A67 was synthesized according to the synthetic method of A1, wherein 2-bromo-1,4-bis(((2-methoxypropan-2-yl)oxy)methyl)benzene (1-9) and p-bromomethylbenzene were replaced by 1-bromo-2,5-bis (((2-methoxypropane-2-yl)oxy)methyl)-4-methylbenzene and 5-(thiophene-2-yl)thiazole.
$^1$H NMR (400 MHz, DMSO-d$_6$) δ 7.72 (s, 1H), 7.53-7.44 (m, 2H), 7.42 (dd, J=7.5, 1.5 Hz, 1H), 7.22 (q, J=1.0 Hz, 1H), 7.03 (t, J=7.5 Hz, 1H), 5.01-4.90 (m, 2H), 4.80 (d, J=5.0 Hz, 1H), 4.68 (dd, J=7.9, 1.0 Hz, 1H), 4.58 (dd, J=8.1, 1.0 Hz, 1H), 4.50 (d, J=5.0 Hz, 1H), 4.23 (dd, J=7.0, 5.0 Hz, 1H), 3.95 (dt, J=12.4, 1.1 Hz, 1H), 3.70 (p, J=6.9 Hz, 1H), 3.56 (td, J=7.0, 5.0 Hz, 1H), 3.32 (td, J=7.0, 5.0 Hz, 1H), 2.43-2.38 (m, 3H), 1.11 (d, J=6.8 Hz, 3H).
LRMS (ESI, m/z): 446 [M+H]+.

Example 68 (1S,3'R,4'S,5'S,6'R)-5,6'-dimethyl-6-((5-(4-fluorophenyl)thiazolyl-2-methyl)-3',4',5',6'-tetrahydro-3H-spiro[isobenzofuran-1,2'-pyran]-3',4',5'-triol (A68)

The target compound A68 was synthesized according to the synthetic method of A1, wherein 2-bromo-1,4-bis(((2-methoxy-propan-2-yl)oxy)methyl)benzene (1-9) and p-bromomethylbenzene were replaced by 1-bromo-2,5-bis (((2-methoxypropane-2-yl)oxy)methyl)-4-methylbenzene and 5-(4-fluorophenyl)thiazole.

$^1$H NMR (400 MHz, DMSO-d$_6$) δ 7.73-7.60 (m, 3H), 7.48 (s, 1H), 7.32-7.18 (m, 3H), 4.98 (d, J=5.0 Hz, 1H), 4.80 (d, J=5.0 Hz, 1H), 4.68 (dd, J=8.0, 1.1 Hz, 2H), 4.64-4.54 (m, 2H), 4.50 (d, J=5.0 Hz, 1H), 4.41 (dt, J=12.4, 1.1 Hz, 1H), 4.26 (dd, J=6.9, 5.0 Hz, 1H), 3.70 (p, J=6.9 Hz, 1H), 3.55 (td, J=7.0, 5.0 Hz, 1H), 3.33 (td, J=7.0, 5.0 Hz, 1H), 2.38-2.33 (m, 3H), 1.11 (d, J=6.8 Hz, 3H).

LRMS (ESI, nm/z): 458 [M+H]$^+$.

Example 69 (1S,3'R,4'S,5'S,6'R)-5,6'-dimethyl-6-((5-phenylthiazolyl)-2-methyl)-3',4',5',6'-tetrahydro-3H-spiro[isobenzofuran-1,2'-pyran]-3',4',5'-triol (A69)

The target compound A69 was synthesized according to the synthetic method of A1, wherein 2-bromo-1,4-bis(((2-methoxypropan-2-yl)oxy)methyl)benzene (1-9) and p-bromomethylbenzene were replaced by 1-bromo-2,5-bis (((2-methoxypropane-2-yl)oxy)methyl)-4-methylbenzene and 5-phenylthiophene.

$^1$H NMR (400 MHz, DMSO-d$_6$) δ 7.93-7.84 (m, 2H), 7.55-7.37 (m, 5H), 7.22 (q, J=1.1 Hz, 1H), 5.01-4.90 (m, 2H), 4.79 (d, J=5.0 Hz, 1H), 4.68 (dd, J=7.9, 1.0 Hz, 1H), 4.58 (dd, J=8.1, 1.0 Hz, 1H), 4.50 (d, J=5.0 Hz, 1H), 4.23 (dd, J=7.0, 5.0 Hz, 1H), 3.96 (dt, J=12.4, 1.0 Hz, 1H), 3.70 (p, J=6.9 Hz, 1H), 3.55 (td, J=7.0, 5.0 Hz, 1H), 3.31 (td, J=7.0, 5.0 Hz, 1H), 2.41 (d, J=1.2 Hz, 3H), 1.11 (d, J=6.8 Hz, 3H).

LRMS (ESI, m/z): 440 [M+H]$^+$.

Example 70 (1S,3'R,4'S,5'S,6'R)-5,6'-dimethyl-6-((5-(4-trifluoromethyl) phenyl) thienyl)-2-methyl)-5-chloro-3',4',5'6'-tetrahydro-3H-spiro[isobenzofuran-1,2'-pyran]-3',4',5'-triol (A70)

The target compound A70 was synthesized according to the synthetic method of A1, wherein 2-bromo-1,4-bis(((2-methoxy-propan-2-yl)oxy)methyl)benzene (1-9) and p-bromomethylbenzene were replaced by 1-bromo-2,5-bis (((2-methoxypropane-2-yl)oxy)methyl)-4-methylbenzene and 2-(4-(trifluoromethyl)phenyl)thiophene.

$^1$H NMR (400 MHz, DMSO-d$_6$) δ 7.74 (s, 4H), 7.51 (d, J=1.2 Hz, 1H), 7.33 (d, J=7.6 Hz, 1H), 7.22 (q, J=1.1 Hz, 1H), 6.92 (dd, J=7.6, 2.5 Hz, 1H), 4.98 (d, J=5.0 Hz, 1H), 4.80 (d, J=5.0 Hz, 1H), 4.68 (dd, J=7.9, 1.0 Hz, 1H), 4.58 (dd, J=8.1, 1.0 Hz, 1H), 4.54-4.45 (m, 2H), 4.23 (dd, J=6.9, 5.0 Hz, 1H), 3.92 (dt, J=12.5, 1.1 Hz, 1H), 3.70 (p, J=6.9 Hz, 1H), 3.56 (td, J=7.0, 5.0 Hz, 1H), 3.32 (td, J=6.9, 5.0 Hz, 1H), 2.40 (d, J=1.5 Hz, 3H), 1.11 (d, J=6.8 Hz, 3H).

LRMS (ESI, nm/z): 507 [M+H]$^+$.

Example 71 (1S,3'R,4'S,5'S,6'R)-5,6'-dimethyl-6-((5-(4-methyl)phenyl)thienyl)-2-methy)-5-chloro-3',4',5',6'-tetrahydro-3H-spiro[isobenzofuran-1,2'-pyran]-3',4',5'-triol (A71)

The target compound A71 was synthesized according to the synthetic method of A1, wherein 2-bromo-1,4-bis(((2-methoxypropan-2-yl)oxy)methyl)benzene (1-9) and p-bromomethylbenzene were replaced by 1-bromo-2,5-bis (((2-methoxypropane-2-yl)oxy)methyl)-4-methylbenzene and 2-(4-methylphenyl)thiophene.

$^1$H NMR (400 MHz, DMSO-d$_6$) δ 7.66-7.59 (m, 2H), 7.33 (d, J=7.6 Hz, 1H), 7.28-7.19 (m, 3H), 7.03 (dd, J=7.5, 1.6 Hz, 1H), 4.98 (d, J=5.0 Hz, 1H), 4.83 (d, J=5.0 Hz, 1H), 4.72-4.60 (m, 2H), 4.60-4.54 (m, 1H), 4.50 (d, J=5.0 Hz, 1H), 4.25 (dd, J=6.9, 5.0 Hz, 1H), 3.93-3.84 (m, 1H), 3.70 (p, J=6.9 Hz, 1H), 3.56 (td, J=7.0, 5.0 Hz, 1H), 3.31 (td, J=6.9, 5.0 Hz, 1H), 2.41-2.30 (m, 6H), 1.11 (d, J=6.9 Hz, 3H).

LRMS (ESI, m/z): 453 [M+H]$^+$.

Example 72 (1S,3'R,4'S,5'S,6'R)-5,6'-dimethyl-6-((5-(3-fluorophenyl)thienyl-2-methyl)-5-chloro-3',3',5',6'-tetrahydro-3H-spiro[isobenzofuran-1,2'-pyran]-3',4',5'-triol (A72)

The target compound A72 was synthesized according to the synthetic method of A1, wherein 2-bromo-1,4-bis(((2-methoxy-propan-2-yl)oxy)methyl)benzene (1-9) and p-bromomethylbenzene were replaced by 1-bromo-2,5-bis (((2-methoxypropane-2-yl)oxy)methyl)benzene and 2-(3-fluorophenyl)thiophene.

$^1$H NMR (400 MHz, DMSO-d$_6$) δ 7.59-7.43 (m, 4H), 7.37-7.19 (m, 3H), 6.93 (dd, J=7.5, 2.5 Hz, 1H), 4.98 (d, J=5.0 Hz, 1H), 4.80 (d, J=5.0 Hz, 1H), 4.68 (dd, J=7.9, 1.0 Hz, 1H), 4.58 (dd, J=8.1, 1.0 Hz, 1H), 4.53-4.44 (m, 2H), 4.23 (dd. J=7.0, 5.0 Hz, 1H), 3.97-3.88 (m, 1H), 3.70 (p, J=6.9 Hz, 1H), 3.55 (td, J=7.0, 5.0 Hz, 1H), 3.32 (td, J=6.9, 5.0 Hz, 1H), 2.40 (d, J=1.4 Hz, 3H), 1.11 (d, J=6.8 Hz, 3H).

LRMS (ESI, m/z): 457 [M+H]$^+$.

Example 73 (1S,3'R,4'S,5'S,6'R)-5,6'-dimethyl-6-((5-(2,4-difluorophenyl)thienyl)-2-methyl)-5-chloro-3',4',5',6'-tetra hydro-3H-spiro[isobenzofuran-1,2'-pyran]-3',4',5'-triol (A73)

The target compound A73 was synthesized according to the synthetic method of A1, wherein 2-bromo-1,4-bis(((2-methoxy-propan-2-yl)oxy)methyl)benzene (1-9) and p-bromomethylbenzene were replaced by 1-bromo-2,5-bis (((2-methoxypropane-2-yl)oxy)methyl)-4-methylbenzene and 2-(2,4-fluorophenyl)thiophene.

$^1$H NMR (400 MHz, DMSO-d$_6$) δ 7.71 (dt, J=7.5, 5.7 Hz, 1H), 7.28-7.20 (m, 2H), 7.16-7.00 (m, 2H), 6.88 (dd, J=7.5, 2.5 Hz, 1H), 4.75 (dd, J=8.8, 5.0 Hz, 2H), 4.68 (dd, J=7.9, 1.0 Hz, 1H), 4.58 (dd, J=8.1, 1.0 Hz, 1H), 4.53-4.44 (m, 2H), 4.22 (dd, J=6.9, 5.0 Hz, 1H), 3.91 (dt, J=12.5, 1.0 Hz, 1H), 3.70 (p, J=6.9 Hz, 1H), 3.56 (td, J=7.0, 5.0 Hz, 1H), 3.30 (td, J=7.0, 5.0 Hz, 1H), 2.42-2.37 (m, 3H), 1.12 (d, J=6.8 Hz, 3H).

LRMS (ESI, nm/z): 475 [M+H]$^+$.

Example 74 (1S,3'R,4'S,5'S,6'R)-5,6'-dimethyl-6-((5-(2-fluorophenyl)thienyl)-2-methyl)-5-chloro-3-3',2',5',6'-tetrahydro-3H-spiro[isobenzofuran-1,2'-pyran]-3',4',5'-triol (A74)

The target compound A74 was synthesized according to the synthetic method of A1, wherein 2-bromo-1,4-bis(((2-methoxy-propan-2-yl)oxy)methyl)benzene (1-9) and p-bromomethylbenzene were replaced by 1-bromo-2,5-bis (((2-methoxypropane-2-yl)oxy)methyl)-4-methylbenzene and 2-(2-fluorophenyl)thiophene.

$^1$H NMR (400 MHz, DMSO-d$_6$) δ 7.70 (ddd, J=7.6, 5.7, 2.1 Hz, 1H), 7.46-7.19 (m, 5H), 6.93 (dd, J=7.6, 2.4 Hz, 1H), 4.98 (d, J=5.0 Hz, 1H), 4.80 (d, J=5.0 Hz, 1H), 4.68 (dd, J=7.9, 1.0 Hz, 1H), 4.62-4.46 (m, 3H), 4.23 (dd, J=7.0, 5.0 Hz, 1H), 3.94 (dt, J=12.4, 1.1 Hz, 1H), 3.70 (p, J=6.9 Hz, 1H), 3.55 (td, J=6.9, 5.0 Hz, 1H), 3.32 (td, J=7.0, 5.0 Hz, 1H), 2.42-2.36 (m, 3H), 1.11 (d, J=6.7 Hz, 3H).

LRMS (ESI, m/z): 457 [M+H]$^+$.

Example 75 (1S,3'R,4'S,5'S,6'R)-5,6'-dimethyl-6-((5-(4-methoxyphenyl)thienyl)-2-methyl)-5-chloro-3',4',5',6'-tetrahydro-3H-spiro[isobenzofuran-1,2'-pyran]-3',4',5'-triol (A75)

The target compound A75 was synthesized according to the synthetic method of A1, wherein 2-bromo-1,4-bis(((2- methoxy-propan-2-yl)oxy)methyl)benzene (1-9) and p-bromomethylbenzene were replaced by 1-bromo-2,5-bis (((2-methoxypropane-2-yl)oxy)methyl)-4-methylbenzene and 2-(4-methoxyphenyl)thiophene.

$^1$H NMR (400 MHz, DMSO-d$_6$) δ 7.73-7.67 (m, 2H), 7.32-7.19 (m, 2H), 7.08-7.02 (m, 2H), 6.93 (dd, J=7.6, 2.5 Hz, 1H), 4.98 (d, J=5.0 Hz, 1H), 4.80 (d, J=5.0 Hz, 1H), 4.68 (dd, J=7.9, 1.0 Hz, 1H), 4.62-4.50 (m, 2H), 4.50 (d, J=3.1 Hz, 1H), 4.23 (dd, J=7.0, 5.0 Hz, 1H), 3.90 (dt, J=12.4, 1.1 Hz, 1H), 3.79 (s, 3H), 3.70 (p, J=6.9 Hz, 1H), 3.56 (td, J=7.0, 5.0 Hz, 1H), 3.32 (td, J=7.0, 5.0 Hz, 1H), 2.43-2.37 (m, 3H), 1.11 (d, J=6.7 Hz, 3H).

LRMS (ESI, m/z): 469 [M+H]$^+$.

Example 76 (1S,3'R,4'S,5'S,6'R)-5,6'-dimethyl-6-((5-methoxythienzyl)-2-methyl)-3',4',5',6'-tetrahydro-3H-spiro[isobenzofuran-1,2'-pyran]-3',4',5'-triol (A76)

The target compound A76 was synthesized according to the synthetic method of A1, wherein 2-bromo-1,4-bis(((2-methoxypropan-2-yl)oxy)methyl)benzene (1-9) and p-bromomethylbenzene were replaced by 1-bromo-2,5-bis (((2-methoxypropane-2-yl)oxy)methyl)-4-methylbenzene and 2-methoxythiophene.

$^1$H NMR (400 MHz, DMSO-d$_6$) δ 7.13 (q, J=1.0 Hz, 1H), 6.62 (dd, J=7.5, 2.5 Hz, 1H), 5.99 (d, J=7.5 Hz, 1H), 4.97 (d, J=5.0 Hz, 1H), 4.79 (d, J=5.0 Hz, 1H), 4.68 (dd, J=7.9, 1.0 Hz, 1H), 4.58 (dd, J=8.1, 1.0 Hz, 1H), 4.50 (d, J=5.0 Hz, 1H), 4.39 (ddt, J=12.3, 2.4, 1.1 Hz, 1H), 4.20 (dd, J=7.0, 5.0 Hz, 1H), 3.85-3.77 (m, 4H), 3.70 (p, J=6.9 Hz, 1H), 3.54 (td, J=7.0, 5.0 Hz, 1H), 3.31 (td, J=6.9, 5.0 Hz, 1H), 2.38-2.32 (m, 3H), 1.10 (d, J=6.8 Hz, 3H).

LRMS (ESI, m/z): 393 [M+H]$^+$.

Example 77 (1S,3'R,4'S,5'S,6'R)-5,6'-dimethyl-6-((5-trifluoromethylthienyl)-2-methyl)-3',4',5',6'-tetrahydro-3H-spiro[isobenzofuran-1,2'-pyran]-3',4',5'-triol (A77)

The target compound A77 was synthesized according to the synthetic method of A1, wherein 2-bromo-1,4-bis(((2-methoxypropan-2-yl)oxy)methyl)benzene (1-9) and p-bromomethylbenzene were replaced by 1-bromo-2,5-bis (((2-methoxypropane-2-yl)oxy)methyl)-4-methylbenzene and 2-trifluoromethylthiophene.

$^1$H NMR (400 MHz, DMSO-d$_6$) δ 7.42 (s, 1H), 7.13 (q, J=1.1 Hz, 1H), 7.05 (d, J=7.4 Hz, 1H), 6.85 (dd, J=7.6, 1.8 Hz, 1H), 4.98 (d, J=5.0 Hz, 1H), 4.79 (d, J=5.0 Hz, 1H), 4.68 (dd, J=7.9, 1.0 Hz, 1H), 4.58 (dd, J=8.1, 1.0 Hz, 1H), 4.54-4.45 (m, 2H), 4.20 (dd, J=7.0, 5.0 Hz, 1H), 3.79 (dt, J=12.5, 1.1 Hz, 1H), 3.70 (p, J=6.9 Hz, 1H), 3.54 (td, J=7.0, 5.0 Hz, 1H), 3.31 (td, J=6.9, 5.0 Hz, 1H), 2.37-2.32 (m, 3H), 1.10 (d, J=6.8 Hz, 3H).

LRMS (ESI, nm/z): 431 [M+H]$^+$.

Example 78 5-(((1S,3'R,4'S,5'S,6'R)-3',4',5'-trihydroxy-5,6'-dimethyl-3',4',5',6-tetrahydro-3H-spiro[isobenzofuran-1,2'-pyran]yl)-6-methyl)thiophene-2-nitrile (A78)

The target compound A78 was synthesized according to the synthetic method of A1, wherein 2-bromo-1,4-bis(((2-methoxypropan-2-yl)oxy)methyl)benzene (1-9) and p-bromomethylbenzene were replaced by 1-bromo-2,5-bis (((2-methoxypropane-2-yl)oxy)methyl)-4-methylbenzene and thiophene-2-cyano.

$^1$H NMR (400 MHz, DMSO-d$_6$) δ 7.50-7.40 (m, 2H), 7.14 (q, J=1.1 Hz, 1H), 7.02 (dd, J=7.5, 2.5 Hz, 1H), 4.97 (d, J=5.0 Hz, 1H), 4.78 (d, J=5.0 Hz, 1H), 4.68 (dd, J=7.9, 1.0 Hz, 1H), 4.58 (dd, J=8.1, 1.0 Hz, 1H), 4.50 (d, J=5.0 Hz, 1H), 4.44 (ddt, J=12.4, 2.4, 1.2 Hz, 1H), 4.20 (dd, J=7.0, 5.0 Hz, 1H), 3.86 (dt, J=12.5, 1.1 Hz, 1H), 3.70 (p, J=6.9 Hz, 1H), 3.55 (td, J=7.0, 5.0 Hz, 1H), 3.30 (td, J=7.0, 5.0 Hz, 1H), 2.37-2.31 (m, 3H), 1.11 (d, J=6.8 Hz, 3H).

LRMS (ESI, m/z): 388 [M+H]$^+$.

Example 79 5-(((1S,3'R,4'S,5'S,6'R)-3',4',5'-trihydroxy-5,6'-dimethyl-3',4',5',6-tetrahydro-3H-spiro[isobenzofuran-1,2'-pyran]yl)-6-methyl)thiophene-2-methyl formate (A79)

The target compound A79 was synthesized according to the synthetic method of A1, wherein 2-bromo-1,4-bis(((2-methoxypropan-2-yl)oxy)methyl)benzene (1-9) and p-bromomethylbenzene were replaced by 1-bromo-2,5-bis (((2-methoxypropane-2-yl)oxy)methyl)-4-methylbenzene and thiophene-2-methyl ester.

$^1$H NMR (400 MHz, DMSO-d$_6$) δ 7.81 (d, J=7.5 Hz, 1H), 7.45 (d, J=1.1 Hz, 1H), 7.16-7.03 (m, 2H), 4.98 (d, J=5.1 Hz, 1H), 4.80 (d, J=5.0 Hz, 1H), 4.68 (dd, J=7.9, 1.0 Hz, 1H), 4.62-4.47 (m, 3H), 4.22 (dd, J=7.0, 5.0 Hz, 1H), 3.87 (s, 3H), 3.82 (dt, J=12.3, 1.0 Hz, 1H), 3.70 (p, J=6.9 Hz, 1H), 3.55 (td, J=7.0, 5.0 Hz, 1H), 3.31 (td, J=7.0, 5.0 Hz, 1H), 2.34 (q, J=1.1 Hz, 3H), 1.11 (d, J=6.9 Hz, 3H).

LRMS (ESI, m/z): 421 [M+H]$^+$.

Example 80 5-(((1S,3'R,4'S,5'S,6'R)-3',4',5'-trihydroxy-5,6'-dimethyl-3',4',5',6-tetrahydro-3H-spiro[isobenzofuran-1,2'-pyran]yl)-6-methyl)thiophene-2-phenyl formate (A80)

The target compound A80 was synthesized according to the synthetic method of A1, wherein 2-bromo-1,4-bis(((2-methoxypropan-2-yl)oxy)methyl)benzene (1-9) and p-bromomethylbenzene were replaced by 1-bromo-2,5-bis (((2-methoxypropane-2-yl)oxy)methyl)-4-methylbenzene and thiophene-2-phenyl ester.

$^1$H NMR (400 MHz, DMSO-d$_6$) δ 7.94 (d, J=7.5 Hz, 1H), 7.40 (t, J=7.4 Hz, 2H), 7.34-7.16 (m, 5H), 4.98 (d, J=5.0 Hz, 1H), 4.82 (d, J=5.0 Hz, 1H), 4.72-4.54 (min, 3H), 4.50 (d, J=5.0 Hz, 1H), 4.25 (dd, J=7.0, 5.0 Hz, 1H), 3.91 (dt, J=12.3, 1.2 Hz, 1H), 3.70 (p, J=6.9 Hz, 1H), 3.56 (td, J=7.0, 5.0 Hz, 1H), 3.31 (td, J=7.0, 5.0 Hz, 1H), 2.38 (d, J=1.9 Hz, 3H), 1.11 (d, J=6.9 Hz, 3H).

LRMS (ESI, nm/z): 483 [M+H]$^+$.

Example 81 N-methyl-5-(((1S,3'R,4'S,5'S,6'R)-3',4',5'-trihydroxy-5,6'-dimethyl-3',4',5',6-tetrahydro-3H-spiro[isobenzofuran-1,2'-pyran]yl)-6-methyl)thiophene-2-formamide (A81)

The target compound A81 was synthesized according to the synthetic method of A1, wherein 2-bromo-1,4-bis(((2-methoxy-propan-2-yl)oxy)methyl)benzene (1-9) and p-bromomethylbenzene were replaced by 1-bromo-2,5-bis (((2-methoxypropane-2-yl)oxy)methyl)-4-methylbenzene and N-methylthiophene-2-formamide.

$^1$H NMR (400 MHz, DMSO-d$_6$) δ 8.46 (s, 1H), 8.21 (d, J=7.5 Hz, 1H), 7.43 (d, J=1.1 Hz, 1H), 7.18-7.11 (m, 2H), 4.98 (d, J=5.0 Hz, 1H), 4.79 (d, J=5.0 Hz, 1H), 4.68 (dd, J=7.9, 1.0 Hz, 1H), 4.62-4.47 (m, 3H), 4.21 (dd, J=6.9, 5.0 Hz, 1H), 3.81 (dt, J=12.3, 1.0 Hz, 1H), 3.70 (p, J=6.9

1H), 3.55 (td, J=7.0, 5.0 Hz, 1H), 3.31 (td, J=7.0, 5.0 Hz, 1H), 2.86 (s, 3H), 2.35 (q, J=1.1 Hz, 3H), 1.11 (d, J=6.8 Hz, 3H).

LRMS (ESI, m/z): 420 [M+H]$^+$.

Example 82 (1S,3'R,4'S,5'S,6'R)-5-ethynyl-6'-methyl-6-(4-methylbenzyl)-3',4',5',6'-tetrahydro-3H-spiro[isobenzofuran-1,2'-pyran]-3',4',5'-triol (A82)

The target compound A82 was synthesized according to the synthetic method of A1, wherein 2-bromo-1,4-bis(((2-methoxy-propan-2-yl)oxy)methyl)benzene (1-9) was replaced by 1-bromo-4-ethynyl-2,5-bis(((2-methoxypropane-2-yl)oxy)methyl)benzene.

$^1$H NMR (400 MHz, DMSO-d$_6$) δ 7.82 (s, 1H), 7.52 (s, 1H), 7.30 (dt, J=7.5, 1.1 Hz, 2H), 7.16-7.08 (m, 2H), 4.90 (d, J=5.0 Hz, 1H), 4.68 (dd, J=7.9, 1.0 Hz, 1H), 4.58 (dd, J=8.1, 1.0 Hz, 1H), 4.47 (dd, J=20.3, 5.0 Hz, 2H), 4.40 (s, 1H), 4.26 (dq, J=12.2, 1.0 Hz, 1H), 4.10 (dd, J=7.0, 5.0 Hz, 1H), 3.87-3.78 (m, 1H), 3.70 (p, J=6.9 Hz, 1H), 3.51 (td, J=7.0, 5.0 Hz, 1H), 3.26 (td, J=7.0, 5.0 Hz, 1H), 2.21 (d, J=1.2 Hz, 3H), 1.09 (d, J=6.7 Hz, 3H).

LRMS (ESI, m/z): 381 [M+H]$^+$.

Example 83 (1S,3'R,4'S,5'S,6'R)-5-ethynyl-6'-methyl-6-((5-(4-fluorophenyl)thienyl)-2-methyl)-3',4',5'6'-tetrahydro-3H-spiro[isobenzofuran-1,2'-pyran]-3',4',5'-triol (A83)

The target compound A83 was synthesized according to the synthetic method of A1, wherein 2-bromo-1,4-bis(((2-methoxypropan-2-yl)oxy)methyl)benzene (1-9) and p-bromomethylbenzene were replaced by 1-bromo-4-ethynyl-2,5-bis (((2-methoxypropane-2-yl)oxy)methyl)benzene and 2-(4-fluorophenyl)thiophene.

$^1$H NMR (400 MHz, DMSO-d$_6$) δ 7.84 (s, 1H), 7.73-7.63 (m, 3H), 7.34-7.21 (m, 3H), 7.17 (d, J=7.5 Hz, 1H), 4.97 (d, J=5.0 Hz, 1H), 4.79 (d, J=5.0 Hz, 1H), 4.72-4.62 (m, 2H), 4.58 (dd, J=8.1, 1.0 Hz, 1H), 4.50 (d, J=5.0 Hz, 1H), 4.31 (s, 1H), 4.26-4.11 (m, 2H), 3.70 (p, J=6.9 Hz, 1H), 3.54 (td, J=7.0, 5.0 Hz, 1H), 3.31 (td, J=7.0, 5.0 Hz, 1H), 1.10 (d, J=6.9 Hz, 3H).

LRMS (ESI, m/z): 467 [M+H]$^+$.

Example 84 (1S,3'R,4'S,5'S,6'R)-5-ethynyl-6'-methyl-6-((5-(2-furyl)thiazolyl)-2-methyl)-3',4',5',6'-tetrrahydro-3H-spiro[isobenzofuran-1,2'-pyran]-3',4',5'-triol (A84)

The target compound A84 was synthesized according to the synthetic method of A1, wherein 2-bromo-1,4-bis(((2-methoxypropan-2-yl)oxy)methyl)benzene (1-9) and p-bromomethylbenzene were replaced by 1-bromo-4-ethynyl-2,5-bis (((2-methoxypropane-2-yl)oxy)methyl)benzene and 5-(furan-2-yl)thiazole.

$^1$H NMR (400 MHz, DMSO-d$_6$) δ 7.83 (s, 1H), 7.70-7.62 (m, 2H), 7.53 (s, 1H), 6.89 (dd, J=7.5, 1.5 Hz, 1H), 6.63 (t, J=7.5 Hz, 1H), 4.98 (d, J=5.0 Hz, 1H), 4.82-4.64 (m, 3H), 4.58 (dd, J=8.1, 1.0 Hz, 1H), 4.54-4.46 (m, 2H), 4.33 (s, 1H), 4.23 (dd, J=6.9, 5.0 Hz, 1H), 3.70 (p, J=6.9 Hz, 1H), 3.54 (td, J=7.0, 5.0 Hz, 1H), 3.32 (td, J=7.0, 5.0 Hz, 1H), 1.10 (d, J=6.8 Hz, 3H).

LRMS (ESI, m/z): 440 [M+H]$^+$.

Example 85 (1S,3'R,4'S,5'S,6'R)-5-ethynyl-6'-methyl-6-((5-ethylthienyl)-2-methyl)-3',4',5',6'-tetrahydro-3H-spiro[isobenzofuran-1,2'-pyran]-3',4',5'-triol (A85)

The target compound A85 was synthesized according to the synthetic method of A1, wherein 2-bromo-1,4-bis(((2-methoxypropan-2-yl)oxy)methyl)benzene (1-9) and p-bromomethylbenzene were replaced by 1-bromo-4-ethynyl-2,5-bis (((2-methoxypropane-2-yl)oxy)methyl)benzene and 2-ethylthiophene.

$^1$H NMR (400 MHz, DMSO-d$_6$) δ 7.76 (d, J=1.3 Hz, 1H), 7.58 (d, J=1.3 Hz, 1H), 6.88 (dd, J=7.5, 1.3 Hz, 1H), 6.73 (d, J=7.5 Hz, 1H), 4.92 (d, J=5.0 Hz, 1H), 4.68 (dd, J=7.9, 1.0 Hz, 1H), 4.62-4.46 (m, 4H), 4.28 (s, 1H), 4.19 (dd, J=6.9, 5.0 Hz, 1H), 4.06 (dt, J=12.5, 1.2 Hz, 1H), 3.70 (p, J=6.9 Hz, 1H), 3.54 (td, J=7.0, 5.0 Hz, 1H), 3.30 (td, J=6.9, 5.0 Hz, 1H), 2.96 (dq, J=12.3, 8.0 Hz, 1H), 2.83 (dq, J=12.4, 8.0 Hz, 1H), 1.30 (t, J=8.0 Hz, 3H), 1.11 (d, J=6.7 Hz, 3H).

LRMS (ESI, m/z): 401 [M+H]$^+$.

Example 86 (1S,3'R,4'S,5'S,6'R)-5-ethynyl-6'-methyl-6-(4-methoxybenzyl)-3',4',5',6'-tetrahydro-3H-spiro[isobenzofuran-1,2'-pyran]-3',4',5'-triol (A86)

The target compound A86 was synthesized according to the synthetic method of A1, wherein 2-bromo-1,4-bis(((2-methoxy-propan-2-yl)oxy)methyl)benzene (1-9) and p-bromomethylbenzene were replaced by 1-bromo-4-ethynyl-2,5-bis (((2-methoxypropane-2-yl)oxy)methyl)benzene and 1-bromo-4-methoxybenzene.

$^1$H NMR (400 MHz, DMSO-d$_6$) δ 7.81 (d, J=1.1 Hz, 1H), 7.55 (d, J=1.3 Hz, 1H), 7.13-7.05 (m, 2H), 6.91-6.83 (m, 2H), 4.96 (d, J=5.0 Hz, 1H), 4.76 (d, J=5.0 Hz, 1H), 4.68 (dd, J=7.9, 1.0 Hz, 1H), 4.58 (dd, J=8.1, 1.0 Hz, 1H), 4.50 (d, J=5.0 Hz, 1H), 4.27 (s, 1H), 4.23-4.11 (m, 2H), 3.83-3.75 (m, 4H), 3.70 (p, J=6.9 Hz, 1H), 3.52 (td, J=7.0, 5.0 Hz, 1H), 3.29 (td, J=7.0, 5.0 Hz, 1H), 1.10 (d, J=6.9 Hz, 3H).

LRMS (ESI, m/z): 397 [M+H]$^+$.

Example 87 (1S,3'R,4'S,5'S,6'R)-5-ethynyl-6'-methyl-6-(4-ethoxybenzyl)-3',4',5',6'-tetrahydro-3H-spiro[isobenzofuran-1,2'-pyran]-3',4',5'-triol (A87)

The target compound A87 was synthesized according to the synthetic method of A1, wherein 2-bromo-1,4-bis(((2-methoxy-propan-2-yl)oxy)methyl)benzene (1-9) and p-bromomethylbenzene were replaced by 1-bromo-4-ethynyl-2,5-bis (((2-methoxypropane-2-yl)oxy)methyl)benzene and 1-bromo-4-ethoxybenzene.

$^1$H NMR (400 MHz, DMSO-d$_6$) δ 7.82 (d, J=1.3 Hz, 1H), 7.09 (dt, J=7.5, 1.1 Hz, 2H), 6.89-6.81 (m, 2H), 4.97 (d, J=5.0 Hz, 1H), 4.79 (d, J=5.0 Hz, 1H), 4.68 (dd, J=7.9, 1.0 Hz, 1H), 4.58 (dd, J=8.1, 1.0 Hz, 1H), 4.50 (d, J=5.0 Hz, 1H), 4.25-3.99 (m, 5H), 3.88-3.79 (m, 1H), 3.70 (p, J=6.9 Hz, 1H), 3.54 (td, J=6.9, 5.0 Hz, 1H), 3.31 (td, J=6.9, 5.0 Hz, 1H), 1.34 (t, J=8.0 Hz, 3H), 1.10 (d, J=6.7 Hz, 3H).

LRMS (ESI, m/z): 411 [M+H]$^+$.

Example 88 (1S,3'R,4'S,5'S,6'R)-3',4',5'-trihydroxy-6'-methyl-6-(4-methylphenyl)-3',4',5',6'-tetrahydro-3H-spiro[isobenzofuran-1,2'-pyran]-5-nitrile (A88)

The target compound A88 was synthesized according to the synthetic method of A1, wherein 2-bromo-1,4-bis(((2- methoxypropan-2-yl)oxy)methyl)benzene (1-9) was replaced by 4-bromo-2,5-bis(((2-methoxypropane-2-yl)oxy) methyl) benzonitrile.

¹H NMR (400 MHz, DMSO-d₆) δ 7.86-7.77 (m, 2H), 7.40-7.31 (m, 2H), 7.16-7.09 (m, 2H), 4.98 (d, J=5.0 Hz, 1H), 4.79 (d, J=5.1 Hz, 1H), 4.68 (dd, J=7.9, 1.0 Hz, 1H), 4.58 (dd, J=8.1, 1.0 Hz, 1H), 4.50 (d, J=5.0 Hz, 1H), 4.22 (dd, J=7.0, 5.0 Hz, 1H), 4.07 (dd, J=12.5, 1.0 Hz, 1H), 4.01-3.93 (m, 1H), 3.70 (p. J=6.9 Hz, 1H), 3.55 (td, J=7.0, 5.0 Hz, 1H), 3.32 (td, J=6.9, 5.0 Hz, 1H), 2.21 (d, J=1.2 Hz, 3H), 1.11 (d, J=6.8 Hz, 3H).

LRMS (ESI, m/z): 382 [M+H]⁺.

Example 89 (1S,3'R,4'S,5'S,6'R)-6-((5-(4-fluorophenyl)thienyl)-2-methyl)-3',4',5'-trihydroxy-6'-methyl-3',4',5',6'-tetrahydro-3H-spiro[isobenzofuran-1,2'-pyran]-5-nitrile (A89)

The target compound A89 was synthesized according to the synthetic method of A1, wherein 2-bromo-1,4-bis(((2-methoxy-propan-2-yl)oxy)methyl)benzene (1-9) and p-bromomethylbenzene were replaced by 4-bromo-2,5-bis (((2-methoxypropane-2-yl)oxy)methyl)benzonitrile and 2-(4-fluorophenyl)thiophene.

¹H NMR (400 MHz, DMSO-d₆) δ 7.88 (s, 1H), 7.82 (s, 1H), 7.73-7.63 (m, 2H), 7.33 (d, J=7.5 Hz, 1H), 7.31-7.18 (m, 3H), 4.98 (d, J=5.0 Hz, 1H), 4.78 (d, J=5.1 Hz, 1H), 4.72-4.60 (m, 2H), 4.58 (dd. J=8.1, 1.0 Hz, 1H), 4.50 (d, J=5.0 Hz, 1H), 4.31-4.19 (m, 2H), 3.70 (p, J=6.9 Hz, 1H), 3.55 (td, J=7.0, 5.0 Hz, 1H), 3.32 (td, J=7.0, 5.0 Hz, 1H), 1.11 (d, J=6.8 Hz, 3H).

LRMS (ESI, m/z): 468 [M+H]⁺.

Example 90 (1S,3'R,4'S,5'S,6'R)-6-((5-(2-furyl)thiazolyl)-2-methyl)-3',2',5'-trihydroxy-6'-methyl-3'4', 5',6'-tetrahydro-3H-spiro[isobenzofuran-1,2'-pyran]-5-nitrile (A90)

The target compound A90 was synthesized according to the synthetic method of A1, wherein 2-bromo-1,4-bis(((2-methoxypropan-2-yl)oxy)methyl)benzene (1-9) and p-bromomethylbenzene were replaced by 4-bromo-2,5-bis (((2-methoxypropane-2-yl)oxy)methyl)benzonitrile and 5-(furan-2-yl)thiazole.

¹H NMR (400 MHz, DMSO-d₆) δ 7.95-7.88 (m, 2H), 7.66 (dd, J=7.5, 1.5 Hz, 1H), 7.53 (s, 1H), 6.90 (dd, J=7.5, 1.4 Hz, 1H), 6.63 (t, J=7.5 Hz, 1H), 4.84 (dd, J=12.5, 1.0 Hz, 1H), 4.75 (dd, J=17.3, 5.0 Hz, 2H), 4.68 (dd, J=7.9, 1.0 Hz, 1H), 4.58 (dd, J=8.1, 1.0 Hz, 1H), 4.54-4.47 (m, 2H), 4.25 (dd, J=7.0, 5.0 Hz, 1H), 3.70 (p, J=6.9 Hz, 1H), 3.56 (td, J=7.0, 5.0 Hz, 1H), 3.32 (td, J=7.0, 5.0 Hz, 1H), 1.12 (d, J=6.7 Hz, 3H).

LRMS (ESI, m/z): 441 [M+H]⁺.

Example 91 (1S,3'R,4'S,5'S,6'R)-6-((5-ethylthienyl)-2-methyl)-3',4',5'-trihydroxy-6'-methyl-3',4',5',6'-tetrahydro-3H-spiro[isobenzofuran-1,2'-pyran]-5-nitrile (A91)

The target compound A91 was synthesized according to the synthetic method of A1, wherein 2-bromo-1,4-bis(((2-methoxypropan-2-yl)oxy)methyl)benzene (1-9) and p-bromomethylbenzene were replaced by 4-bromo-2,5-bis (((2-methoxypropane-2-yl)oxy)methyl)benzonitrile and 2-ethylthiophene.

¹H NMR (400 MHz, DMSO-d₆) δ 7.79 (s, 1H), 7.72 (d, J=1.3 Hz, 1H), 6.90 (dd, J=7.5, 1.1 Hz, 1H), 6.75 (d, J=7.5 Hz, 1H), 4.98 (d, J=5.0 Hz, 1H), 4.79 (d, J=5.0 Hz, 1H), 4.68 (dd, J=7.9, 1.0 Hz, 1H), 4.58 (dd, J=8.1, 1.0 Hz, 1H), 4.54-4.45 (m, 2H), 4.21 (dd, J=6.9, 5.0 Hz, 1H), 4.15 (dd, J=12.5, 1.0 Hz, 1H), 3.70 (p, J=6.9 Hz, 1H), 3.55 (td, J=7.0, 5.0 Hz, 1H), 3.31 (td, J=7.0, 5.0 Hz, 1H), 2.97 (dq, J=12.4, 8.0 Hz, 1H), 2.82 (dq, J=12.5, 8.0 Hz, 1H), 1.30 (t, J=8.0 Hz, 3H), 1.11 (d, J=6.8 Hz, 3H).

LRMS (ESI, m/z): 402 [M+H]⁺.

Example 92 (1S,3'R,4'S,5'S,6'R)-3',4',5'-trihydroxy-6-(4-methoxyphenyl)-6'-methyl-3',4',5'-trihydroxy-6'-methyl-3',4',5',6'-tetrahydro-3H-spiro[isobenzofuran-1,2'-pyran]-5-nitrile (A92)

The target compound A92 was synthesized according to the synthetic method of A1, wherein 2-bromo-1,4-bis(((2-methoxypropan-2-yl)oxy)methyl)benzene (1-9) and p-bromomethylbenzene were replaced by 4-bromo-2,5-bis (((2-methoxypropane-2-yl)oxy)methyl)benzonitrile and 1-bromo-4-methoxybenzene.

¹H NMR (400 MHz, DMSO-d₆) δ 7.82 (dt, J=13.3, 1.2 Hz, 2H), 7.13-7.05 (m, 2H), 6.92-6.84 (m, 2H), 4.98 (d, J=5.0 Hz, 1H), 4.79 (d, J=5.0 Hz, 1H), 4.68 (dd, J=7.9, 1.0 Hz, 1H), 4.58 (dd, J=8.1, 1.0 Hz, 1H), 4.50 (d, J=5.0 Hz, 1H), 4.22 (dd, J=6.9, 5.0 Hz, 1H), 4.07 (dd, J=12.4, 1.0 Hz, 1H), 4.01-3.93 (m, 1H), 3.79 (s, 3H), 3.70 (p, J=6.9 Hz, 1H), 3.55 (td, J=7.0, 5.0 Hz, 1H), 3.32 (td, J=7.0, 5.0 Hz, 1H), 1.11 (d, J=6.7 Hz, 3H).

LRMS (ESI, m/z): 398 [M+H]⁺.

Example 93 (1S,3'R,4'S,5'S,6'R)-3',4',5,5-trihydroxy-6-(4-ethoxyphenyl)-6'-methyl-3',4',5'-trihydroxy-6'-methyl-3',4',5',6'-tetrahydro-3H-spiro[isobenzofuran-1,2'-pyran]-5-nitrile (A93)

The target compound A93 was synthesized according to the synthetic method of A1, wherein 2-bromo-1,4-bis(((2-methoxypropan-2-yl)oxy)methyl)benzene (1-9) and p-bromomethylbenzene were replaced by 4-bromo-2,5-bis (((2-methoxypropane-2-yl)oxy)methyl)benzonitrile and 1-bromo-4-ethoxybenzene.

¹H NMR (400 MHz, DMSO-d₆) δ 7.82 (dt, J=14.2, 1.1 Hz, 2H), 7.13-7.05 (m, 2H), 6.89-6.81 (m, 2H), 4.98 (d, J=5.0 Hz, 1H), 4.79 (d, J=5.0 Hz, 1H), 4.68 (dd, J=7.9, 1.0 Hz, 1H), 4.58 (dd, J=8.1, 1.0 Hz, 1H), 4.50 (d, J=5.0 Hz, 1H), 4.22 (dd, J=6.9, 5.0 Hz, 1H), 4.18-4.01 (m, 3H), 4.01-3.93 (m, 1H), 3.70 (p, J=6.9 Hz, 1H), 3.55 (td, J=6.9, 5.0 Hz, 1H), 3.32 (td, J=7.0, 5.0 Hz, 1H), 1.34 (t, J=8.0 Hz, 3H), 1.11 (d, J=6.8 Hz, 3H).

LRMS (ESI, nm/z): 412 [M+H]⁺.

Example 94 (1S,3'R,4'S,5'S,6'R)-6'-methyl-6-(4-methylbenzyl)-5-bromo-3',4',5',6'-tetrahydro-3H-spiro[isobenzofuran-1,2'-pyran]-3',4',5'-triol (A94)

The target compound A94 was synthesized according to the synthetic method of A1, wherein 2-bromo-1,4-bis(((2-methoxypropan-2-yl)oxy)methyl)benzene (1-9) was replaced by 1,4-dibromo-2,5-bis(((2-methoxypropane-2-yl)oxy)methyl)benzene.

¹H NMR (400 MHz, DMSO-d₆) δ 7.60 (d, J=1.0 Hz, 1H), 7.43 (s, 1H), 7.36-7.28 (m, 2H), 7.17-7.10 (m, 2H), 4.95 (d, J=5.0 Hz, 1H), 4.77-4.64 (m, 2H), 4.58 (dd, J=8.1, 1.0 Hz, 1H), 4.50 (d, J=5.0 Hz, 1H), 4.31-4.22 (m, 1H), 4.10 (dd, J=6.9, 5.0 Hz, 1H), 3.83 (dd, J=12.5, 1.0 Hz, 1H), 3.70 (p, J=6.9 Hz, 1H), 3.51 (td, J=7.0, 5.0 Hz, 1H), 3.27 (td, J=7.0, 5.0 Hz, 1H), 2.21 (d, J=1.2 Hz, 3H), 1.09 (d, J=6.7 Hz, 3H).

LRMS (ESI, m/z): 435 [M+H]⁺.

Example 95 (1S,3'R,4'S,5'S,6'R)-6'-methyl-6-((5-(4-fluorophenyl)thienyl)-2-methyl)-5-bromo-3-3',4',5', 6'-tetrahydro-3H-spiro[isobenzofuran-1,2'-pyran]-3', 4',5'-triol (A95)

The target compound A95 was synthesized according to the synthetic method of A1, wherein 2-bromo-1,4-bis(((2- methoxy-propan-2-yl)oxy)methyl)benzene (1-9) and p-bromomethylbenzene were replaced by 1,4-dibromo-2,5-bis (((2-methoxypropane-2-yl)oxy)methyl)benzene and 2-(4-fluorophenyl)thiophene.

$^1$H NMR (400 MHz, DMSO-d$_6$) δ 7.73-7.64 (m, 2H), 7.62 (dt, J=7.0, 1.1 Hz, 2H), 7.34-7.21 (m, 3H), 7.02 (dd, J=7.4, 1.5 Hz, 1H), 4.93 (d, J=5.0 Hz, 1H), 4.72-4.55 (m, 3H), 4.51 (dd, J=7.3, 5.0 Hz, 2H), 4.25 (dd, J=7.0, 5.0 Hz, 1H), 4.04 (dd, J=12.3, 1.0 Hz, 1H), 3.70 (p, J=6.9 Hz, 1H), 3.56 (td, J=7.0, 5.0 Hz, 1H), 3.30 (td, J=7.0, 5.0 Hz, 1H), 1.11 (d, J=6.7 Hz, 3H).

LRMS (ESI, m/z): 521 [M+H]$^+$.

Example 96 (1S,3'R,4'S,5'S,6'R)-6'-methyl-6-((5-(2-furyl)thiazolyl)-2-methyl)-5-bromo-3'4',5',6'-tetrahydro-3H-spiro[isobenzofuran-1,2'-pyran]-3',4',5'-triol (A96)

The target compound A96 was synthesized according to the synthetic method of A1, wherein 2-bromo-1,4-bis(((2-methoxypropan-2-yl)oxy)methyl)benzene (1-9) and p-bromomethylbenzene were replaced by 1,4-dibromo-2,5-bis (((2-methoxypropane-2-yl)oxy)methyl)benzene and 5-(furan-2-yl)thiazole.

$^1$H NMR (400 MHz, DMSO-d$_6$) δ 7.70-7.57 (m, 3H), 7.54 (s, 1H), 6.86 (dd, J=7.5, 1.5 Hz, 1H), 6.63 (t, J=7.5 Hz, 1H), 5.02 (dd, J=12.5, 1.0 Hz, 1H), 4.92 (d, J=5.1 Hz, 1H), 4.68 (dd, J=7.9, 1.0 Hz, 1H), 4.58 (dd, J=8.1, 1.0 Hz, 1H), 4.51 (t, J=4.8 Hz, 2H), 4.27-4.16 (m, 2H), 3.70 (p, J=6.9 Hz, 1H), 3.56 (td, J=7.0, 5.0 Hz, 1H), 3.31 (td, J=7.0, 5.0 Hz, 1H), 1.12 (d, J=6.8 Hz, 3H).

LRMS (ESI, m/z): 494 [M+H]$^+$.

Example 97 (1S,3'R,4'S,5'S,6'R)-6'-methyl-6-((5-ethylthienyl)-2-methyl)-5-fluoro-3,4',5',6'-tetrahydro-3H-spiro[iso benzofuran-1,2'-pyran]-3',4',5'-triol (A97)

The target compound A97 was synthesized according to the synthetic method of A1, wherein 2-bromo-1,4-bis(((2-methoxypropan-2-yl)oxy)methyl)benzene (1-9) and p-bromomethylbenzene were replaced by 1,4-dibromo-2,5-bis (((2-methoxypropane-2-yl)oxy)methyl)benzene and 2-ethylthiophene.

$^1$H NMR (400 MHz, DMSO-d$_6$) δ 7.55-7.47 (m, 2H), 6.81-6.70 (m, 2H), 4.97 (d, J=5.0 Hz, 1H), 4.79 (d, J=5.0 Hz, 1H), 4.68 (dd, J=7.9, 1.0 Hz, 1H), 4.58 (dd, J=8.1, 1.0 Hz, 1H), 4.54-4.46 (m, 2H), 4.20 (dd, J=6.9, 5.0 Hz, 1H), 3.92 (dd, J=12.5, 1.0 Hz, 1H), 3.70 (p, J=6.9 Hz, 1H), 3.54 (td. J=7.0, 5.0 Hz, 1H), 3.30 (td. J=7.0, 5.0 Hz, 1H), 2.97 (dq, J=12.5, 8.0 Hz, 1H), 2.83 (dq, J=12.3, 8.0 Hz, 1H), 1.30 (t, J=8.0 Hz, 3H), 1.10 (d, J=6.8 Hz, 3H).

LRMS (ESI, nm/z): 455 [M+H]$^+$.

Example 98 (1S,3'R,4'S,5'S,6'R)-6'-methyl-6-(4-methoxybenzyl)-5-bromo-3',4',5',6'-tetrahydro-3H-spiro[isobenzofuran-1,2'-pyran]-3',4',5'-triol (A98)

The target compound A98 was synthesized according to the synthetic method of A1, wherein 2-bromo-1,4-bis(((2-methoxypropan-2-yl)oxy)methyl)benzene (1-9) and p-bromomethylbenzene were replaced by 1,4-dibromo-2,5-bis (((2-methoxypropane-2-yl)oxy)methyl)benzene and 1-bromo-4-methoxybenzene.

$^1$H NMR (400 MHz, DMSO-d$_6$) δ 7.58 (dt, J=15.5, 1.1 Hz, 2H), 7.09 (dt, J=7.5, 1.1 Hz, 2H), 6.90-6.82 (m, 2H), 4.91 (d, J=5.0 Hz, 1H), 4.68 (dd, J=7.9, 1.0 Hz, 1H), 4.58 (dd, J=8.1, 1.0 Hz, 1H), 4.49 (dd, J=11.1, 5.0 Hz, 2H), 4.30-4.22 (m, 1H), 4.15 (dd, J=7.0, 5.0 Hz, 1H), 3.79 (s, 3H), 3.76-3.64 (m, 2H), 3.54 (td, J=7.0, 5.0 Hz, 1H), 3.28 (td, J=7.0, 5.0 Hz, 1H), 1.11 (d, J=6.9 Hz, 3H).

LRMS (ESI, m/z): 451 [M+H]$^+$.

Example 99 (1S,3'R,4'S,5'S,6'R)-6'-methyl-6-(4-ethoxybenzyl)-5-bromo-3',4',5',6'-tetrahydro-3H-spiro[isobenzofuran-1,2'-pyran]-3',4',5'-triol (A99)

The target compound A99 was synthesized according to the synthetic method of A1, wherein 2-bromo-1,4-bis(((2-methoxypropan-2-yl)oxy)methyl)benzene (1-9) and p-bromomethylbenzene were replaced by 1,4-dibromo-2,5-bis (((2-methoxypropane-2-yl)oxy)methyl)benzene and 1-bromo-4-ethoxybenzene.

$^1$H NMR (400 MHz, DMSO-d$_6$) δ 7.57 (dt, J=4.8, 1.1 Hz, 2H), 7.09 (dt, J=7.5, 1.1 Hz, 2H), 6.89-6.81 (m, 2H), 4.97 (d, J=5.0 Hz, 1H), 4.77 (d, J=5.0 Hz, 1H), 4.68 (dd, J=7.9, 1.0 Hz, 1H), 4.58 (dd, J=8.1, 1.0 Hz, 1H), 4.50 (d, J=5.0 Hz, 1H), 4.23-4.10 (m, 4H), 3.77-3.64 (m, 2H), 3.54 (td, J=7.0, 5.0 Hz, 1H), 3.30 (td, J=7.0, 5.0 Hz, 1H), 1.34 (t, J=8.0 Hz, 3H), 1.10 (d, J=6.8 Hz, 3H).

LRMS (ESI, m/z): 465 [M+H]$^+$.

Example 100 (1S,3'R,4'S,5'S,6'R)-5-methoxy-6'-methyl-6-(4-methylbenzyl)-3',4',5',6'-tetrahydro-3H-spiro[isobenzofuran-1,2'-pyran]-3',4',5'-triol (A100)

The target compound A100 was synthesized according to the synthetic method of A1, wherein 2-bromo-1,4-bis(((2-methoxypropan-2-yl)oxy)methyl)benzene (1-9) was replaced by 1-bromo-4-methoxy-2,5-bis(((2-methoxypropane-2-yl)oxy)methyl)benzene.

$^1$H NMR (400 MHz, DMSO-d$_6$) δ 7.35-7.27 (m, 2H), 7.10 (dt, J=7.4, 1.1 Hz, 2H), 6.95 (s, 1H), 4.97 (d, J=5.0 Hz, 1H), 4.77 (d, J=5.0 Hz, 1H), 4.68 (dd, J=7.9, 1.0 Hz, 1H), 4.58 (dd, J=8.1, 1.0 Hz, 1H), 4.50 (d, J=5.0 Hz, 1H), 4.17 (dd, J=7.0, 5.0 Hz, 1H), 3.74 (s, 3H), 3.72-3.64 (m, 1H), 3.62-3.47 (m, 2H), 3.40 (dd, J=12.4, 1.0 Hz, 1H), 3.29 (td, J=6.9, 5.0 Hz, 1H), 2.21 (d, J=1.2 Hz, 3H), 1.08 (d, J=6.8 Hz, 3H).

LRMS (ESI, m/z): 387 [M+H]$^+$.

Example 101 (1S,3'R,4'S,5'S,6'R)-6-((5-(4-fluorophenyl) thienyl)-2-methyl)-5-methoxy-6'-methyl-3',4',5',6'-tetrahydro-3H-spiro[isobenzofuran-1,2'-pyran]-3',4',5'-triol (A101)

The target compound A101 was synthesized according to the synthetic method of A1, wherein 2-bromo-1,4-bis(((2-methoxypropan-2-yl)oxy)methyl)benzene (1-9) and p-bromomethylbenzene were replaced by 1-bromo-4-methoxy-2, 5-bis (((2-methoxypropane-2-yl)oxy)methyl)benzene and 2-(4-fluorophenyl)thiophene.

$^1$H NMR (400 MHz, DMSO-d$_6$) δ 7.73-7.63 (m, 2H), 7.61 (t, J=1.1 Hz, 1H), 7.32-7.21 (m, 3H), 7.07 (dd, J=7.5, 1.1 Hz, 1H), 6.98 (d, J=1.3 Hz, 1H), 4.97 (d, J=5.0 Hz, 1H), 4.78 (d, J=5.0 Hz, 1H), 4.68 (dd, J=7.9, 1.0 Hz, 1H), 4.58 (dd, J=8.1, 1.0 Hz, 1H), 4.50 (d, J=5.0 Hz, 1H), 4.22 (dd, J=7.0, 5.0 Hz, 1H), 3.99 (dd, J=12.3, 1.0 Hz, 1H), 3.82 (dt, J=12.5, 1.2 Hz, 1H), 3.74 (s, 3H), 3.72-3.64 (m, 1H), 3.54 (td, J=7.0, 5.0 Hz, 1H), 3.31 (td, J=7.0, 5.0 Hz, 1H), 1.10 (d, J=6.9 Hz, 3H).

LRMS (ESI, m/z): 473 [M+H]$^+$.

Example 102 (1S,3'R,4'S,5'S,6'R)-6-((5-(2-furyl) thiazolyl)-2-methyl)-5-methoxy-6'-methyl-3',4',5',6'-tetrahydro-3H-spiro[isobenzofuran-1,2'-pyran]-3',4', 5'-triol (A102)

The target compound A102 was synthesized according to the synthetic method of A1, wherein 2-bromo-1,4-bis(((2-methoxypropan-2-yl)oxy)methyl)benzene (1-9) and p-bromomethylbenzene were replaced by 1-bromo-4-methoxy-2,5-bis (((2-methoxypropane-2-yl)oxy)methyl)benzene and 5-(furan-2-yl)thiazole.

$^1$H NMR (400 MHz, DMSO-d$_6$) δ 7.66 (dd, J=7.6, 1.6 Hz, 1H), 7.57-7.50 (m, 2H), 6.98 (t, J=1.1 Hz, 1H), 6.86 (dd, J=7.5, 1.5 Hz, 1H), 6.62 (t, J=7.5 Hz, 1H), 4.98 (d, J=5.0 Hz, 1H), 4.79 (d, J=5.0 Hz, 1H), 4.68 (dd. J=7.9, 1.0 Hz, 1H), 4.58 (dd, J=8.1, 1.0 Hz, 1H), 4.50 (d, J=5.0 Hz, 1H), 4.33 (dd, J=12.4, 1.0 Hz, 1H), 4.22 (dd, J=7.0, 5.0 Hz, 1H), 4.04 (dd, J=12.5, 1.0 Hz, 1H), 3.74 (s, 3H), 3.69 (q, J=6.8 Hz, 2H), 3.55 (td, J=7.0, 5.0 Hz, 1H), 3.32 (td, J=7.0, 5.0 Hz, 1H), 1.12 (d, J=6.7 Hz, 3H).

LRMS (ESI, nm/z): 446 [M+H]$^+$.

Example 103 (1S,3'R,4'S,5'S,6'R)-6-((5-ethylthienyl)-2-methyl)-5-methoxy-6'-methyl-3',4',5',6'-tetrahydro-3H-spiro[isobenzofuran-1,2'-pyran]-3',4',5'-triol (A103)

The target compound A103 was synthesized according to the synthetic method of A1, wherein 2-bromo-1,4-bis(((2-methoxypropan-2-yl)oxy)methyl)benzene (1-9) and p-bromomethylbenzene were replaced by 1-bromo-4-methoxy-2,5-bis (((2-methoxypropane-2-yl)oxy)methyl)benzene and 2-ethylthiophene.

$^1$H NMR (400 MHz, DMSO-d$_6$) δ 7.52 (d, J=1.1 Hz, 1H), 6.89 (t, J=1.1 Hz, 1H), 6.79 (dd, J=7.5, 1.0 Hz, 1H), 6.72 (d, J=7.5 Hz, 1H), 4.98 (d, J=5.0 Hz, 1H), 4.80 (d, J=5.0 Hz, 1H), 4.68 (dd, J=7.9, 1.0 Hz, 1H), 4.58 (dd, J=8.1, 1.0 Hz, 1H), 4.50 (d, J=5.0 Hz, 1H), 4.22 (dd, J=7.0, 5.0 Hz, 1H), 3.86 (dd, J=12.4, 1.0 Hz, 1H), 3.76-3.64 (m, 5H), 3.54 (td, J=7.0, 5.0 Hz, 1H), 3.31 (td, J=7.0, 5.0 Hz, 1H), 2.96 (dq, J=12.4, 8.0 Hz, 1H), 2.83 (dq, J=12.3, 8.0 Hz, 1H), 1.30 (t, J=8.0 Hz, 3H), 1.11 (d, J=6.8 Hz, 3H).

LRMS (ESI, m/z): 407 [M+H]$^+$.

Example 104 (1S,3'R,4'S,5'S,6'R)-5-methoxy-6-((4-methoxyphenyl)-6'-methyl)-3',4',5',6'-tetrahydro-3H-spiro[isobenzofuran-1,2'-pyran]-3',4',5'-triol (A104)

The target compound A104 was synthesized according to the synthetic method of A1, wherein 2-bromo-1,4-bis(((2-methoxy-propan-2-yl)oxy)methyl)benzene (1-9) and p-bromomethylbenzene were replaced by 1-bromo-4-methoxy-2,5-bis (((2-methoxypropane-2-yl)oxy)methyl)benzene and 1-bromo-4-methoxybenzene.

$^1$H NMR (400 MHz, DMSO-d$_6$) δ 7.49 (d, J=1.0 Hz, 1H), 7.13-7.05 (m, 2H), 6.96 (s, 1H), 6.89-6.81 (m, 2H), 4.96 (d, J=5.0 Hz, 1H), 4.77 (d, J=5.0 Hz, 1H), 4.68 (dd, J=7.9, 1.0 Hz, 1H), 4.58 (dd, J=8.1, 1.0 Hz, 1H), 4.50 (d, J=5.0 Hz, 1H), 4.15 (dd, J=6.9, 5.0 Hz, 1H), 3.79 (s, 3H), 3.74 (s, 3H), 3.69 (q, J=6.8 Hz, 1H), 3.63-3.47 (m, 2H), 3.39 (dd, J=12.4, 1.0 Hz, 1H), 3.29 (td, J=7.0, 5.0 Hz, 1H), 1.10 (d, J=6.7 Hz, 3H).

LRMS (ESI, n/i): 403 [M+H]$^+$.

Example 105 (1S,3'R,4'S,5'S,6'R)-5-methoxy-6-(4-ethoxyphenyl)-6'-methyl)-3',4',5',6'-tetrahydro-3H-spiro[isobenzofuran-1,2'-pyran]-3',4',5'-triol (A105)

The target compound A105 was synthesized according to the synthetic method of A1, wherein 2-bromo-1,4-bis(((2-methoxy-propan-2-yl)oxy)methyl)benzene (1-9) and p-bromomethylbenzene were replaced by 1-bromo-4-methoxy-2,5-bis (((2-methoxypropane-2-yl)oxy)methyl)benzene and 1-bromo-4-ethoxybenzene.

$^1$H NMR (400 MHz, DMSO-d$_6$) δ 7.51 (t, J=1.1 Hz, 1H), 7.09 (dd, J=7.4, 1.2 Hz, 2H), 6.95 (d, J=1.1 Hz, 1H), 6.88-6.82 (m, 2H), 4.97 (d, J=5.0 Hz, 1H), 4.77 (d, J=5.0 Hz, 1H), 4.68 (dd, J=7.9, 1.0 Hz, 1H), 4.58 (dd, J=8.1, 1.0 Hz, 1H), 4.50 (d, J=5.0 Hz, 1H), 4.22-4.04 (m, 3H), 3.74 (s, 3H), 3.69 (q, J=6.8 Hz, 1H), 3.61-3.48 (m, 2H), 3.45-3.36 (m, 1H), 3.29 (td, J=7.0, 5.0 Hz, 1H), 1.34 (t, J=8.0 Hz, 3H), 1.08 (d, J=6.7 Hz, 3H).

LRMS (ESI, m/z): 417 [M+H]$^+$.

Example 106 (1S,3'R,4'S,5'S,6'R)-6-(benzofuran-5-ylmethyl)-5-chloro-6'-methyl-3',4',5',6'-tetrahydro-3H-spiro[isobenzofuran-1,2'-pyran]-3',4',5'-triol (A106)

The target compound A106 was synthesized according to the synthetic method of A1, wherein 2-bromo-1,4-bis(((2-methoxypropan-2-yl)oxy)methyl)benzene (1-9) and p-bromomethylbenzene were replaced by 1-bromo-4-chloro-2,5-bis (((2-methoxypropane-2-yl)oxy)methyl)benzene and 5-bromobenzofuran.

$^1$H NMR (400 MHz, DMSO-d$_6$) δ 7.49-7.31 (m, 4H), 7.17 (m, 2H), 6.43 (t, J=1.1 Hz, 1H), 5.11 (d, J=2.7 Hz, 2H), 4.29 (s, 2H), 3.85 (dq, J=9.8, 6.2 Hz, 1H), 3.73-3.65 (m, 2H), 3.12 (m, 1H), 1.20 (d, J=6.3 Hz, 3H).

LRMS (ESI, m/z): 417 [M+H]$^+$.

Example 107 (1S,3'R,4'S,5'S,6'R)-5-chloro-6-(4-ethoxyl-3-fluorophenyl)-6'-methyl-3',4',5',6'-tetrahydro-3H-spiro[isobenzofuran-1,2'-pyran]-3',4',5'-triol (A107)

The target compound A107 was synthesized according to the synthetic method of A1, wherein 2-bromo-1,4-bis(((2-methoxypropan-2-yl)oxy)methyl)benzene (1-9) and p-bromomethylbenzene were replaced by 1-bromo-4-chloro-2,5-bis (((2-methoxypropane-2-yl)oxy)methyl)benzene and 4-bromo-2-fluorophenetole.

$^1$H NMR (400 MHz, DMSO-d$_6$) δ 7.38 (d, J=3.7 Hz, 1H), 7.23 (s, 1H), 7.02-6.90 (m, 3H), 5.16-5.06 (m, 2H), 4.07 (m, 4H), 3.88 (ddd, J=8.7, 6.2, 2.1 Hz, 1H), 3.77-3.68 (m, 2H), 3.16 (ddd, J=9.6, 6.4, 2.9 Hz, 1H), 1.40 (td, J=7.0, 2.7 Hz, 3H), 1.23 (d, J=6.2 Hz, 3H).

LRMS (ESI, m/z): 439 [M+H]$^+$.

Example 108 1-(4-(((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)methyl)phenyl) cyclopropane-1-formonitrile (A108)

The target compound A108 was synthesized according to the synthetic method of A1, wherein 2-bromo-1,4-bis(((2-methoxypropan-2-yl)oxy)methyl)benzene (1-9) and p-bromomethylbenzene were replaced by 1-bromo-4-chloro-2,5-bis (((2-methoxypropane-2-yl)oxy)methyl)benzene and 1-(4-bromophenyl)cyclopropanecarbonitrile.

$^1$H NMR (400 MHz, DMSO-d$_6$) δ 7.39 (s, 1H), 7.29-7.21 (m, 5H). 5.16-5.07 (m, 2H), 4.15 (s, 2H), 3.92-3.83 (m, 1H), 3.76-3.67 (m, 2H), 3.20-3.11 (m, 1H), 1.70 (m, 2H), 1.49-1.43 (m, 2H), 1.22 (d, J=6.2 Hz, 3H).

LRMS (ESI, m/z): 442 [M+H]$^+$.

Example 109 1-(5-(((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)methyl)thiophen-2-yl)cyclopropane-1-formonitrile (A109)

The target compound A109 was synthesized according to the synthetic method of A1, wherein 2-bromo-1,4-bis(((2-methoxy-propan-2-yl)oxy)methyl)benzene (1-9) and p-bromomethylbenzene were replaced by 1-bromo-4-chloro-2,5-bis (((2-methoxypropane-2-yl)oxy)methyl)benzene and 1-thiophene-2-ylcyclopropaneformonitrile.

$^1$H NMR (400 MHz, DMSO-$d_6$) δ 7.40 (s, 1H), 7.33 (s, 1H), 6.88 (d, J=3.5 Hz, 1H), 6.72 (d, J=3.6 Hz, 1H), 5.11 (d, J=2.5 Hz, 2H), 4.27 (d, J=2.2 Hz, 2H), 3.88 (dd, J=9.7, 6.3 Hz, 1H), 3.78-3.67 (m, 2H), 3.17 (ddd, J=9.3, 7.9, 1.1 Hz, 1H), 1.74-1.68 (m, 2H), 1.46-1.41 (m, 2H), 1.23 (d, J=6.2 Hz, 3H).

LRMS (ESI, m/z): 448 [M+H]$^+$.

Example 110 (1S,3'R,4'S,5'S,6'R)-5-chloro-6'-methyl-6-(4-trifluoromethylphenyl)-3',4',5',6'-tetrahydro-3H-spiro[isobenzofuran-1,2'-pyran]-3',4',5'-triol (A110)

The target compound A110 was synthesized according to the synthetic method of A1, wherein 2-bromo-1,4-bis(((2-methoxypropan-2-yl)oxy)methyl)benzene (1-9) and p-bromomethylbenzene were replaced by 1-bromo-4-chloro-2,5-bis (((2-methoxypropane-2-yl)oxy)methyl)benzene and 4-bromotrifluorotoluene.

$^1$H NMR (600 MHz, DMSO-$d_6$) δ 7.58 (d, J=8.1 Hz, 2H), 7.41 (s, 1H), 7.40 (s, 2H), 7.31 (s, 1H), 5.16-5.09 (m, 2H), 4.25 (s, 2H), 3.89 (dd, J=9.6, 6.3 Hz, 1H), 3.77-3.70 (m, 2H), 3.16 (ddd, J=9.3, 7.9, 1.1 Hz, 1H), 1.23 (d, J=6.3 Hz, 3H).

LRMS (ESI, m/z): 445 [M+H]$^+$.

Example 111 ((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)(4-(trifluoromethyl)phenyl)ketone (A11)

The target compound A111 was synthesized according to the synthetic method of A1, wherein 2-bromo-1,4-bis(((2-methoxypropan-2-yl)oxy)methyl)benzene (1-9) and p-bromomethylbenzene were replaced by 1-bromo-4-chloro-2,5-bis (((2-methoxypropane-2-yl)oxy)methyl)benzene and 4-bromotrifluorotoluene.

$^1$H NMR (400 MHz, DMSO-$d_6$) δ 8.00 (d, J=8.2 Hz, 1H), 7.86 (d, J=8.0 Hz, 2H), 7.56 (s, 1H), 7.49 (s, 1H), 5.23 (t, J=1.4 Hz, 2H), 3.91 (dq, J=9.6, 6.2 Hz, 1H), 3.83-3.70 (m, 2H), 3.17 (dd, J=9.6, 8.5 Hz, 1H), 1.25 (d, J=6.2 Hz, 3H).

LRMS (ESI, nm/z): 459 [M+H]$^+$.

Example 112 ((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)(3-fluoro-4-(trifluoromethyl)phenyl)ketone (A112)

The target compound A112 was synthesized according to the synthetic method of A1, wherein 2-bromo-1,4-bis(((2-methoxypropan-2-yl)oxy)methyl)benzene (1-9) and p-bromomethylbenzene were replaced by 1-bromo-4-chloro-2,5-bis (((2-methoxypropane-2-yl)oxy)methyl)benzene and 4-bromo-2-fluorotrifluorotoluene.

$^1$H NMR (400 MHz, DMSO-$d_6$) δ 7.93-7.83 (m, 2H), 7.80 (d, J=1.1 Hz, 1H), 7.71-7.62 (m, 1H), 7.57 (dd, J=7.5, 2.0 Hz, 1H), 5.03 (d, J=5.0 Hz, 1H), 4.80 (d, J=5.0 Hz, 1H), 4.73-4.53 (m, 3H), 4.50 (d, J=5.0 Hz, 1H), 3.79-3.64 (m, 2H), 3.36 (td, J=7.0, 5.0 Hz, 1H), 1.10 (d, J=6.8 Hz, 3H).

LRMS (ESI, m/z): 477 [M+H]$^+$.

Example 113 ((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)(5-ethylthiophene-2-yl)ketone (A113)

The target compound A113 was synthesized according to the synthetic method of A1, wherein 2-bromo-1,4-bis(((2-methoxy-propan-2-yl)oxy)methyl)benzene (1-9) and p-bromomethylbenzene were replaced by 1-bromo-4-chloro-2,5-bis (((2-methoxypropane-2-yl)oxy)methyl)benzene and 2-ethylthiophene.

$^1$H NMR (400 MHz, DMSO-$d_6$) δ 7.53 (s, 1H), 7.45 (s, 1H), 7.33 (d, J=3.8 Hz, 1H), 6.96 (d, J=3.9 Hz, 1H), 5.21 (dd, J=2.2, 1.0 Hz, 2H), 3.90 (dq, J=9.6, 6.2 Hz, 1H), 3.82-3.71 (m, 2H), 3.17 (dd, J=9.7, 8.5 Hz, 1H), 2.97 (qd, J=7.5, 0.9 Hz, 2H), 1.37 (t, J=7.5 Hz, 4H), 1.25 (d, J=6.3 Hz, 3H).

LRMS (ESI, m/z): 425 [M+H]$^+$.

Example 114 (1S,3'R,4'S,5'S,6'R)-5-chloro-6-((5-(2-methoxyethyl)thiophene-2-yl)methyl)-6'-methyl-3-3',4',5',6'-tetrahydro-3H-spiro[isobenzofuran-1,2'-pyran]-3',4',5'-triol (A114)

The target compound A114 was synthesized according to the synthetic method of A1, wherein 2-bromo-1,4-bis(((2-methoxy-propan-2-yl)oxy)methyl)benzene (1-9) and p-bromomethylbenzene were replaced by 1-bromo-4-chloro-2,5-bis (((2-methoxypropane-2-yl)oxy)methyl)benzene and 2-(2-methoxyethyl)thiophene.

$^1$H NMR (400 MHz, DMSO-$d_6$) δ 7.35 (s, 1H), 7.26 (s, 1H), 6.68-6.60 (m, 2H), 5.08 (d, J=2.2 Hz, 2H), 4.21 (d, J=3.7 Hz, 2H), 3.85 (dq, J=9.7, 6.2 Hz, 1H), 3.73-3.65 (m, 2H), 3.56 (t, J=6.6 Hz, 2H), 3.32 (s, 3H), 3.14 (ddd, J=9.3, 6.7, 2.3 Hz, 1H), 2.96 (t, J=6.6 Hz, 2H), 1.20 (d, J=6.3 Hz, 3H).

LRMS (ESI, m/z): 441 [M+H]$^+$.

Example 115 (1S,3'R,4'S,5'S,6'R)-5-chloro-6-((5-(2-ethoxyethyl)thiophene-2-yl)methyl)-6'-methyl-3',4',5',6'-tetrahydro-3H-spiro[isobenzofuran-1,2'-pyran]-3',4',5'-triol (A115)

The target compound A115 was synthesized according to the synthetic method of A1, wherein 2-bromo-1,4-bis(((2-methoxy-propan-2-yl)oxy)methyl)benzene (1-9) and p-bromomethylbenzene were replaced by 1-bromo-4-chloro-2,5-bis (((2-methoxypropane-2-yl)oxy)methyl)benzene and 2-(2-ethoxyethyl)thiophene.

$^1$H NMR (400 MHz, DMSO-$d_6$) δ 7.38 (s, 1H), 7.29 (s, 1H), 6.70-6.63 (m, 2H), 5.11 (d, J=2.6 Hz, 2H), 4.25 (d, J=5.2 Hz, 2H), 3.87 (dd, J=9.6, 6.3 Hz, 1H), 3.75-3.67 (m, 2H), 3.63 (t, J=6.7 Hz, 2H), 3.52 (q, J=7.0 Hz, 2H), 3.16 (ddd, J=9.2, 6.4, 2.5 Hz, 1H), 3.03-2.95 (m, 2H), 1.23 (d, J=6.2 Hz, 3H), 1.19 (t, J=7.0 Hz, 3H).

LRMS (ESI, m/z): 455 [M+H]$^+$.

Example 116 (1S,3'R,4'S,5'S,6'R)-5-chloro-6-((5-(2-propoxyethyl)thiophene-2-yl)methyl)-6'-methyl-3',4',5',6'-tetrahydro-3H-spiro[isobenzofuran-1,2'-pyran]-3',4',5'-triol (A116)

The target compound A116 was synthesized according to the synthetic method of A1, wherein 2-bromo-1,4-bis(((2- methoxy-propan-2-yl)oxy)methyl)benzene (1-9) and p-bromomethylbenzene were replaced by 1-bromo-4-chloro-2,5-bis (((2-methoxypropane-2-yl)oxy)methyl)benzene and 2-(2-propoxyethyl)thiophene.

¹H NMR (400 MHz, DMSO-d₆) δ 7.38 (s, 1H), 7.29 (s, 1H), 6.66 (d, J=4.4 Hz, 2H), 5.11 (d, J=2.8 Hz, 2H), 4.25 (d, J=6.2 Hz, 2H), 3.94-3.83 (m, 1H), 3.76-3.67 (m, 2H), 3.62 (t, J=6.6 Hz, 2H), 3.43 (t, J=6.6 Hz, 2H), 3.16 (ddd, J=9.3, 6.5, 2.4 Hz, 1H), 3.00 (t, J=6.6 Hz, 2H), 1.59 (h, J=7.1 Hz, 2H), 1.23 (d, J=6.2 Hz, 3H), 0.93 (t, J=7.4 Hz, 3H).

LRMS (ESI, m/z): 469 [M+H]⁺.

Example 117 1-(5-((((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)methyl)thiophene-2-yl)ethanone (A117)

The target compound A117 was synthesized according to the synthetic method of A1, wherein 2-bromo-1,4-bis(((2-methoxy-propan-2-yl)oxy)methyl)benzene (1-9) and p-bromomethylbenzene were replaced by 1-bromo-4-chloro-2,5-bis (((2-methoxypropane-2-yl)oxy)methyl)benzene and 2-acetylthiophene.

¹H NMR (400 MHz, DMSO-d₆) δ 7.68 (d, J=3.8 Hz, 1H), 7.39 (s, 1H), 7.34 (s, 1H), 6.96-6.89 (m, 1H), 5.10 (d, J=2.6 Hz, 2H), 4.34 (t, J=1.3 Hz, 2H), 3.85 (dq, J=9.6, 6.2 Hz, 1H), 3.76-3.65 (m, 2H), 3.18-3.10 (m, 1H), 2.48 (s, 3H), 1.20 (d, J=6.2 Hz, 3H).

LRMS (ESI, m/z): 425 [M+H]⁺.

Example 118 (1S,3'R,4'S,5'S,6'R)-5-chloro-6-((5-(1-hydroxyethyl)thiophene-2-yl)methyl)-6'-methyl-3',4',5',6'-tetrahydro-3H-spiro[isobenzofuran-1,2'-pyran]-3',4',5'-triol (A118)

The target compound A118 was synthesized according to the synthetic method of A1, wherein 2-bromo-1,4-bis(((2-methoxy-propan-2-yl)oxy)methyl)benzene (1-9) and p-bromomethylbenzene were replaced by 1-bromo-4-chloro-2,5-bis (((2-methoxypropane-2-yl)oxy)methyl)benzene and 1-(thiophene-2-yl)-1-ethanol.

¹H NMR (400 MHz, DMSO-d₆) δ 7.37 (s, 1H), 7.29 (s, 1H), 6.67 (s, 2H), 5.10 (d, J=2.3 Hz, 2H), 4.24 (d, J=3.6 Hz, 2H), 3.88 (dq, J=9.4, 6.2 Hz, 1H), 3.79-3.67 (m, 4H), 3.17 (ddd, J=9.3, 6.8, 2.1 Hz, 1H), 2.95 (t, J=6.8 Hz, 2H), 1.23 (d, J=6.2 Hz, 3H).

LRMS (ESI, nm/z): 427 [M+H]⁺.

Example 119 (1S,3'R,4'S,5'S,6'R)-5-chloro-6-((5-(2-hydroxyethyl)thiophene-2-yl)methyl)-6'-methyl-3',4',5',6'-tetrahydro-3H-spiro[isobenzofuran-1,2'-pyran]-3',4',5'-triol (A119)

The target compound A119 was synthesized according to the synthetic method of A1, wherein 2-bromo-1,4-bis(((2-methoxy-propan-2-yl)oxy)methyl)benzene (1-9) and p-bromomethylbenzene were replaced by 1-bromo-4-chloro-2,5-bis (((2-methoxypropane-2-yl)oxy)methyl)benzene and 2-thiopheneethanol.

¹H NMR (400 MHz, DMSO-d₆) δ 7.35 (s, 1H), 7.27 (s, 1H), 6.76 (d, J=3.5 Hz, 1H), 6.66 (dd, J=3.5, 1.0 Hz, 1H), 5.08 (d, J=2.4 Hz, 2H), 4.32-4.14 (m, 2H), 3.85 (dd, J=9.6, 6.2 Hz, 1H), 3.76-3.62 (m, 2H), 3.13 (ddd, J=9.3, 6.5, 2.4 Hz, 1H), 1.47 (d, J=6.5 Hz, 3H), 1.20 (d, J=6.3 Hz, 3H).

LRMS (ESI, m/z): 427 [M+H]⁺.

Example 120 (1S,3'R,4'S,5'S,6'R)-5-chloro-6-((5-ethylthiophene-2-yl)(hydroxymethyl)-6'-methyl-1-3',4',5',6'-tetrahydro-3H-spiro[isobenzofuran-1,2'-pyran]-3',4',5'-triol (A120)

The target compound A120 was synthesized according to the synthetic method of A1, wherein 2-bromo-1,4-bis(((2-methoxy-propan-2-yl)oxy)methyl)benzene (1-9) and p-bromomethylbenzene were replaced by 1-bromo-4-chloro-2,5-bis (((2-methoxypropane-2-yl)oxy)methyl)benzene and 2-ethylthiophene.

¹H NMR (400 MHz, DMSO-d₆) δ 7.72 (s, 1H), 7.36 (s, 1H), 6.62 (dd, J=3.5, 0.8 Hz, 1H), 6.61-6.58 (m, 1H), 6.28 (s, 1H), 5.14 (s, 2H), 3.92-3.85 (m, 1H), 3.81-3.70 (m, 2H), 3.19 (t, J=9.2 Hz, 1H), 2.79 (qd, J=7.5, 1.0 Hz, 2H), 1.27 (t, J=7.5 Hz, 3H), 1.23 (d, J=6.3 Hz, 3H).

LRMS (ESI, m/z): 427 [M+H]⁺.

Example 121 2-(5-(((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)methyl)thiophene-2-yl)acetic acid (A121)

The target compound A121 was synthesized according to the synthetic method of A1, wherein 2-bromo-1,4-bis(((2-methoxypropan-2-yl)oxy)methyl)benzene (1-9) and p-bromomethylbenzene were replaced by 1-bromo-4-chloro-2,5-bis (((2-methoxypropane-2-yl)oxy)methyl)benzene and 2-thiopheneacetic acid.

¹H NMR (400 MHz, DMSO-d₆) δ 11.25 (s, 1H), 7.62 (dt, J=11.5, 1.1 Hz, 2H), 6.91-6.79 (m, 2H), 5.08 (d, J=5.1 Hz, 1H), 4.80 (d, J=5.1 Hz, 1H), 4.68 (dd, J=18.2, 1.1 Hz, 1H), 4.64-4.53 (m, 3H), 4.50 (d, J=4.9 Hz, 1H), 4.07 (d, J=12.5 Hz, 1H), 3.94 (d, J=12.3 Hz, 1H), 3.85 (dt, J=12.4, 1.1 Hz, 1H), 3.80-3.64 (m, 2H), 3.35 (td, J=7.0, 5.0 Hz, 1H), 1.09 (d, J=6.8 Hz, 3H).

LRMS (ESI, m/z): 441 [M+H]⁺.

Example 122 2-(5-(((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)methyl)thiophene-2-yl)methylacetate (A122)

The target compound A122 was synthesized according to the synthetic method of A1, wherein 2-bromo-1,4-bis(((2-methoxypropan-2-yl)oxy)methyl)benzene (1-9) and p-bromomethylbenzene were replaced by 1-bromo-4-chloro-2,5-bis (((2-methoxypropane-2-yl)oxy)methyl)benzene and 2-thiophenemethylacetate.

¹H NMR (400 MHz, DMSO-d₆) δ 7.76 (d, J=1.0 Hz, 1H), 7.60 (d, J=1.0 Hz, 1H), 6.81-6.70 (m, 2H), 5.23 (d, J=4.9 Hz, 1H), 4.88 (d, J=5.1 Hz, 1H), 4.69 (dd, J=18.2, 1.0 Hz, 1H), 4.65-4.53 (m, 2H), 4.53-4.43 (m, 2H), 4.36 (dd, J=12.5, 1.0 Hz, 1H), 4.27 (d, J=12.4 Hz, 1H), 3.94 (dd, J=12.3, 2.1 Hz, 1H), 3.81-3.64 (m, 2H), 3.61-3.49 (m, 4H), 1.11 (d, J=6.8 Hz, 3H).

LRMS (ESI, nm/z): 455 [M+H]⁺.

Example 123 2-(5-(((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)methyl)thiophene-2-yl)ethylacetate (A123)

The target compound A123 was synthesized according to the synthetic method of A1, wherein 2-bromo-1,4-bis(((2-methoxypropan-2-yl)oxy)methyl)benzene (1-9) and p-bromomethylbenzene were replaced by 1-bromo-4-chloro-2,5-bis (((2-methoxypropane-2-yl)oxy)methyl)benzene and 2-thiopheneethylacetate.

$^1$H NMR (400 MHz, DMSO-d$_6$) δ 7.74 (t, J=1.0 Hz, 1H), 7.61 (s, 1H), 6.77 (dd, J=7.5, 1.3 Hz, 1H), 6.69 (dd, J=7.5, 2.0 Hz, 1H), 5.08 (d, J=5.1 Hz, 1H), 4.91-4.77 (m, 2H), 4.73-4.53 (m, 4H), 4.49 (qd, J=8.7, 8.0, 6.2 Hz, 2H), 4.25 (d, J=12.3 Hz, 1H), 3.95 (ddd, J=16.6, 12.3, 1.5 Hz, 2H), 3.79 (td, J=7.0, 5.0 Hz, 1H), 3.70 (p, J=6.8 Hz, 1H), 3.36 (td, J=7.0, 5.0 Hz, 1H), 1.20 (t, J=7.9 Hz, 3H), 1.10 (d, J=6.8 Hz, 3H).

LRMS (ESI, m/z): 469 [M+H]$^+$.

Example 124 2-(5-(((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)methyl)thiophene-2-yl)-N-methylacetamide (A124)

The target compound A124 was synthesized according to the synthetic method of A1, wherein 2-bromo-1,4-bis(((2-methoxy-propan-2-yl)oxy)methyl)benzene (1-9) and p-bromomethylbenzene were replaced by 1-bromo-4-chloro-2,5-bis (((2-methoxypropane-2-yl)oxy)methyl)benzene and N-methyl-2-thiopheneacetamide.

$^1$H NMR (400 MHz, DMSO-d$_6$) δ 7.78 (s, 1H), 7.60 (s, 1H), 6.85-6.71 (m, 2H), 6.20 (s, 1H), 5.22 (d, J=5.1 Hz, 1H), 4.89 (d, J=5.1 Hz, 1H), 4.69 (dd, J=18.2, 1.0 Hz, 1H), 4.66-4.53 (m, 2H), 4.53-4.42 (m, 2H), 4.34 (dd, J=12.5, 1.0 Hz, 1H), 4.09 (d, J=12.4 Hz, 1H), 3.81-3.64 (m, 3H), 3.55 (td, J=7.0, 5.0 Hz, 1H), 2.79 (s, 3H), 1.11 (d, J=6.8 Hz, 3H).

LRMS (ESI, m/z): 454 [M+H]$^+$.

Example 125 2-(5-(((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)methyl)thiophene-2-yl)-N-ethylacetamide (A125)

The target compound A125 was synthesized according to the synthetic method of A1, wherein 2-bromo-1,4-bis(((2-methoxypropan-2-yl)oxy)methyl)benzene (1-9) and p-bromomethylbenzene were replaced by 1-bromo-4-chloro-2,5-bis (((2-methoxypropane-2-yl)oxy)methyl)benzene and N-ethyl-2-thiopheneacetamide.

$^1$H NMR (400 MHz, DMSO-d$_6$) δ 8.15 (s, 1H), 7.63 (dt, J=10.2, 1.1 Hz, 2H), 6.84 (dd, J=7.4, 1.1 Hz, 1H), 6.77 (dd, J=7.4, 1.0 Hz, 1H), 5.25 (d, J=4.9 Hz, 1H), 4.87 (d, J=5.1 Hz, 1H), 4.73-4.53 (m, 4H), 4.50 (d, J=4.9 Hz, 1H), 3.93-3.62 (m, 5H), 3.52 (td, J=6.9, 5.0 Hz, 1H), 3.32 (dq, J=12.5, 8.1 Hz, 1H), 2.92 (dq, J=12.3, 7.9 Hz, 1H), 1.12 (d, J=6.8 Hz, 3H), 0.99 (t, J=8.0 Hz, 3H).

LRMS (ESI, m/z): 468 [M+H]$^+$.

Example 126 2-(5-(((1S,3'R,4'S,5'S,6'R)-5-chloro-3',4',5'-trihydroxy-6'-methyl-3'4',5',6'-tetrahydro-3H-spiro[isobenzofuran-1,2'-pyran]-6-yl)methyl)thiophene-2-yl)-N,N-dimethylacetamide (A126)

The target compound A126 was synthesized according to the synthetic method of A1, wherein 2-bromo-1,4-bis(((2-methoxypropan-2-yl)oxy)methyl)benzene (1-9) and p-bromomethylbenzene were replaced by 1-bromo-4-chloro-2,5-bis (((2-methoxypropane-2-yl)oxy)methyl)benzene and N,N-dimethyl-2-thiopheneacetamide.

$^1$H NMR (400 MHz, DMSO-d$_6$) δ 7.67 (d, J=1.1 Hz, 1H), 7.60 (d, J=1.1 Hz, 1H), 6.87-6.76 (m, 2H), 4.93 (dd, J=11.0, 5.0 Hz, 2H), 4.68 (dd, J=18.4, 1.0 Hz, 1H), 4.62-4.52 (m, 2H), 4.50 (d, J=4.9 Hz, 1H), 4.26 (dd, J=6.9, 5.0 Hz, 1H), 4.08-3.96 (m, 2H), 3.76-3.60 (m, 3H), 3.38 (td, J=6.9, 5.0 Hz, 1H), 2.94 (s, 6H), 1.10 (d, J=6.8 Hz, 3H).

LRMS (ESI, m/z): 468 [M+H]$^+$.

Example 127 2-(5-(((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)methyl)thiophene-2-yl)-1-(pyrrolidine-1-yl)ethyl-1-one (A127)

The target compound A127 was synthesized according to the synthetic method of A1, wherein 2-bromo-1,4-bis(((2-methoxy-propan-2-yl)oxy)methyl)benzene (1-9) and p-bromomethylbenzene were replaced by 1-bromo-4-chloro-2,5-bis (((2-methoxypropane-2-yl)oxy)methyl)benzene and 1-(pyrrole-1-yl)-2-thiopheneethylketone.

$^1$H NMR (400 MHz, DMSO-d$_6$) δ 7.62 (d, J=16.6 Hz, 6H), 6.86-6.74 (m, 6H), 5.34 (d, J=4.9 Hz, 3H), 4.87 (d, J=4.9 Hz, 3H), 4.73-4.58 (m, 11H), 4.58-4.47 (m, 4H), 4.35 (d, J=12.4 Hz, 3H), 3.89-3.81 (m, 8H), 3.81 (s, 1H), 3.80-3.64 (m, 7H), 3.61-3.48 (m, 6H), 3.11-3.01 (m, 6H), 1.86-1.61 (m, 12H), 1.12 (d, J=6.7 Hz, 9H).

LRMS (ESI, m/z): 494 [M+H]$^+$.

Example 128 2-(5-(((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)methyl)thiophene-2-yl)-1-morpholine-ethyl-1-one (A128)

The target compound A128 was synthesized according to the synthetic method of A1, wherein 2-bromo-1,4-bis(((2-methoxy-propan-2-yl)oxy)methyl)benzene (1-9) and p-bromomethylbenzene were replaced by 1-bromo-4-chloro-2,5-bis (((2-methoxypropane-2-yl)oxy)methyl)benzene and 1-(morpholine-1-yl)-2-thiophene-ethylketone.

$^1$H NMR (400 MHz, DMSO-d$_6$) δ 7.66 (s, 1H), 7.60 (s, 1H), 6.83-6.71 (m, 2H), 4.96 (d, J=5.1 Hz, 1H), 4.89 (d, J=5.1 Hz, 1H), 4.73-4.61 (m, 2H), 4.57 (dd, J=18.4, 1.0 Hz, 1H), 4.50 (d, J=4.9 Hz, 1H), 4.37-4.23 (m, 2H), 4.22-3.93 (m, 6H), 3.87 (dd, J=12.3, 1.0 Hz, 1H), 3.76-3.57 (m, 3H), 3.39 (td. J=7.0, 5.0 Hz, 1H), 3.27-3.15 (m, 2H), 1.11 (d, J=6.7 Hz, 3H).

LRMS (ESI, m/z): 510 [M+H]$^+$.

Example 129 5-(((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)methyl)thiophene-2-carboxaldehyde (A129)

The target compound A129 was synthesized according to the synthetic method of A1, wherein 2-bromo-1,4-bis(((2-methoxypropan-2-yl)oxy)methyl)benzene (1-9) and p-bromomethylbenzene were replaced by 1-bromo-4-chloro-2,5-bis (((2-methoxypropane-2-yl)oxy)methyl)benzene and 2-thiophenecarboxaldehyde.

$^1$H NMR (400 MHz, DMSO-d$_6$) δ 9.79 (s, 1H), 7.77 (d, J=3.8 Hz, 1H), 7.41 (d, J=16.2 Hz, 2H), 7.05 (d, J=3.8 Hz, 1H), 5.13 (d, J=2.7 Hz, 2H), 4.42 (s, 2H), 3.94-3.83 (m, 1H), 3.80-3.66 (m, 2H), 3.17 (t, J=8.9 Hz, 1H), 1.23 (d, J=6.3 Hz, 3H).

LRMS (ESI, m/z): 411 [M+H]$^+$.

Example 130 (1S,3'R,4'S,5'S,6'R)-5-chloro-6-((5-(hydroxymethyl)thiophene-2-yl)methyl)-6'-methyl-3',4',5',6'-tetrahydro-3H-spiro[isobenzofuran-1,2'-pyran]-3',4',5'-triol (A130)

The target compound A130 was synthesized according to the synthetic method of A1, wherein 2-bromo-1,4-bis(((2- methoxy-propan-2-yl)oxy)methyl)benzene (1-9) and p-bromomethylbenzene were replaced by 1-bromo-4-chloro-2,5-bis (((2-methoxypropane-2-yl)oxy)methyl)benzene and 2-thiophenemethanol.

$^1$H NMR (400 MHz, DMSO-d$_6$) δ 7.62 (dd, J=2.6, 1.2 Hz, 2H), 7.02 (dt, J=7.6, 1.8 Hz, 1H), 6.74 (dd, J=7.5, 2.2 Hz, 1H), 5.15 (t, J=5.5 Hz, 1H), 5.01 (dd, J=5.0, 3.0 Hz, 1H), 4.91-4.77 (m, 2H), 4.73-4.53 (m, 3H), 4.50 (d, J=4.9 Hz, 1H), 4.44 (dd, J=12.3, 1.0 Hz, 1H), 3.91 (ddd, J=12.3, 2.2, 1.0 Hz, 1H), 3.78-3.64 (m, 2H), 3.36 (td, J=6.9, 5.0 Hz, 1H), 1.09 (d, J=6.8 Hz, 3H).

LRMS (ESI, m/z): 413 [M+H]$^+$.

Example 131 (1S,3'R,4'S,5'S,6'R)-5-chloro-6-((5-(difluoromethyl)thiophene-2-yl)methyl)-6'-methyl-1-3',4',5',6'-tetrahydro-3H-spiro[isobenzofuran-1,2'-pyran]-3',4',5'-triol (A131)

The target compound A131 was synthesized according to the synthetic method of A1, wherein 2-bromo-1,4-bis(((2-methoxy-propan-2-yl)oxy)methyl)benzene (1-9) and p-bromomethylbenzene were replaced by 1-bromo-4-chloro-2,5-bis (((2-methoxypropane-2-yl)oxy)methyl)benzene and 2-difluoromethylthiophene.

$^1$H NMR (400 MHz, DMSO-d$_6$) δ 7.72 (t, J=1.0 Hz, 1H), 7.61 (s, 1H), 7.12 (d, J=7.6 Hz, 1H), 6.83 (d, J=7.6 Hz, 1H), 4.95 (dd, J=7.0, 5.1 Hz, 2H), 4.69 (dd, J=19.2, 1.0 Hz, 1H), 4.57 (dd, J=18.9, 1.0 Hz, 1H), 4.50 (d, J=4.9 Hz, 1H), 4.41 (d, J=1.2 Hz, 2H), 4.31 (d, J=6.9, 5.0 Hz, 1H), 3.76-3.60 (m, 2H), 3.40 (td, J=7.0, 5.1 Hz, 1H), 1.12 (d, J=6.8 Hz, 3H).

LRMS (ESI, m/z): 433 [M+H]$^+$.

Example 132 (1S,3'R,4'S,5'S,6'R)-5-chloro-6'-methyl-6-((5-(pyrrolidine-1-ylmethyl)thiophene-2-yl)methyl)-3',4',5',6'-tetrahydro-3H-spiro[isobenzofuran-1,2'-pyran]-3',4',5'-triol (A132)

The target compound A132 was synthesized according to the synthetic method of A1, wherein 2-bromo-1,4-bis(((2-methoxy-propan-2-yl)oxy)methyl)benzene (1-9) and p-bromomethylbenzene were replaced by 1-bromo-4-chloro-2,5-bis (((2-methoxypropane-2-yl)oxy)methyl)benzene and 1-(thiophene-2-yl)-methylpyrrole.

$^1$H NMR (400 MHz, DMSO-d$_6$) δ 7.76 (t, J=0.9 Hz, 1H), 6.79 (qd, J=7.4, 1.3 Hz, 2H), 5.48 (d, J=5.1 Hz, 1H), 4.97 (d, J=5.1 Hz, 1H), 4.69 (dd, J=18.5, 1.0 Hz, 1H), 4.62-4.40 (m, 4H), 4.29 (ddd, J=16.5, 12.5, 1.3 Hz, 2H), 3.82-3.64 (m, 2H), 3.43-3.24 (m, 4H), 1.99 (td, J=9.6, 7.2 Hz, 2H), 1.92-1.78 (m, 2H), 1.67 (dhept, J=13.3, 3.3 Hz, 2H), 1.10 (d, J=6.8 Hz, 3H).

LRMS (ESI, m/z): 466 [M+H]$^+$.

Example 133 (1S,3'R,4'S,5'S,6'R)-5-chloro-6'-methyl-6-((5-(morpholinemethyl)thiophene-2-yl)methyl)-3',4',5',6'-tetrahydro-3H-spiro[isobenzofuran-1,2'-pyran]-3',4',5'-triol (A133)

The target compound A133 was synthesized according to the synthetic method of A1, wherein 2-bromo-1,4-bis(((2-methoxy-propan-2-yl)oxy)methyl)benzene (1-9) and p-bromomethylbenzene were replaced by 1-bromo-4-chloro-2,5-bis (((2-methoxypropane-2-yl)oxy)methyl)benzene and 4-(thiophene-2-yl)-methylmorpholine.

$^1$H NMR (400 MHz, DMSO-d$_6$) δ 7.62 (d, J=11.3 Hz, 1H), 6.72 (s, 1H), 4.80-4.64 (m, 2H), 4.62-4.40 (m, 2H), 4.35-4.17 (m, 2H), 4.00-3.86 (m, 3H), 3.76-3.61 (m, 1H), 2.76 (ddd, J=12.5, 8.8, 6.4 Hz, 1H), 2.52 (dt, J=12.5, 2.0 Hz, 1H), 1.10 (d, J=6.6 Hz, 2H).

LRMS (ESI, m/z): 482 [M+H]$^+$.

Example 134 2-(5-(((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl) thiophene-2-methyl formate (A134)

The target compound A134 was synthesized according to the synthetic method of A1, wherein 2-bromo-1,4-bis(((2-methoxy-propan-2-yl)oxy)methyl)benzene (1-9) and p-bromomethylbenzene were replaced by 1-bromo-4-chloro-2,5-bis (((2-methoxypropane-2-yl)oxy)methyl)benzene and 2-thiophenemethylformate.

$^1$H NMR (400 MHz, DMSO-d$_6$) δ 7.82 (d, J=7.6 Hz, 1H), 7.63 (dt, J=10.1, 1.1 Hz, 2H), 7.14 (d, J=7.4 Hz, 1H), 5.24 (d, J=4.9 Hz, 1H), 4.86 (d, J=4.9 Hz, 1H), 4.69 (dd, J=18.2, 1.0 Hz, 1H), 4.66-4.47 (m, 4H), 4.01 (d, J=12.4 Hz, 1H), 3.87 (s, 3H), 3.82-3.64 (m, 2H), 3.51 (td, J=6.9, 5.0 Hz, 1H), 1.11 (d, J=6.8 Hz, 3H).

LRMS (ESI, m/z): 441 [M+H]$^+$.

Example 135 2-(5-(((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)methyl)thiophene-2-ethylformate (A135)

The target compound A135 was synthesized according to the synthetic method of A1, wherein 2-bromo-1,4-bis(((2-methoxy-propan-2-yl)oxy)methyl)benzene (1-9) and p-bromomethylbenzene were replaced by 1-bromo-4-chloro-2,5-bis (((2-methoxypropane-2-yl)oxy)methyl)benzene and 2-thiopheneethylformate.

$^1$H NMR (400 MHz, DMSO-d$_6$) δ 7.85 (d, J=7.4 Hz, 1H), 7.73 (s, 1H), 7.61 (d, J=1.2 Hz, 1H), 7.12 (d, J=7.4 Hz, 1H), 5.21 (d, J=5.1 Hz, 1H), 4.86 (d, J=5.1 Hz, 1H), 4.68 (dd, J=18.2, 1.0 Hz, 1H), 4.65-4.53 (m, 2H), 4.53-4.45 (m, 2H), 4.37-4.22 (m, 2H), 4.08 (dq, J=12.3, 8.0 Hz, 1H), 3.80-3.64 (m, 2H), 3.52 (td, J=7.0, 5.0 Hz, 1H), 1.33 (t, J=8.0 Hz, 3H), 1.11 (d, J=6.8 Hz, 3H).

LRMS (ESI, nm/z): 455 [M+H]$^+$.

Example 136 (5-(((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)methyl)thiophene-2-yl)(pyrrolidine-1-yl)ketone (A136)

The target compound A136 was synthesized according to the synthetic method of A1, wherein 2-bromo-1,4-bis(((2-methoxy-propan-2-yl)oxy)methyl)benzene (1-9) and p-bromomethylbenzene were replaced by 1-bromo-4-chloro-2,5-bis (((2-methoxypropane-2-yl)oxy)methyl)benzene and (1-pyrrole)(2-thiophene)ketone.

$^1$H NMR (400 MHz, DMSO-d$_6$) δ 7.87 (d, J=7.4 Hz, 1H), 7.63 (dt, J=16.5, 1.1 Hz, 2H), 7.14 (dd, J=7.4, 1.8 Hz, 1H), 5.09 (d, J=4.9 Hz, 1H), 4.81 (d, J=4.9 Hz, 1H), 4.73-4.64 (m, 1H), 4.64-4.50 (m, 3H), 4.49 (d, J=1.3 Hz, 1H), 3.96 (dt, J=12.3, 1.3 Hz, 1H), 3.82-3.64 (m, 2H), 3.54 (ddd, J=10.8, 9.3, 5.9 Hz, 2H), 3.36 (td, J=6.9, 5.0 Hz, 1H), 3.15 (dd, J=9.4, 6.7 Hz, 2H), 1.77 (tdd, J=11.3, 6.1, 2.7 Hz, 2H), 1.64-1.55 (m, 2H), 1.10 (d, J=6.6 Hz, 3H).

LRMS (ESI, m/z): 480 [M+H]$^+$.

Example 137 (5-(((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)methyl)thiophene-2-yl)(morpholinyl)ketone (A137)

The target compound A137 was synthesized according to the synthetic method of A1, wherein 2-bromo-1,4-bis(((2- methoxy-propan-2-yl)oxy)methyl)benzene (1-9) and p-bromomethylbenzene were replaced by 1-bromo-4-chloro-2,5-bis (((2-methoxypropane-2-yl)oxy)methyl)benzene and morpholine (2-thiophene)ketone.

¹H NMR (400 MHz, DMSO-d₆) δ 7.90 (d, J=7.4 Hz, 1H), 7.64 (dt. J=20.5, 1.1 Hz, 2H), 7.23 (d, J=7.4 Hz, 1H), 5.16 (d, J=5.1 Hz, 1H), 4.87 (d, J=5.1 Hz, 1H), 4.73-4.53 (m, 4H), 4.50 (d, J=4.9 Hz, 1H), 4.13-4.02 (m, 2H), 3.95-3.82 (m, 3H), 3.80-3.64 (m, 4H), 3.54 (td, J=7.0, 5.0 Hz, 1H), 3.11 (ddd, J=12.5, 2.6, 1.1 Hz, 2H), 1.10 (d, J=6.8 Hz, 3H). LRMS (ESI, nm/z): 496 [M+H]⁺.

Example 138 (5-(((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)methyl)-N-methylthiophene-2-formamide (A138)

The target compound A138 was synthesized according to the synthetic method of A1, wherein 2-bromo-1,4-bis(((2-methoxypropan-2-yl)oxy)methyl)benzene (1-9) and p-bromomethylbenzene were replaced by 1-bromo-4-chloro-2,5-bis (((2-methoxypropane-2-yl)oxy)methyl)benzene and N-methyl-2-thiopheneformamide.

¹H NMR (400 MHz, DMSO-d₆) δ 8.17 (s, 1H), 7.86 (d, J=7.6 Hz, 1H), 7.63 (dt, J=9.7, 1.1 Hz, 2H), 7.21 (d, J=7.6 Hz, 1H), 5.24 (d, J=4.9 Hz, 1H), 4.76 (d, J=4.9 Hz, 1H), 4.69 (dd, J=18.2, 1.0 Hz, 1H), 4.64-4.53 (m, 3H), 4.50 (d, J=4.9 Hz, 1H), 3.99 (d, J=12.5 Hz, 1H), 3.82-3.64 (m, 2H), 3.50 (td, J=7.0, 5.0 Hz, 1H), 2.86 (s, 3H), 1.12 (d, J=6.8 Hz, 3H). LRMS (ESI, m/z): 440 [M+H]⁺.

Example 139 (5-(((1S,3'R,4'S,5'S,6'R)-5-chloro-33',4',5'-trihydroxy-6'-methyl-3',4',5',6'-tetrahydro-3H-spiro[isobenzofuran-1,2'-pyran]-6-yl)methyl)-N-ethylthiophene-2-formamide (A139)

The target compound A139 was synthesized according to the synthetic method of A1, wherein 2-bromo-1,4-bis(((2-methoxypropan-2-yl)oxy)methyl)benzene (1-9) and p-bromomethylbenzene were replaced by 1-bromo-4-chloro-2,5-bis (((2-methoxypropane-2-yl)oxy)methyl)benzene and N-ethyl-2-thiopheneforinamide.

¹H NMR (400 MHz, DMSO-d₆) δ 8.40 (s, 1H), 7.84 (d, J=7.6 Hz, 1H), 7.71 (s, 1H), 7.61 (s, 1H), 7.24 (dd, J=7.5, 1.1 Hz, 1H), 4.88 (d, J=4.9 Hz, 1H), 4.76 (d, J=5.0 Hz, 1H), 4.73-4.53 (m, 4H), 4.50 (d, J=4.9 Hz, 1H), 3.91 (dd, J=12.3, 1.0 Hz, 1H), 3.80-3.64 (m, 2H), 3.59 (td, J=6.9, 4.9 Hz, 1H), 3.34 (dq, J=12.5, 8.0 Hz, 1H), 2.83 (dq, J=12.3, 8.0 Hz, 1H), 1.11 (d, J=6.8 Hz, 3H), 1.03 (t, J=8.0 Hz, 3H). LRMS (ESI, m/z): 454 [M+H]⁺.

Example 140 (5-(((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)methyl)-N,N-dimethylthiophene-2-formamide (A140)

The target compound A140 was synthesized according to the synthetic method of A1, wherein 2-bromo-1,4-bis(((2-methoxypropan-2-yl)oxy)methyl)benzene (1-9) and p-bromomethylbenzene were replaced by 1-bromo-4-chloro-2,5-bis (((2-methoxypropane-2-yl)oxy)methyl)benzene and N,N-dimethyl-2-thiopheneformamide.

¹H NMR (400 MHz, DMSO-d₆) δ 7.92 (d, J=7.4 Hz, 4H), 7.62 (dt, J=6.5, 1.1 Hz, 8H), 7.18 (d, J=7.5 Hz, 4H), 5.25 (d, J=5.1 Hz, 4H), 4.86 (d, J=4.9 Hz, 4H), 4.68 (dd, J=18.2, 1.0 Hz, 4H), 4.63 (s, 4H), 4.62-4.53 (m, 10H), 4.53-4.47 (m, 5H), 4.04-3.95 (m, 4H), 3.81-3.64 (m, 8H), 3.51 (td, J=6.9, 5.0 Hz, 4H), 2.89 (s, 23H), 1.11 (d, J=6.8 Hz, 12H). LRMS (ESI, m/z): 454 [M+H]⁺.

Example 141 (1S,3'R,4'S,5'S,6'R)-5-chloro-6-((5-ethyl-4-methylthiophene-2-yl)methyl)-6'-methyl-3',4',5',6'-tetrahydro-3H-spiro[isobenzofuran-1,2'-pyran]-3',4',5'-triol (A141)

The target compound A141 was synthesized according to the synthetic method of A1, wherein 2-bromo-1,4-bis(((2-methoxy-propan-2-yl)oxy)methyl)benzene (1-9) and p-bromomethylbenzene were replaced by 1-bromo-4-chloro-2,5-bis (((2-methoxypropane-2-yl)oxy)methyl)benzene and 2-ethyl-3-methylthiophene.

¹H NMR (400 MHz, DMSO-d₆) δ 7.70 (s, 1H), 7.60 (s, 1H), 6.78 (s, 1H), 5.23 (d, J=4.9 Hz, 1H), 4.87 (d, J=5.0 Hz, 1H), 4.68 (dd, J=8.0, 1.0 Hz, 1H), 4.65-4.55 (m, 2H), 4.55-4.46 (m, 2H), 4.17 (dd, J=12.2, 1.1 Hz, 1H), 3.81-3.64 (m, 2H), 3.53 (td, J=6.9, 5.0 Hz, 1H), 3.16 (dqd, J=12.4, 7.9, 1.1 Hz, 1H), 2.62 (dqd, J=12.5, 8.0, 1.1 Hz, 1H), 2.22 (d, J=1.2 Hz, 3H), 1.30 (t, J=7.9 Hz, 3H), 1.11 (d, J=6.8 Hz, 3H). LRMS (ESI, m/z): 425 [M+H]⁺.

Example 142 (1S,3'R,4'S,5'S,6'R)-5-chloro-6-((5-(2-hydroxyethyl)-4-methylthiophene-2-yl)methyl)-6'-methyl-3',4',5',6'-tetrahydro-3H-spiro[isobenzofuran-1,2'-pyran]-3',4',5'-triol (A142)

The target compound A142 was synthesized according to the synthetic method of A1, wherein 2-bromo-1,4-bis(((2-methoxy-propan-2-yl)oxy)methyl)benzene (1-9) and p-bromomethylbenzene were replaced by 1-bromo-4-chloro-2,5-bis (((2-methoxypropane-2-yl)oxy)methyl)benzene and 2-hydroxyethyl-3-methylthiophene.

¹H NMR (400 MHz, DMSO-d₆) δ 7.68 (s, 1H), 6.79 (s, 1H), 5.23 (d, J=5.1 Hz, 1H), 4.87 (d, J=4.9 Hz, 1H), 4.68 (dd. J=8.0, 1.0 Hz, 1H), 4.65-4.54 (m, 3H), 4.54-4.46 (m, 2H), 4.11 (dd, J=12.3, 1.0 Hz, 1H), 4.11-3.92 (m, 2H), 3.81-3.64 (m, 2H), 3.52 (td, J=7.0, 5.0 Hz, 1H), 3.28-3.16 (m, 1H), 2.72 (dddd, J=12.4, 11.0, 3.9, 1.0 Hz, 1H), 2.21 (d, J=2.1 Hz, 1H), 2.21 (s, 2H), 1.11 (d, J=6.8 Hz, 3H). LRMS (ESI, nm/z): 441 [M+H]⁺.

Example 143 (1S,3'R,4'S,5'S,6'R)-5-chloro-6-((5-ethyl-4-fluorothiophene-2-yl)methyl)-6'-methyl-3',4',5',6'-tetrahydro-3H-spiro[isobenzofuran-1,2'-pyran]-3',4',5'-triol (A143)

The target compound A143 was synthesized according to the synthetic method of A1, wherein 2-bromo-1,4-bis(((2-methoxy-propan-2-yl)oxy)methyl)benzene (1-9) and p-bromomethylbenzene were replaced by 1-bromo-4-chloro-2,5-bis (((2-methoxypropane-2-yl)oxy)methyl)benzene and 2-ethyl-3-fluorothiophene.

¹H NMR (400 MHz, DMSO-d₆) δ 7.83 (d, J=1.3 Hz, 1H), 7.33 (d, J=1.3 Hz, 1H), 6.44 (d, J=8.0 Hz, 1H), 4.91 (d, J=4.9 Hz, 1H), 4.68 (dd, J=8.0, 1.0 Hz, 1H), 4.62-4.51 (m, 2H), 4.50 (d, J=4.9 Hz, 1H), 4.45 (dd, J=3.0, 0.9 Hz, 2H), 4.28 (dd, J=6.9, 5.0 Hz, 1H), 3.70 (tt, J=6.9, 2.6 Hz, 2H), 3.60 (td, J=7.0, 5.0 Hz, 1H), 2.87 (q, J=8.1 Hz, 2H), 1.30 (t, J=8.0 Hz, 3H), 1.14 (d, J=6.8 Hz, 3H). LRMS (ESI, m/z): 429 [M+H]⁺.

Example 144 (1S,3'R,4'S,5'S,6'R)-5-chloro-6-((4-fluoro-5-(2-hydroxyethyl)thiophene-2-yl)methyl)-6'-methyl-3',4',5',6'-tetrahydro-3H-spiro[isobenzofuran-1,2'-pyran]-3',4',5'-triol (A144)

The target compound A144 was synthesized according to the synthetic method of A1, wherein 2-bromo-1,4-bis(((2- methoxy-propan-2-yl)oxy)methyl)benzene (1-9) and p-bromomethylbenzene were replaced by 1-bromo-4-chloro-2,5-bis (((2-methoxypropane-2-yl)oxy)methyl)benzene and 2-(3-fluorothiophene-2-yl)ethanol.

$^{1}$H NMR (400 MHz, DMSO-d$_{6}$) δ 7.83 (s, 1H), 7.33 (s, 1H), 6.46 (d, J=8.0 Hz, 1H), 4.91 (d, J=4.9 Hz, 1H), 4.72-4.59 (m, 2H), 4.62-4.51 (m, 2H), 4.50 (d, J=4.9 Hz, 1H), 4.45 (dd, J=3.0, 1.0 Hz, 2H), 4.28 (dd, J=6.9, 5.0 Hz, 1H), 3.70 (tt, J=6.9, 2.6 Hz, 2H), 3.60 (td, J=7.2, 5.6 Hz, 3H), 3.01 (t, J=7.1 Hz, 2H), 1.14 (d, J=6.8 Hz, 3H).

LRMS (ESI, m/z): 445 [M+H]$^{+}$.

Example 145 (1S,3'R,4'S,5'S,6'R)-5-chloro-6-((4,5-dimethylthiophene-2-yl)methyl)-6'-methyl-3',4',5',6'-tetrahydro-3H-spiro[isobenzofuran-1,2'-pyran]-3',4',5'-triol (A145)

The target compound A145 was synthesized according to the synthetic method of A1, wherein 2-bromo-1,4-bis(((2-methoxy-propan-2-yl)oxy)methyl)benzene (1-9) and p-bromomethylbenzene were replaced by 1-bromo-4-chloro-2,5-bis (((2-methoxypropane-2-yl)oxy)methyl)benzene and 2,3-dimethylthiophene.

$^{1}$H NMR (400 MHz, DMSO-d$_{6}$) δ 7.73 (s, 1H), 7.60 (s, 1H), 6.74 (d, J=0.8 Hz, 1H). 4.96 (dd, J=5.1, 1.4 Hz, 2H), 4.68 (dd, J=8.0, 1.0 Hz, 1H), 4.58 (dd, J=8.0, 1.0 Hz, 1H), 4.50 (d, J=4.9 Hz, 1H), 4.44 (dd, J=12.3, 1.0 Hz, 1H), 4.42-4.33 (m, 1H), 4.31 (dd, J=7.0, 4.9 Hz, 1H), 3.76-3.60 (m, 2H), 3.40 (td, J=6.9, 5.0 Hz, 1H), 2.41 (s, 3H), 2.24 (s, 3H), 1.12 (d, J=6.8 Hz, 3H).

LRMS (ESI, m/z): 411 [M+H]$^{+}$.

Example 146 (1S,3'R,4'S,5'S,6'R)-5-chloro-6-((5-chloro-4-methylthiophene-2-yl)methyl)-6'-methyl-3',4',5',6'-tetrahydro-3H-spiro[isobenzofuran-1,2'-pyran]-3',4',5'-triol (A146)

The target compound A146 was synthesized according to the synthetic method of A1, wherein 2-bromo-1,4-bis(((2-methoxy-propan-2-yl)oxy)methyl)benzene (1-9) and p-bromomethylbenzene were replaced by 1-bromo-4-chloro-2,5-bis (((2-methoxypropane-2-yl)oxy)methyl)benzene and 2-chloro-3-methylthiophene.

$^{1}$H NMR (400 MHz, DMSO-d$_{6}$) δ 7.62 (dt, J=9.6, 1.1 Hz, 2H), 6.76 (s, 1H), 5.25 (d, J=5.1 Hz, 1H), 4.86 (d, J=4.9 Hz, 1H), 4.68 (dd, J=8.0, 1.0 Hz, 1H), 4.65-4.47 (m, 4H), 4.00 (dd, J=12.4, 1.1 Hz, 1H), 3.81-3.64 (m, 2H), 3.50 (td, J=7.0, 5.0 Hz, 1H), 2.19 (s, 3H), 1.11 (d, J=6.8 Hz, 3H).

LRMS (ESI, m/z): 431 [M+H]$^{+}$.

Example 147 (1S,3'R,4'S,5'S,6'R)-5-chloro-6-((5-fluoro-4-methylthiophene-2-yl)methyl)-6'-methyl-3',4'5',6'-tetrahydro-3H-spiro[isobenzofuran-1,2'-pyran]-3',4',5'-triol (A147)

The target compound A147 was synthesized according to the synthetic method of A1, wherein 2-bromo-1,4-bis(((2-methoxy-propan-2-yl)oxy)methyl)benzene (1-9) and p-bromomethylbenzene were replaced by 1-bromo-4-chloro-2,5-bis (((2-methoxypropane-2-yl)oxy)methyl)benzene and 2-fluoro-3-methylthiophene.

$^{1}$H NMR (400 MHz, DMSO-d$_{6}$) δ 7.83 (d, J=1.2 Hz, 1H), 7.33 (d, J=1.3 Hz, 1H), 6.25 (d, J=5.1 Hz, 1H), 4.91 (d, J=4.9 Hz, 1H), 4.68 (dd, J=8.0, 1.0 Hz, 1H), 4.62-4.51 (m, 2H), 4.50 (d, J=4.9 Hz, 1H), 4.45 (d, J=3.0, 1.0 Hz, 2H), 4.28 (dd, J=6.9, 5.0 Hz, 1H), 3.70 (tt, J=6.9, 2.6 Hz, 2H), 3.60 (td, J=7.0, 5.0 Hz, 1H), 2.26 (s, 3H), 1.14 (d, J=6.8 Hz, 3H).

LRMS (ESI, nm/z): 415 [M+H]$^{+}$.

Example 148 (1S,3'R,4'S,5'S,6'R)-5-chloro-6-((5-((R)-1-hydroxyethyl)thiophene-2-yl)methyl)-6'-methyl-3',4',5,6'-tetrahydro-3H-spiro[isobenzofuran-1,2'-pyran]-3',4',5'-triol (A148)

The target compound A148 was synthesized according to the synthetic method of A1, wherein 2-bromo-1,4-bis(((2-methoxy-propan-2-yl)oxy)methyl)benzene (1-9) and p-bromomethylbenzene were replaced by 1-bromo-4-chloro-2,5-bis (((2-methoxypropane-2-yl)oxy)methyl)benzene and (R)-1-(thiophene-2-yl)-1-ethanol.

$^{1}$H NMR (400 MHz, DMSO-d$_{6}$) δ 7.37 (s, 1H), 7.29 (s, 1H), 6.67 (s, 2H), 5.10 (d, J=2.3 Hz, 2H), 4.24 (d, J=3.6 Hz, 2H), 3.88 (dq, J=9.4, 6.2 Hz, 1H), 3.79-3.67 (m, 4H), 3.17 (ddd, J=9.3, 6.8, 2.1 Hz, 1H), 2.95 (t, J=6.8 Hz, 2H), 1.23 (d, J=6.2 Hz, 3H).

LRMS (ESI, m/z): 427 [M+H]$^{+}$.

Example 149 (1S,3'R,4'S,5'S,6'R)-5-chloro-6-((5-((S)-1-hydroxyethyl)thiophene-2-yl)methyl)-6'-methyl-3'-4',5',6'-tetrahydro-3H-spiro[isobenzofuran-1,2'-pyran]-3',4',5'-triol (A149)

The target compound A149 was synthesized according to the synthetic method of A1, wherein 2-bromo-1,4-bis(((2-methoxy-propan-2-yl)oxy)methyl)benzene (1-9) and p-bromomethylbenzene were replaced by 1-bromo-4-chloro-2,5-bis (((2-methoxypropane-2-yl)oxy)methyl)benzene and (S)-1-(thiophene-2-yl)-1-ethanol.

$^{1}$H NMR (400 MHz, DMSO-d$_{6}$) δ 7.37 (s, 1H), 7.29 (s, 1H), 6.67 (s, 2H), 5.10 (d, J=2.3 Hz, 2H), 4.24 (d, J=3.6 Hz, 2H), 3.88 (dq, J=9.4, 6.2 Hz, 1H), 3.79-3.67 (m, 4H), 3.17 (ddd, J=9.3, 6.8, 2.1 Hz, 1H), 2.95 (t, J=6.8 Hz, 2H), 1.23 (d, J=6.2 Hz, 3H).

LRMS (ESI, m/z): 427 [M+H]$^{+}$.

Example 150 (1S,3'R,4'S,5'S,6'R)-5-chloro-6-((S)-(5-ethylthiophene-2-yl)(hydroxy)methyl)-6'-methyl-3',5',5',6'-tetrahydro-3H-spiro[isobenzofuran-1,2'-pyran]-3',4',5'-triol (A150)

The target compound A150 was synthesized according to the synthetic method of A1, wherein 2-bromo-1,4-bis(((2-methoxy-propan-2-yl)oxy)methyl)benzene (1-9) and p-bromomethylbenzene were replaced by 1-bromo-4-chloro-2,5-bis (((2-methoxypropane-2-yl)oxy)methyl)benzene and 2-ethylthiophene.

$^{1}$H NMR (400 MHz, DMSO-d$_{6}$) δ 7.72 (s, 1H), 7.36 (s, 1H), 6.62 (dd, J=3.5, 0.8 Hz, 1H), 6.61-6.58 (m, 1H), 6.28 (s, 1H), 5.14 (s, 2H), 3.92-3.85 (m, 1H), 3.81-3.70 (m, 2H), 3.19 (t, J=9.2 Hz, 1H), 2.79 (qd, J=7.5, 1.0 Hz, 2H), 1.27 (t, J=7.5 Hz, 3H), 1.23 (d, J=6.3 Hz, 3H).

LRMS (ESI, m/z): 427 [M+H]$^{+}$.

Example 151 (1S,3'R,4'S,5'S,6'R)-5-chloro-6-((R)-(5-ethylthiophene-2-yl)(hydroxy)methyl)-6'-methyl-3',5',5',6'-tetra hydro-3H-spiro[isobenzofuran-1,2'-pyran]-3',4',5'-triol (A151)

The target compound A151 was synthesized according to the synthetic method of A1, wherein 2-bromo-1,4-bis(((2-methoxy-propan-2-yl)oxy)methyl)benzene (1-9) and p-bromomethylbenzene were replaced by 1-bromo-4-chloro-2,5-bis (((2-methoxypropane-2-yl)oxy)methyl)benzene and 2-ethylthiophene.

$^{1}$H NMR (400 MHz, DMSO-d$_{6}$) δ 7.72 (s, 1H), 7.36 (s, 1H), 6.62 (dd, J=3.5, 0.8 Hz, 1H), 6.61-6.58 (m, 1H), 6.28 (s, 1H), 5.14 (s, 2H), 3.92-3.85 (m, 1H), 3.81-3.70 (m, 2H), 3.19 (t, J=9.2 Hz, 1H), 2.79 (qd, J=7.5, 1.0 Hz, 2H), 1.27 (t, J=7.5 Hz, 3H), 1.23 (d, J=6.3 Hz, 3H).

LRMS (ESI, m/z): 427 [M+H]$^{+}$.

Physical and Chemical Properties Example

TABLE 1 physicochemical properties of the compounds

Chemical properties

| No. | LogP | CLogP | tPSA |
|---|---|---|---|
| A1 | 3.13 | 3.083 | 79.15 |
| A2 | 3.55 | 3.612 | 79.15 |
| A3 | 3.97 | 4.141 | 79.15 |
| A4 | 3.55 | 3.612 | 79.15 |
| A5 | 2.52 | 2.503 | 88.38 |
| A6 | 2.86 | 3.032 | 88.38 |
| A7 | 2.82 | 2.729 | 79.15 |
| A8 | 3.31 | 3.258 | 79.15 |
| A9 | 3.73 | 3.787 | 79.15 |
| A10 | 2.86 | 2.985 | 79.15 |
| A11 | 4.38 | 4.4794 | 79.15 |
| A12 | 4.22 | 4.328 | 79.15 |
| A13 | 3.31 | 3.08 | 91.51 |
| A14 | 3.64 | 3.758 | 79.15 |
| A15 | 3.18 | 2.954 | 79.15 |
| A16 | 2.17 | 3.144 | 88.38 |
| A17 | 2.07 | 2.412 | 100.74 |
| A18 | 3.43 | 2.9174 | 91.51 |
| A19 | 3.61 | 3.17576 | 91.51 |
| A20 | 3.45 | 3.026 | 91.51 |
| A21 | 3.69 | 3.796 | 79.15 |
| A22 | 4.11 | 4.325 | 79.15 |
| A23 | 4.52 | 4.854 | 79.15 |
| A24 | 4.44 | 4.724 | 79.15 |
| A25 | 3.08 | 3.216 | 88.38 |
| A26 | 3.41 | 3.745 | 88.38 |
| A27 | 3.38 | 3.442 | 79.15 |
| A28 | 3.87 | 3.971 | 79.15 |
| A29 | 4.29 | 4.5 | 79.15 |
| A30 | 3.42 | 3.698 | 79.15 |
| A31 | 4.94 | 5.1924 | 79.15 |
| A32 | 4.78 | 5.041 | 79.15 |
| A33 | 3.86 | 3.793 | 91.51 |
| A34 | 4.2 | 4.471 | 79.15 |
| A35 | 4.1 | 4.327 | 79.15 |
| A36 | 2.73 | 3.857 | 88.38 |
| A37 | 2.63 | 3.125 | 100.74 |
| A38 | 3.29 | 3.226 | 79.15 |
| A39 | 2.68 | 2.646 | 88.38 |
| A40 | 3.01 | 3.175 | 88.38 |
| A41 | 2.98 | 2.872 | 79.15 |
| A42 | 3.47 | 3.401 | 79.15 |
| A43 | 3.02 | 3.128 | 79.15 |
| A44 | 4.54 | 4.6224 | 79.15 |
| A45 | 4.38 | 4.471 | 79.15 |
| A46 | 3.46 | 3.223 | 91.51 |
| A47 | 3.7 | 3.757 | 79.15 |
| A48 | 2.33 | 3.287 | 88.38 |
| A49 | 2.23 | 2.555 | 100.74 |
| A50 | 3.62 | 3.532 | 79.15 |
| A51 | 4.04 | 4.061 | 79.15 |
| A52 | 4.45 | 4.59 | 79.15 |
| A53 | 4.37 | 4.46 | 79.15 |
| A54 | 3 | 2.952 | 88.38 |
| A55 | 3.34 | 3.481 | 88.38 |
| A56 | 3.31 | 3.178 | 79.15 |
| A57 | 3.8 | 3.707 | 79.15 |
| A58 | 4.21 | 4.236 | 79.15 |
| A59 | 3.35 | 3.434 | 79.15 |
| A60 | 4.86 | 4.9284 | 79.15 |
| A61 | 4.71 | 4.777 | 79.15 |
| A62 | 3.79 | 3.529 | 91.51 |
| A63 | 4.13 | 4.207 | 79.15 |
| A64 | 4.03 | 4.063 | 79.15 |
| A65 | 2.66 | 3.593 | 88.38 |
| A66 | 2.56 | 2.861 | 100.74 |
| A67 | 3.92 | 3.3664 | 91.51 |
| A68 | 4.1 | 3.62476 | 91.51 |
| A69 | 3.94 | 3.475 | 91.51 |
| A70 | 5.63 | 5.6747 | 79.15 |
| A71 | 5.19 | 5.276 | 79.15 |
| A72 | 4.86 | 4.9284 | 79.15 |
| A73 | 5.02 | 5.07434 | 79.15 |
| A74 | 4.86 | 4.9284 | 79.15 |
| A75 | 4.58 | 4.7211 | 88.38 |
| A76 | 3.04 | 2.7235 | 88.38 |
| A77 | 3.95 | 3.6355 | 79.15 |
| A78 | 3.06 | 2.2095 | 102.94 |
| A79 | 2.85 | 2.7245 | 105.45 |
| A80 | 4.51 | 4.2335 | 105.45 |
| A81 | 2.17 | 1.59 | 108.25 |
| A82 | 3.29 | 3.353 | 79.15 |
| A83 | 4.54 | 4.7494 | 79.15 |
| A84 | 2.73 | 2.682 | 100.74 |
| A85 | 3.47 | 3.528 | 79.15 |
| A86 | 2.68 | 2.773 | 88.38 |
| A87 | 3.01 | 3.302 | 88.38 |
| A88 | 3.16 | 2.656 | 102.94 |
| A89 | 4.41 | 4.0524 | 102.94 |
| A90 | 2.1 | 1.985 | 124.53 |
| A91 | 3.34 | 2.831 | 102.94 |
| A92 | 2.55 | 2.076 | 112.17 |
| A93 | 2.89 | 2.605 | 112.17 |
| A94 | 3.96 | 3.946 | 79.15 |
| A95 | 5.21 | 5.3424 | 79.15 |
| A96 | 2.9 | 3.275 | 100.74 |
| A97 | 4.14 | 4.121 | 79.15 |
| A98 | 3.35 | 3.366 | 88.38 |
| A99 | 3.68 | 3.895 | 88.38 |
| A100 | 3 | 3.002 | 88.38 |
| A101 | 4.25 | 4.3984 | 88.38 |
| A102 | 1.94 | 2.331 | 109.97 |
| A103 | 3.18 | 3.177 | 88.38 |
| A104 | 2.39 | 2.422 | 97.61 |
| A105 | 2.73 | 2.951 | 97.61 |
| A106 | 2.81 | 3.857 | 88.38 |
| A107 | 3.57 | 3.828 | 88.38 |
| A108 | 3.95 | 3.063 | 102.94 |
| A109 | 3.85 | 2.709 | 102.94 |
| A110 | 4.12 | 4.18 | 79.15 |
| A111 | 3.24 | 3.04976 | 96.22 |
| A112 | 3.4 | 3.20202 | 96.22 |
| A113 | 3.12 | 2.853 | 96.22 |
| A114 | 2.99 | 2.85 | 88.38 |
| A115 | 3.33 | 3.239 | 88.38 |
| A116 | 3.82 | 3.768 | 88.38 |
| A117 | 2.41 | 2.5125 | 96.22 |
| A118 | 2.85 | 2.214 | 99.38 |
| A119 | 2.63 | 2.134 | 99.38 |
| A120 | 3.05 | 2.214 | 99.38 |
| A121 | 2.6 | 2.215 | 116.45 |
| A122 | 2.87 | 2.621 | 105.45 |
| A123 | 3.2 | 3.15 | 105.45 |
| A124 | 2.19 | 1.491 | 108.25 |
| A125 | 2.53 | 2.02 | 108.25 |
| A126 | 2.42 | 1.767 | 99.46 |
| A127 | 2.74 | 2.491 | 99.46 |
| A128 | 2.02 | 2.046 | 108.69 |
| A129 | 2.85 | 2.471 | 96.22 |
| A130 | 2.53 | 1.905 | 99.38 |
| A131 | 3.37 | 3.138 | 79.15 |
| A132 | 3.36 | 3.411 | 82.39 |
| A133 | 2.64 | 2.69 | 91.62 |
| A134 | 2.92 | 2.9885 | 105.45 |
| A135 | 3.26 | 3.5175 | 105.45 |
| A136 | 2.8 | 2.1725 | 99.46 |
| A137 | 2.08 | 1.7035 | 108.69 |
| A138 | 2.24 | 1.854 | 108.25 |
| A139 | 2.58 | 2.383 | 108.25 |
| A140 | 2.48 | 1.5385 | 99.46 |
| A141 | 4.36 | 4.42 | 79.15 |
| A142 | 3.12 | 2.583 | 99.38 |
| A143 | 4.03 | 4.156 | 79.15 |
| A144 | 2.79 | 2.319 | 99.38 |

TABLE 1-continued physicochemical properties of the compounds

| | Chemical properties | | |
|---|---|---|---|
| No. | LogP | CLogP | tPSA |
| A145 | 3.87 | 3.891 | 79.15 |
| A146 | 3.91 | 4.197 | 79.15 |
| A147 | 3.63 | 3.627 | 79.15 |
| A148 | 2.85 | 2.214 | 99.38 |
| A149 | 2.85 | 2.214 | 99.38 |
| A150 | 3.05 | 2.214 | 99.38 |
| A151 | 3.05 | 2.214 | 99.38 |
| dapagliflozin | 2.27 | 3.3687 | 99.38 |

Note:
The physicochemical properties of compounds (LogP, CLogP, and tPSA values are the Chemdraw software forecasts in the ChemOffice package.) "—" refers to none
Conclusion: The physicochemical properties of these compounds (LogP, CLogP and tPSA, etc.) are comparable to those of positive drugs (dapagliflozin), and also have good druggability.

Pharmacological Activity Test Example

Experimental Example 1

Inhibition of the compounds of formula I against human sodium-glucose cotransporter 2 (SGLT2) was determined experimentally and the experimental procedures were carried out as reference[1]. The experimental data is shown in Table 1.

(1) Reagents and Equipment

Main Reagents:
Methyl-α-D-[U-$^{14}$C] glucopyranoside (Perkin Elmer)
Dimethylsulfoxide (Genebase, Prod No: 0231)
Main Instrument:
Perkin Elmer 1450-023
Grouping and Dose Setting
Dose Setting Basis:
The test concentration gradients of the compounds and the replicate wells were set according to the requirements of the primary screening and IC$_{50}$ test.
Dose Setting and Groups:
(1) Primary screening of hSGLT2 are conducted with two concentrations, 100 nM and 10 nM;
(2) The concentrations of all tested compounds of hSGLT2 IC$_{50}$ test were started from 100 nM, and diluted by 3-fold in increments at 6 concentrations and 3 replicate wells were set for each concentration; hSGLT1 test concentrations for all test compounds were started from 100 uM, and diluted by 3-fold in increments at 6 concentrations and 3 replicate wells were set for each concentration.

(2) Experimental Principle

SGLT2 transports D-glucose at 1:1 sodium-glucose ratio, glucose is replaced by the non-metabolic and isotope labeled methyl-aD-[U-$^{14}$C] glucopyranoside and methyl-aD-glucopyranoside, and the amount of isotope transferred into the cells was determined.

(3) Experimental Steps 1) 0.2% gelatin in a 96-well plate was put in a 37° C. incubator for further use;

2) NIH3T3-hSGLT2 cells were injected into 96-well plates, 40000/well, and 100 μL culture medium per well:

3) the fluid was changed in the next day, and sodium butyrate was added into medium at a final concentration of 2 mM;

4) wash the cells with 100 μL of KRH—Na$^+$ for 3 times and incubate cells with 50 μL for 30 minutes. Cells were changed to 50 μL of compound in KRH—Na$^+$, uptake buffer (KRH—Na$^+$ and methyl-α-D-[U-$^{14}$C]glucopyranoside and ⅙ mM methyl-α-D-glucopyranoside at 10 μL per well) was added; KRH-acetylcholine solution was used as background control instead of KRH-Na$^+$ 5) washed with 100 μL PBS for 3 times, dried, 50 μL lysate and 150 μL scintillation fluid were added, the membrane was covered and flattened, shaken on a shaker to mix thoroughly, centrifuged at 1500 rpm at 4° C. for 3 min, taken out and read;

6) the results were analyses.

(4) Data Processing and Statistic Analysis

The inhibition rate (% Inhibiton) of each sample at each concentration was calculated by dividing the value of the compound well value minus the background value by the value of the DMSO control well value minus the background value.

$$\text{Inhibition}\% = \left(1 - \frac{LSample - LBackground}{LControl - LBackground}\right) \times 100$$

IC$_{50}$ is calculated as follows:

$$y = \text{bottom} + \frac{\text{top} - \text{bottom}}{1 + (\overline{x}/IC_{50})^{slope}}$$

The y value is the activity or inhibition percent, the x value is the concentration of the corresponding compound, top (the maximum y value of the curve), bottom (the minimum y value of the curve).

TABLE 1

Results of in vitro SGLT2 inhibition rate test

| | % Inhibition rate ± SD | |
|---|---|---|
| Compound | 100 nM | 10 nM |
| A1 | 26.9 ± 9.1 | 21.2 ± 14.4 |
| A2 | 62.6 ± 2.0 | 51.4 ± 2.1 |
| A3 | 31.0 ± 9.7 | 23.1 ± 18.5 |
| A4 | 42.2 ± 3.5 | 34.1 ± 23.6 |
| A5 | 28.9 ± 7.2 | 26.0 ± 14.0 |
| A6 | 27.6 ± 3.1 | 27.0 ± 15.7 |
| A7 | 27.9 ± 1.9 | 15.7 ± 25.2 |
| A8 | 59.1 ± 5.3 | 30.4 ± 4.8 |
| A9 | 52.8 ± 15.5 | 34.7 ± 24.0 |
| A10 | 45.8 ± 10.2 | 28.1 ± 25.8 |
| A11 | 31.4 ± 8.1 | 29.4 ± 11.1 |
| A12 | 49.1 ± 20.0 | 20.4 ± 28.4 |
| A13 | 46.9 ± 8.6 | 31.0 ± 30.5 |
| A14 | 55.8 ± 13.2 | 25.8 ± 15.0 |
| A15 | 50.8 ± 4.4 | 46.9 ± 4.0 |
| A16 | 39.0 ± 16.1 | 27.5 ± 19.6 |

TABLE 1-continued

Results of in vitro SGLT2 inhibition rate test

| Compound | % Inhibition rate ± SD | |
|---|---|---|
| | 100 nM | 10 nM |
| A22 | 79.8 ± 8.5 | 25.0 ± 3.1 |
| A25 | 100.7 ± 2.2 | 91.8 ± 5.1 |
| A26 | 90.5 ± 4.1 | 51.5 ± 10.7 |
| A28 | 86.1 ± 2.4 | 67.0 ± 4.9 |
| A31 | 91.5 ± 11.7 | 67.5 ± 5.7 |
| A33 | 20.7 ± 7.5 | 25.0 ± 9.3 |
| A35 | 95.7 ± 2.0 | 22.4 ± 7.5 |
| A36 | 102.8 ± 3.7 | 24.4 ± 8.8 |
| A42 | 103.5 ± 2.8 | 62.4 ± 11.8 |
| A46 | 63.6 ± 2.4 | 16.0 ± 14.8 |
| A47 | 50.2 ± 10.8 | 19.4 ± 0.5 |
| A48 | 33.2 ± 10.1 | 13.1 ± 8.4 |
| A57 | 95.4 ± 2.8 | 31.1 ± 7.4 |
| A85 | 50.4 ± 16.9 | 33.9 ± 14.1 |
| A106 | 50.8 ± 7.5 | 4.8 ± 3.9 |
| A107 | 72.7 ± 3.3 | 93.0 ± 1.8 |
| A108 | 96.2 ± 3.4 | 100.4 ± 0.9 |
| A109 | 62.6 ± 7.2 | 86.8 ± 1.6 |
| A110 | 71.5 ± 7.2 | 93.0 ± 5.9 |
| A111 | 39.9 ± 10.8 | 46.2 ± 11.1 |
| A112 | 44.3 ± 15.6 | 34.9 ± 23.0 |
| A113 | 22.5 ± 10.7 | 20.9 ± 16.3 |
| A114 | 71.4 ± 2.8 | 18.3 ± 2.2 |
| A115 | 53.8 ± 5.5 | 78.1 ± 5.1 |
| A116 | 62.3 ± 6.0 | 89.4 ± 1.5 |
| A117 | 22.6 ± 8.3 | 30.1 ± 1.0 |
| A118 | 91.8 ± 3.5 | 22.1 ± 3.0 |
| A119 | 80.0 ± 2.7 | 22.0 ± 3.1 |
| A120 | 22.8 ± 8.1 | 4.0 ± 9.2 |
| dapagliflozin | 103.3 ± 2.8 | 59.6 ± 11.3 |

TABLE 2

Results of in vitro SGLT2 inhibitory activity and selectivity test

| Compound | IC50 ± SD (nM) | | Selectivity[a] |
|---|---|---|---|
| | SGLT2 | SGLT1 | |
| A2 | 63.5 ± 7.1 | 22340 ± 4260 | 351 |
| A8 | 285.1 ± 116.7 | ND[b] | ND[b] |
| A22 | 29.7 ± 18.4 | 410 ± 50 | 13 |
| A26 | 15.7 ± 2.1 | 920 ± 90 | 58 |
| A28 | 1.42 ± 0.20 | 2060 ± 210 | 1450 |
| A31 | 3.6 ± 0.7 | 70140 ± 7900 | 19483 |
| A35 | 24.0 ± 2.4 | 1950 ± 130 | 81 |
| A36 | 32.4 ± 8.2 | 5400 ± 660 | 166 |
| A42 | 26.7 ± 2.0 | 25900 ± 4290 | 988 |
| A57 | 8.4 ± 0.7 | 1930 ± 160 | 779 |
| A114 | 43.5 ± 11.3 | 3.6 ± 0.26 | 83 |
| A118 | 43.4 ± 12.9 | 7.2 ± 0.6 | 166 |
| A119 | 3.6 ± 0.8 | 0.6 ± 0.08 | 167 |
| dapagliflozin | 7.1 ± 0.4 | 10.8 ± 0.6 | 1521 |

[a]Selectivity is calculated by $IC_{50}$ SGLT1/$IC_{50}$ SGLT2;
[b]ND is not tested.

Experimental Example 2

Experimental Method:

(1) Acutely Administering Compound to Observed the Urinary Glucose Changes in SD Rats Thirty-eight male normal SD rats were selected and randomly divided into 5 groups according to body weight and blood glucose, 6-8 in each group. Under normal conditions, the rats were orally administered with positive drug of dapagliflozin 1 mg/kg, and test compound 1 mg/kg respectively, and the blank control group was orally administered with 0.5% MC solution. After oral gavage, the rats were placed in rats metabolic cages, and urine was collected after 24 h, and the urine volume was recorded, the urine sugar concentration was determined, and urinary sugar content was calculated according to the following formula.

Urine content=urinary sugar concentration×urine volume (2) Detection of Glucose Concentration Glucose levels in urine are measured by the glucose assay kit.

(3) Data Processing and Statistic Analysis

Data were expressed as mean±standard deviation ($\bar{x}$±s), and Student's t test was used for statistical analysis of the data, p<0.05 was considered statistically significant.

Figure 2:
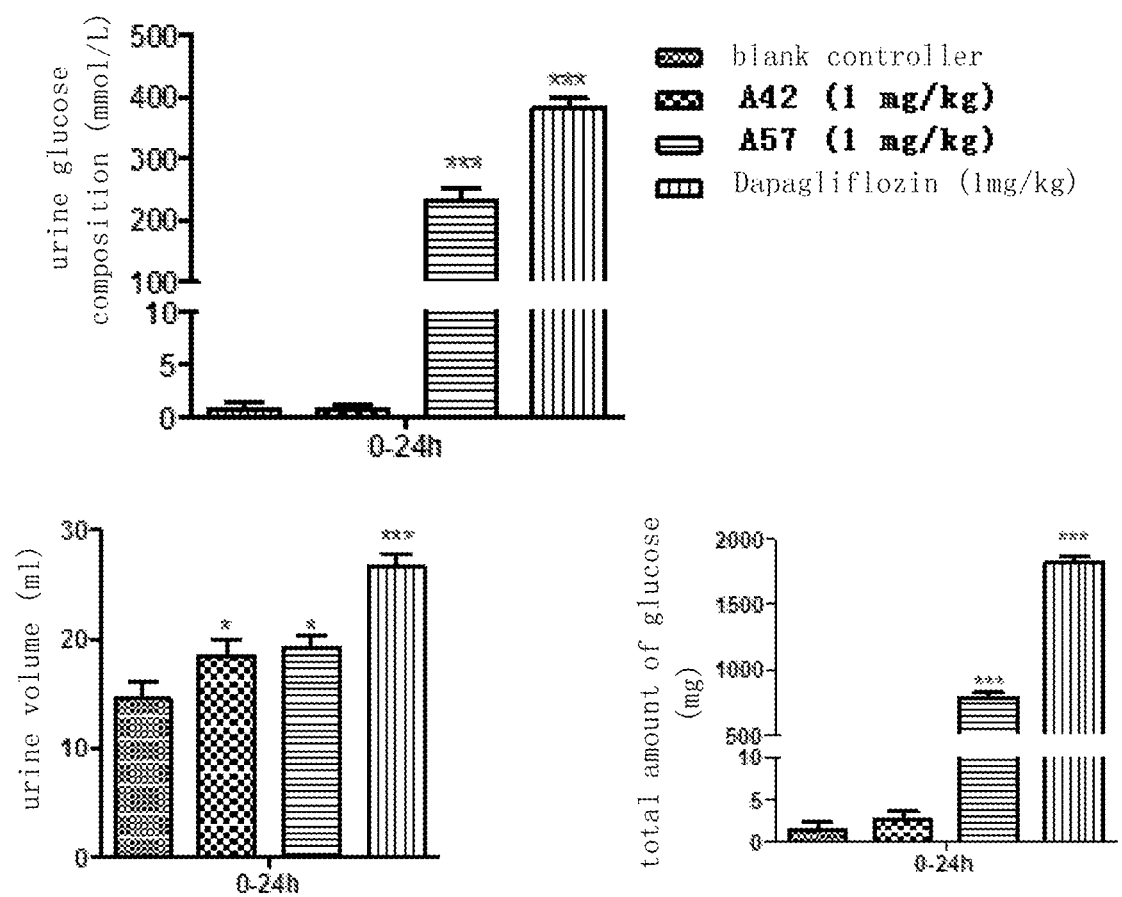
FIG. 2. Effect of single administration of test substance on each index in urine of SD rats; note: *: $p<0.05$; , $p<0.01$; *, $p<0.001$, compared with the blank control.

The experimental results are as shown in the following table and FIG. 1, FIG. 2:

TABLE 3

Influence of single administration of test substance on each index in urine of SD rats

| Group | Dose (mg/kg) | Number of animals | After 24 h administration | | |
|---|---|---|---|---|---|
| | | | Urine glucose concentration | Urine volume | The total amount of glucose excreted |
| Blank control group | 0.5% MC | 8 | 0.99 ± 0.56 | 19.63 ± 4.96 | 3.72 ± 2.83 |
| A28 | 1 | 8 | 76.29 ± 71.20* | 24 ± 6.63 | 337.10 ± 313.7* |
| A31 | 1 | 8 | 1.50 ± 0.60 | 33.13 ± 9.99* | 9.41 ± 6.18*** |
| dapagliflozin | 1 | 8 | 251.92 ± 52.98*** | 40.75 ± 8.60*** | 1860.61 ± 575.28*** |

Note:
p value <0.01; *p value <0.001; compared with the blank control group

TABLE 4

Influence of single administration of test substance on each index in urine of SD rats

| Group | Dose (mg/kg) | Number of animals | Urine glucose concentration | After 24 h administration Urine volume | The total amount of glucose excreted |
|---|---|---|---|---|---|
| Blank control group | 0.5% MC | 6 | 0.78 ± 1.50 | 14.67 ± 3.61 | 1.40 ± 2.31 |
| A42 | 1 | 6 | 0.82 ± 0.73 | 18.5 ± 3.51* | 2.56 ± 2.37 |
| A57 | 1 | 6 | 232.39 ± 50.5*** | 19.17 ± 2.71* | 786.39 ± 96.43*** |
| dapagliflozin | 1 | 6 | 382.41 ± 35.64*** | 26.67 ± 3.01*** | 1822.21 ± 112.97*** |

Note:
p value <0.01; *p value <0.001; compared with the blank control group

Experimental Example 3

Experimental Method:

Six healthy rats were randomly divided into two groups, three for each group. A28 was administered orally and intravenously, and the drug was grounded and dissolved in 0.5% MC. Fasted for 8 h before testing.

Three rats were intravenously administrated with 2 mg/kg of test compound A28, and 3 rats were orally administered with 10 mg/kg of test compound A28. Blood was collected from the orbital venous plexus of rats before administration, at 15 min, 30 min, 1 hour, 2 hours, 4 hours, 8 hours, 24 hours after administration, respectively. Blood sample were taken from three rats at each time point for each dose, and the plasma was immediately centrifuged.

Experimental Results:

After intravenous injection and intragastric administration of A28 in rats, the mean pharmacokinetic parameters are shown in Table 5.

Rats were intragastrically administered 10 mg/kg A28, average plasma concentration peak time $T_{max}$ was 1.67 h, maximal concentration $C_{max}$ was 272.7 ng/ml; area under the curve $AUC_{0-t}$ was 1348.7 ng·h/ml; terminal elimination half-life $t_{1/2}$ is 1.69 h. After intravenous injection of 2 mg/kg A28, the $AUC_{0-t}$ was 251.9 ng·h/ml; the absolute bioavailability after intragastric administration of 10 mg/kg A28 in rats was 107% after dose normalization.

Compared with the existing drug dapagliflozin, the absolute bioavailability of compound A28 of the present invention (107%) is superior to that of dapagliflozin (84%), which indicates that the compound has good pharmacokinetic properties and can be used in the following development.

Experimental Example 4

Acute Administration of A28 at Multiple Doses to Observe its Effect on Urinary Glucose of SD Rats Experimental Method:

(1) 72 normal male SD rats were selected and randomly divided into 9 groups according to body weight and blood glucose, 8 in each group. Under normal conditions, the rats were orally administered with positive drug Dapagliflozin 1 and 3 mg/kg, and 0.3, 1, 3 and 10 mg/kg of compound A28 respectively, and the solvent control group was orally administered with 0.5% MC solution. After oral gavage, the rats were placed in rats metabolic cages, and urine was collected after 24 h, and the urine volume was recorded, then preserved under −20° C. Rats take food and water freely during the experimental period.

(2) Index Determination: Glucose levels in urine are measured by the glucose assay kit.

TABLE 5

Mean pharmacokinetic parameters of rats after intragastric and intravenous administration of A28

| administration route | dose mg/kg | $T_{max}$ h | $C_{max}$ ng/mL | $AUC_{0-t}$ ng/mL*h | $AUC_{0-\infty}$ ng/mL*h | MRT h | $t_{1/2}$ h | CLz L/h/kg | F % |
|---|---|---|---|---|---|---|---|---|---|
| vein | 2 | 0.25 | 201.3 | 251.9 | 251.9 | 0.982 | 1.53 | 8.03 | / |
| Gavage | 10 | 1.67 | 272.7 | 1348.7 | 1349.7 | 3.785 | 1.69 | / | 107 |

Experimental Results:

| Group | Dose (mg/kg) | Number of animals | Urine concentration (mmol/L) | Urine volume (ml) | Total sugar excretion (mg/100 g) |
|---|---|---|---|---|---|
| Vehicle | 0.5% MC | 8 | 0.45 ± 0.18 | 17.63 ± 1.22 | 0.58 ± 0.26 |
| A28 | 0.3 | 8 | 8.70 ± 1.98** | 16.25 ± 1.50 | 10.55 ± 10.05* |
|  | 1 | 8 | 105.56 ± 0.00** | 19.25 ± 0.00 | 149.08 ± 0.00** |
|  | 3 | 8 | 257.69 ± 32.96** | 25.00 ± 2.06** | 441.27 ± 50.75** |
|  | 10 | 8 | 359.48 ± 29.43** | 39.75 ± 1.57** | 1028.20 ± 83.93** |
| Dapa | 1 | 8 | 313.13 ± 16.92** | 31.38 ± 1.99** | 706.69 ± 39.98** |
|  | 3 | 8 | 327.16 ± 24.63** | 36.88 ± 1.55** | 859.30 ± 41.55** |

Results:

After orally administering a single dose of 0.3, 1, 3 and 10 mg/kg of compound A28, the urine glucose excretion in SD rats was significantly promoted in a dose-dependent manner within 24 h.

Experimental Example 5

Acute administration of A28 at multiple doses to observe its effect on glucose tolerance of SD rats Experimental Method:

(1) 80 SD rats were selected and starved overnight, took water freely, then randomly divided into 10 groups according to body weight and random blood glucose, 8 rats in each group. The rats were orally administered with positive drug Dapagliflozin 1 and 3 mg/kg, 0.3, 1, 3 and 10 mg/kg of compound A28 respectively, and the blank control group and solvent control group were orally administered with 0.5% MC solution. 1 h after oral gavage, 3 g/kg of glucose was orally administered to each group except blank control group, and the blood glucose level was monitored before the sugar administration, and at 15, 30, 60, 90 and 120 minutes after the sugar administration.

(2) Determination of blood glucose: the blood glucose levels before sugar administration, and at 15, 30, 60, 90 and 120 minutes after sugar administration were determined, and the area under the blood glucose curve (AUC) within 120 minutes was calculated:

$$AUC\ (mmol/L \cdot h) = (BG_0 + BG_{15}) \times 0.25/2 + (BG_{15} + BG_{30}) \times 0.25/2 + (BG_{30} + BG_{60}) \times 0.5/2 + (BG_{60} + BG_{10}) \times 1.0/2$$

Note: $BG_0$, $BG_{15}$, $BG_{30}$, $BG_{60}$ and $BG_{120}$ represent the blood glucose levels before the sugar administration, and at 15, 30, 60, and 120 min after sugar administration, respectively.

Average hypoglycemic rate %=(AUC$_{0-120\ min}$ of solvent control group−AUC$_{0-120\ min}$ of administration group)/(AUC$_{0-120\ min}$ of solvent control group−AUC$_{0-120\ min}$ of blank control group)*100%

Experimental Results:

Results:

After orally administering a single dose of 0.3, 1, 3 and 10 mg/kg of A28, the 2 h blood glucose levels in SD rats of each administration group were significantly reduced except the low dose of 0.3 mg/kg. And the A28 has shown equivalent 2 h hypoglycemic effect to positive Dapagliflozin.

Experimental Example 6

Acute Administration of A28 at Multiple Doses to Observe its Effect on Urinary Glucose of C57 Mice Experimental Method:

(1) 90 normal male C57BL/6J mice were selected and randomly divided into 9 groups according to body weight and blood glucose, 10 in each group. Under normal conditions, the mice were orally administered with positive drug Dapagliflozin 1 and 3 mg/kg, and 0.3, 1, 3 and 10 mg/kg of compound A28 respectively, and the solvent control group was orally administered with 0.5% MC solution. After oral gavage, the mice were placed in rats (mice) metabolic cages, after oral gavage, the mice were placed in mice metabolic cages, and urine was collected after 24 h, and the urine volume was recorded, then preserved under −20° C. Rats take food and water freely during the experimental period.

(2) Index Determination: Glucose levels in urine are measured by the glucose assay kit.

| Group | Dose (mg/kg) | Blood glucose level (mmol/L) | | | | | | | Average hypoglycemic rate % (0-2 h) |
|---|---|---|---|---|---|---|---|---|---|
| | | 0 | 15 min | 30 min | 60 min | 90 min | 120 min | AUC0-2 h | |
| Vehicle | 0.5% MC | 5.1 ± 0.4 | 8.7 ± 1.5 | 12.0 ± 0.9 | 11.5 ± 1.8 | 10.2 ± 1.1 | 8.3 ± 1.3 | 20.2 ± 1.2 | — |
| A28 | 0.3 | 5.0 ± 0.7 | 7.6 ± 0.8 | 10.1 ± 1.6* | 11.1 ± 1.3 | 10.5 ± 0.8 | 8.1 ± 1.3 | 19.1 ± 1.77 | 10.3 |
|  | 1 | 4.4 ± 0.3** | 5.4 ± 0.9** | 6.5 ± 1.1** | 8.4 ± 0.6** | 9.6 ± 1.2 | 9.0 ± 1.3 | 15.6 ± 0.9** | 45.0 |
|  | 3 | 3.7 ± 0.4 | 3.6 ± 0.5** | 4.3 ± 0.3** | 5.6 ± 0.7** | 7.4 ± 0.6** | 8.4 ± 1.6 | 11.6 ± 0.9** | 83.7 |
|  | 10 | 3.1 ± 0.4** | 3.0 ± 0.4** | 3.4 ± 0.4** | 4.3 ± 1.8** | 4.2 ± 0.4** | 3.7 ± 0.9** | 7.6 ± 0.9** | 122.4 |
| Dapa | 1 | 4.9 ± 0.4 | 6.6 ± 0.7** | 7.8 ± 0.9** | 9.4 ± 1.1* | 9.5 ± 1.0 | 7.9 ± 1.3 | 16.6 ± 1.2** | 35.1 |
|  | 3 | 4.0 ± 0.6** | 4.7 ± 0.2** | 6.9 ± 1.0** | 8.6 ± 1.0** | 8.6 ± 1.3* | 8.3 ± 1.2 | 14.9 ± 1.0** | 51.5 |

Experimental Results:

| Group | Dose (mg/kg) | Number of animals | Urine concentration (mmol/L) | Urine volume (mL) | Total sugar excretion (mg/100 g) |
|---|---|---|---|---|---|
| Vehicle | 0.5% MC | 10 | 0.07 ± 0.02 | 2.0 ± 0.6 | 0.11 ± 0.04 |
| A28 | 0.3 | 10 | 7.91 ± 2.50** | 2.1 ± 0.7 | 10.31 ± 3.26** |
|  | 1 | 10 | 133.28 ± 42.18** | 1.8 ± 0.6 | 175.49 ± 55.53** |
|  | 3 | 10 | 265.71 ± 84.09** | 2.1 ± 0.7 | 440.02 ± 139.25** |
|  | 10 | 10 | 344.07 ± 108.88** | 2.5 ± 0.8 | 712.00 ± 225.32** |
| Dapa | 1 | 10 | 142.82 ± 45.20** | 2.3 ± 0.7 | 258.20 ± 81.71** |
|  | 3 | 10 | 177.86 ± 56.29** | 2.3 ± 0.7 | 315.49 ± 99.84** |

Results Analysis:

Within 24 hours of a single oral administration of 0.3, 1, 3 and 10 mg/kg dose, test compound A28 significantly promoted the urine glucose excretion of C57BL/6J mice in a dose-dependent manner, of which the effective dose was 0.3 mg/kg or less. At the same dose, the urinary exclusion effect of A28 was equal to or stronger than positive control Dapagliflozin.

Experimental Example 7

Acute Administration of A28 at Multiple Doses to Observe its Effect on Urinary Glucose of C57 Mice Experimental Method:

(1) Experimental Methods: 56 C57BL/6J mice were selected and starved for 6 h, took water freely, then randomly divided into 7 groups according to body weight and random blood glucose, 8 rats in each group. The mice were orally administered with 0.3, 1 and 3 mg/kg of compound A28, and 0.1, 1 and 3 mg/kg of positive Dapagliflozin, respectively, and the solvent control group was orally administered with 0.5% MC solution. 1 h after oral gavage, 3 g/kg of glucose was orally administered to each group, and the blood glucose level was monitored before the sugar administration, and at 15, 30, 60, 90 and 120 minutes after the sugar administration.

(2) Determination of blood glucose: the blood glucose levels before sugar administration, and at 15, 30, 60, 90 and 120 minutes after sugar administration were determined, and the area under the blood glucose curve (AUC) within 120 minutes was calculated:

AUC (mmol/L·h)=(BG$_0$+BG$_{15}$)×0.25/2+(BG$_{15}$+BG$_{30}$)×0.25/2+(BG$_{30}$+BG$_{60}$)×0.5/2+(BG$_{60}$+BG$_{10}$)×1.0/2

Note: BG$_0$, BG$_{15}$, BG$_{30}$, BG$_{60}$ and BG$_{120}$ represent the blood glucose levels before the sugar administration, and at 15, 30, 60, and 120 min after sugar administration, respectively.

Average hypoglycemic rate %=(AUC$_{0-120\ min}$ of solvent control group−AUC$_{0-120\ min}$ of administration group)/(AUC$_{0-120\ min}$ of solvent control group−AUC$_{0-120\ min}$ of blank control group)* 100%

Experimental Results:

| Group | dose (mg/kg) | Blood glucose level (mmol/L) | | | | | | AUC$_{0-2\ h}$ | Average hypoglycemic rate % (0-2 h) |
|---|---|---|---|---|---|---|---|---|---|
|  |  | 0 | 15 min | 30 min | 60 min | 90 min | 120 min |  |  |
| Vehcile | 0.5% MC | 6.9 ± 0.6 | 15.6 ± 1.3 | 13.7 ± 1.4 | 10.8 ± 1.1 | 9.1 ± 0.5 | 8.7 ± 0.9 | 22.0 ± 1.3 | — |
| A28 | 0.3 | 7.5 ± 0.4 | 14.2 ± 2.1 | 13.0 ± 1.7 | 11.2 ± 0.8 | 9.1 ± 1.0 | 8.3 ± 1.0 | 21.6 ± 1.5 | 2.0 |
|  | 1 | 7.1 ± 0.6 | 12.5 ± 1.6** | 12.0 ± 0.8* | 9.9 ± 0.9 | 8.7 ± 0.7 | 7.9 ± 0.7* | 19.8 ± 1.0** | 10.0 |
|  | 3 | 6.4 ± 0.7** | 10.4 ± 1.0** | 11.3 ± 1.1* | 9.5 ± 0.7* | 8.4 ± 0.7* | 7.4 ± 0.6** | 18.5 ± 0.6** | 16.2 |
| Dapa | 0.3 | 7.1 ± 0.4 | 13.4 ± 2.3* | 12.1 ± 1.0* | 10.6 ± 1.0 | 9.3 ± 1.1 | 8.8 ± 0.8 | 20.9 ± 1.6 | 4.9 |
|  | 1 | 6.5 ± 0.9 | 12.3 ± 1.1** | 12.0 ± 1.1* | 9.1 ± 1.1* | 8.4 ± 0.9 | 8.5 ± 0.9** | 19.3 ± 1.3** | 12.4 |
|  | 3 | 6.1 ± 1.0* | 11.6 ± 0.9** | 11.6 ± 1.1** | 8.9 ± 1.4* | 7.9 ± 1.1* | 7.0 ± 0.6** | 18.2 ± 1.6** | 17.5 |

Results Analysis:

After once administrated, compound A28 dose-dependently reduced the area under the curve of blood glucose level (AUC) of C57BL/6J mice within 2 h after sugar administration, of which the effective dose was 1 mg/kg, equal to the acute hypoglycemic effect of Dapagliflozin at 0.3-3 mg/kg.

Experimental Example 8

Acute Administration of Compound at Multiple Doses to Observe its Effect on the Random Blood Glucose in Db/Db Mice Experimental Method:

(1) 127 db/db mice (half male and half female) entered the animal laboratory of the institute at 7 weeks of age and were grouped at 10 weeks of age. Random blood glucose and random body weight of all db/db mice were determined at 9:00 am, and then fasted for 6 hours (free drinking). Fasting blood glucose and fasting body weight were determined, and blood was collected (10 μl EDTA+20 μl tail blood, centrifugated to collect supernatant) to determine the insulin content. 80 mice with random blood glucose over 11.1 mmol/l were selected and divided into 7 groups according to the random blood glucose, random body weight, fasting blood glucose, fasting body weight and insulin content, 10 in each group (half male and half female): model control group, two positive groups (1 mg/kg and 3 mg/kg of Dapagliflozin) and test group at four doses (0.3, 1, 3 and 10 mg/kg of A28), another group of normal mice (wild type, WT) of db/db mice from the same brood as a normal control. The db/db mice were once orally administered at a dose of 10 mL/kg. Blood glucose levels were measured before administration, and at 1 h, 2 h, 3 h, 4 h, 6 h after administration, and the administration times and body weights were recorded. Mice took food and water freely during the experiment.

(2) Calculate the area under the blood glucose curve (AUC) within 360 min:

$$AUC\ (mmol/L \cdot h) = (BG_0 + BG_{60}) \times 0.25/2 + (BG_{60} + BG_{120}) \times 0.25/2 + (BG_{120} + BG_{180}) \times 0.5/2 + (BG_{180} + BG_{240}) \times 0.5/2 + (BG_{240} + BG_{360}) \times 0.5/2$$

Note: $BG_0$, $BG_{60}$, $BG_{120}$, $BG_{180}$, $BG_{240}$ and $BG_{360}$ represent the blood glucose levels before the sugar administration, and at 15, 30, 60, and 120 min after sugar administration, respectively.

Average hypoglycemic rate %=(model control group−administration group)/(model control group−blank control group)*100%

Experimental Results:

of starvation, the fasting blood glucose in each group was measured. Free drinking during the hunger process. The rate of decrease of blood glucose was calculated according to the following formula: Average hypoglycemic rate %=(Blood glucose of model control group−Blood glucose of administration group)/Model control group×100%

(3) Random Weight and Fasting Weight

Random weights were determined before daily administration. Random weight and fasting weight of mice in each group were measured before determination of random blood glucose and fasting blood glucose.

(4) Food Intake:

The food intake of each mouse was determined every day.

(5) Oral Glucose Tolerance

The glucose tolerance of mice of normal control group, model control group, test substance group and positive control group were determined 3 weeks after administration

| Group | dose mg/kg | Blood glucose level (mmol/L) | | | | | | |
|---|---|---|---|---|---|---|---|---|
| | | 0 h | 1 h | 2 h | 3 h | 4 h | 6 h | AUC0-6 h |
| Vehicle | 0.5% MC | 19.4 ± 1.0 | 16.8 ± 2.4 | 18.8 ± 1.6 | 16.0 ± 2.5 | 15.8 ± 2.9 | 15.0 ± 2.1 | 100.0 ± 12.5 |
| A28 | 0.3 | 17.9 ± 1.5 | 19.4 ± 1.2 | 18.0 ± 0.9 | 17.2 ± 1.5 | 16.5 ± 1.5 | 15.4 ± 1.7 | 103.7 ± 7.7 |
| | 1 | 16.8 ± 1.2 | 15.9 ± 0.7 | 13.7 ± 0.6** | 14.6 ± 0.9 | 14.9 ± 1.1 | 12.3 ± 0.9 | 87.3 ± 4.8 |
| | 3 | 18.7 ± 1.2 | 11.2 ± 1.2* | 9.1 ± 0.5** | 10.2 ± 0.7* | 8.7 ± 0.6* | 9.7 ± 0.8* | 62.7 ± 3.3** |
| | 10 | 18.3 ± 1.7 | 8.2 ± 0.4** | 6.0 ± 0.6** | 7.1 ± 0.5** | 7.2 ± 0.6** | 6.1 ± 0.4** | 47.2 ± 1.7** |
| Dapa | 1 | 19.3 ± 1.3 | 13.0 ± 0.7 | 11.4 ± 0.6** | 10.2 ± 0.6* | 9.8 ± 0.7* | 8.8 ± 0.6* | 67.8 ± 2.5* |
| | 3 | 17.5 ± 1.3 | 11.8 ± 0.5* | 8.5 ± 0.4** | 8.6 ± 0.5** | 8.5 ± 0.3* | 9.4 ± 0.7* | 59.7 ± 1.7** |
| WT | 0.5% MC | 7.0 ± 0.2 | 8.8 ± 0.3 | 7.0 ± 0.3 | 7.8 ± 0.3 | 8.9 ± 0.3 | 7.8 ± 0.5 | 48.3 ± 1.3 |

Results Analysis:

There was no significant effect on db/db blood glucose within 6 h after single administration of 0.3 mg/kg of A28, and the blood glucose level at 2 h after a single administration of 1 mg/kg was significantly reduced. A single administration of 3 mg/kg and 10 mg/kg significantly decreased blood glucose levels at each time point, therefore, single administration of compound A28 also reduced blood glucose levels in db/db mice in a dose-dependent manner, of which the effective dose was 3 mg/kg. At 1 mg/kg, the hypoglycemic effect of A28 within 6 h was weaker than that of positive control Dapagliflozin, while the hypoglycemic effect of 3 mg/kg of A28 within 6 h was equivalent to the positive control Dapagliflozin. Therefore, dose-dependency of A28 is stronger than Dapagliflozin.

Experimental Example 9

Chronic Administration of Compound at Multiple Doses to Observe its Effect on the Blood Glucose and the Like in Db/Db Mice Experimental Method:

Grouped db/db mice (model control group, two positive groups (1 mg/kg and 3 mg/kg of Dapagliflozin), and the test group at 4 doses (0.3, 1, 3 and 10 mg/kg of A28)) in experimental example 8 were orally gavaged, and another group of normal mice (WT) of db/db mice from the same brood were used as normal control.

(1) Dosage, Administration Mode and Frequency

Oral gavage administrated, daily dose volume was 10 mL/kg, administered once daily. Administration time was 9: 00-10:00 daily, and the administration period was 5 weeks.

(2) Random Blood Glucose and Fasting Blood Glucose

The random blood glucose of mice in the normal control group, model control group, test substance administration group and positive control group were determined on the 7th, 14th, 21st, 28th day (9: 00-10:00) every week after the first administration, and food was removed and after 6 hours of drug, oral administrated with 1.5 g/kg of glucose, and taken 2 µL of blood on the tail. 4 µL of normal saline was added to 96 well sharp bottom plate to dilute evenly, and then the blood glucose was measured. The blood glucose levels before the sugar administration and at 15, 30, 60, 90 and 120 min after the sugar administration were measured. The true blood glucose level was calculated and the area under the blood glucose curve within 120 min was calculated by the following formula:

$$AUC_{0-2h}\ (mmol/L \cdot h) = (BG_0 + BG_{15}) \times 0.25/2 + (BG_{15} + BG_{30}) \times 0.25/2 + (BG_{30} + BG_{60}) \times 0.5/2 + (BG_{60} + BG_{10}) \times 1.0/2$$

Note: $BG_0$, $BG_{15}$, $BG_{30}$, $BG_{60}$ and $BG_{120}$ represent the blood glucose levels before the sugar administration, and at 15, 30, 60, and 120 min after sugar administration, respectively.

Average hypoglycemic rate %=(solvent control group $AUC_{0-2h}$−administration group $AUC_{0-2h}$)/ solvent control group $AUC_{0-2h}$*100%

(6) Glucose-Stimulated Insulin Release

The fourth week after administration, the mice were starved for 6 hours after morning administration and were orally administrated with glucose (1.5 g/kg), and blood was collected from the tail (10 µL EDTA+20 µL tail blood). Centrifuged and the supernatant was taken, stored at −20° C. for insulin test.

(7) Urine Output and Urine Glucose Amount

The mice of normal control group, model control group, test substance group and positive control group were placed in metabolic cages in batches 5 weeks after administration, 24 h urine was collected, and mice took food and water freely. Glucose oxidase method kit was used to assay 24 h urinary glucose content of animals in each group, and the total amount of urinary glucose excretion of mice in each group was calculated.

(8) Anatomy:

In the end of the above experiment, the orbital blood was taken from animals of each group and divided into two tubes, one was centrifuged to take blood cells for the determination of glycated hemoglobin content, the other tube was added with 25 μL EDTA in advance, centrifuged and the supernatant was taken to determine the indexes such as triglyceride (TG), total cholesterol (TC), total protein (TP), albumin, low density lipoprotein (LDL), high density lipoprotein (HDL), non-esterified fatty acid (NEFA) and so on.

Mice were dislocate executed after taken blood, and tissues such as liver, kidney, pancreas, subcutaneous fat, epididymal fat and perirenal fat were weighed and of which the ratio to body weight was calculated. Tissues such as blood, liver, kidney, pancreas, subcutaneous fat, epididymal fat and perirenal fat were weighed and of which the ratio to body weight was calculated.

(9) Determination of Various Biochemical Indicators

The content of triglyceride, total cholesterol, total protein, albumin, low density lipoprotein and high density lipoprotein in serum were measured by biochemical analyzer. The uric acid and other indexes were measured manually with kit.

Experimental Results:

(1) Chronic administration of compound A28 at multiple doses to observe its effect on the fasting blood-glucose in db/db mice PPG

| Group | Dose mg/kg | After administration (weeks)/fasting blood glucose (mmol/L) | | | | | Hypoglycemic rate % | | | |
|---|---|---|---|---|---|---|---|---|---|---|
| | | Pre | 1 | 2 | 3 | 4 | 1 | 2 | 3 | 4 |
| Vehicle | — | 13.2 ± 1.4 | 13.5 ± 1.0 | 22.0 ± 1.9** | 17.8 ± 1.0 | 16.0 ± 1.2 | — | — | — | — |
| A28 | 0.3 | 13.2 ± 0.7 | 10.6 ± 0.9** | 10.5 ± 0.8** | 12.3 ± 0.9** | 12.6 ± 1.2** | 21.4 | 52.3 | 30.6 | 21.1 |
| | 1 | 13.2 ± 1.3 | 8.7 ± 0.6** | 9.4 ± 0.9** | 10.4 ± 1.0** | 10.0 ± 0.7** | 35.0 | 57.2 | 41.5 | 37.8 |
| | 3 | 13.5 ± 1.5 | 8.6 ± 0.5** | 6.8 ± 0.6** | 8.1 ± 0.5** | 8.5 ± 0.6** | 36.2 | 69.2 | 54.2 | 46.8 |
| | 10 | 13.8 ± 1.2 | 7.6 ± 0.6** | 6.9 ± 0.5** | 7.2 ± 0.6** | 7.3 ± 0.5** | 43.2 | 68.9 | 59.5 | 54.5 |
| Dapa | 1 | 14.0 ± 1.0 | 9.4 ± 0.6** | 9.0 ± 0.6** | 10.0 ± 1.0** | 9.7 ± 0.7** | 30.3 | 59.0 | 43.9 | 39.5 |
| | 3 | 13.8 ± 1.2 | 8.1 ± 0.6** | 7.7 ± 0.6** | 8.6 ± 0.4** | 7.8 ± 0.4** | 39.8 | 65.1 | 51.6 | 51.0 |
| WT | — | 7.0 ± 0.4 | 6.4 ± 0.6 | 7.2 ± 0.4 | 7.7 ± 0.3 | 7.4 ± 0.4 | — | — | — | — |

(2) Chronic Administration of Compound A28 at Multiple Doses to Observe its Effect on the Random Blood-Glucose in Db/Db Mice

| Group | Dose mg/kg | After administration (weeks)/random blood glucose (mmol/L) | | | | | Hypoglycemic rate % | | | |
|---|---|---|---|---|---|---|---|---|---|---|
| | | Pre | 1 | 2 | 3 | 4 | 1 | 2 | 3 | 4 |
| Vehicle | — | 19.4 ± 0.9 | 19.6 ± 0.6 | 19.4 ± 1.3 | 20.3 ± 1.2 | 20.7 ± 1.7 | — | — | — | — |
| A28 | 0.3 | 17.9 ± 1.4 | 16.9 ± 1.3 | 15.7 ± 1.3* | 16.7 ± 1.5 | 19.1 ± 1.6 | 14.0 | 19.1 | 18.0 | 7.8 |
| | 1 | 16.8 ± 1.2 | 16.1 ± 1.0* | 16.3 ± 1.2 | 15.9 ± 1.1* | 15.1 ± 1.4* | 17.9 | 16.0 | 21.8 | 27.0 |
| | 3 | 18.7 ± 1.2 | 14.7 ± 0.9** | 13.0 ± 0.8** | 12.4 ± 1.0** | 13.2 ± 0.9** | 25.4 | 33.1 | 39.0 | 36.6 |
| | 10 | 18.3 ± 1.6 | 12.9 ± 0.6** | 10.6 ± 0.5** | 9.1 ± 0.4** | 9.7 ± 0.7** | 34.3 | 45.3 | 55.3 | 53.1 |
| Dapagliflozin | 1 | 19.3 ± 1.2 | 14.9 ± 0.9** | 14.9 ± 1.1* | 14.9 ± 1.0** | 14.4 ± 1.1** | 24.0 | 23.6 | 26.4 | 30.5 |
| | 3 | 17.5 ± 1.2 | 13.4 ± 0.8** | 14.1 ± 0.8** | 15.2 ± 1.2** | 11.7 ± 1.0** | 32.0 | 27.7 | 25.4 | 43.8 |
| WT | — | 7.0 ± 0.2 | 7.3 ± 0.5 | 7.1 ± 0.3 | 7.4 ± 0.4 | 6.9 ± 0.3 | — | — | — | — |

(3) Chronic Administration of Compound A28 at Multiple Doses to Observe its Effect on the Level of Glycosylated Hemoglobin in Db/Db Mice

| Group | Dose (mg/kg) | Number of animals | HbA1c (%) | Decline rate % |
|---|---|---|---|---|
| Vehicle | — | 10 | 7.59 ± 0.25 | — |
| A28 | 0.3 | 10 | 5.83 ± 0.36** | 23.2 |
| | 1 | 10 | 6.02 ± 0.30** | 20.7 |
| | 3 | 10 | 4.95 ± 0.37** | 34.8 |
| | 10 | 10 | 4.50 ± 0.27** | 40.7 |
| Dapa | 1 | 10 | 5.79 ± 0.32** | 23.7 |
| | 3 | 10 | 5.32 ± 0.26** | 29.9 |
| WT | — | 10 | 3.09 ± 0.13** | — |

(4) Chronic Administration of Compound A28 at Multiple Doses to Observe its Effect on Glucose Tolerance in Db/Db Mice

| Group | Dose mg/kg | Blood glucose (mmol/L) | | | | | | $AUC_{0-2\,h}$ | $AUC_{0-2\,h}$ reduction rate (%) |
|---|---|---|---|---|---|---|---|---|---|
| | | 0 min | 15 min | 30 min | 60 min | 90 min | 120 min | | |
| Veh | — | 17.8 ± 1.0 | 33.7 ± 1.3 | 33.1 ± 1.1 | 23.4 ± 1.0 | 22.6 ± 1.7 | 16.8 ± 1.6 | 14.7 ± 1.6 | — |
| A28 | 0.3 | 12.3 ± 0.9** | 22.7 ± 1.4** | 21.4 ± 1.1** | 13.5 ± 0.7** | 12.5 ± 0.9* * | 10.9 ± 1.0* * | 6.3 ± 1.3** | 57.2 |
| | 1 | 10.4 ± 1.0** | 16.9 ± 0.8** | 18.7 ± 0.7** | 11.1 ± 0.5** | 10.4 ± 0.6* * | 8.7 ± 0.5** | 4.7 ± 1.9** | 68.2 |
| | 3 | 8.1 ± 1.0** | 16.1 ± 2.4** | 17.4 ± 2.6** | 9.1 ± 1.0** | 8.9 ± 0.8** | 6.9 ± 0.8** | 6.1 ± 0.9** | 58.9 |
| | 10 | 7.2 ± 0.6** | 11.3 ± 0.6** | 12.3 ± 1.0** | 7.1 ± 0.5** | 6.5 ± 0.3** | 6.2 ± 0.5** | 2.3 ± 0.8** | 84.6 |
| Dapa | 1 | 10.0 ± 1.0** | 19.9 ± 1.0** | 20.3 ± 1.1** | 11.1 ± 0.5** | 10.8 ± 0.4* * | 11.8 ± 0.5* * | 7.9 ± 1.7** | 48.9 |
| | 3 | 8.6 ± 0.4** | 19.0 ± 1.2** | 20.2 ± 1.8** | 12.0 ± 1.4** | 9.9 ± 0.8** | 9.1 ± 0.6** | 9.4 ± 1.7* | 36.1 |
| WT | — | 7.7 ± 0.3** | 12.0 ± 0.5** | 9.8 ± 0.6** | 8.3 ± 0.4** | 6.5 ± 0.3** | 7.8 ± 0.4** | 1.5 ± 0.7** | — |

(5) Chronic Administration of Compound A28 at Multiple Doses to Observe its Effect on Glucose-Stimulated Insulin Release in Db/Db Mice

| Group | Dose mg/kg | Number of animals | Insulin (ng/ml) | | | | | AUC |
|---|---|---|---|---|---|---|---|---|
| | | | pre | 0 min | 15 min | 30 min | 60 min | |
| vehicle | — | 10 | 7.96 ± 0.88 | 10.90 ± 1.14 | 28.37 ± 2.86 | 29.32 ± 6.47 | 23.71 ± 2.25 | 25.38 ± 3.47 |
| A28 | 0.3 | 10 | 7.68 ± 0.79 | 21.58 ± 2.48** | 51.67 ± 7.86** | 46.22 ± 8.10 | 43.61 ± 4.85** | 43.85 ± 5.69** |
| | 1 | 10 | 7.86 ± 0.94 | 17.47 ± 2.20** | 41.94 ± 8.42 | 40.07 ± 7.01 | 32.89 ± 3.69* | 35.92 ± 5.00* |
| | 3 | 10 | 7.92 ± 1.60 | 17.57 ± 4.54** | 38.42 ± 8.58* | 36.06 ± 8.77 | 28.68 ± 8.81 | 32.49 ± 5.92 |
| | 10 | 10 | 7.45 ± 1.00 | 9.02 ± 0.59 | 16.70 ± 2.42** | 13.42 ± 1.94* | 27.45 ± 4.43 | 17.20 ± 1.59 |
| Dapa | 1 | 10 | 8.05 ± 1.10 | 12.92 ± 1.17 | 35.99 ± 5.34 | 29.85 ± 4.97 | 24.33 ± 2.90 | 27.89 ± 3.63 |
| | 3 | 10 | 8.15 ± 0.91 | 8.41 ± 1.07 | 21.29 ± 3.11 | 22.60 ± 3.22 | 31.36 ± 5.44 | 22.69 ± 2.89 |
| WT | — | 10 | −1.24 ± 0.07*** | 1.54 ± 0.07*** | 1.75 ± 0.07*** | 0.36 ± 0.12*** | 0.02 ± 0.06*** | 0.78 ± 0.06*** |

Results Analysis:

Four weeks after chronic administration of A28, the fasting blood glucose, random blood glucose and HbA1c levels were significantly and dose-dependently reduced in db/db mice with an effective dose of 0.3 mg/kg, which was comparable to that of Dapagliflozin at the same dose. After 3 weeks of chronic administration, A28 has significantly improved the oral glucose tolerance of db/db mice in a dose-dependent manner, and the effect was stronger than that of Dapagliflozin of the same dose. After four weeks of chronic administration, 0.3 mg/kg and 1 mg/kg dose of A28 has significantly improved glucose-stimulated insulin release in db/db mice in a dose-dependent manner.

All literatures mentioned in the present application are incorporated herein by reference, as though each one is individually incorporated by reference. Additionally, it should be understood that after reading the above teachings, those skilled in the art can make various changes and modifications to the present invention. These equivalents also fall within the scope defined by the appended claims.

The invention claimed is:

1. A compound of formula (I):

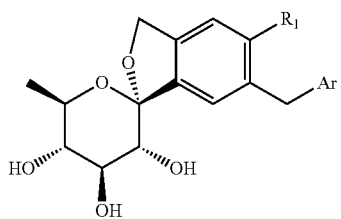

Formula I wherein:

$R_1$ is a hydrogen, halogen, or a substituted or unsubstituted group selected from the group consisting of $C_1$-$C_6$ alkyl, $C_2$-$C_6$ alkenyl, $C_1$-$C_6$ alkoxy, $C_2$-$C_6$ alkynyl, $C_3$-$C_{10}$ cycloalkyl, ($C_{2-10}$) alkoxycarbonyl, carbonyl ($C_{1-3}$) alkyl, thiocarbonyl ($C_{1-3}$) alkyl, sulfonyl ($C_{1-3}$) alkyl, sulfinyl ($C_{1-3}$) alkyl, imino ($C_{1-3}$) alkyl, amino, and cyano;

Ar is a group selected from the group consisting of substituted or unsubstituted $C_6$-$C_{12}$ aryl, and substituted or unsubstituted 3-12 membered heterocyclic group;

wherein the substitution means that one or more hydrogen atoms on the group are substituted by a substituent selected from the group consisting of cyano, $C_1$-$C_6$ alkyl, $C_1$-$C_6$ alkoxy, halogen, $C_1$-$C_6$ haloalkyl, carbonyl ($C_{2-10}$) alkoxy, carbonyl ($C_{7-10}$) aryloxy, acylamino ($C_{2-10}$) alkyl, $C_6$-$C_{12}$ aryl and 3-12 membered heterocyclic group, wherein each of the $C_6$-$C_{12}$ aryl and 3-12 membered heterocyclic group is unsubstituted or substituted by 1 to 3 substituents selected from the group consisting of halogen, unsubstituted or halogenated $C_1$-$C_6$ alkyl, and $C_1$-$C_6$ alkoxy.

2. A compound of formula (II):

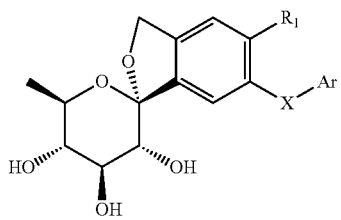

formula II wherein:
R₁ is a hydrogen, halogen, or a substituted or unsubstituted group selected from the group consisting of $C_1$-$C_6$ alkyl, $C_2$-$C_6$ alkenyl, $C_1$-$C_6$ alkoxy, $C_2$-$C_6$ alkynyl, $C_3$-$C_{10}$ cycloalkyl, ($C_{2-10}$) alkoxycarbonyl, carbonyl ($C_{1-3}$) alkyl, thiocarbonyl ($C_{1-3}$) alkyl, sulfonyl ($C_{1-3}$) alkyl, sulfinyl ($C_{1-3}$) alkyl, imino ($C_{1-3}$) alkyl, amino, and cyano;

X is selected from the group consisting of —CH₂—, —C(=O)—, and —CH(—OH)—;

Ar is a group selected from the group consisting of substituted or unsubstituted $C_6$-$C_{12}$ aryl, and substituted or unsubstituted 3-12 membered heterocyclic group;

wherein the substitution means that one or more hydrogen atoms on the group are substituted with a substituent selected from the group consisting of cyano, $C_1$-$C_6$ alkyl, $C_1$-$C_6$ alkoxy, $C_2$-$C_{10}$ ether group, $C_2$-$C_{10}$ ester group, $C_1$-$C_{10}$ hydroxyalkyl, $C_1$-$C_{10}$ carboxyalkyl, $C_2$-$C_6$ acyl, $C_3$-$C_{10}$ ester-alkyl, $C_1$-$C_4$ alkyl-3-12 membered heterocyclic group, halogen, $C_1$-$C_6$ haloalkyl, carbonyl ($C_{2-10}$) alkoxy, carbonyl ($C_{7-10}$) aryloxy, carbonyl ($C_{7-10}$) heterocyclic group, amido ($C_{2-10}$) alkyl, acyl ($C_{2-10}$) 3-12 membered heterocyclic group, $C_3$-$C_6$ cycloalkyl, $C_6$-$C_{12}$ aryl, and 3-12 membered heterocyclic group; wherein the $C_3$-$C_6$ cycloalkyl, $C_6$-$C_{12}$ aryl or 3-12 membered heterocyclic group are unsubstituted or substituted by 1 to 3 substituents selected from the group consisting of halogen, cyano, unsubstituted or halogenated $C_1$-$C_6$ alkyl, $C_1$-$C_6$ haloalkyl, and $C_1$-$C_6$ alkoxy.

3. The compound of claim 1, wherein R₁ is a hydrogen, halogen, or a substituted or unsubstituted group selected from the group consisting of $C_1$-$C_6$ alkyl, $C_2$-$C_6$ alkenyl, $C_1$-$C_6$ alkoxy, $C_2$-$C_6$ alkynyl, $C_3$-$C_{10}$ cycloalkyl, ($C_{2-10}$) alkoxycarbonyl, carbonyl ($C_{1-3}$) alkyl, thiocarbonyl ($C_{1-3}$) alkyl, sulfonyl ($C_{1-3}$) alkyl, sulfinyl ($C_{1-3}$) alkyl, and cyano; and/or Ar is a substituted or unsubstituted group selected from the group consisting of phenyl, furanyl, thiophenyl, pyrrolyl, pyrazolyl, triazolyl, isoxazolyl, oxazolyl, thiazolyl, isothiazolyl, oxadiazolyl, pyridinyl, pyridazinyl, pyrimidinyl, benzofuranyl, isobenzofuranyl, benzothiophenyl, isobenzothiophenyl, imidazolyl, benzoimidazolyl, indolyl, isoindolyl, quinolinyl, isoquinolinyl, naphthyridinyl, pyridopyridinyl, and benzothiazolyl.

4. The compound of claim 1, wherein R₁ is a hydrogen, halogen, or a substituted or unsubstituted group selected from the group consisting of methyl, methoxy, ethyl, ethylenyl, amino, cyano, ester group, amide, acetyl, carboxamido, carbamoyl, formyloxy, methoxycarbonyl, trifluoromethyl and trifluoromethoxy; and/or Ar is a substituted or unsubstituted group selected from the group consisting of phenyl, furanyl, thiophenyl, pyrrolyl, thiazolyl, isothiazolyl, pyridinyl, pyridazinyl, pyrimidinyl, benzofuranyl, isobenzofuranyl, benzothiophenyl, isobenzothiophenyl, imidazolyl, benzoimidazolyl, indolyl, isoindolyl, quinolinyl, isoquinolinyl, naphthyridinyl, pyridopyridinyl, and benzothiazolyl.

5. The compound of claim 1, wherein R₁ is a hydrogen, halogen, or a substituted or unsubstituted group selected from the group consisting of methyl, methoxy, ethyl, ethylenyl, amino, cyano, ester group, amide, acetyl, carboxamido, trifluoromethyl and trifluoromethoxy; and/or Ar is a substituted or unsubstituted group selected from the group consisting of phenyl, furanyl, thiophenyl, pyrrolyl, thiazolyl, isothiazolyl, benzofuranyl, and benzothiophenyl.

6. The compound of claim 1, wherein R₁ is selected from the group consisting of hydrogen, halogen, methyl, and ethyl; and/or Ar is a substituted or unsubstituted group selected from the group consisting of phenyl, thiophenyl, benzofuranyl, and benzothiophenyl; wherein the substitution means that one or more hydrogen atoms on the group are substituted by a substituent selected from the group consisting of halogen, $C_1$-$C_4$ alkyl, and phenyl unsubstituted or substituted by 1-3 halogen atoms.

7. A method for preparing the compound of formula (I) of claim 1, the method comprising:

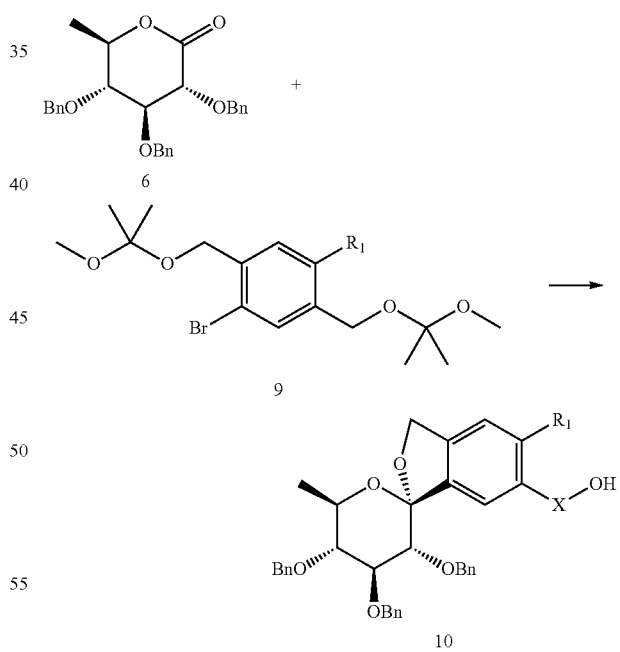

(a) reacting a compound of formula 6 in an inert solvent with a compound of formula 9, thus obtaining a compound of formula 10; and (b) preparing the compound of formula (I) using the compound of formula 10.

8. The method of claim 7, wherein the compound of formula 6 is prepared by the following method:

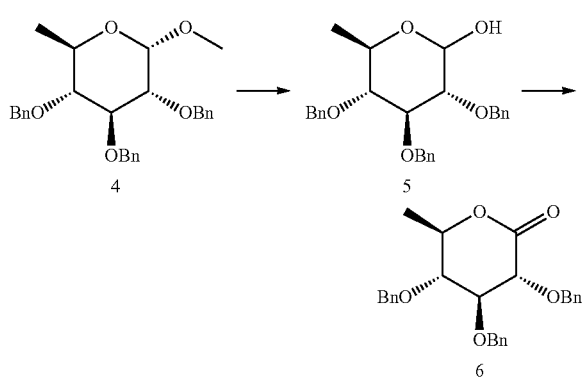

(b1) reacting a compound of formula 4 in an inert solvent and in the presence of acid to form a compound of formula 5;

(b2) reacting the compound of formula 5 in an inert solvent and in the presence of acetic anhydride to form the compound of formula 6.

9. A pharmaceutical composition comprising a therapeutically effective amount of the compound of formula (I) of claim 1, or a pharmaceutically acceptable salt, racemate, R-isomer, S-isomer thereof, or a mixture thereof, and optionally at least one of a pharmaceutically acceptable carrier, vehicle, adjuvant, excipient and diluent.

10. A method of inhibiting a sodium-glucose cotransporter 2 or decreasing the expression of sodium-glucose cotransporter 2 in a subject, the method comprising administering to the subject the pharmaceutical composition of claim 9.

11. A method of treating a metabolic disorder associated with sodium-glucose cotransporter 2 in a subject, the method comprising administering to the subject the pharmaceutical composition of claim 9, wherein the metabolic disorder is diabetes, atherosclerosis or obesity.

12. The compound of claim 2, wherein $R_1$ is a hydrogen, halogen, or a substituted or unsubstituted group selected from the group consisting of $C_1$-$C_6$ alkyl, $C_2$-$C_6$ alkenyl, $C_1$-$C_6$ alkoxy, $C_2$-$C_6$ alkynyl, $C_3$-$C_{10}$ cycloalkyl, ($C_{2-10}$) alkoxycarbonyl, carbonyl ($C_{1-3}$) alkyl, thiocarbonyl ($C_{1-3}$) alkyl, sulfonyl ($C_{1-3}$) alkyl, sulfinyl ($C_{1-3}$) alkyl, and cyano; and/or Ar is a substituted or unsubstituted group selected from the group consisting of phenyl, furanyl, thiophenyl, pyrrolyl, pyrazolyl, triazolyl, isoxazolyl, oxazolyl, thiazolyl, isothiazolyl, oxadiazolyl, pyridinyl, pyridazinyl, pyrimidinyl, benzofuranyl, isobenzofuranyl, benzothiophenyl, isobenzothiophenyl, imidazolyl, benzoimidazolyl, indolyl, isoindolyl, quinolinyl, isoquinolinyl, naphthyridinyl, pyridopyridinyl, and benzothiazolyl.

13. The compound of claim 2, wherein $R_1$ is a hydrogen, halogen, or a substituted or unsubstituted group selected from the group consisting of methyl, methoxy, ethyl, ethylenyl, amino, cyano, ester group, amide, acetyl, carboxamido, carbamoyl, formyloxy, methoxycarbonyl, trifluoromethyl and trifluoromethoxy; and/or Ar is a substituted or unsubstituted group selected from the group consisting of phenyl, furanyl, thiophenyl, pyrrolyl, thiazolyl, isothiazolyl, pyridinyl, pyridazinyl, pyrimidinyl, benzofuranyl, isobenzofuranyl, benzothiophenyl, isobenzothiophenyl, imidazolyl, benzoimidazolyl, indolyl, isoindolyl, quinolinyl, isoquinolinyl, naphthyridinyl, pyridopyridinyl, and benzothiazolyl.

14. The compound of claim 2, wherein $R_1$ is a hydrogen, halogen, or a substituted or unsubstituted group selected from the group consisting of methyl, methoxy, ethyl, ethylenyl, amino, cyano, ester group, amide, acetyl, carboxamido, trifluoromethyl and trifluoromethoxy; and/or Ar is a substituted or unsubstituted group selected from the group consisting of phenyl, furanyl, thiophenyl, pyrrolyl, thiazolyl, isothiazolyl, benzofuranyl, and benzothiophenyl.

15. The compound of claim 2, wherein $R_1$ is selected from the group consisting of hydrogen, halogen, methyl, and ethyl; and/or Ar is a substituted or unsubstituted group selected from the group consisting of phenyl, thiophenyl, benzofuranyl, and benzothiophenyl; wherein the substitution means that one or more hydrogen atoms on the group are substituted by a substituent selected from the group consisting of halogen, $C_1$-$C_4$ alkyl, and phenyl unsubstituted or substituted by 1-3 halogen atoms.

16. A pharmaceutical composition comprising a therapeutically effective amount of the compound of formula (I) of claim 2, or a pharmaceutically acceptable salt, racemate, R-isomer, S-isomer thereof, or a mixture thereof, and optionally at least one of a pharmaceutically acceptable carrier, vehicle, adjuvant, excipient and diluent.

17. A method of inhibiting a sodium-glucose cotransporter 2 or decreasing the expression of sodium-glucose cotransporter 2 in a subject, the method comprising administering to the subject the pharmaceutical composition of claim 16.

18. A method of treating a metabolic disorder associated with sodium-glucose cotransporter 2 in a subject, the method comprising administering to the subject the pharmaceutical composition of claim 16, wherein the metabolic disorder is diabetes, atherosclerosis, or obesity.

19. The compound according to claim 2, wherein $R_1$ is a hydrogen, halogen, or a substituted or unsubstituted group selected from the group consisting of $C_1$-$C_6$ alkyl and $C_2$-$C_6$ alkynyl.

20. A compound selected from the group consisting of:

| No. | Name | Structure |
|-----|------|-----------|
| A1 | (1S,3'R,4'S,5'S,6'R)-6'-methyl-6-(4-methylbenzyl)-3',4',5',6'-tetrahydro-3H-spiro[isobenzofuran-1,2'-pyran]-3',4',5'-triol | A1 |

-continued

| No. | Name | Structure |
|---|---|---|
| A2 | (1S,3'R,4'S,5'S,6'R)-6'-methyl-6-(4-ethylbenzyl)-3',4',5',6'-tetrahydro-3H-spiro[isobenzofuran-1,2'-pyran]-3',4',5'-triol | 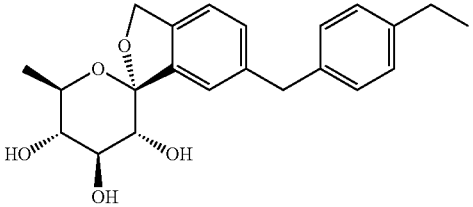 A2 |
| A3 | (1S,3'R,4'S,5'S,6'R)-6'-methyl-6-(4-propylbenzyl)-3',4',5',6'-tetrahydro-3H-spiro[isobenzofuran-1,2'-pyran]-3',4',5'-triol | 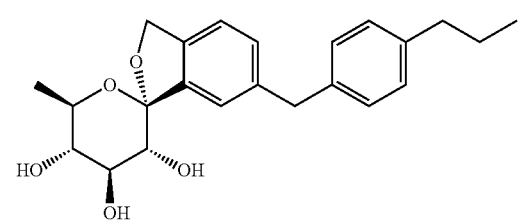 A3 |
| A4 | (1S,3'R,4'S,5'S,6'R)-6'-methyl-6-(4-isopropylbenzyl)-3',4',5',6'-tetrahydro-3H-spiro[isobenzofuran-1,2'-pyran]-3',4',5'-triol | 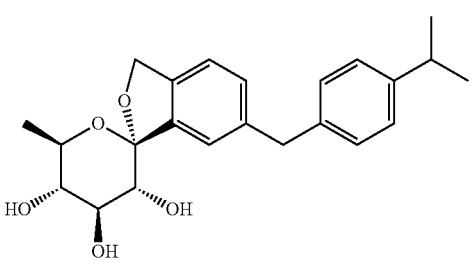 A4 |
| A5 | (1S,3'R,4'S,5'S,6'R)-6'-methyl-6-(4-methoxybenzyl)-3',4',5',6'-tetrahydro-3H-spiro[isobenzofuran-1,2'-pyran]-3',4',5'-triol | 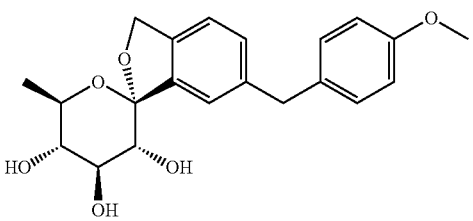 A5 |
| A6 | (1S,3'R,4'S,5'S,6'R)-6'-methyl-6-(4-ethyoxylbenzyl)-3',4',5',6'-tetrahydro-3H-spiro[isobenzofuran-1,2'-pyran]-3',4',5'-triol | 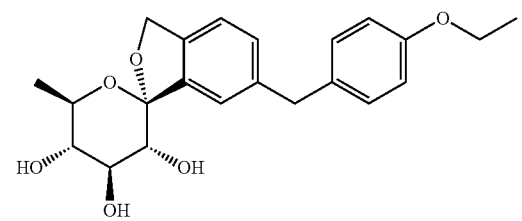 A6 |
| A7 | (1S,3'R,4'S,5'S,6'R)-6'-methyl-6-((5-methylthienyl)-2-methyl)-3',4',5',6'-tetrahydro-3H-spiro[isobenzofuran-1,2'-pyran]-3',4',5'-triol | 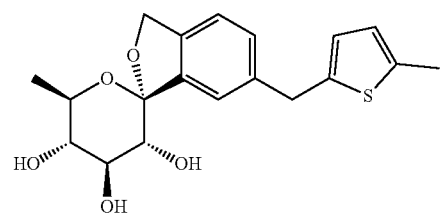 A7 |

| No. | Name | Structure |
|---|---|---|
| A8 | (1S,3'R,4'S,5'S,6'R)-6'-methyl-6-((5-ethylthienyl)-2-methyl)-3',4',5',6'-tetrahydro-3H-spiro[isobenzofuran-1,2'-pyran]-3',4',5'-triol | 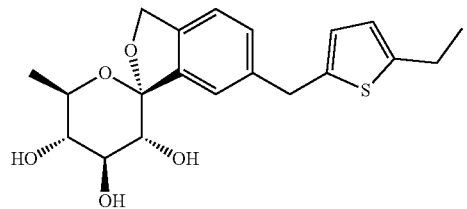 A8 |
| A9 | (1S,3'R,4'S,5'S,6'R)-6'-methyl-6-((5-propylthienyl)-2-methyl)-3',4',5',6'-tetrahydro-3H-spiro[isobenzofuran-1,2'-pyran]-3',4',5'-triol | 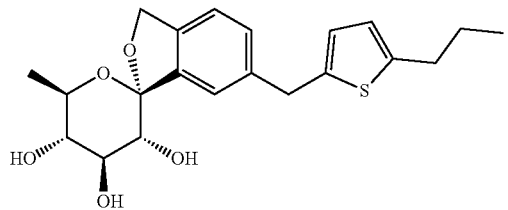 A9 |
| A10 | (1S,3'R,4'S,5'S,6'R)-6'-methyl-6-((5-chlorothienyl)-2-methyl)-3',4',5',6'-tetrahydro-3H-spiro[isobenzofuran-1,2'-pyran]-3',4',5'-triol | 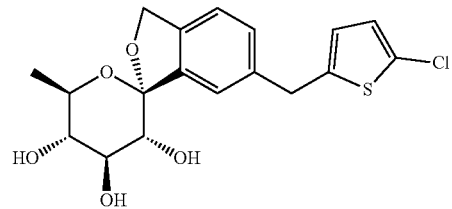 A10 |
| A11 | (1S,3'R,4'S,5'S,6'R)-6'-methyl-6-((5-(4-fluorophenyl)thienyl)-2-methyl)-3',4',5',6'-tetrahydro-3H-spiro[isobenzofuran-1,2'-pyran]-3',4',5'-triol | 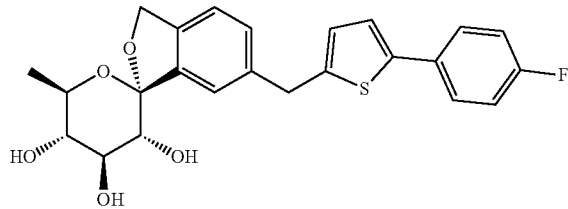 A11 |
| A12 | (1S,3'R,4'S,5'S,6'R)-6'-methyl-6-((5-phenylthienyl)-2-methyl)-3',4',5',6'-tetrahydro-3H-spiro[isobenzofuran-1,2'-pyran]-3',4',5'-triol | 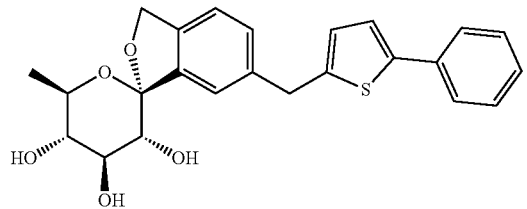 A12 |
| A13 | (1S,3'R,4'S,5'S,6'R)-6'-methyl-6-((5-(2-pyridyl)thienyl)-2-methyl)-3',4',5',6'-tetrahydro-3H-spiro[isobenzofuran-1,2'-pyran]-3',4',5'-triol | 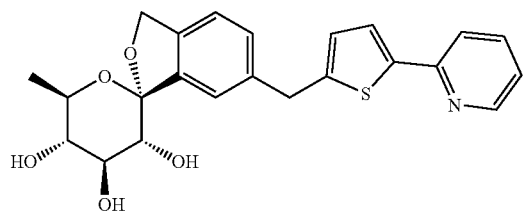 A13 |

-continued

| No. | Name | Structure |
|---|---|---|
| A14 | (1S,3'R,4'S,5'S,6'R)-6'-methyl-6-(naphthyl-2-methyl)-3',4',5',6'-tetrahydro-3H-spiro[isobenzofuran-1,2'-pyran]-3',4',5'-triol | 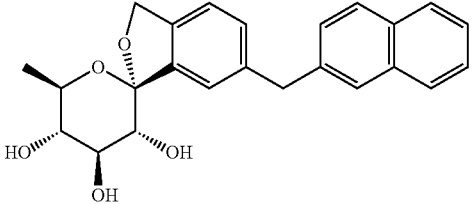 [SMILES: C[C@H]1O[C@]2(OCc3ccc(Cc4ccc5ccccc5c4)cc32)[C@H](O)[C@@H](O)[C@@H]1O]<br>A14 |
| A15 | (1S,3'R,4'S,5'S,6'R)-6'-methyl-6-(benzo[b]thiophene-2-methyl)-3',4',5',6'-tetrahydro-3H-spiro[isobenzofuran-1,2'-pyran]-3',4',5'-triol | 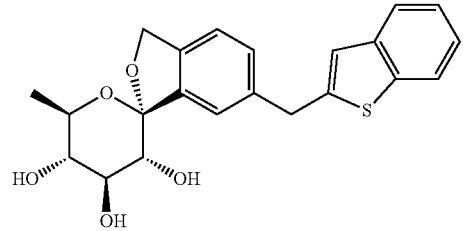 [SMILES: C[C@H]1O[C@]2(OCc3ccc(Cc4cc5ccccc5s4)cc32)[C@H](O)[C@@H](O)[C@@H]1O]<br>A15 |
| A16 | (1S,3'R,4'S,5'S,6'R)-6'-methyl-6-(benzo[b]furan-2-methyl)-3',4',5',6'-tetrahydro-3H-spiro[isobenzofuran-1,2'-pyran]-3',4',5'-triol | 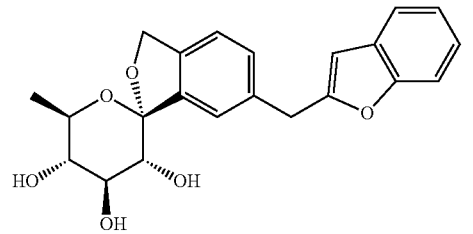<br>A16 |
| A17 | (1S,3'R,4'S,5'S,6'R)-6'-methyl-6-((5-(2-furyl)thiazolyl)-2-methyl)-3',4',5',6'-tetrahydro-3H-spiro[isobenzofuran-1,2'-pyran]-3',4',5'-triol | 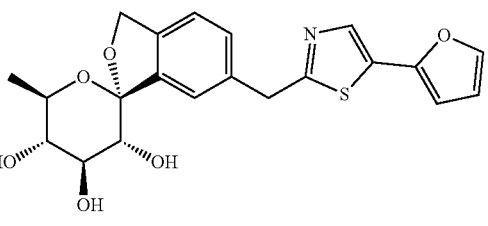<br>A17 |
| A18 | (1S,3'R,4'S,5'S,6'R)-6'-methyl-6-((5-(2-thienyl)thiazolyl)-2-methyl)-3',4',5',6'-tetrahydro-3H-spiro[isobenzofuran-1,2'-pyran]-3',4',5'-triol | 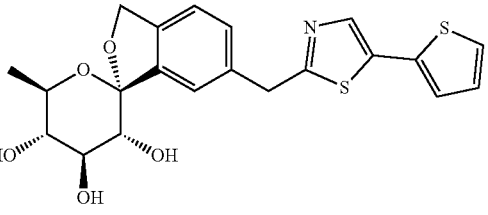<br>A18 |
| A19 | (1S,3'R,4'S,5'S,6'R)-6'-methyl-6-((5-(4-fluorophenyl)thiazolyl)-2-methyl)-3',4',5',6'-tetrahydro-3H-spiro[isobenzofuran-1,2'-pyran]-3',4',5'-triol | 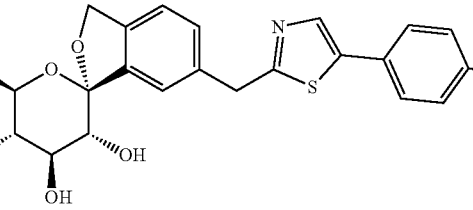<br>A19 |

-continued

| No. | Name | Structure |
|---|---|---|
| A20 | (1S,3'R,4'S,5'S,6'R)-6'-methyl-6-((5-phenylthiazolyl)-2-methyl)-3',4',5',6'-tetrahydro-3H-spiro[isobenzofuran-1,2'-pyran]-3',4',5'-triol | A20 |
| A21 | (1S,3'R,4'S,5'S,6'R)-6'-methyl-6-(4-methylbenzyl)-5-chloro-3',4',5',6'-tetrahydro-3H-spiro[isobenzofuran-1,2'-pyran]-3',4',5'-triol | A21 |
| A22 | (1S,3'R,4'S,5'S,6'R)-6'-methyl-6-(4-ethylbenzyl)-5-chloro-3',4',5',6'-tetrahydro-3H-spiro[isobenzofuran-1,2'-pyran]-3',4',5'-triol | A22 |
| A23 | (1S,3'R,4'S,5'S,6'R)-6'-methyl-6-(4-propylbenzyl)-5-chloro-3',4',5',6'-tetrahydro-3H-spiro[isobenzofuran-1,2'-pyran]-3',4',5'-triol | A23 |
| A24 | (1S,3'R,4'S,5'S,6'R)-6'-methyl-6-(4-isopropylbenzyl)-5-chloro-3',4',5',6'-tetrahydro-3H-spiro[isobenzofuran-1,2'-pyran]-3',4',5'-triol | A24 |
| A25 | (1S,3'R,4'S,5'S,6'R)-6'-methyl-6-(4-methoxybenzyl)-5-chloro-3',4',5',6'-tetrahydro-3H-spiro[isobenzofuran-1,2'-pyran]-3',4',5'-triol | A25 |

| No. | Name | Structure |
|---|---|---|
| A26 | (1S,3'R,4'S,5'S,6'R)-6'-methyl-6-(4-ethyoxylbenzyl)-5-chloro-3',4',5',6'-tetrahydro-3H-spiro[isobenzofuran-1,2'-pyran]-3',4',5'-triol | 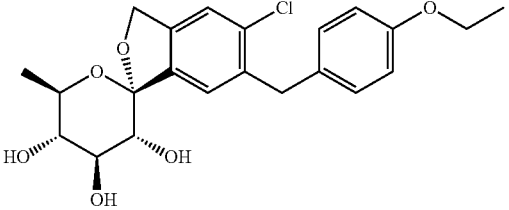 A26 |
| A27 | (1S,3'R,4'S,5'S,6'R)-6'-methyl-6-((5-methylthienyl)-2-methyl)-5-chloro-3',4',5',6'-tetrahydro-3H-spiro[isobenzofuran-1,2'-pyran]-3',4',5'-triol | 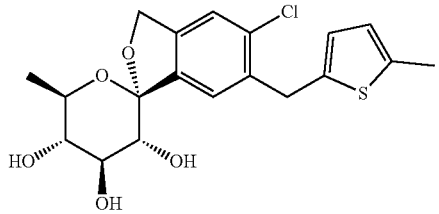 A27 |
| A28 | (1S,3'R,4'S,5'S,6'R)-6'-methyl-6-((5-ethylthienyl)-2-methyl)-5-chloro-3',4',5',6'-tetrahydro-3H-spiro[isobenzofuran-1,2'-pyran]-3',4',5'-triol | 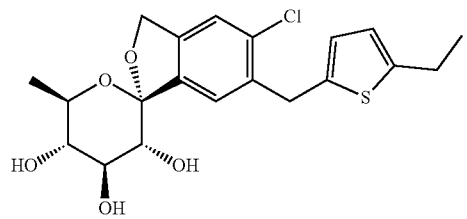 A28 |
| A29 | (1S,3'R,4'S,5'S,6'R)-6'-methyl-6-((5-propylthienyl)-2-methyl)-5-chloro-3',4',5',6'-tetrahydro-3H-spiro[isobenzofuran-1,2'-pyran]-3',4',5'-triol | 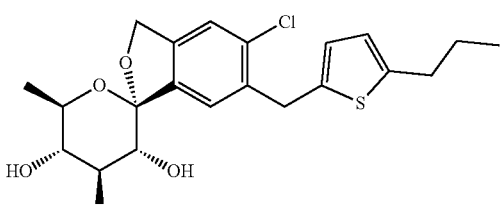 A29 |
| A30 | (1S,3'R,4'S,5'S,6'R)-6'-methyl-6-((5-chlorothienyl)-2-methyl)-5-chloro-3',4',5',6'-tetrahydro-3H-spiro[isobenzofuran-1,2'-pyran]-3',4',5'-triol | 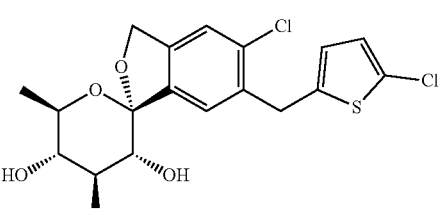 A30 |
| A31 | (1S,3'R,4'S,5'S,6'R)-6'-methyl-6-((5-(4-fluorophenyl)thienyl)-2-methyl)-5-chloro-3',4',5',6'-tetrahydro-3H-spiro[isobenzofuran-1,2'-pyran]-3',4',5'-triol | 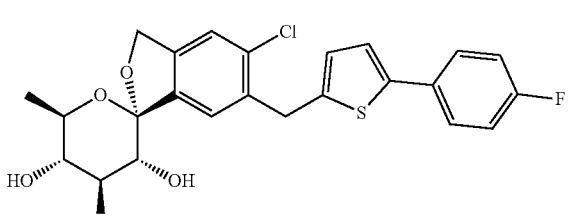 A31 |

| No. | Name | Structure |
|---|---|---|
| A32 | (1S,3'R,4'S,5'S,6'R)-6'-methyl-6-((5-phenylthienyl)-2-methyl)-5-chloro-3',4',5',6'-tetrahydro-3H-spiro[isobenzofuran-1,2'-pyran]-3',4',5'-triol | 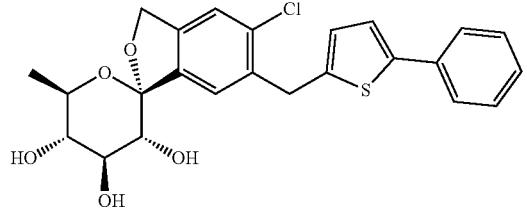<br>A32 |
| A33 | (1S,3'R,4'S,5'S,6'R)-6'-methyl-6-((5-(2-pyridyl)thienyl)-2-methyl)-5-chloro-3',4',5',6'-tetrahydro-3H-spiro[isobenzofuran-1,2'-pyran]-3',4',5'-triol | 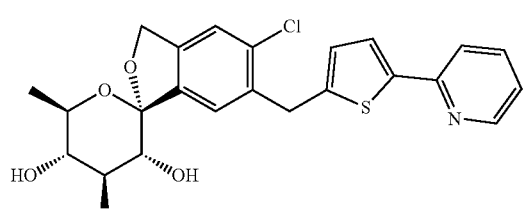<br>A33 |
| A34 | (1S,3'R,4'S,5'S,6'R)-6'-methyl-6-(naphthyl-2-methyl)-5-chloro-3',4',5',6'-tetrahydro-3H-spiro[isobenzofuran-1,2'-pyran]-3',4',5'-triol | 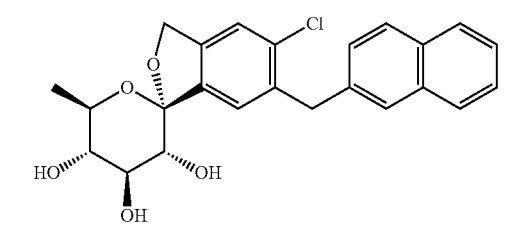<br>A34 |
| A35 | (1S,3'R,4'S,5'S,6'R)-6'-methyl-6-(benzo[b]thiophene-2-methyl)-5-chloro-3',4',5',6'-tetrahydro-3H-spiro[isobenzofuran-1,2'-pyran]-3',4',5'-triol | 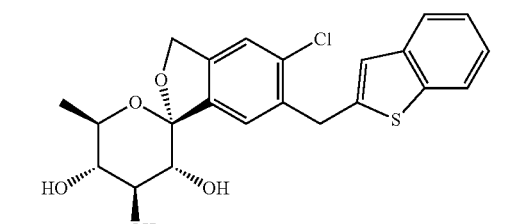<br>A35 |
| A36 | (1S,3'R,4'S,5'S,6'R)-6'-methyl-6-(benzo[b]furan-2-methyl)-5-chloro-3',4',5',6'-tetrahydro-3H-spiro[isobenzofuran-1,2'-pyran]-3',4',5'-triol | 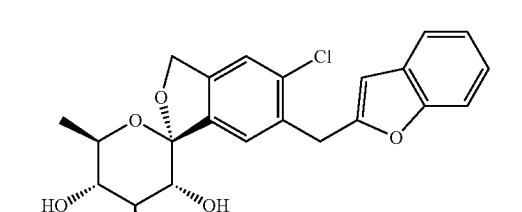<br>A36 |
| A37 | (1S,3'R,4'S,5'S,6'R)-6'-methyl-6-((5-(2-furyl)thiazolyl)-2-methyl)-5-chloro-3',4',5',6'-tetrahydro-3H-spiro[isobenzofuran-1,2'-pyran]-3',4',5'-triol | 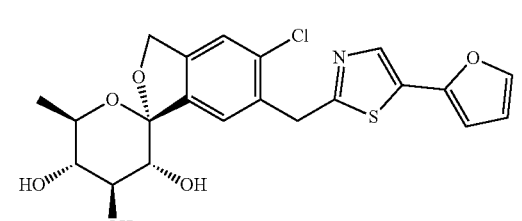<br>A37 |

-continued

| No. | Name | Structure |
|---|---|---|
| A38 | (1S,3'R,4'S,5'S,6'R)-6'-methyl-6-(4-methylbenzyl)-5-fluoro-3',4',5',6'-tetrahydro-3H-spiro[isobenzofuran-1,2'-pyran]-3',4',5'-triol | 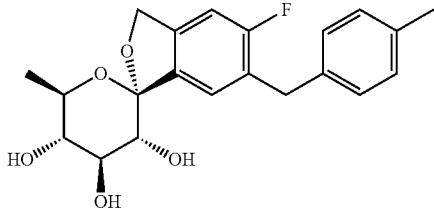<br>A38 |
| A39 | (1S,3'R,4'S,5'S,6'R)-6'-methyl-6-(4-methoxybenzyl)-5-fluoro-3',4',5',6'-tetrahydro-3H-spiro[isobenzofuran-1,2'-pyran]-3',4',5'-triol | 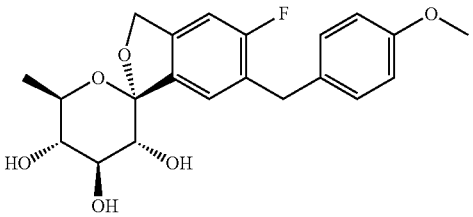<br>A39 |
| A40 | (1S,3'R,4'S,5'S,6'R)-6'-methyl-6-(4-ethyoxylbenzyl)-5-fluoro-3',4',5',6'-tetrahydro-3H-spiro[isobenzofuran-1,2'-pyran]-3',4',5'-triol | 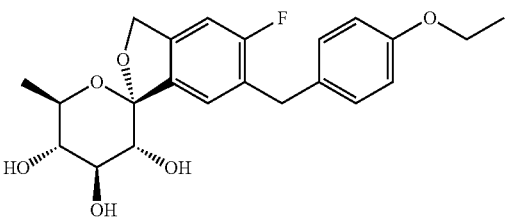<br>A40 |
| A41 | (1S,3'R,4'S,5'S,6'R)-6'-methyl-6-((5-methylthienyl)-2-methyl)-5-fluoro-3',4',5',6'-tetrahydro-3H-spiro[isobenzofuran-1,2'-pyran]-3',4',5'-triol | 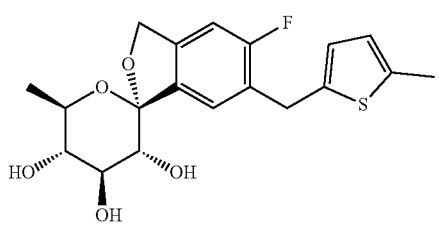<br>A41 |
| A42 | (1S,3'R,4'S,5'S,6'R)-6'-methyl-6-((5-ethylthienyl)-2-methyl)-5-fluoro-3',4',5',6'-tetrahydro-3H-spiro[isobenzofuran-1,2'-pyran]-3',4',5'-triol | 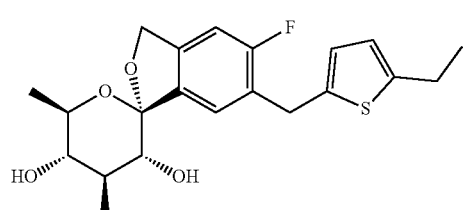<br>A42 |
| A43 | (1S,3'R,4'S,5'S,6'R)-6'-methyl-6-((5-chlorothienyl)-2-methyl)-5-fluoro-3',4',5',6'-tetrahydro-3H-spiro[isobenzofuran-1,2'-pyran]-3',4',5'-triol | 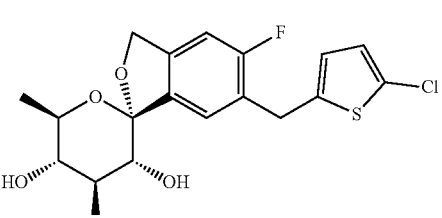<br>A43 |

-continued

| No. | Name | Structure |
|---|---|---|
| A44 | (1S,3'R,4'S,5'S,6'R)-6'-methyl-6-((5-(4-fluorophenyl)thienyl)-2-methyl)-5-fluoro-3',4',5',6'-tetrahydro-3H-spiro[isobenzofuran-1,2'-pyran]-3',4',5'-triol | 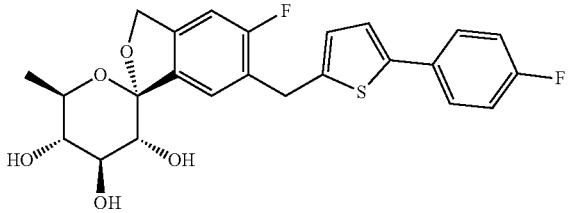<br>A44 |
| A45 | (1S,3'R,4'S,5'S,6'R)-6'-methyl-6-((5-phenylthienyl)-2-methyl)-5-fluoro-3',4',5',6'-tetrahydro-3H-spiro[isobenzofuran-1,2'-pyran]-3',4',5'-triol | 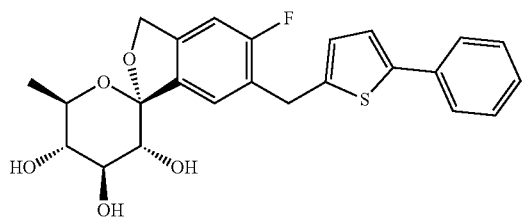 [SMILES: C[C@H]1O[C@]2(OCc3cc(Cl)c(Cc4ccc(-c5ccccc5)s4)cc32)[C@H](O)[C@@H](O)[C@@H]1O]<br>A45 |
| A46 | (1S,3'R,4'S,5'S,6'R)-6'-methyl-6-((5-(2-pyridyl)thienyl)-2-methyl)-5-fluoro-3',4',5',6'-tetrahydro-3H-spiro[isobenzofuran-1,2'-pyran]-3',4',5'-triol | 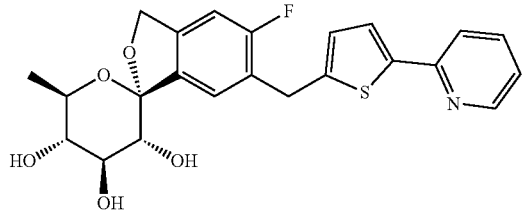 [SMILES: C[C@H]1O[C@]2(OCc3cc(Cl)c(Cc4ccc(-c5ccccn5)s4)cc32)[C@H](O)[C@@H](O)[C@@H]1O]<br>A46 |
| A47 | (1S,3'R,4'S,5'S,6'R)-6'-methyl-6-(benzo[b]thiophene-2-methyl)-5-fluoro-3',4',5',6'-tetrahydro-3H-spiro[isobenzofuran-1,2'-pyran]-3',4',5'-triol | 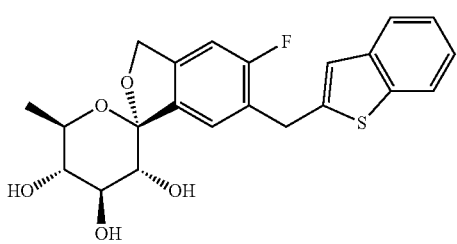 [SMILES: C[C@H]1O[C@]2(OCc3cc(Cl)c(Cc4cc5ccccc5s4)cc32)[C@H](O)[C@@H](O)[C@@H]1O]<br>A47 |
| A48 | (1S,3'R,4'S,5'S,6'R)-6'-methyl-6-(benzo[b]furan-2-methyl)-5-fluoro-3',4',5',6'-tetrahydro-3H-spiro[isobenzofuran-1,2'-pyran]-3',4',5'-triol | 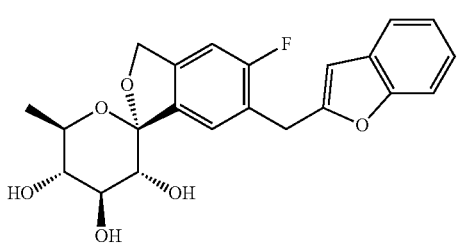 [SMILES: C[C@H]1O[C@]2(OCc3cc(Cl)c(Cc4cc5ccccc5o4)cc32)[C@H](O)[C@@H](O)[C@@H]1O]<br>A48 |
| A49 | (1S,3'R,4'S,5'S,6'R)-6'-methyl-6-((5-(2-furyl)thiazolyl)-2-methyl)-5-fluoro-3',4',5',6'-tetrahydro-3H-spiro[isobenzofuran-1,2'-pyran]-3',4',5'-triol | 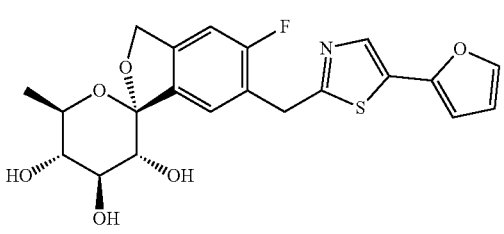<br>A49 |

-continued

| No. | Name | Structure |
|---|---|---|
| A50 | (1S,3'R,4'S,5'S,6'R)-5,6'-dimethyl-6-(4-methylbenzyl)-3',4',5',6'-tetrahydro-3H-spiro[isobenzofuran-1,2'-pyran]-3',4',5'-triol | 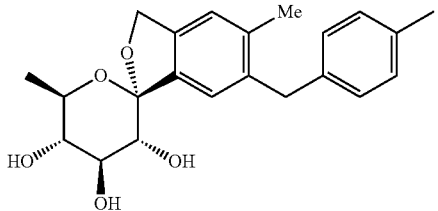 A50 |
| A51 | (1S,3'R,4'S,5'S,6'R)-5,6'-dimethyl-6-(4-ethylbenzyl)-3',4',5',6'-tetrahydro-3H-spiro[isobenzofuran-1,2'-pyran]-3',4',5'-triol | 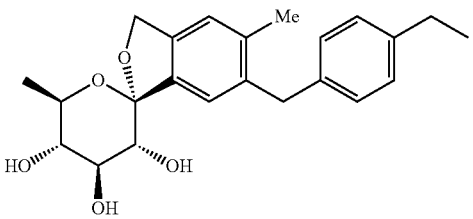 A51 |
| A52 | (1S,3'R,4'S,5'S,6'R)-5,6'-dimethyl-6-(4-propylbenzyl)-3',4',5',6'-tetrahydro-3H-spiro[isobenzofuran-1,2'-pyran]-3',4',5'-triol | 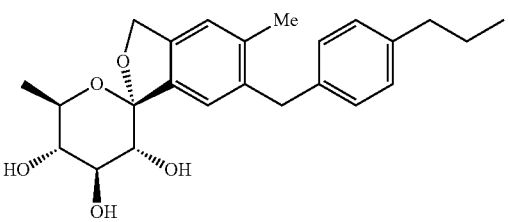 A52 |
| A53 | (1S,3'R,4'S,5'S,6'R)-5,6'-dimethyl-6-(4-isopropylbenzyl)-3',4',5',6'-tetrahydro-3H-spiro[isobenzofuran-1,2'-pyran]-3',4',5'-triol | 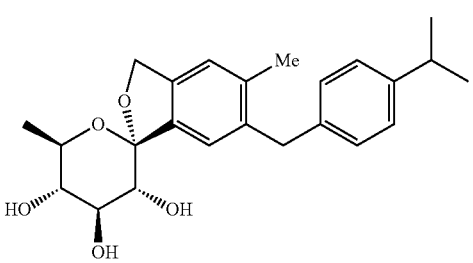 A53 |
| A54 | (1S,3'R,4'S,5'S,6'R)-5,6'-dimethyl-6-(4-methoxybenzyl)-3',4',5',6'-tetrahydro-3H-spiro[isobenzofuran-1,2'-pyran]-3',4',5'-triol | 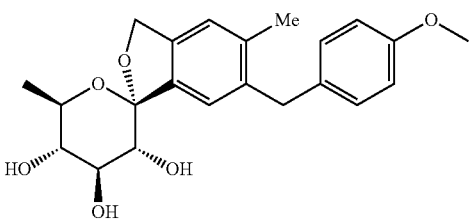 A54 |
| A55 | (1S,3'R,4'S,5'S,6'R)-5,6'-dimethyl-6-(4-ethyoxylbenzyl)-3',4',5',6'-tetrahydro-3H-spiro[isobenzofuran-1,2'-pyran]-3',4',5'-triol | 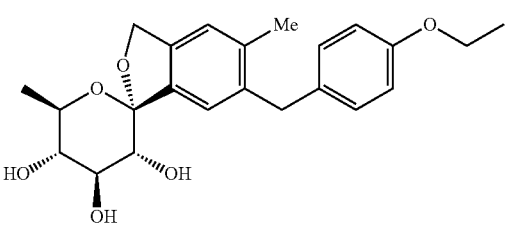 A55 |

| No. | Name | Structure |
|---|---|---|
| A56 | (1S,3'R,4'S,5'S,6'R)-5,6'-dimethyl-6-((5-methylthienyl)-2-methyl)-3',4',5',6'-tetrahydro-3H-spiro[isobenzofuran-1,2'-pyran]-3',4',5'-triol | 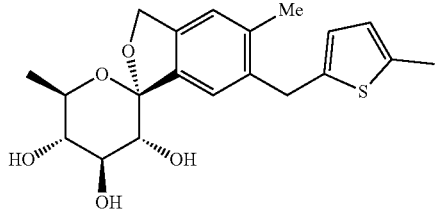 A56 |
| A57 | (1S,3'R,4'S,5'S,6'R)-5,6'-dimethyl-6-((5-ethylthienyl)-2-methyl)-3',4',5',6'-tetrahydro-3H-spiro[isobenzofuran-1,2'-pyran]-3',4',5'-triol | 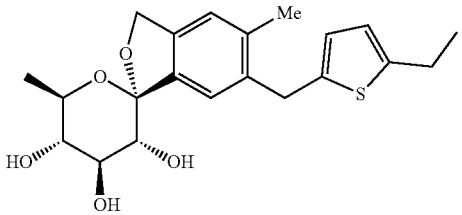 A57 |
| A58 | (1S,3'R,4'S,5'S,6'R)-5,6'-dimethyl-6-((5-propylthienyl)-2-methyl)-3',4',5',6'-tetrahydro-3H-spiro[isobenzofuran-1,2'-pyran]-3',4',5'-triol | 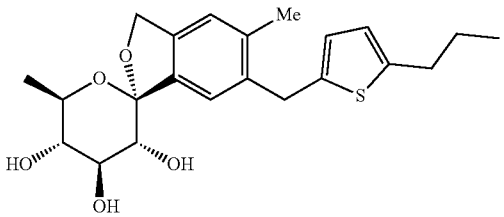 A58 |
| A59 | (1S,3'R,4'S,5'S,6'R)-5,6'-dimethyl-6-((5-chlorothienyl)-2-methyl)-3',4',5',6'-tetrahydro-3H-spiro[isobenzofuran-1,2'-pyran]-3',4',5'-triol | 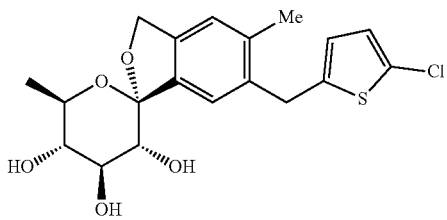 A59 |
| A60 | (1S,3'R,4'S,5'S,6'R)-5,6'-dimethyl-6-((5-(4-fluorophenyl)thienyl)-2-methyl)-5-chloro-3',4',5',6'-tetrahydro-3H-spiro[isobenzofuran-1,2'-pyran]-3',4',5'-triol | 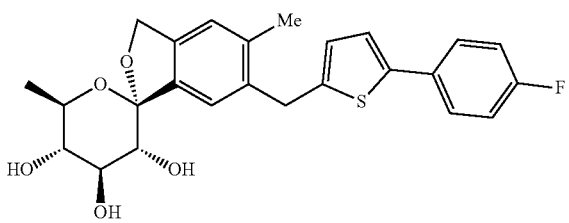 A60 |
| A61 | (1S,3'R,4'S,5'S,6'R)-5,6'-dimethyl-6-((5-phenylthienyl)-2-methyl)-3',4',5',6'-tetrahydro-3H-spiro[isobenzofuran-1,2'-pyran]-3',4',5'-triol | 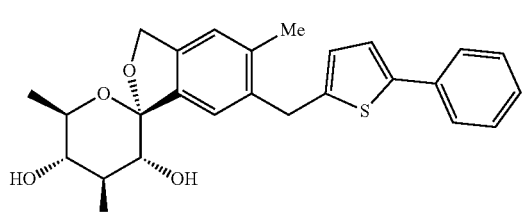 A61 |

| No. | Name | Structure |
|---|---|---|
| A62 | (1S,3'R,4'S,5'S,6'R)-5,6'-dimethyl-6-((5-(2-pyridyl)thienyl)-2-methyl)-3',4',5',6'-tetrahydro-3H-spiro[isobenzofuran-1,2'-pyran]-3',4',5'-triol | 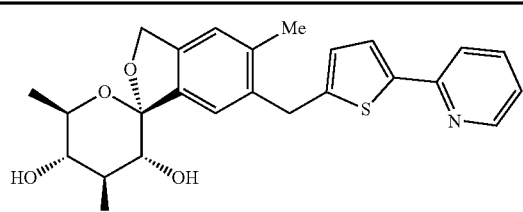 A62 |
| A63 | (1S,3'R,4'S,5'S,6'R)-5,6'-dimethyl-6-(naphthyl-2-methyl)-3',4',5',6'-tetrahydro-3H-spiro[isobenzofuran-1,2'-pyran]-3',4',5'-triol | 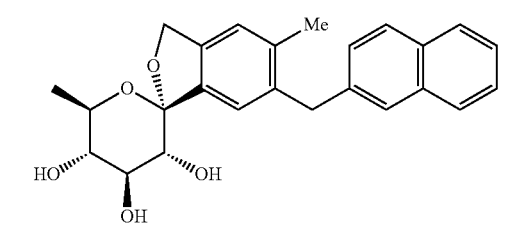 A63 |
| A64 | (1S,3'R,4'S,5'S,6'R)-5,6'-dimethyl-6-(benzo[b]thiophene-2-methyl)-3',4',5',6'-tetrahydro-3H-spiro[isobenzofuran-1,2'-pyran]-3',4',5'-triol | 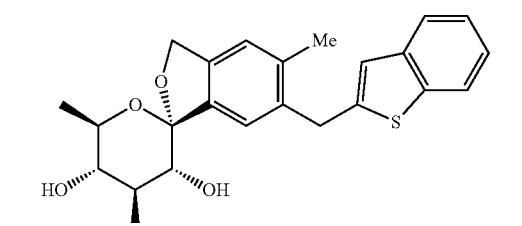 A64 |
| A65 | (1S,3'R,4'S,5'S,6'R)-5,6'-dimethyl-6-(benzo[b]furan-2-methyl)-3',4',5',6'-tetrahydro-3H-spiro[isobenzofuran-1,2'-pyran]-3',4',5'-triol | 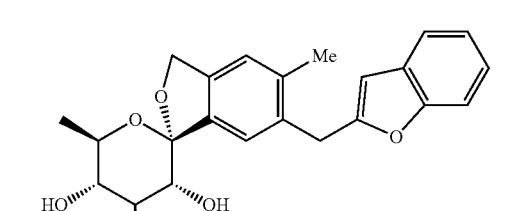 A65 |
| A66 | (1S,3'R,4'S,5'S,6'R)-5,6'-dimethyl-6-((5-(2-furyl)thiazolyl)-2-methyl)-3',4',5',6'-tetrahydro-3H-spiro[isobenzofuran-1,2'-pyran]-3',4',5'-triol | 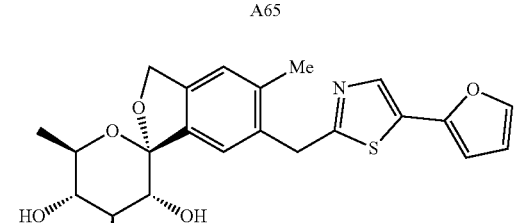 A66 |
| A67 | (1S,3'R,4'S,5'S,6'R)-5,6'-dimethyl-6-((5-(2-thienyl)thiazolyl)-2-methyl)-3',4',5',6'-tetrahydro-3H-spiro[isobenzofuran-1,2'-pyran]-3',4',5'-triol | 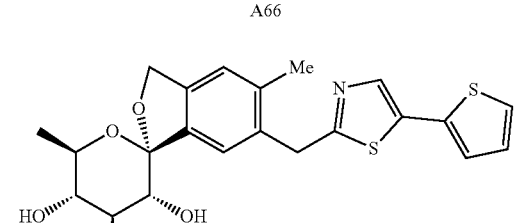 A67 |

-continued

| No. | Name | Structure |
|---|---|---|
| A68 | (1S,3'R,4'S,5'S,6'R)-5,6'-dimethyl-6-((5-(4-fluorophenyl)thiazolyl)-2-methyl)-3',4',5',6'-tetrahydro-3H-spiro[isobenzofuran-1,2'-pyran]-3',4',5'-triol | 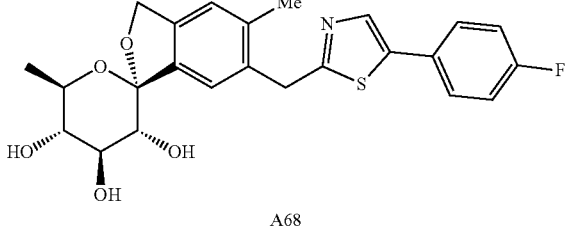 A68 |
| A69 | (1S,3'R,4'S,5'S,6'R)-5,6'-dimethyl-6-((5-phenylthiazolyl)-2-methyl)-3',4',5',6'-tetrahydro-3H-spiro[isobenzofuran-1,2'-pyran]-3',4',5'-triol | 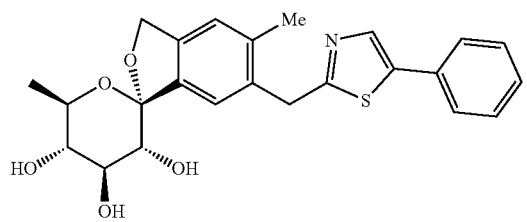 A69 |
| A70 | (1S,3'R,4'S,5'S,6'R)-5,6'-dimethyl-6-((5-(4-trifluoromethyl)phenyl)thienyl)-2-methyl)-5-chloro-3',4',5',6'-tetrahydro-3H-spiro[isobenzofuran-1,2'-pyran]-3',4',5'-triol | 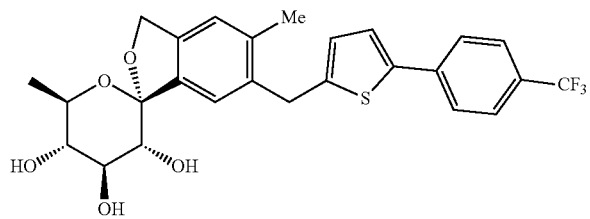 A70 |
| A71 | (1S,3'R,4'S,5'S,6'R)-5,6'-dimethyl-6-((5-(4-methyl)phenyl)thienyl)-2-methyl)-5-chloro-3',4',5',6'-tetrahydro-3H-spiro[isobenzofuran-1,2'-pyran]-3',4',5'-triol | 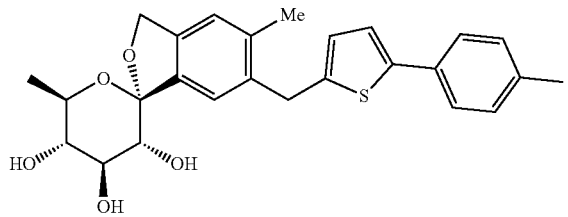 A71 |
| A72 | (1S,3'R,4'S,5'S,6'R)-5,6'-dimethyl-6-((5-(3-fluorophenyl)thienyl)-2-methyl)-5-chloro-3',4',5',6'-tetrahydro-3H-spiro[isobenzofuran-1,2'-pyran]-3',4',5'-triol | 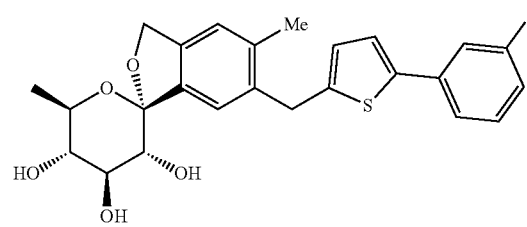 A72 |
| A73 | (1S,3'R,4'S,5'S,6'R)-5,6'-dimethyl-6-((5-(2,4-difluorophenyl)thienyl)-2-methyl)-5-chloro-3',4',5',6'-tetrahydro-3H-spiro[isobenzofuran-1,2'-pyran]-3',4',5'-triol | 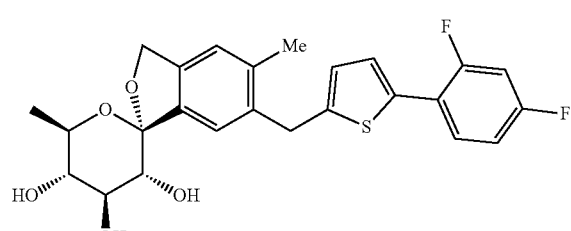 A73 |

| No. | Name | Structure |
| --- | --- | --- |
| A74 | (1S,3'R,4'S,5'S,6'R)-5,6'-dimethyl-6-((5-(2-fluorophenyl)thienyl)-2-methyl)-5-chloro-3',4',5',6'-tetrahydro-3H-spiro[isobenzofuran-1,2'-pyran]-3',4',5'-triol | 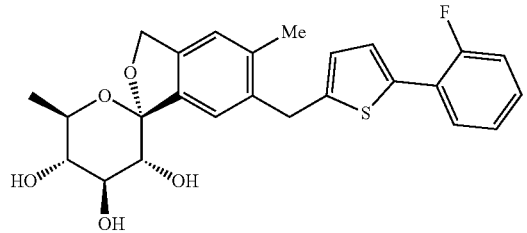 [SMILES: Cc1cc2c(cc1Cc1ccc(-c3ccccc3F)s1)[C@]1(OC2)O[C@H](C)[C@@H](O)[C@H](O)[C@H]1O] |
| A75 | (1S,3'R,4'S,5'S,6'R)-5,6'-dimethyl-6-((5-(4-methoxyphenyl)thienyl)-2-methyl)-5-chloro-3',4',5',6'-tetrahydro-3H-spiro[isobenzofuran-1,2'-pyran]-3',4',5'-triol | 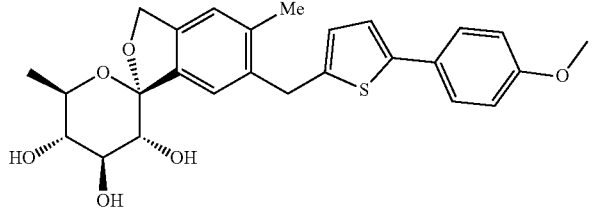 |
| A76 | (1S,3'R,4'S,5'S,6'R)-5,6'-dimethyl-6-((5-methoxythienyl)-2-methyl)-3',4',5',6'-tetrahydro-3H-spiro[isobenzofuran-1,2'-pyran]-3',4',5'-triol | 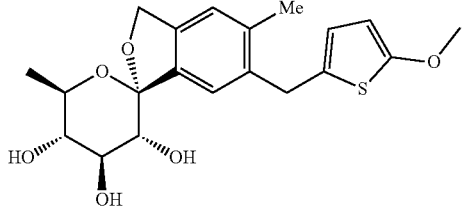 |
| A77 | (1S,3'R,4'S,5'S,6'R)-5,6'-dimethyl-6-((5-trifluoromethylthienyl)-2-methyl)-3',4',5',6'-tetrahydro-3H-spiro[isobenzofuran-1,2'-pyran]-3',4',5'-triol | 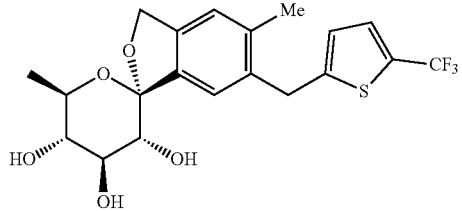 [SMILES: Cc1cc2c(cc1Cc1ccc(C(F)(F)F)s1)[C@]1(OC2)O[C@H](C)[C@@H](O)[C@H](O)[C@H]1O] |
| A78 | 5-(((1S,3'R,4'S,5'S,6'R)-3',4',5'-trihydroxy-5,6'-dimethyl-3',4',5',6'-tetrahydro-3H-spiro[isobenzofuran-1,2'-pyran]yl)-6-methyl)thiophene-2-nitrile | 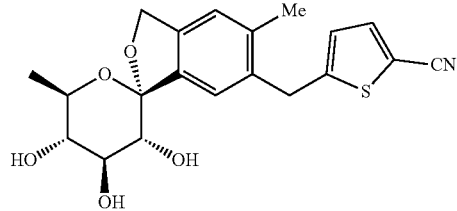 [SMILES: Cc1cc2c(cc1Cc1ccc(C#N)s1)[C@]1(OC2)O[C@H](C)[C@@H](O)[C@H](O)[C@H]1O] |
| A79 | 5-(((1S,3'R,4'S,5'S,6'R)-3',4',5'-trihydroxy-5,6'-dimethyl--3',4',5',6'-tetrahydro-3H-spiro[isobenzofuran-1,2'-pyran]yl)-6-methyl)thiophene-2-methyl formate | 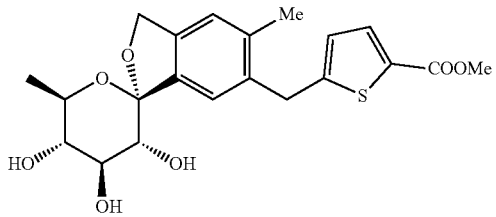 [SMILES: COC(=O)c1ccc(Cc2cc3c(cc2C)CO[C@]32O[C@H](C)[C@@H](O)[C@H](O)[C@H]2O)s1] |

| No. | Name | Structure |
|---|---|---|
| A80 | 5-(((1S,3'R,4'S,5'S,6'R)-3',4',5'-trihydroxy-5,6'-dimethyl-3',4',5',6'-tetrahydro-3H-spiro[isobenzofuran-1,2'-pyran]yl)-6-methyl)thiophene-2-phenyl formate | 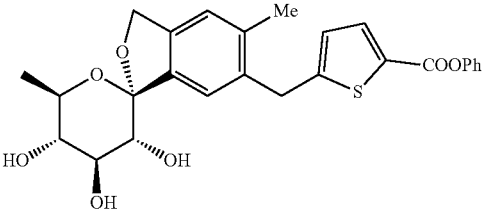<br>A80 |
| A81 | N-methyl-5-(((1S,3'R,4'S,5'S,6'R)-3',4',5'-trihydroxy-5,6'-dimethyl--3',4',5',6'-tetrahydro-3H-spiro[isobenzofuran-1,2'-pyran]yl)-6-methyl)thiophene-2-formamide | 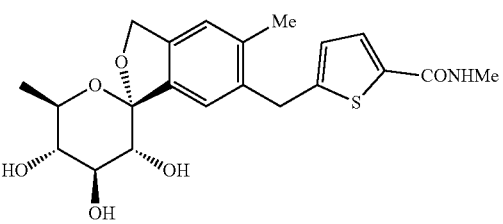<br>A81 |
| A82 | (1S,3'R,4'S,5'S,6'R)-5-ethynyl-6'-methyl-6-(4-methylbenzyl)-3',4',5',6'-tetrahydro-3H-spiro[isobenzofuran-1,2'-pyran]-3',4',5'-triol | 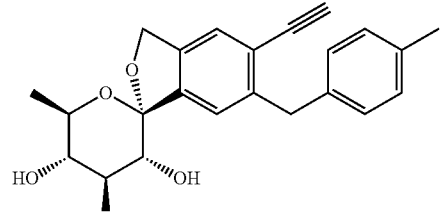<br>A82 |
| A83 | (1S,3'R,4'S,5'S,6'R)-5-ethynyl-6'-methyl-6-((5-(4-fluorophenyl)thienyl)-2-methyl)-3',4',5',6'-tetrahydro-3H-spiro[isobenzofuran-1,2'-pyran]-3',4',5'-triol | 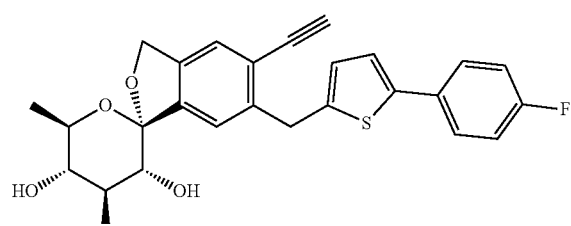<br>A83 |
| A84 | (1S,3'R,4'S,5'S,6'R)-5-ethynyl-6'-methyl-6-((5-(2-furyl)thiazolyl)-2-methyl)-3',4',5',6'-tetrahydro-3H-spiro[isobenzofuran-1,2'-pyran]-3',4',5'-triol | 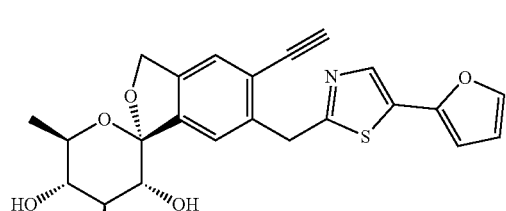<br>A84 |
| A85 | (1S,3'R,4'S,5'S,6'R)-5-ethynyl-6'-methyl-6-((5-ethylthienyl)-2-methyl)-3',4',5',6'-tetrahydro-3H-spiro[isobenzofuran-1,2'-pyran]-3',4',5'-triol | 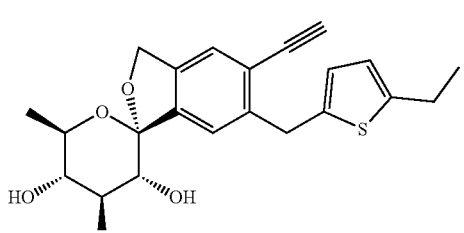<br>A85 |

-continued

| No. | Name | Structure |
|---|---|---|
| A86 | (1S,3'R,4'S,5'S,6'R)-5-ethynyl-6'-methyl-6-(4-methoxybenzyl)-3',4',5',6'-tetrahydro-3H-spiro[isobenzofuran-1,2'-pyran]-3',4',5'-triol | 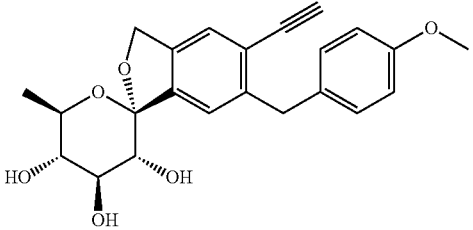<br>A86 |
| A87 | (1S,3'R,4'S,5'S,6'R)-5-ethynyl-6'-methyl-6-(4-ethyoxylbenzyl)-3',4',5',6'-tetrahydro-3H-spiro[isobenzofuran-1,2'-pyran]-3',4',5'-triol | 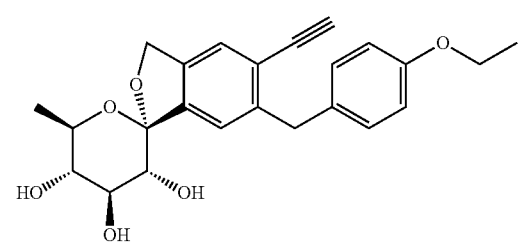 [SMILES: C#Cc1cc2c(cc1Cc1ccc(OCC)cc1)[C@]1(OC2)O[C@H](C)[C@@H](O)[C@H](O)[C@H]1O]<br>A87 |
| A88 | (1S,3'R,4'S,5'S,6'R)-3',4',5'-trihydroxy-6'-methyl-6-(4-methylphenyl)-3',4',5',6'-tetrahydro-3H-spiro[isobenzofuran-1,2'-pyran]-5-nitrile | 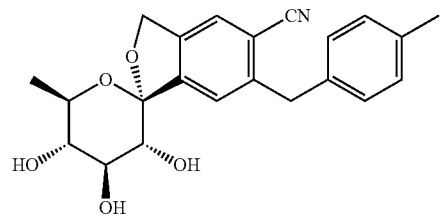<br>A88 |
| A89 | (1S,3'R,4'S,5'S,6'R)-6-((5-(4-fluorophenyl)thienyl)-2-methyl)-3',4',5'-trihydroxy-6'-methyl-3',4',5',6'-tetrahydro-3H-spiro[isobenzofuran-1,2'-pyran]-5-nitrile | 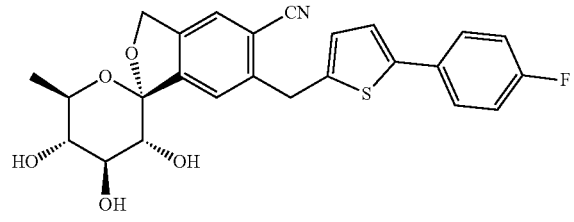 [SMILES: C[C@H]1O[C@]2(OCc3cc(C#N)c(Cc4ccc(-c5ccc(F)cc5)s4)cc32)[C@H](O)[C@@H](O)[C@@H]1O]<br>A89 |
| A90 | (1S,3'R,4'S,5'S,6'R)-6-((5-(2-furyl)thiazolyl)-2-methyl)-3',4',5'-trihydroxy-6'-methyl-3',4',5',6'-tetrahydro-3H-spiro[isobenzofuran-1,2'-pyran]-5-nitrile | 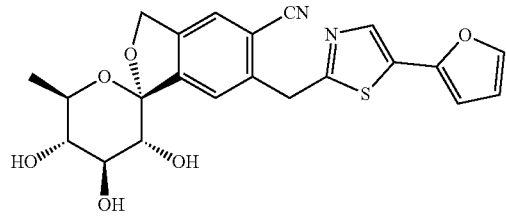 [SMILES: C[C@H]1O[C@]2(OCc3cc(C#N)c(Cc4ncc(-c5ccco5)s4)cc32)[C@H](O)[C@@H](O)[C@@H]1O]<br>A90 |
| A91 | (1S,3'R,4'S,5'S,6'R)-6-((5-ethylthienyl)-2-methyl)-3',4',5'-trihydroxy-6'-methyl-3',4',5',6'-tetrahydro-3H-spiro[isobenzofuran-1,2'-pyran]-5-nitrile | 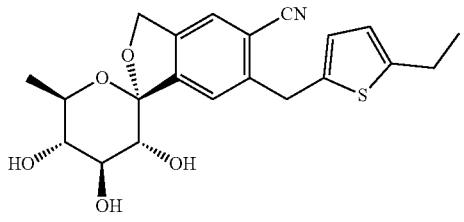 [SMILES: CCc1ccc(Cc2cc3c(cc2C#N)CO[C@]32O[C@H](C)[C@@H](O)[C@H](O)[C@H]2O)s1]<br>A91 |

| No. | Name | Structure |
|---|---|---|
| A92 | (1S,3'R,4'S,5'S,6'R)-3',4',5'-trihydroxy-6-(4-methoxyphenyl)-6'-methyl-3',4',5'-trihydroxy-6'-methyl-3',4',5',6'-tetrahydro-3H-spiro[isobenzofuran-1,2'-pyran]-5-nitrile | 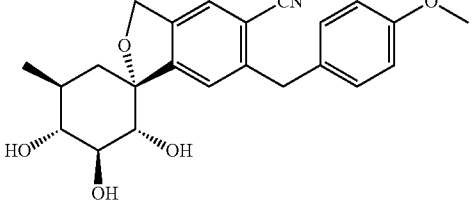 |
| A93 | (1S,3'R,4'S,5'S,6'R)-3',4',5'-trihydroxy-6-(4-ethyoxylphenyl)-6'-methyl-3',4',5'-trihydroxy-6'-methyl-3',4',5',6'-tetrahydro-3H-spiro[isobenzofuran-1,2'-pyran]-5-nitrile | 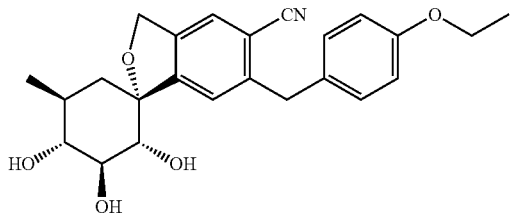 [SMILES: CCOc1ccc(Cc2cc3c(cc2C#N)CO[C@]32C[C@H](C)[C@@H](O)[C@H](O)[C@H]2O)cc1] |
| A94 | (1S,3'R,4'S,5'S,6'R)-6'-methyl-6-(4-methylbenzyl)-5-bromo-3',4',5',6'-tetrahydro-3H-spiro[isobenzofuran-1,2'-pyran]-3',4',5'-triol | 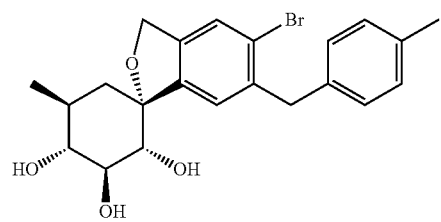 |
| A95 | (1S,3'R,4'S,5'S,6'R)-6'-methyl-6-((5-(4-fluorophenyl)thienyl)-2-methyl)-5-bromo-3',4',5',6'-tetrahydro-3H-spiro[isobenzofuran-1,2'-pyran]-3',4',5'-triol | 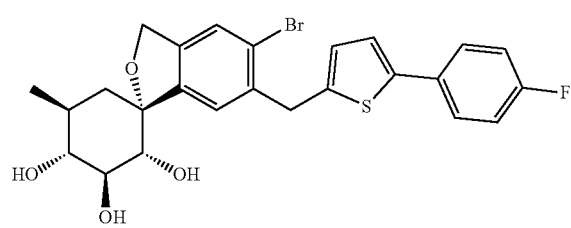 [SMILES: C[C@H]1C[C@]2(OCc3cc(Br)c(Cc4ccc(-c5ccc(F)cc5)s4)cc32)[C@H](O)[C@@H](O)[C@@H]1O] |
| A96 | (1S,3'R,4'S,5'S,6'R)-6'-methyl-6-((5-(2-furyl)thiazolyl)-2-methyl)-5-bromo-3',4',5',6'-tetrahydro-3H-spiro[isobenzofuran-1,2'-pyran]-3',4',5'-triol | 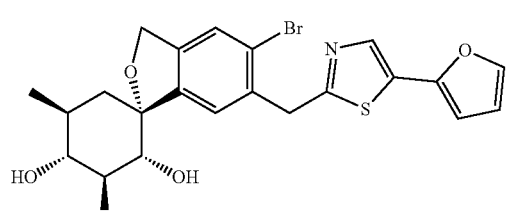 |
| A97 | (1S,3'R,4'S,5'S,6'R)-6'-methyl-6-((5-ethylthienyl)-2-methyl)-5-fluoro-3',4',5',6'-tetrahydro-3H-spiro[isobenzofuran-1,2'-pyran]-3',4',5'-triol | 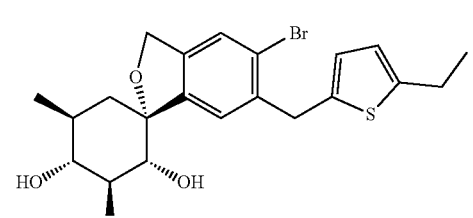 |

| No. | Name | Structure |
|---|---|---|
| A98 | (1S,3'R,4'S,5'S,6'R)-6'-methyl-6-(4-methoxybenzyl)-5-bromo-3',4',5',6'-tetrahydro-3H-spiro[isobenzofuran-1,2'-pyran]-3',4',5'-triol | 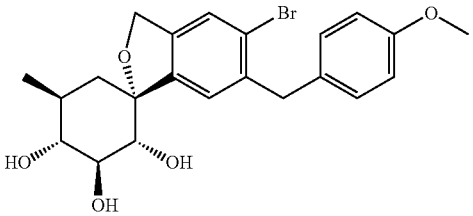 |
| A99 | (1S,3'R,4'S,5'S,6'R)-6'-methyl-6-(4-ethyoxylbenzyl)-5-bromo-3',4',5',6'-tetrahydro-3H-spiro[isobenzofuran-1,2'-pyran]-3',4',5'-triol | 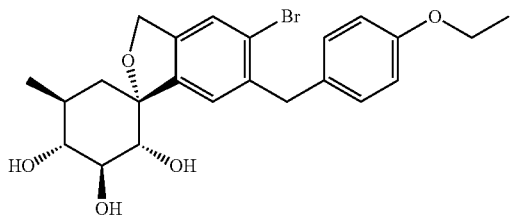 |
| A100 | (1S,3'R,4'S,5'S,6'R)-5-methoxy-6'-methyl-6-(4-methylbenzyl)-3',4',5',6'-tetrahydro-3H-spiro[isobenzofuran-1,2'-pyran]-3',4',5'-triol | 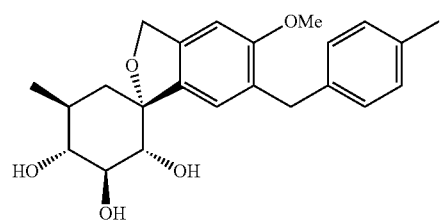 |
| A101 | (1S,3'R,4'S,5'S,6'R)-6-((5-(4-fluorophenyl)thienyl)-2-methyl)-5-methoxy-6'-methyl-3',4',5',6'-tetrahydro-3H-spiro[isobenzofuran-1,2'-pyran]-3',4',5'-triol | 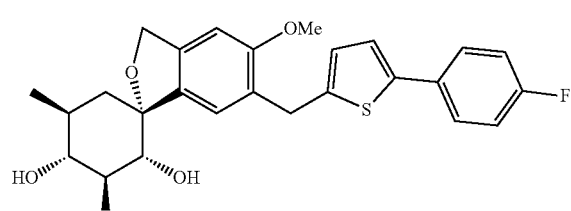 |
| A102 | (1S,3'R,4'S,5'S,6'R)-6-((5-(2-furyl)thiazolyl)-2-methyl)-5-methoxy-6'-methyl-3',4',5',6'-tetrahydro-3H-spiro[isobenzofuran-1,2'-pyran]-3',4',5'-triol | 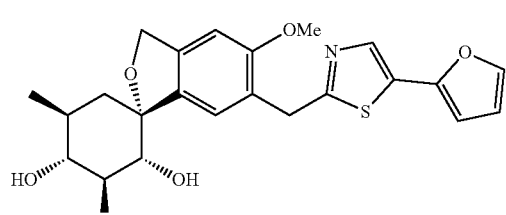 |
| A103 | (1S,3'R,4'S,5'S,6'R)-6-((5-ethylthienyl)-2-methyl)-5-methoxy-6'-methyl-3',4',5',6'-tetrahydro-3H-spiro[isobenzofuran-1,2'-pyran]-3',4',5'-triol | 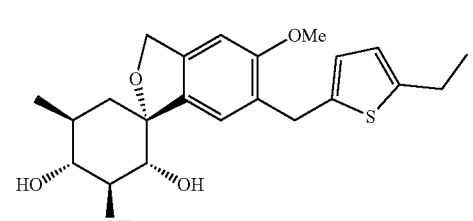 |

-continued

| No. | Name | Structure |
|---|---|---|
| A104 | (1S,3'R,4'S,5'S,6'R)-5-methoxy-6-(4-methoxyphenyl)-6'-methyl-3',4',5',6'-tetrahydro-3H-spiro[isobenzofuran-1,2'-pyran]-3',4',5'-triol | 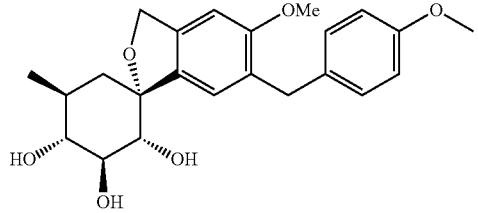<br>A104 |
| A105 | (1S,3'R,4'S,5'S,6'R)-5-methoxy-6-(4-ethyoxylphenyl)-6'-methyl-3',4',5',6'-tetrahydro-3H-spiro[isobenzofuran-1,2'-pyran]-3',4',5'-triol | 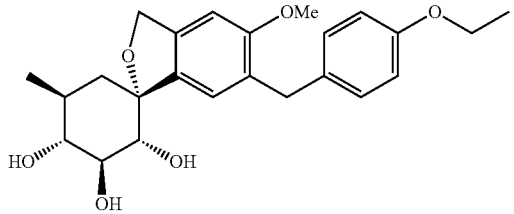 [SMILES: CCOc1ccc(Cc2cc3c(cc2OC)CO[C@]32C[C@H](C)[C@@H](O)[C@H](O)[C@H]2O)cc1]<br>A105 |
| A106 | (1S,3'R,4'S,5'S,6'R)-6-(benzofuran-5-ylmethyl)-5-chloro-6'-methyl-3',4',5',6'-tetrahydro-3H-spiro[isobenzofuran-1,2'-pyran]-3',4',5'-triol | 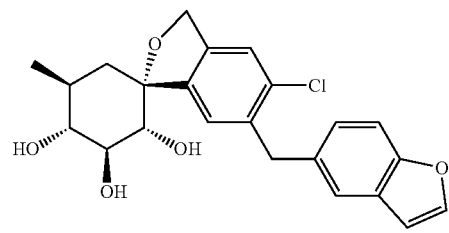 [SMILES: C[C@H]1C[C@]2(OCc3cc(Cl)c(Cc4ccc5occc5c4)cc32)[C@H](O)[C@@H](O)[C@@H]1O]<br>A106 |
| A107 | (1S,3'R,4'S,5'S,6'R)-5-chloro-6-(4-ethyoxyl-3-fluorophenyl)-6'-methyl-3',4',5',6'-tetrahydro-3H-spiro[isobenzofuran-1,2'-pyran]-3',4',5'-triol | 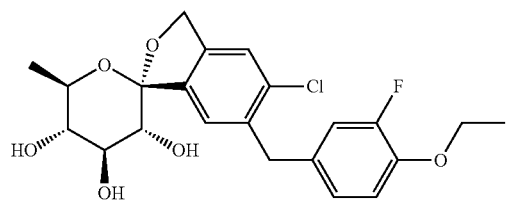 [SMILES: CCOc1ccc(Cc2cc3c(cc2Cl)CO[C@]32O[C@H](C)[C@@H](O)[C@H](O)[C@H]2O)cc1F]<br>A107 |
| A108 | 1-(4-(((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)methyl)phenyl)cyclopropane-1-formonitrile | 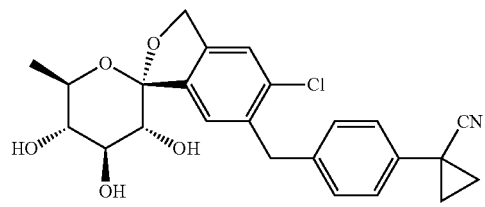 [SMILES: C[C@H]1O[C@]2(OCc3cc(Cl)c(Cc4ccc(C5(C#N)CC5)cc4)cc32)[C@H](O)[C@@H](O)[C@@H]1O]<br>A108 |
| A109 | 1-(5-(((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)methyl)thiophene-2-yl)cyclopropane-1-formonitrile | 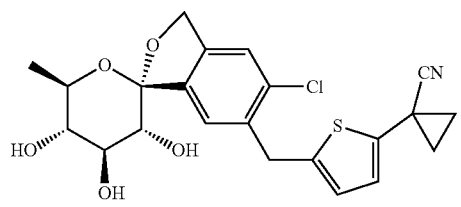 [SMILES: C[C@H]1O[C@]2(OCc3cc(Cl)c(Cc4ccc(C5(C#N)CC5)s4)cc32)[C@H](O)[C@@H](O)[C@@H]1O]<br>A109 |

| No. | Name | Structure |
|---|---|---|
| A110 | (1S,3'R,4'S,5'S,6'R)-5-chloro-6'-methyl-6-(4-trifluoromethylphenyl)-3',4',5',6'-tetrahydro-3H-spiro[isobenzofuran-1,2'-pyran]-3',4',5'-triol | 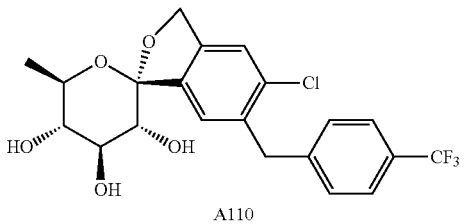 |
| A111 | ((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)(4-(trifluoromethyl)phenyl)ketone | 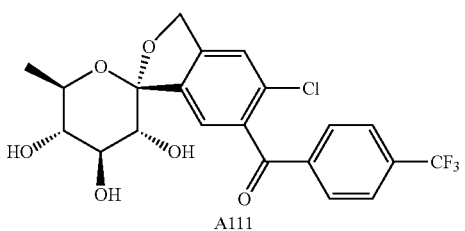 |
| A112 | ((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)(3-fluoro-4-(trifluoromethyl)phenyl)ketone | 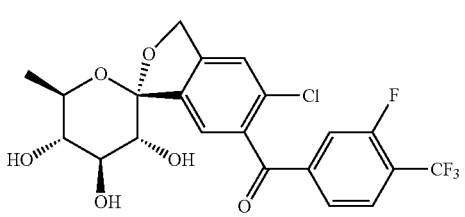 [SMILES: C[C@H]1O[C@]2(OCc3cc(Cl)c(C(=O)c4ccc(C(F)(F)F)c(F)c4)cc32)[C@H](O)[C@@H](O)[C@@H]1O] |
| A113 | ((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)(5-ethylthiophene-2-yl)ketone | 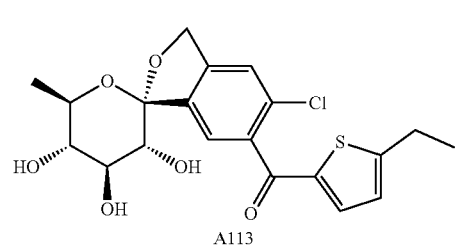 |
| A114 | (1S,3'R,4'S,5'S,6'R)-5-chloro-6-((5-(2-methoxyethyl)thiophene-2-yl)methyl)-6'-methyl-3',4',5',6'-tetrahydro-3H-spiro[isobenzofuran-1,2'-pyran]-3',4',5'-triol | 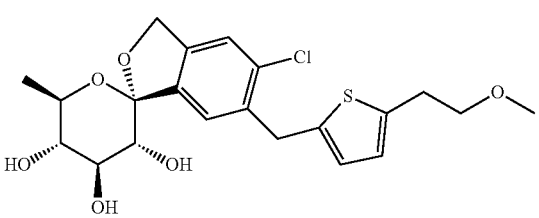 |
| A115 | (1S,3'R,4'S,5'S,6'R)-5-chloro-6-((5-(2-ethyoxyethyl)thiophene-2-yl)methyl)-6'-methyl-3',4',5',6'-tetrahydro-3H-spiro[isobenzofuran-1,2'-pyran]-3',4',5'-triol | 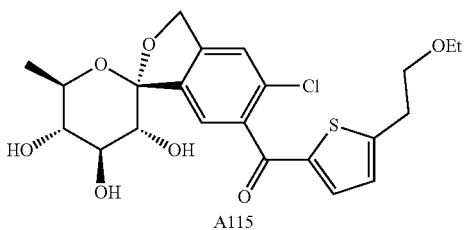 |

| No. | Name | Structure |
|---|---|---|
| A116 | (1S,3'R,4'S,5'S,6'R)-5-chloro-6-((5-(2-propoxyethyl)thiophene-2-yl)methyl)-6'-methyl-3',4',5',6'-tetrahydro-3H-spiro[isobenzofuran-1,2'-pyran]-3',4',5'-triol | 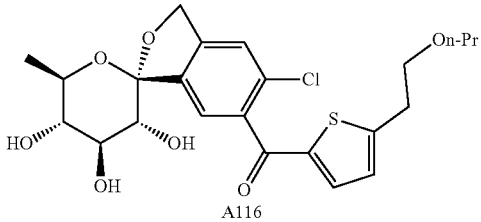 |
| A117 | 1-(5-(((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)methyl)thiophene-2-yl)ethanone | 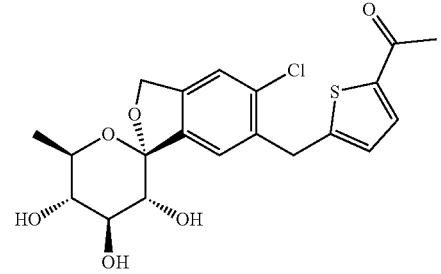 [SMILES: CC(=O)c1ccc(Cc2cc3c(cc2Cl)CO[C@]32O[C@H](C)[C@@H](O)[C@H](O)[C@H]2O)s1] |
| A118 | (1S,3'R,4'S,5'S,6'R)-5-chloro-6-((5-(1-hydroxy-ethyl)thiophene-2-yl)methyl)-6'-methyl-3',4',5',6'-tetrahydro-3H-spiro[isobenzofuran-1,2'-pyran]-3',4',5'-triol | 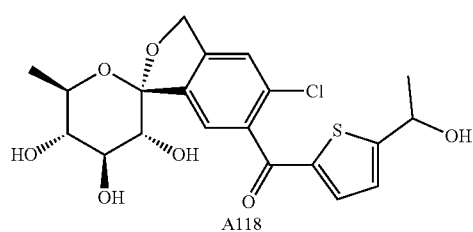 |
| A119 | (1S,3'R,4'S,5'S,6'R)-5-chloro-6-((5-(2-hydroxy-ethyl)thiophene-2-yl)methyl)-6'-methyl-3',4',5',6'-tetrahydro-3H-spiro[isobenzofuran-1,2'-pyran]-3',4',5'-triol | 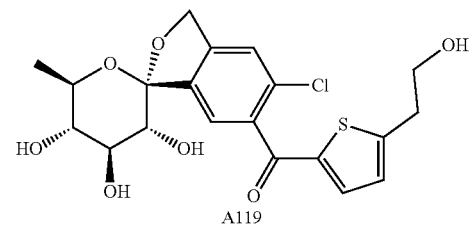 |
| A120 | (1S,3'R,4'S,5'S,6'R)-5-chloro-6-((5-ethylthiophene-2-yl)(hydroxymethyl)-6'-methyl-3',4',5',6'-tetrahydro-3H-spiro[isobenzofuran-1,2'-pyran]-3',4',5'-triol | 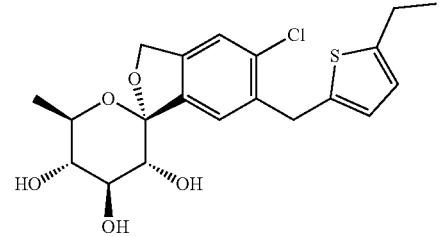 [SMILES: CCc1ccc(Cc2cc3c(cc2Cl)CO[C@]32O[C@H](C)[C@@H](O)[C@H](O)[C@H]2O)s1] |
| A121 | 2-(5-(((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)methyl)thiophene-2-yl) acetic acid | 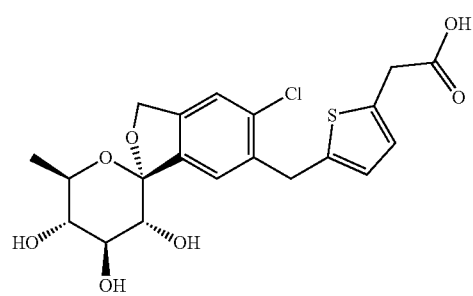 [SMILES: C[C@H]1O[C@]2(OCc3cc(Cl)c(Cc4ccc(CC(=O)O)s4)cc32)[C@H](O)[C@@H](O)[C@@H]1O] |

-continued

| No. | Name | Structure |
|---|---|---|
| A122 | 2-(5-(((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)methyl)thiophene-2-yl)methyl acetate | 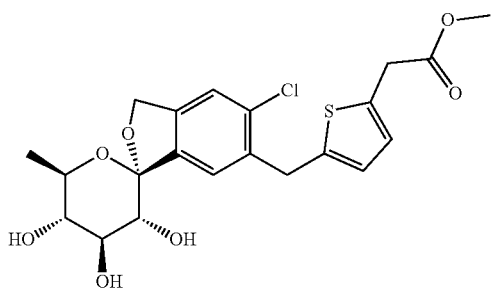 A122 |
| A123 | 2-(5-(((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)methyl)thiophene-2-yl)ethyl acetate | 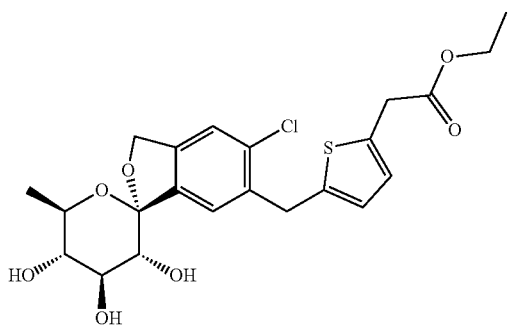 A123 |
| A124 | 2-(5-(((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)methyl)thiophene-2-yl)-N-methylacetamide | 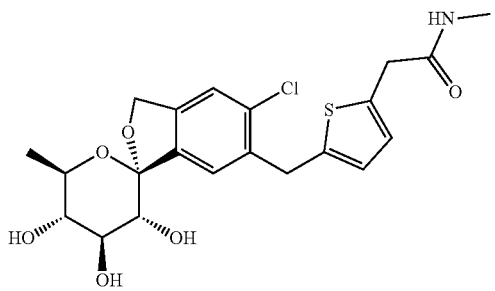 A124 |
| A125 | 2-(5-(((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)methyl)thiophene-2-yl)-N-ethylacetamide | 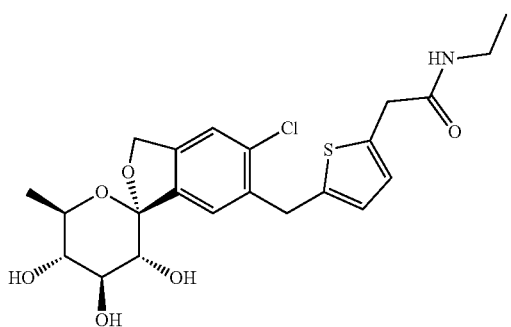 A125 |

| No. | Name | Structure |
|---|---|---|
| A126 | 2-(5-(((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)methyl)thiophene-2-yl)-N,N-dimethylacetamide | 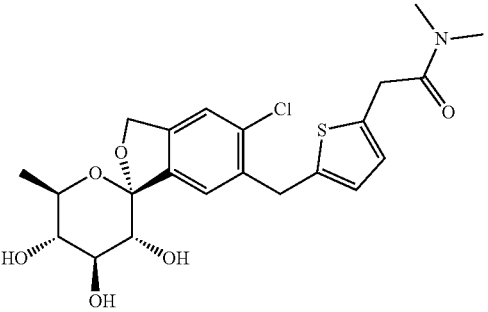 |
| A127 | 2-(5-(((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)methyl(thiophene-2-yl)-1-(pyrrolidine-1-yl)ethyl-1-one | 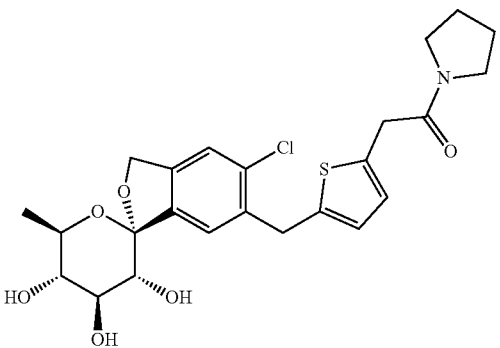 [SMILES: C[C@H]1O[C@]2(OCc3cc(Cl)c(Cc4ccc(CC(=O)N5CCCC5)s4)cc32)[C@H](O)[C@@H](O)[C@@H]1O] |
| A128 | 2-(5-(((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)methyl)thiophene-2-yl)-1-morpholineethyl-1-one | 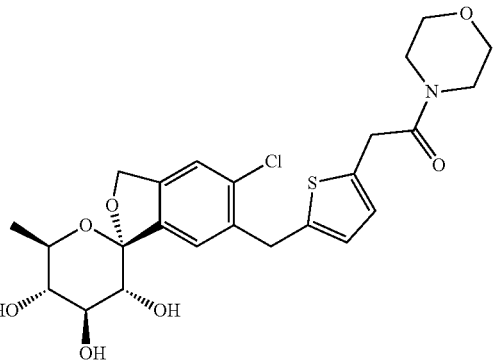 |
| A129 | 5-(((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)methyl)thiophene-2-formaldehyde | 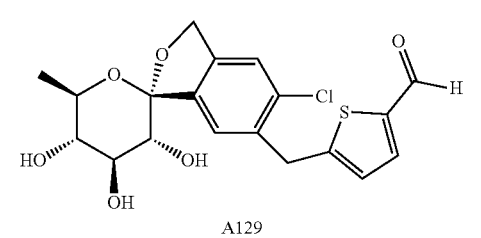 |
| A130 | (1S,3'R,4'S,5'S,6'R)-5-chloro-6-((5-(hydroxymethyl)thiophene-2-yl)methyl)-6'-methyl-3',4',5',6'-tetrahydro-3H-spiro[isobenzofuran-1,2'-pyran]-3',4',5'-triol | 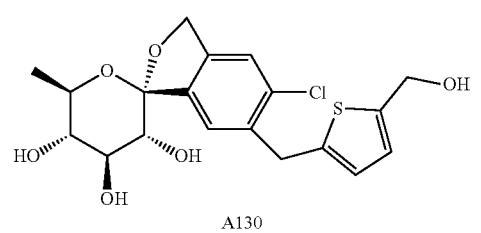 |

| No. | Name |
|---|---|
| A131 | (1S,3'R,4'S,5'S,6'R)-5-chloro-6-((5-(difluoromethyl)thiophene-2-yl)methyl)-6'-methyl-3',4',5',6'-tetrahydro-3H-spiro[isobenzofuran-1,2'-pyran]-3',4',5'-triol |
| A132 | (1S,3'R,4'S,5'S,6'R)-5-chloro-6'-methyl-6-((5-(pyrrolidine-1-ylmethyl)thiophene-2-yl)methyl)-3',4',5',6'-tetrahydro-3H-spiro[isobenzofuran-1,2'-pyran]-3',4',5'-triol |
| A133 | (1S,3'R,4'S,5'S,6'R)-5-chloro-6'-methyl-6-((5-morpholinemethyl)thiophene-2-yl)methyl)-3',4',5',6'-tetrahydro-3H-spiro[isobenzofuran-1,2'-pyran]-3',4',5'-triol |
| A134 | 2-(5-(((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)methyl)thiophene-2-methyl formate |
| A135 | 2-(5-(((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)methyl)thiophene-2-ethyl formate |
| A136 | (5-(((1S,3'R,4'S,5',S,6'R)-5-chloro-3',4',5'-trihydroxy-6'-methyl-3',4',5',6'-tetrahydro-3H-spiro[isobenzofuran-1,2'-pyran]-6-yl)methypthiophene-2-yl)(pyrrolidine-1-yl)ketone |
| A137 | (5-(((1S,3'R,4'S,5',S,6'R)-5-chloro-3',4',5'-trihydroxy-6'-methyl-3',4',5',6'-tetrahydro-3H-spiro[isobenzofuran-1,2'-pyran]-6-yl)methyl)thiophene-2-yl)(morpholineyl)ketone |

-continued

| No. | Name | Structure |
|---|---|---|
| A138 | (5-((((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)methyl)-N-methylthiophene-2-formamide | 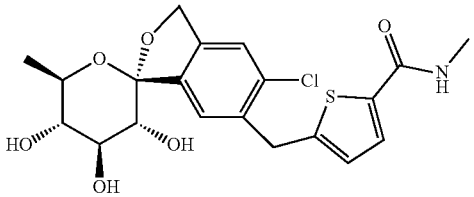 A138 |
| A139 | (5-((((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)methyl)-N-ethylthiophene-2-formamide | 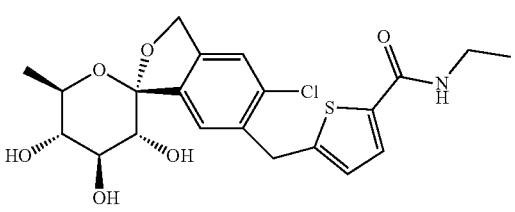 A139 |
| A140 | (5-((((1S,3'R,4'S,5'S,6'R)-5-chloro-3',4',5'-trihydroxy-6'-methyl-3',4',5',6'-tetrahydro-3H-spiro[isobenzofuran-1,2'-pyran]-6-yl)methyl)-N,N-dimethylthiophene-2-formamide | 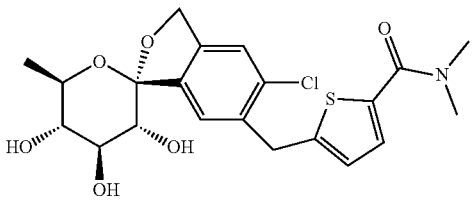 A140 |
| A141 | (1S,3'R,4'S,5'S,6'R)-5-chloro-6-((5-ethyl-4-methylthiophene-2-yl)methyl)-6'-methyl-3',4',5',6'-tetrahydro-3H-spiro[isobenzofuran-1,2'-pyran]-3',4',5'-triol | 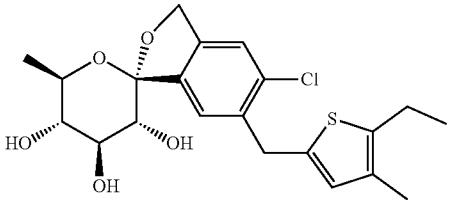 A141 |
| A142 | (1S,3'R,4'S,5'S,6'R)-5-chloro-6-((5-(2-hydroxyethyl)-4-methylthiophene-2-yl)methyl)-6'-methyl-3',4',5',6'-tetrahydro-3H-spiro[isobenzofuran-1,2'-pyran]-3',4',5'-triol | 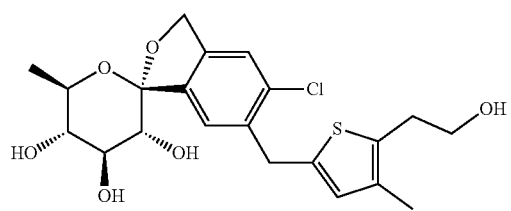 A142 |
| A143 | (1S,3'R,4'S,5'S,6'R)-5-chloro-6-((5-ethyl-4-fluorothiophene-2-yl)methyl)-6'-methyl-3',4',5',6'-tetrahydro-3H-spiro[isobenzofuran-1,2'-pyran]-3',4',5'-triol | 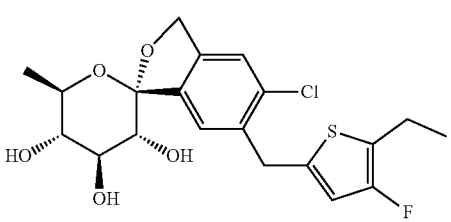 A143 |

-continued

| No. | Name | Structure |
|---|---|---|
| A144 | (1S,3'R,4'S,5'S,6'R)-5-chloro-6-((4-fluoro-5-(2-hydroxyethyl)thiophene-2-yl)methyl)-6'-methyl-3',4',5',6'-tetrahydro-3H-spiro[isobenzofuran-1,2'-pyran]-3',4',5'-triol | 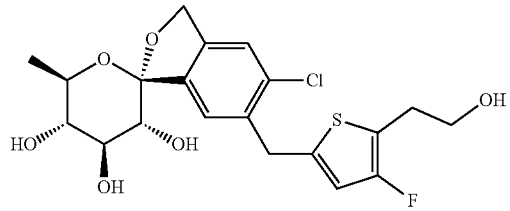 [SMILES: C[C@H]1O[C@]2(OCc3cc(Cl)c(Cc4cc(F)c(CCO)s4)cc32)[C@H](O)[C@@H](O)[C@@H]1O] |
| A145 | (1S,3'R,4'S,5'S,6'R)-5-chloro-6-((4,5-dimethylthiophene-2-yl)methyl)-6'-methyl-3',4',5',6'-tetrahydro-3H-spiro[isobenzofuran-1,2'-pyran]-3',4',5'-triol | 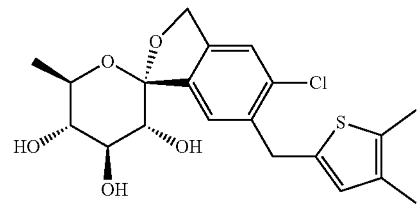 |
| A146 | (1S,3'R,4'S,5'S,6'R)-5-chloro-6-((5-chloro-4-methylthiophene-2-yl)methyl)-6'-methyl-3',4',5',6'-tetrahydro-3H-spiro[isobenzofuran-1,2'-pyran]-3',4',5'-triol | 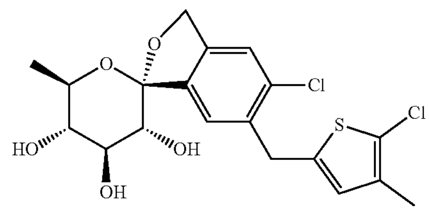 |
| A147 | (1S,3'R,4'S,5'S,6'R)-5-chloro-6-((5-fluoro-4-methylthiophene-2-yl)methyl)-6'-methyl-3',4',5',6'-tetrahydro-3H-spiro[isobenzofuran-1,2'-pyran]-3',4',5'-triol | 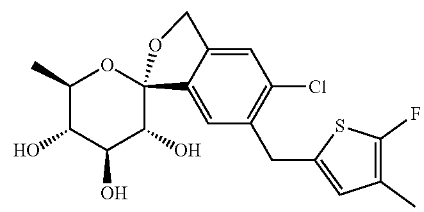 |
| A148 | (1S,3'R,4'S,5'S,6'R)-5-chloro-6-((5-((R)-1-hydroxyethyl)thiophene-2-yl)methyl)-6'-methyl-3',4',5',6'-tetrahydro-3H-spiro[isobenzofuran-1,2'-pyran]-3',4',5'-triol | 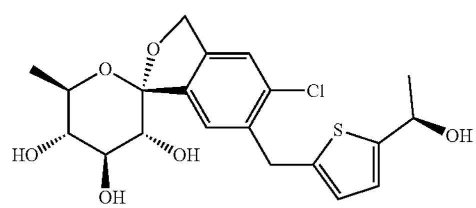 [SMILES: C[C@@H](O)c1ccc(Cc2cc3c(cc2Cl)CO[C@]32O[C@H](C)[C@@H](O)[C@H](O)[C@H]2O)s1] |
| A149 | (1S,3'R,4'S,5'S,6'R)-5-chloro-6-((5-((S)-1-hydroxyethyl)thiophene-2-yl)methyl)-6'-methyl-3',4',5',6'-tetrahydro-3H-spiro[isobenzofuran-1,2'-pyran]-3',4',5'-triol | 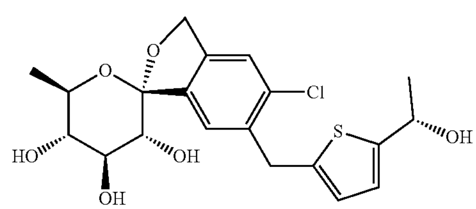 |

| No. | Name | Structure |
|---|---|---|
| A150 | (1S,3'R,4'S,5'S,6'R)-5-chloro-6-((S)-(5-ethylthiophene-2-yl)(hydroxyl)methyl)-6'-methyl-3',4',5',6'-tetrahydro-3H-spiro[isobenzofuran-1,2'-pyran]-3',4',5'-triol | 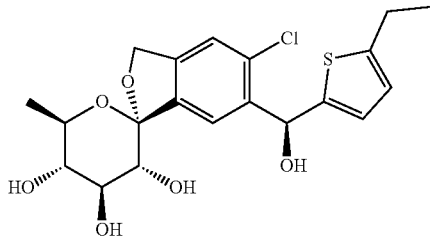 A150 |
| A151 | (1S,3'R,4'S,5'S,6'R)-5-chloro-6-((R)-(5-ethylthiophene-2-yl)(hydroxyl)methyl)-6'-methyl-3',4',5',6'-tetrahydro-3H-spiro[isobenzofuran-1,2'-pyran]-3',4',5'-triol | 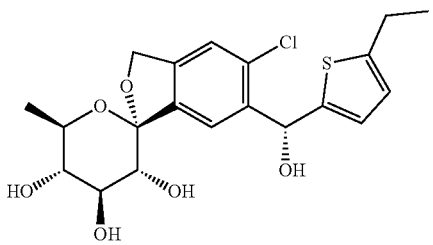 A151 |
or a pharmaceutically acceptable salt thereof.
* * * * *